(12) United States Patent
Von Kreudenstein et al.

(10) Patent No.: US 10,875,931 B2
(45) Date of Patent: Dec. 29, 2020

(54) STABLE HETERODIMERIC ANTIBODY DESIGN WITH MUTATIONS IN THE FC DOMAIN

(71) Applicant: Zymeworks Inc., Vancouver (CA)

(72) Inventors: Thomas Spreter Von Kreudenstein, Vancouver (CA); Eric Escobar-Cabrera, Burnaby (CA); Surjit Bhimarao Dixit, Richmond (CA); Paula Irene Lario, Vancouver (CA); David Kai Yuen Poon, Richmond (CA)

(73) Assignee: ZYMEWORKS, INC., Vancouver (CA)

( * ) Notice: Subject to any disclaimer, the term of this patent is extended or adjusted under 35 U.S.C. 154(b) by 227 days.

(21) Appl. No.: 15/409,456

(22) Filed: Jan. 18, 2017

(65) Prior Publication Data

US 2018/0194860 A1  Jul. 12, 2018

Related U.S. Application Data

(63) Continuation of application No. 13/289,934, filed on Nov. 4, 2011, now Pat. No. 9,562,109.

(60) Provisional application No. 61/497,861, filed on Jun. 16, 2011, provisional application No. 61/491,846, filed on May 31, 2011, provisional application No. 61/475,614, filed on Apr. 14, 2011, provisional application No. 61/439,341, filed on Feb. 3, 2011, provisional application No. 61/425,375, filed on Dec. 21, 2010, provisional application No. 61/410,746, filed on Nov. 5, 2010.

(51) Int. Cl.
| | | |
|---|---|---|
| *C07K 16/00* | (2006.01) | |
| *C12P 21/08* | (2006.01) | |
| *A61K 39/395* | (2006.01) | |
| *C07K 16/46* | (2006.01) | |
| *C07K 16/32* | (2006.01) | |
| *C07K 1/00* | (2006.01) | |

(52) U.S. Cl.
CPC ............ *C07K 16/468* (2013.01); *C07K 16/00* (2013.01); *C07K 16/32* (2013.01); *C07K 2317/30* (2013.01); *C07K 2317/524* (2013.01); *C07K 2317/526* (2013.01); *C07K 2317/64* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,624,821 A | 4/1997 | Winter et al. |
| 5,731,168 A | 3/1998 | Carter et al. |
| 5,807,706 A | 9/1998 | Carter et al. |
| 5,821,333 A | 10/1998 | Carter et al. |
| 5,885,573 A | 3/1999 | Bluestone et al. |
| 6,194,551 B1 | 2/2001 | Idusogie et al. |
| 6,331,415 B1 | 12/2001 | Cabilly et al. |
| 6,737,056 B1 | 5/2004 | Presta |
| 6,809,185 B1 | 10/2004 | Schoonjans et al. |
| 7,183,076 B2 | 2/2007 | Arathoon et al. |
| 7,635,472 B2 | 12/2009 | Kufer et al. |
| 7,642,228 B2 | 1/2010 | Carter et al. |
| 7,695,936 B2 | 4/2010 | Carter et al. |
| 7,769,573 B2 | 8/2010 | Fejes et al. |
| 7,923,221 B1 | 4/2011 | Cabilly et al. |
| 7,951,917 B1 | 5/2011 | Arathoon et al. |
| 8,501,185 B2 | 8/2013 | Heitner Hansen et al. |
| 8,592,562 B2 | 11/2013 | Kannan et al. |
| 8,623,361 B2 | 1/2014 | Beirnaert et al. |
| 8,771,988 B2 | 7/2014 | Kopetzki et al. |
| 9,079,965 B2 | 7/2015 | Zhou et al. |
| 9,499,634 B2 | 11/2016 | Dixit et al. |
| 9,527,927 B2 | 12/2016 | Chowdry et al. |
| 9,562,109 B2 | 2/2017 | Von Kreudenstein et al. |
| 9,574,010 B2 | 2/2017 | Spreter Von Kreudenstein et al. |
| 9,732,155 B2 | 8/2017 | Spreter Von Kreudenstein et al. |
| 9,914,785 B2 | 3/2018 | Corper et al. |
| 9,988,460 B2 | 6/2018 | Spreter Von Kreudenstein et al. |
| 10,077,298 B2 | 9/2018 | Corper et al. |
| 2003/0190311 A1 | 10/2003 | Dall'acqua et al. |
| 2004/0071696 A1 | 4/2004 | Adams et al. |
| 2005/0069549 A1 | 3/2005 | Herman et al. |
| 2005/0227324 A1 | 10/2005 | Huang et al. |

(Continued)

FOREIGN PATENT DOCUMENTS

| | | |
|---|---|---|
| CA | 2548757 | 7/2005 |
| CN | 1176659 | 3/1998 |

(Continued)

OTHER PUBLICATIONS

U.S. Appl. No. 15/355,019: Non-Final Office Action dated Jan. 8, 2019, 5 pages.

(Continued)

*Primary Examiner* — Chun W Dahle

(74) *Attorney, Agent, or Firm* — Kilpatrick Townsend & Stockton LLP

(57) ABSTRACT

The provided scaffolds have heavy chains that are asymmetric in the various domains (e.g. CH2 and CH3) to accomplish selectivity between the various Fc receptors involved in modulating effector function, beyond those achievable with a natural homodimeric (symmetric) Fc molecule, and increased stability and purity of the resulting variant Fc heterodimers. These novel molecules comprise complexes of heterogeneous components designed to alter the natural way antibodies behave and that find use in therapeutics.

8 Claims, 88 Drawing Sheets

Specification includes a Sequence Listing.

(56) References Cited

U.S. PATENT DOCUMENTS

| | | |
|---|---|---|
| 2006/0074225 A1 | 4/2006 | Chamberlain et al. |
| 2006/0106905 A1 | 5/2006 | Chren et al. |
| 2006/0160184 A1 | 7/2006 | Mattheus Hoogenboom et al. |
| 2006/0263882 A1 | 11/2006 | Fazio et al. |
| 2007/0041987 A1 | 2/2007 | Carter et al. |
| 2007/0196363 A1 | 8/2007 | Arathoon et al. |
| 2007/0274985 A1 | 11/2007 | Dubel et al. |
| 2007/0276791 A1 | 11/2007 | Fejes et al. |
| 2007/0278170 A1 | 12/2007 | Wiebe et al. |
| 2008/0050370 A1 | 2/2008 | Glaser et al. |
| 2008/0147360 A1 | 6/2008 | Fejes et al. |
| 2009/0162360 A1 | 6/2009 | Klein et al. |
| 2009/0182127 A1 | 7/2009 | Kjaergaard et al. |
| 2009/0226466 A1 | 9/2009 | Fong et al. |
| 2009/0232811 A1 | 9/2009 | Klein et al. |
| 2009/0263392 A1 | 10/2009 | Iagawa et al. |
| 2010/0104564 A1 | 4/2010 | Hansen et al. |
| 2010/0105874 A1 | 4/2010 | Schuurman et al. |
| 2010/0166749 A1 | 7/2010 | Presta |
| 2010/0196265 A1 | 8/2010 | Adams et al. |
| 2010/0256338 A1 | 10/2010 | Brinkmann et al. |
| 2010/0286374 A1 | 11/2010 | Kannan et al. |
| 2010/0322934 A1 | 12/2010 | Imhof-Jung et al. |
| 2010/0322935 A1 | 12/2010 | Croasdale et al. |
| 2010/0331527 A1 | 12/2010 | Davis et al. |
| 2011/0008345 A1 | 1/2011 | Ashman et al. |
| 2011/0053261 A1 | 3/2011 | Lario et al. |
| 2011/0059076 A1 | 3/2011 | McDonagh et al. |
| 2011/0200596 A1 | 8/2011 | Huang et al. |
| 2011/0274691 A1 | 11/2011 | Arvedson et al. |
| 2011/0275787 A1 | 11/2011 | Kufer et al. |
| 2011/0287009 A1 | 11/2011 | Scheer et al. |
| 2011/0293613 A1 | 12/2011 | Brinkmann et al. |
| 2012/0076728 A1 | 3/2012 | Wu et al. |
| 2012/0149876 A1 | 6/2012 | Von Kreudenstein et al. |
| 2012/0244577 A1 | 9/2012 | Dixit et al. |
| 2012/0244578 A1 | 9/2012 | Kannan et al. |
| 2012/0270801 A1 | 10/2012 | Frejd et al. |
| 2013/0078249 A1 | 3/2013 | Ast et al. |
| 2013/0195849 A1 | 8/2013 | Spreter Von Kreudenstein et al. |
| 2013/0238299 A1 | 9/2013 | Ohrn |
| 2013/0245963 A1 | 9/2013 | Ohrn et al. |
| 2013/0336973 A1 | 12/2013 | Spreter Von Kreudenstein et al. |
| 2014/0051835 A1 | 2/2014 | Dixit et al. |
| 2014/0154253 A1 | 6/2014 | Ng et al. |
| 2014/0200331 A1 | 7/2014 | Corper et al. |
| 2015/0051889 A1 | 2/2015 | Ohrn et al. |
| 2015/0125449 A1 | 5/2015 | Ng et al. |
| 2015/0142326 A1 | 5/2015 | Lakatos et al. |
| 2015/0211001 A1 | 7/2015 | Ohrn et al. |
| 2015/0220681 A1 | 8/2015 | Dixit |
| 2015/0284470 A1 | 10/2015 | Spreter Von Kreudenstein et al. |
| 2015/0307594 A1 | 10/2015 | Corper et al. |
| 2016/0083480 A1 | 3/2016 | Ng et al. |
| 2016/0114057 A1 | 4/2016 | Dixit et al. |
| 2016/0257763 A1 | 9/2016 | Von Kreudenstein et al. |
| 2017/0158779 A1 | 6/2017 | Dixit et al. |
| 2018/0016347 A1 | 1/2018 | Spreter Von Kreudenstein et al. |
| 2018/0030150 A1 | 2/2018 | Spreter Von Kreudenstein et al. |
| 2018/0179296 A1 | 6/2018 | Corper et al. |

FOREIGN PATENT DOCUMENTS

| | | |
|---|---|---|
| EP | 368684 | 5/1990 |
| EP | 1870459 | 12/2007 |
| WO | 9308829 | 5/1993 |
| WO | 9404690 | 3/1994 |
| WO | 9627011 | 9/1996 |
| WO | 97/34631 | 9/1997 |
| WO | 9958572 | 11/1999 |
| WO | 0042072 | 7/2000 |
| WO | 03031464 | 4/2003 |
| WO | 2004029207 | 4/2004 |
| WO | 2004068820 | 8/2004 |
| WO | 2005018629 | 3/2005 |
| WO | 2006003388 | 1/2006 |
| WO | 2006030220 | 3/2006 |
| WO | 2007110205 | 10/2007 |
| WO | 2008131242 | 10/2008 |
| WO | 2008141449 A1 | 11/2008 |
| WO | 2009089004 | 7/2009 |
| WO | 2010068722 | 6/2010 |
| WO | 2010085682 | 7/2010 |
| WO | 2010115553 | 10/2010 |
| WO | 2011005621 | 1/2011 |
| WO | 2011028952 | 3/2011 |
| WO | 2011063348 | 5/2011 |
| WO | 2011066655 | 6/2011 |
| WO | 2011120134 | 10/2011 |
| WO | 2011120135 | 10/2011 |
| WO | 2011143545 | 11/2011 |
| WO | 2012058768 | 11/2011 |
| WO | 2011133886 | 12/2011 |
| WO | 2011147982 | 12/2011 |
| WO | 2012006635 | 1/2012 |
| WO | 2012037659 | 3/2012 |
| WO | 2012040833 | 9/2012 |
| WO | 2012116453 | 9/2012 |
| WO | 2012143523 | 10/2012 |
| WO | 2013002362 | 1/2013 |
| WO | 2013063702 | 5/2013 |
| WO | 2013166594 | 11/2013 |
| WO | 2013166604 | 11/2013 |
| WO | 2014004586 | 1/2014 |
| WO | 2014012082 | 1/2014 |
| WO | 2014012085 | 1/2014 |
| WO | 2014018572 | 1/2014 |
| WO | 2014067011 | 5/2014 |
| WO | 2014082179 | 6/2014 |
| WO | 2014182970 | 11/2014 |
| WO | 2014186905 | 11/2014 |
| WO | 2015006749 | 1/2015 |
| WO | 2015181805 | 12/2015 |

OTHER PUBLICATIONS

U.S. Appl. No. 13/289,934, "Restriction Requirement", dated Sep. 16, 2014.

U.S. Appl. No. 13/289,934, "Non-Final Office Action", dated Feb. 27, 2015.

U.S. Appl. No. 13/289,934, "Non-Final Office Action", dated May 13, 2015.

U.S. Appl. No. 13/289,934, "Final Office Action", dated Nov. 16, 2015.

U.S. Appl. No. 13/289,934, "Advisory Action", dated Feb. 5, 2016.

U.S. Appl. No. 13/289,934, "Notice of Allowance", dated Apr. 25, 2016.

U.S. Appl. No. 13/289,934, Notice of Allowance, dated Sep. 29, 2016.

U.S. Appl. No. 13/668,098, "Restriction Requirement", dated Dec. 5, 2014.

U.S. Appl. No. 13/668,098 , "Non-Final Office Action", dated Apr. 3, 2015, 18 pages.

U.S. Appl. No. 13/668,098 , "Final Office Action", dated Nov. 17, 2015, 16 pages.

U.S. Appl. No. 13/668,098, "Notice of Allowance", dated Sep. 23, 2016.

U.S. Appl. No. 13/892,198, "Restriction Requirement", dated Jul. 10, 2015, 12 pages.

U.S. Appl. No. 13/892,198, "Non-Final Office Action", dated Oct. 6, 2015, 23 pages.

U.S. Appl. No. 13/927,065, "Restriction Requirement", dated Apr. 15, 2015, 9 pages.

U.S. Appl. No. 13/927,065, "Non-Final Office Action", dated Oct. 7, 2015, 10 pages.

U.S. Appl. No. 13/927,065, "Final Office Action", dated Feb. 22, 2016, 6 pages.

U.S. Appl. No. 13/927,065, "Notice of Allowance", dated Aug. 26, 2016.

(56) References Cited

OTHER PUBLICATIONS

U.S. Appl. No. 14/439,532, "Restriction Requirement", dated Nov. 8, 2016.
U.S. Appl. No. 14/439,532, "Notice of Allowance", dated Feb. 9, 2017.
U.S. Appl. No. 14/439,532, Notice of Allowance, dated Apr. 1, 2017.
U.S. Appl. No. 14/439,532, "Notice of Allowance", dated May 19, 2017.
U.S. Appl. No. 15/675,248, "Notice of Allowance", dated Mar. 22, 2018.
U.S. Appl. No. 14/893,706, "Restriction Requirement", dated Apr. 4, 2017.
U.S. Appl. No. 14/893,706, "Non-Final Office Action", dated Jun. 30, 2017.
U.S. Appl. No. 14/893,706, "Final Office Action", dated Dec. 1, 2017.
U.S. Appl. No. 14/893,706, "Restriction Requirement", dated Aug. 24, 2018.
U.S. Appl. No. 14/989,648, "Restriction Requirement", dated Jan. 9, 2018.
U.S. Appl. No. 14/989,648, "Non-final Office Action", dated Apr. 18, 2018.
U.S. Appl. No. 14/989,648, "Final Office Action", dated Sep. 26, 2018.
U.S. Appl. No. 13/941,449, "Restriction Requirement", dated Dec. 3, 2015, 10 pages.
U.S. Appl. No. 13/941,449, "Non-Final Office Action", dated Apr. 13, 2016, 41 pages.
U.S. Appl. No. 13/941,449, "Final Office Action", dated Oct. 31, 2016.
U.S. Appl. No. 13/941,449, "Advisory Action", dated Mar. 30, 2017.
U.S. Appl. No. 13/941,449, "Non-Final Office Action", dated Dec. 21, 2017.
U.S. Appl. No. 13/941,449, "Final Office Action", dated Jul. 24, 2018.
U.S. Appl. No. 15/355,019, "Non-Final Office Action", dated Jul. 21, 2017, 7 pages.
U.S. Appl. No. 15/355,019, "Notice of Allowance", dated Nov. 17, 2017, 7 pages.
U.S. Appl. No. 15/355,019, "Notice of Allowance", dated May 22, 2018, 6 pages.
U.S. Appl. No. 15/298,625, "Restriction Requirement", dated Jan. 17, 2018.
U.S. Appl. No. 15/298,625, "Non-Final Office Action", dated Jun. 1, 2018.
U.S. Appl. No. 14/888,580, "Restriction Requirement", dated Jan. 30, 2017.
U.S. Appl. No. 14/888,580, "Non-Final Office Action", dated Apr. 12, 2017.
U.S. Appl. No. 14/888,580, "Final Office Action", dated Sep. 7, 2017.
U.S. Appl. No. 14/888,580, "Non-Final Office Action", dated Mar. 1, 2018.
U.S. Appl. No. 14/888,580, "Final Office Action", dated Aug. 7, 2018.
U.S. Appl. No. 14/888,580, "Notice of Allowance", dated Nov. 15, 2018.
Alegre et al., A Non-Activating "Humanized" Anti-Cd3 Monoclonal Antibody Retains Immunosuppressive Properties In Vivo. Transplantation, Jun. 15, 1994, vol. 57, No. 11, pp. 1537-1543.
Altintas et al., "Targeting epidermal growth factor receptor in tumors: from conventional monoclonal antibodies via heavy chain-only antibodies to nanobodies", Eur J Pharm Sci., vol. 45, No. 4, Oct. 28, 2011, pp. 399-407.
Aitman et al., Copy Number Polymorphism in Fcgr3 Predisposes to Glomerulonephritis in Rats and Humans, Nature, Feb. 16, 2006, vol. 439, No. 7078, pp. 851-855.

Arnold et al., "The impact of glycosylation on the biological function and structure of human immunoglobulins", Annu Rev Immunol., vol. 25, 2007, pp. 21-50.
Atwell et al., Stable Heterodimers From Remodeling The Domain Interface of a Homodimer Using a Phage Display Library, J Mol Biol., Jul. 4, 1997, vol. 270 No. 1, pp. 26-35.
Barthelemy et al., "Comprehensive analysis of the factors contributing to the stability and solubility of autonomous human VH domains", J. Bioi. Chem., vol. 283, No. 6, Feb. 2008, pp. 3639-3654.
Beck et al., "Strategies and challenges for the next generation of therapeutic antibodies," Nature Reviews Immunology, vol. 10, No. 5, 2010, pp. 345-352.
Beckman, R. A., et al., Antibody constructs in cancer therapy: protein engineering strategies to improve exposure in solid tumors. Cancer. Jan. 15, 2007; 109(2):170-9.
Bell et al., "Differential tumor-targeting abilities of three single-domain antibody formats", Cancer Letters, vol. 289, 2009, pp. 81-90.
Bolon et al., Specificity Versus Stability in Computational Protein Design. Proc Natl Acad Sci US A., 2005 Sep. 6, 2005, vol. 102 No. 36, Epub Aug. 29, 2005, pp. 12724-12729.
Carter et al., Humanization of an Anti-p185HER2 Antibody for Human Cancer Therapy. Proc Natl Acad Sci U S A., May 15, 1992, vol. 89, No. 10, pp. 4285-4289.
Carter, "Introduction to current and future protein therapeutics: A protein engineering perspective," Experimental Cell Research, vol. 317, No. 9, 2011, pp. 1261-1269.
Cespedes, M.V., et al., Mouse models in oncogenesis and cancer therapy. Clin Transl Oncol. May 2006; 8(5):318-29.
Chames et al., "Therapeutic antibodies: successes, limitations and hopes for the future", British Journal of Pharmacology, vol. 157, No. 2, 2009, pp. 220-223.
Cochlovius et al., "Treatment of human B cell lymphoma xenografts with a CD3 x CD19 diabody and T cells", Journal of Immunology, vol. 165, No. 2, 2000, pp. 888-895.
Colbere-Garapin et al., "A new dominant hybrid selective marker for higher eukaryotic cell", Journal of Molecular Biology, vol. 150, No. 1, Jul. 25, 1981, pp. 1-14.
Colman , "Effects of amino acid sequence changes on antibody-antigen interactions", Research in Immunology, vol. 145, No. 1, 1994, 33-36.
Coloma et al., Design and Production of Novel Tetravalent Bispecific Antibodies, Nat Biotechnol., Feb. 1997, vol. 15, No. 2, pp. 159-163.
Dall'Acqua et al., Contribution of Domain Interface Residues to the Stability of Antibody CH3 Domain Homodimers. Biochemistry, 1998, vol. 37, No. 26, pp. 9266-9273.
Davis et al., SEED bodies: Fusion Proteins Based on Strand-Exchange Engineered Domain (SEED) Ch3 Heterodimers in an Fc Analogue Platform for Asymmetric Binders or Immunofusions and Bispecific Antibodies, Protein Eng Des Sel., Apr. 2010, vol. 23, No. 4, Doi: 10.1093/protein/gzp094, Epub Feb. 4, 2010, pp. 195-202.
De Kruif et al., Leucine Zipper Dimerized Bivalent and Bispecific ScFv Antibodies From A Semi-Synthetic Antibody Phage Display Library, J Biol Chern., Mar. 29, 1996, vol. 271, No. 13, pp. 7630-7634.
Demarest et al., "Antibody therapeutics, antibody engineering, and the merits of protein stability," Current Opinion in Drug Discovery and Development vol. 11, No. 5, 2008, pp. 675-687.
Demarest et al., "Optimization of the Antibody CH3 Domain by Residue Frequency Analysis of IgG Sequences", Journal of Molecular Biology, vol. 335, No. 1, Jan. 2, 2004, pp. 41-48.
Dennis, C., Cancer: Off by a whisker. Nature. Aug. 16, 2006; 442; 739-741.
Dockal et al., "Conformational Transitions of the Three Recombinant Domains of Human Serum Albumin Depending on pH", The Journal of Biological Chemistry, vol. 275, No. 5, Feb. 4, 2000, pp. 3042-3050.
Dockal et al., "Five recombinant fragments of human serum albumin-tools for the characterization of the warfarin binding site", Protein Science, vol. 9, No. 8, 2000, pp. 1455-1465.

(56) References Cited

OTHER PUBLICATIONS

Ducry et al. "Antibody-Drug Conjugates: Linking Cytotoxic Payloads to Monoclonal Antibodies", *Bioconjugate Chem.* 2010, vol. 21, pp. 5-13.
Duncan, et al., Localization of the Binding Site for the Human High-Affinity Fc Receptor on IgG. Nature, 1988, vol. 332, No. 7, pp. 563-564.
Durocher et al., "High-level and high-throughput recombinant protein production by transient transfection of suspension-growing human HEK293-EBNA1 cells", Nucleic acids research, vol. 30, No. 2, Jan. 2002, p. e9.
Fujimori, J., et al., A modeling analysis of monoclonal antibody percolation through tumors: a binding-site barrier. J Nucl Med. Jul. 1990; 3(17):1191-8.
Grabulovski et al., "A novel, non-immunogenic Fyn SH3-derived binding protein with tumor vascular targeting properties", J Bioi Chem., vol. 282, No. 5, Feb. 2007, pp. 3196-3204.
Groot et al., "Identification by phage display of single-domain antibody fragments specific for the ODD domain in hypoxia-inducible factor 1 alpha", Lab Invest vol. 86, No. 4, Apr. 2006, pp. 345-356.
Gunasekaran et al., Enhancing Antibody Fc Heterodimer Formation Through Electrostatic Steering Effects: Applications to Bispecific Molecules and Monovalent Igg. J Biol Chern., Jun. 18, 2010, vol. 285 No. 25, Doi: 10.1074/jbc.M110.117382, Epub Apr. 16, 2010, pp. 19637-19646.
Guss et al., "Structure of the IgG-binding regions of streptococcal protein G", The EMBO Journal, vol. 5, No. 7, 1986, pp. 1567-1575.
Hardy et al., "Valency of Antibody Binding to Enveloped Virus Particles as Determined by Surface Plasmon Resonance", J Viral., vol. 77, No. 2, 2003, pp. 1649-1652.
Havnarek et al., Automated Design of Specificity in Molecular Recognition. Nat Struct Biol., 2003, vol. 10, No. 1, pp. 5-52.
Hennecke et al., "Composition and arrangement of genes define the strength of IRES-driven translation in bicistronic mRNAs", Nucleic Acids Res., vol. 29, No. 16, Aug. 15, 2001, pp. 3327-3334.
Holt et al., "Domain antibodies: proteins for therapy", Trends in Biotechnology, Elsevier Publications, Cambridge, GB, vol. 21, No. 11, Nov. 2003, pp. 484-490.
Huang et al., A De Novo Designed Protein Protein Interface, Protein Sci., Dec. 2007, vol. 16, No. 12, pp. 2770-2774.
Huang, C., et al., Recombinant immuno-therapeutics: current state and perspectives regarding the feasibility and market. Appl Microbiol Biotechnol. Jun. 2010; 87(2):401-410.
Hust et al., "Single chain Fab (scFab) fragment", BMC Biotech-nology, vol. 7, No. 14. Available online at httn://www.biomedcentral.com/1472-6750/7/14, 2007, pp. 1-15.
Hutchins et al, Improved Biodistribution, Tumor Targeting, and Reduced Immunogenicity in Mice With A Gamma 4 Variant of Campath-1H, Proc Natl Acad Sci USA., Dec. 19, 1995, vol. 92, No. 26, pp. 11980-11984.
Idusogie et al., Engineered Antibodies With Increased Activity to Recruit Complement. J Immunol., Feb. 15, 2001, vol. 166, No. 4, pp. 2571-2575.
Idusogie et al., Mapping of the C1q Binding Site on Rituxan, a Chimeric Antibody with a Human IgG1 Fc. J Immunol., Apr. 15, 2000, vol. 164, No. 8, pp. 4178-4184.
Igawa et al., "VH/VL interface engineering to promote selective expression and inhibit conformational isomerization of thrombopoietin receptor against single-chain diabody", Protein Engineering, Design & Selection, vol. 23, No. 8, Aug. 2010, pp. 667-677.
Jackman et al., "Development of a Two-part Strategy to Identify a Therapeutic Human Bispecific Antibody That Inhibits IgE Receptor Signaling", J Biol Chem., vol. 285, No. 27, Jul. 2, 2010, pp. 20850-20859.
Janeway et al., "Structure of the Antibody Molecule and Immunoglobulin Genes", Immunology Third Edition, Garland Publishing Inc. Chapter 3, tructure of the Antibody Molecule and Immunoglobulin Genes, 1997, pp. 3:1-3:11.

Jefferis et al., Interaction Sites on Human IgG-Fc for FcgammaR: Current Models, Immunol Lett., 2002, vol. 82, No. 1-2, pp. 57-65.
Jefferis et al., Modulation of Fc(gamma)R and Human Complement Activation by Igg3-Core Oligosaccharide Interaction, Immunol Lett., 1996, vol. 54, No. 2-3, pp. 101-104.
Jefferis et al., Recognition Sites on Human IgG for Fc Gamma Receptors: The Role of Glycosylation. Immunol Lett., 1995, vol. 44, No. 2-3, pp. 111-117.
Jin et al., "MetMAb, the one-armed 5D5 anti-c-met antibody, inhibits orthotopic pancreatic tumor growth and improves survival", Cancer Res., vol. 68, No. 11, Jun. 1, 2008, pp. 4360-4368.
Kabat, E.A., et al., Sequences of proteins of immunological interest, DIANE publishing, 5th ed., vol. 1, 1991, NIH Publication 91-3242; See pp. 688-695.
Kelley, Very large Scale Monoclonal Antibody Purification: The Case for Conventional Unit Operations, Biotechnol Prog., 2007, vol. 23, No. 5, pp. 995-1008.
Klein et al., "Progress in overcoming the chain association issue in bispecific heterodimeric IgG antibodies", MABS,vol. 4, No. 6 Nov./Dec. 2012, pp. 653-663.
Kontermann, "Dual targeting strategies with bispecific antibodies.", mAbs, vol. 4, No. 2, Mar.-Apr. 2012, pp. 182-197.
Lewis Phillips et al. "Targeting HER2-Positive Breast Cancer with Trastuzumab-DM1, and Antibody-Cytotoxic Drug Conjugate" *Cancer Res.* 2008, vol. 68, pp. 9280-9290.
Lindhofer et al., Preferential Species-Restricted Heavy/light Chain Pairing in Rat/mouse Quadromas. Implications for a Single-step purification of Bispecific Antibodies, J Immunol., 1995, vol. 155, No. 1, pp. 219-225.
LoRusso et al. "Trastuzumab Emtansine: A Unique Antibody-Drug Conjugate in Development for Human Epidermal Growth Factor Receptor 2-Positive Cancer", *Clin. Cancer Res.* 2011, vol. 17, pp. 6437-6447.
Lu et al., "Fab-scFv fusion protein: an efficient approach to production of bispecific antibody fragments", Journal of Immunological Methods, vol. 267, No. 2, 2002, pp. 213-226.
Lund et al., Human Fc gamma RI and Fc gamma RII Interact with Distinct but Overlapping Sites on Human IgG., J Immunol., Oct. 15, 1991, vol. 147, No. 8, pp. 2657-2662.
Lund et al., Multiple Binding Sites on the Ch2 Domain of IgG for Mouse Fc Gamma RII., Mol Immunol., 1992, vol. 29, No. 1, pp. 53-59.
Lund et al., Multiple Interactions of IgG with its Core Oligosaccharide Can Modulate Recognition by Complement and Human Fc Gamma Receptor I and Influence the Synthesis of its Oligosaccharide Chains, J Immunol., 1996, vol. 157, No. 11, pp. 4963-4969.
Lund et al., Oligosaccharide-protein Interactions in IgG can Modulate Recognition by Fc Gamma Receptors, FASEB J., Jan. 1995, vol. 9, No. 1, pp. 115-119.
Maccallum et al., "Antibody-antigen interactions: Contact analysis and binding site topography", Journal of Molecular Biology, vol. 262 (5), Oct. 1996, pp. 732-745.
Marqusee et al., "Helix stabilization by Glu- . . . Lys+ salt bridges in short peptides of de novo design", Proc Natl Acad Sci U S A., No. 84, No. 24, 1987, pp. 8898-8902.
Mcdonagh, et al., "Antitumor activity of a novel bispecific antibody that targets the ErbB2/ErbB3 oncogenic unit and inhibits heregulin-induced activation of ErbB3", Mol. Cancer Ther., vol. 11, No. 3, Jan. 2012, pp. 582-593.
Merchant et al., An efficient Route to Human Bispecific IgG. Nature Biotechnology, 1998, vol. 16, No. 7, pp. 677-681.
Milstein et al., Hybrid Hybridomas and their use in Immunohistochemistry, Nature, 1983, vol. 305, No. 6, pp. 537-540.
Moore et al., "A novel bispecific antibody format enables simultaneous bivalent and monovalent co-engagement of distinct target antigens", MAbs, vol. 3, No. 6, 2011, pp. 546-557.
Moore et al., "Engineered Fc variant antibodies with enhanced ability to recruit complement and mediate effector functions", MABS, Landes Biosciences, vol. 2, No. 2, Mar. 2010, pp. 181-189.
Omidfar et al., "Single domain antibodies: A new concept for epidermal growth factor receptor and EGFRvIII targeting", vol. 31, No. 6, 2012.

(56) References Cited

OTHER PUBLICATIONS

Omidfar et al., "Studies of thermostability in Camelus bactrianus (Bactrian camel) single-domain antibody specific for the mutant epidermal-growth-factor receptor expressed by Pichia.", Biotechnol. Appl. Biochem., vol. 46,, Jan. 2007, pp. 41-49.
Osborn et al., "Pharmacokinetic and Pharmacodynamics Studies of a Human Serum Albumin-Interferon-A Fusion Protein in Cynomolgus Monkeys", J. Pharamcology and Experiemental Therapeutics, vol. 330, 2002, pp. 540-548.
Paul , "Protein and polypeptide antigenic determinants", Fundamental Immunology, 3d ed, 1993, p. 242.
Pham et al., "Large-scale transfection of mammalian cells for the fast production of recombinant protein", Molecular Biotechnology, vol. 34, No. 2, 2006, pp. 225-237.
Pluckthun , "Antibodies from *Escherichia coli*. In: The Pharmacology of Monoclonal Antibodies", Rosenburg and Moore eds, Springer-Verlag, vol. 113, chapter 11, 1994, pp. 269-315.
Portolano et al., "Lack of promiscuity in autoantigen-specific H and L chain combinations as revealed by human H and L chain "roulette".", J Immunol., vol. 150, No. 3, Feb. 1, 1993, pp. 880-887.
Presta et al., Engineering Therapeutic Antibodies for Improved Function, Biochem Soc Trans., Aug. 2002, vol. 30, No. 4, pp. 487-490.
Rakestraw et al., "Secretion-and-capture cell-surface display for selection of target-binding proteins", Protein Engineering, Design and Selection, vol. 24, No. 6, 2011, pp. 525-530.
Raymond et al., "A simplified polyethylenimine-mediated transfection process for large-scale and high-throughput applications", Methods, vol. 55, No. 1, 2011, pp. 44-51.
Reddy et al., Elimination of Fc Receptor-Dependent Effector Functions of a Modified IgG4 Monoclonal Antibody to Human CD4, J Immunol., Feb. 15, 2000, vol. 164, No. 4, pp. 1925-1933.
Ridgway et al., 'Knobs-into-holes' Engineering of Antibody CH3 Domains for Heavy Chain Heterodimerization, Protein Eng., Jul. 1996, vol. 9, No. 7, pp. 617-621.
Robinson et al., "Targeting ErbB2 and ErbB3 with a bispecific single-chain Fv enhances 1-5 targeting selectivity and induces a therapeutic effect in vitro", Br. J. Cancer, vol. 99, Oct. 7, 2008, 1415-1425.
Rudikoff et al., "Single Amino Acid Substitution altering Antigen-binding Specificity", Proc. Natl Acad Sci., vol. 79,No. 6, 1982, pp. 1979-1983.
Segal et al., Introduction: Bispecific Antibodies, J Immunol Methods, 2001, vol. 248, No. 1-2, pp. 1-6.
Shields et al., High Resolution Mapping of the Binding Site on Human IgG1 for Fc Gamma RI, Fc Gamma RII, Fc Gamma RIII, and Fern and Design of IgG1 Variants With Improved Binding to the Fc Gamma R., J Biol Chern, Mar. 2, 2001, vol. 276, No. 9, Epub Nov. 28, 2000, pp. 6591-6604.
Stancovski et al., Mechanistic Aspects of the Opposing effects of Monoclonal Antibodies to the ERBB2 receptor on Tumor Growth, Proceedings of the National Academy of Sciences, vol. 88, Nov. 1991, pp. 8691-8695.
Stanglmaier et al., "Bi20 (FBTA05), A Novel Trifunctional Bispecific Antibody (anti-CD20 3 anti-CD3), Mediates Efficient Killing of B-cell Lymphoma Cells Even With Very Low CD20 Expression Levels", International Journal of Cancer, vol. 123, 2008, pp. 1181-1189.
Strohl et al., "Cell Line Development", 2012, 154.
Strop et al., "Generating bispecific human IgG1 and IgG2 antibodies from any antibody pair.", Journal of Molecular Biology, vol. 420, No. 3,, Jul. 13, 2012, pp. 204-219.
Suresh et al., Bispecific Monoclonal Antibodies From Hybrid Hybridomas, Methods in Enzymol, 1983, vol. 121, pp. 210-228.
Talmadge, J.E., et al., Murine models to evaluate novel and conventional therapeutic strategies for cancer. Am J Pathol. Mar. 2007; 170(3):793-804.
Tamaskovic et al., "Designed ankyrin repeat proteins (DARPins): From reserach to therapy", Methods in Enzymology, vol. 503, 2012, 101-134.
Thurber, G.M., et al., Antibody tumor penetration: transport opposed by systemic and antigen-mediated clearance. Adv Drug Deliv Rev. Sep. 2008; 60(12):1421-34.
Traunecker et al., Bispecific Single Chain Molecules (Janusins) Target Cytotoxic Lymphocytes on HIV Infected Cells, EMBO J., Dec. 1991, vol. 10, No. 12, pp. 3655-3659.
Troise et al., "Differential binding of human immunoagents and Herceptin to the ErbB2 receptor", FEBS Journal, vol. 275, No. 20, 2008, pp. 4967-4979.
Verheesen et al., "Selection of phange display of single domain antibodies specifics to antigens in their native conformation", Methods Mo Bio. , Chapter 6, vol. 911, 2012, pp. 81-104.
Vie et al., "Human fusion proteins between interleukin 2 and IgM heavy chain are cytotoxic for cells expressing the interleukin 2 receptor", Proc. Natl. Acad. Sci., vol. 89, 1992, pp. 11337-11341.
Vitetta, E., and Ghetie, V. F., Considering Therapeutic Antibodies. Science. 2006; 313: 308-309.
Von Kreudenstein, T. S., et al., Improving biophysical properties of a bispecific antibody scaffold to aid developability: quality by molecular design. MAbs. Sep.-Oct. 2013; 5(5):646-654.
Von Kreudenstein et al., Protein Engineering and the Use of Molecular Modelling and Simulation: The case Ofheterodimeric Fc Engineering, Methods, 2014, vol. 65, No. 1, pp. 77-94.
Voskoglou-Nomikos, T., et al., Clinical predictive value of the in vitro cell line, human xenograft, and mouse allograft preclinical cancer models. Clin Can Res. Sep. 15, 2006; 9(11):4227-39.
Wang, "Protein aggregation and its inhibition in biopharmaceutics," International Journal of Pharmaceutics, vol. 289, 2005, pp. 1-30.
Ward et al., "Binding activities of a repertoire of single immunoglobulin variable domains secreted from *Escherichia coli*", Nature, 334, 1989, pp. 544-546.
Wesolowski et al., "Single domain antibodies: promising experimental and therapeutic tools in infection and immunity", Med Microbiol Immunol., vol. 198, No. 3, 2009, pp. 157-174.
Wiens et al., "Mutation of a single conserved residue in VH complementarity-determining region 2 results in a severe Ig secretion defect.", J Immunology, vol. 167, No. 4, Aug. 2001, pp. 2179-2186.
Woods et al., LC-MS Characterization and Purity Assessment of a Prototype Bispecific Antibody, MABS, 2013, vol. 5, No. 5, pp. 711-722.
Wu et al. "Arming antibodies: prospects and challenges for immunoconjugates", *Nature Biotech.*, 2005, vol. 23(9), pp. 1137-1146.
Wu et al., "Humanization of a Murine Monoclonal Antibody by Simultaneous Optimization of Framework and CDR Residues", Journal of Molecular Biology, vol. 294, Nov. 1999, pp. 151-162.
Xu et al., In Vitro Characterization of Five Humanized OKT3 Effector Function Variant Antibodies, Cell Immunol. 2000, vol. 200, No. 1, pp. 16-26.
Zhu et al., "Remodeling domain interfaces to enhance heterodimer formation", Protein Science, vol. 6, No. 4, Apr. 1997, pp. 781-788.
U.S. Appl. No. 15/411,799: Restriction Requirement dated Jan. 25, 2019.
U.S. Appl. No. 14/989,648: Non-Final Office Action dated Mar. 29, 2019.
U.S. Appl. No. 15/355,019: Notice of Allowance dated Jul. 29, 2019.
U.S. Appl. No. 15/896,170, Restriction Requirement dated Jun. 26, 2019.
U.S. Appl. No. 15/896,170, Non-Final Office Action dated Sep. 18, 2019.
U.S. Appl. No. 15/298,625 Final Office Action dated Dec. 3, 2018.
U.S. Appl. No. 15/298,625 Non-Final Office Action dated Apr. 18, 2019.
U.S. Appl. No. 15/298,625 Final Office Action dated Sep. 4, 2019.

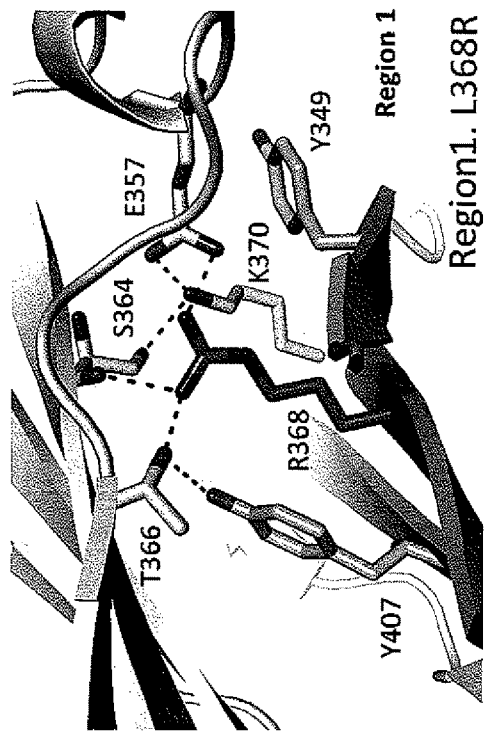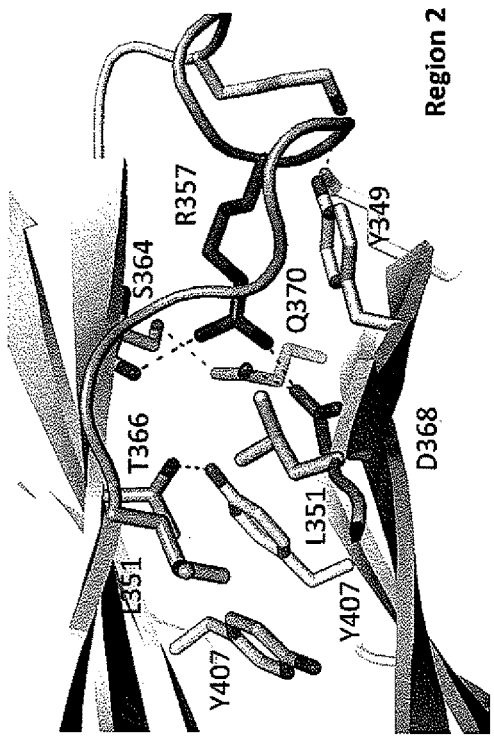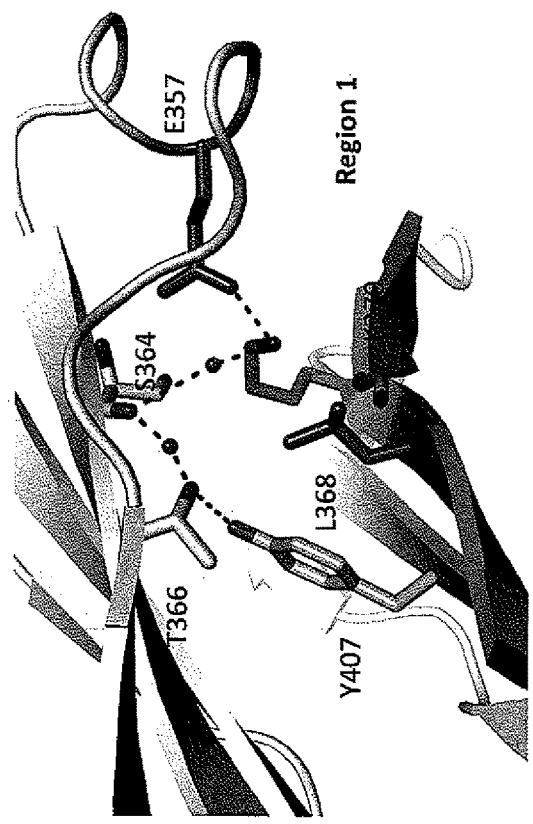
FIGURE 4
ZYMEWORKS VARIANT: AZ1
WT ● Chain A   ● Chain B
- L368 faces a critical natural cavity
- L368R increases stability by improving packing in Region 1
- Additional mutations create favorable electrostatic interactions

ZYMEWORKS VARIANT: AZ2, AZ3

L368R_E357R / L368D_K370Q_L351I

- Chain A
- Chain B
- Variants AZ 2 and 3 build on AZ 1
- L351I (AZ2) is designed and favors heterodimer formation by improving packing

FIGURE 7
ZYMEWORKS VARIANT: AZ2, AZ3
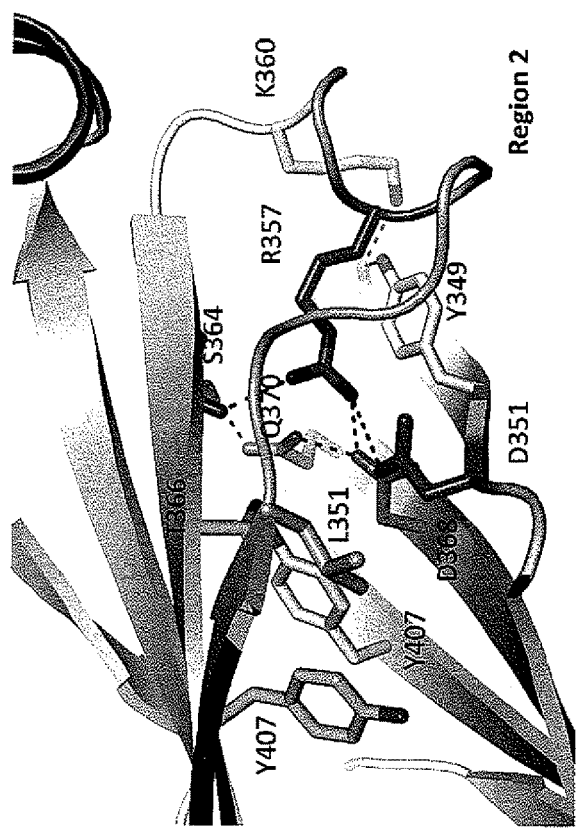
L368R_E357R / L368D_K370Q_L351I
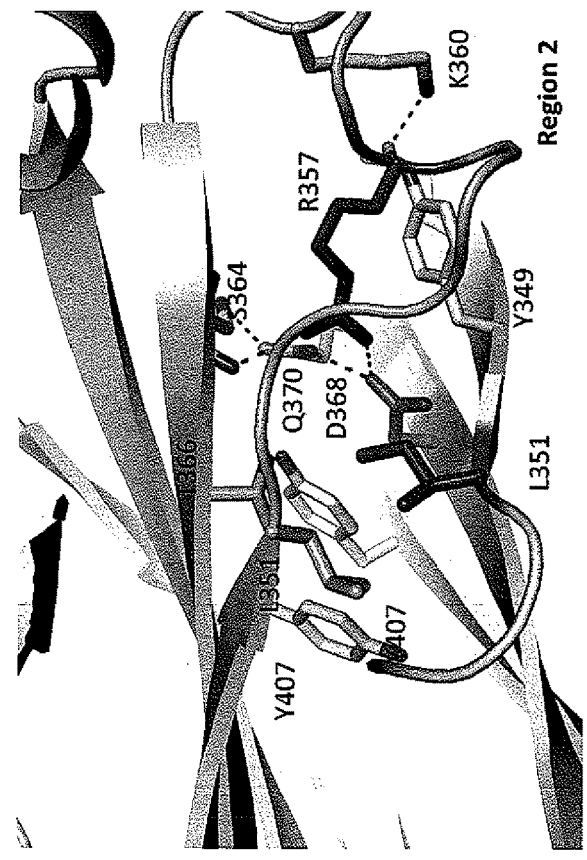
L368R_E357R / L368D_K370Q_L351D
● Chain A    ● Chain B
- Variants AZ 2 and 3 build on AZ 1
- L351I (AZ2) is designed and favors heterodimer formation by improving packing
- L351D (AZ3) is designed and favors heterodimers formation by improving electrostatic interactions

FIG. 12

ZYMEWORKS VARIANT: AZ4, AZ5, AZ6

| | | clash score (kcal/mol) − wt + | Δ interface area (Å²) − wt + | Δ packing (sd) − wt + | Δ electrostatics (kcal/mol) − wt + | affinity score − wt + |
|---|---|---|---|---|---|---|
| Heterodimer | Control 2 | -10.8 | 8.4 | -0.1 | 18.1 | 0.7 |
| | AZ4 | -3.5 | -31.1 | 0.2 | 3.0 | -0.7 |
| | AZ5 | -5.1 | -25.1 | 0.2 | -5.5 | -0.8 |
| | AZ6 | -13.8 | -32.5 | 0.0 | -11.7 | -0.3 |
| Homodimer | Control 2 (chain A) | 15.2 | -4.7 | N/A | 15.6 | N/A |
| | Control 2 (chain B) | 8.3 | 71.2 | -0.3 | 2.3 | N/A |
| | AZ4 (chain A) | 55.6 | 1.1 | N/A | 32.1 | N/A |
| | AZ4 (chain B) | 5.6 | -13.5 | -0.5 | 6.9 | N/A |
| | AZ5 (chain A) | 37.9 | -44.3 | N/A | 35.5 | N/A |
| | AZ6 (chain B) | 25.2 | -10.9 | -0.3 | -16.1 | N/A |

Black Favorable
Gray Unfavorable

FIG. 18
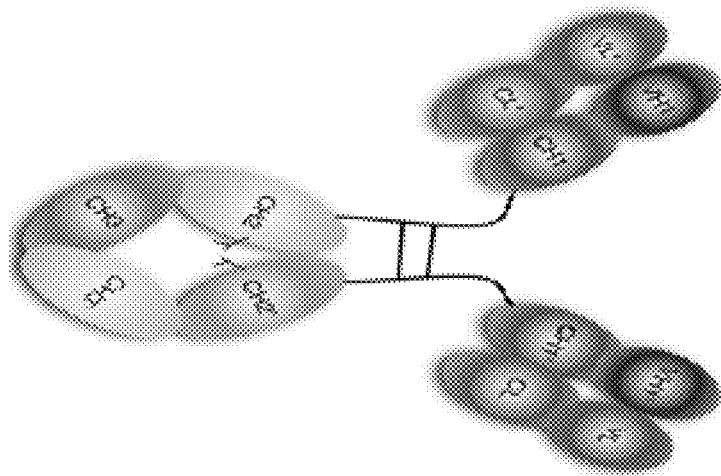
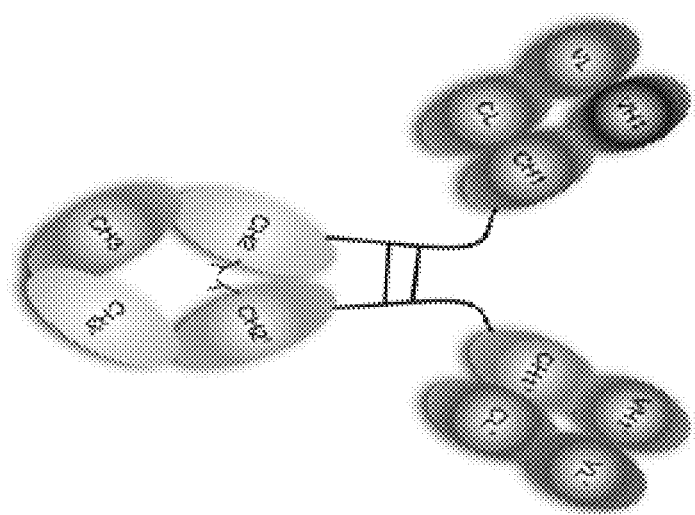

FIG. 19
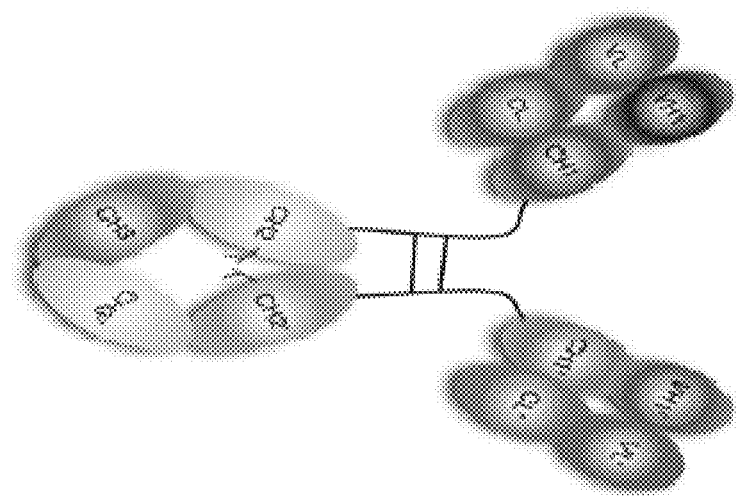
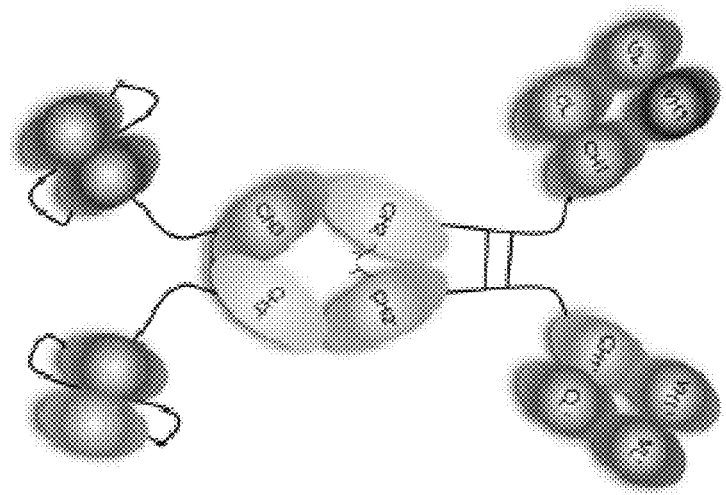

FIG. 20
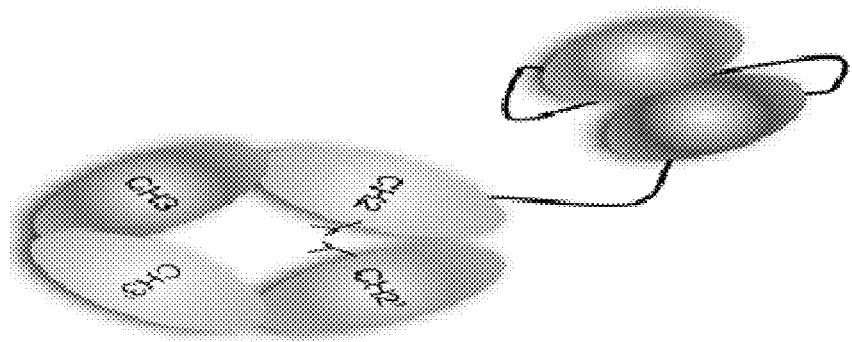
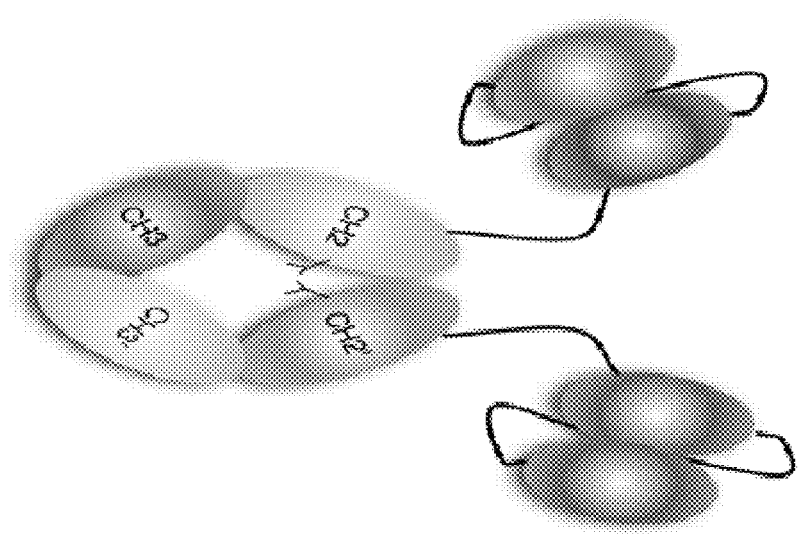

FIG. 21
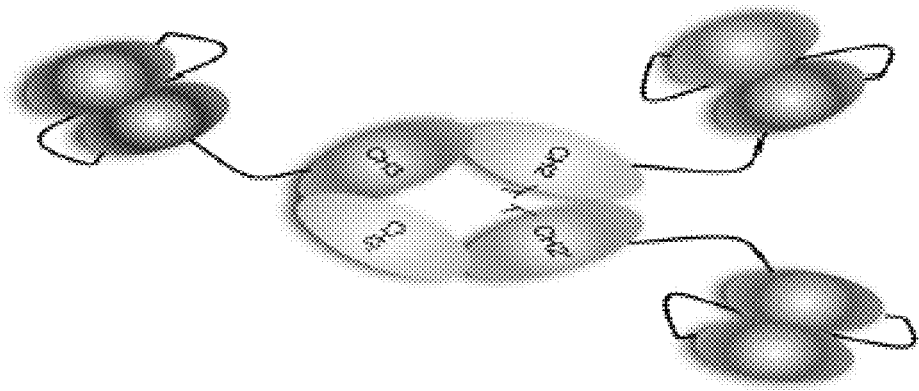
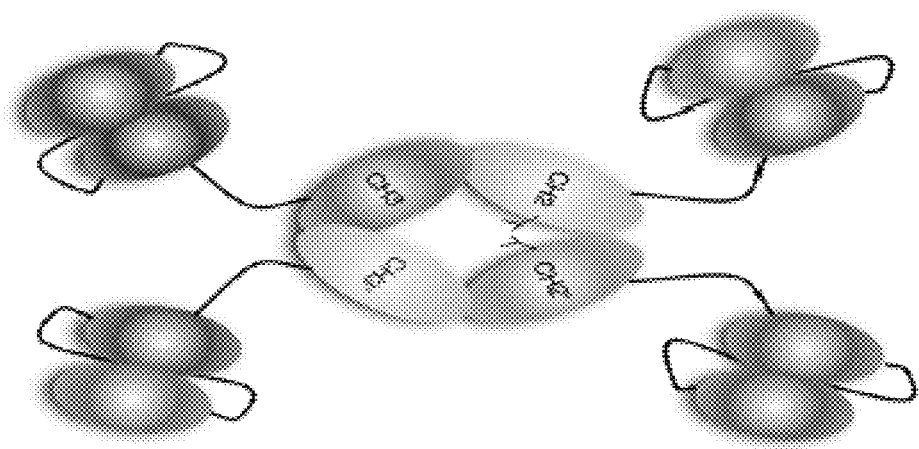

Figure 23: Parental wild-type heavy chain IgG1 sequence

GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTVDKS
RWQQGNVFSCSVMHEALHNHYTQKSLSLSPGK

Figure 24: Iterative strategy of heterodimer Fc design

Figure 25A: Non-reducing SDS-PAGE assay to determine heterodimer purity

Figure 25B & C: Non-reducing SDS-PAGE assay to determine heterodimer purity

FIG. 26:
Heterodimer Purity Determination after Protein A purification using non-reducing SDS-PAGE
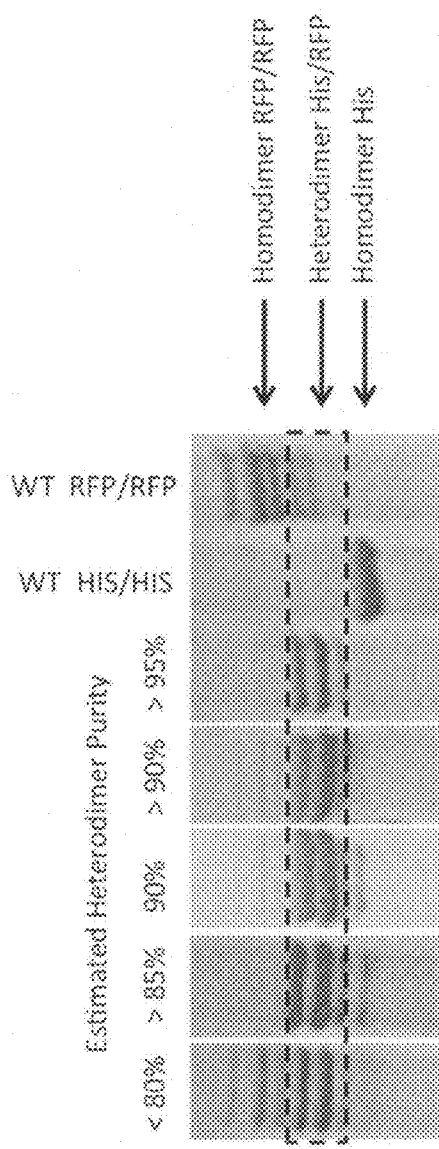
FIG. 26 A
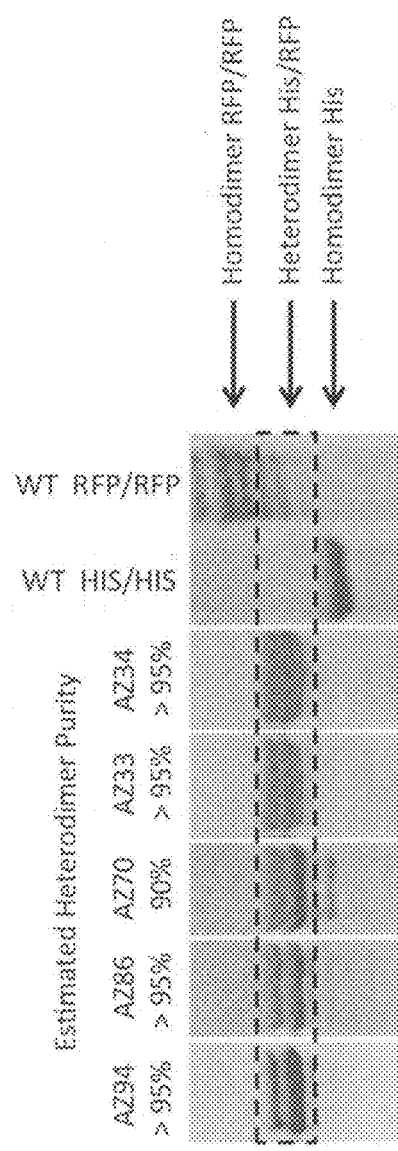
FIG. 26 B FIG. 29: In silico analysis of initial negative design variants and independent positive design optimizations: Scaffold 1 – hydrophobic core

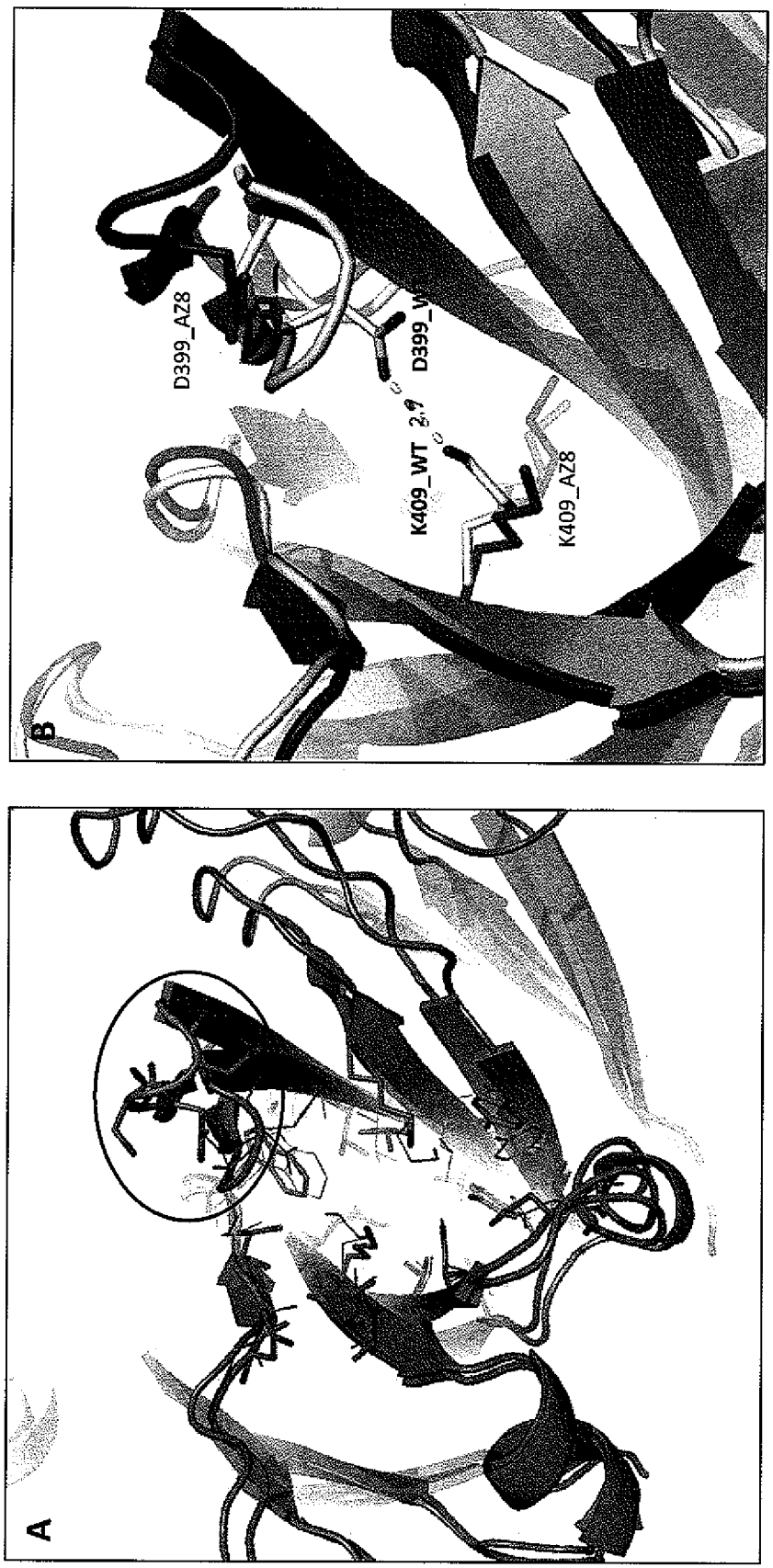
Figure 30 In silico analysis of initial negative design variants and independent positive design optimizations: Scaffold 1 – stabilizing 399-400 loop conformation

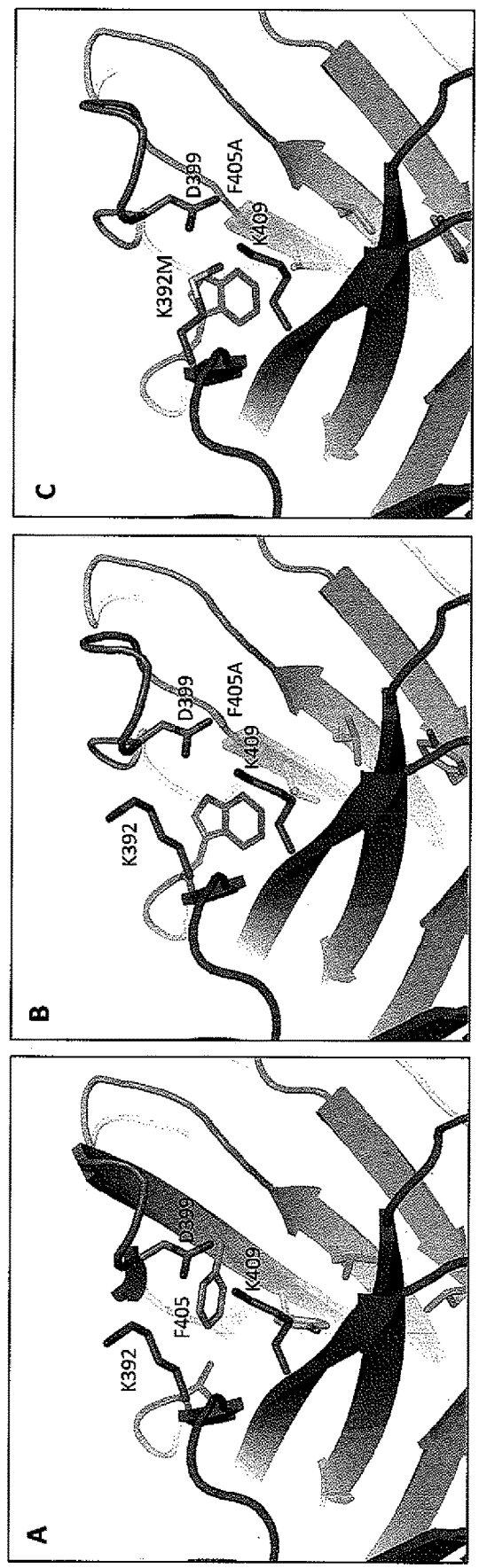
Figure 31 In silico analysis of initial negative design variants and independent positive design optimizations: Scaffold 1 – stabilizing 399-400 loop conformation FIG. 33 In silico analysis of initial negative design variants and independent positive design optimizations: Scaffold 2 – hydrophobic packing FIG. 34 In silico analysis of initial negative design variants and independent positive design optimizations: Scaffold 2 – stabilizing 399-400 loop conformation

FIG. 37

Table 6

| Variant | Fc mutations chain A | Fc mutations chain B |
|---|---|---|
| AZ133 | L351Y_F405A_Y407V | T366L_K392M_T394W |
| AZ134 | Q347R_T350V_L351Y_F405A_Y407V | T350V_K360E_T366L_K392M_T394W_T411R |
| AZ135 | L351L_F405A_Y407I | T366L_K392L_T394W |
| AZ136 | L351L_F405A_Y407I | T366L_K392M_T394W |
| AZ137 | L351L_F405A_Y407I | T366L_K392F_T394W |
| AZ138 | L351L_F405A_Y407V | T366L_K392L_T394W |
| AZ139 | L351L_F405A_Y407V | T366L_K392M_T394W |
| AZ140 | L351L_F405A_Y407V | T366L_K392F_T394W |
| AZ141 | L351L_F405S_Y407I | T366L_K392L_T394W |
| AZ142 | L351L_F405S_Y407I | T366L_K392M_T394W |
| AZ143 | L351L_F405S_Y407I | T366L_K392F_T394W |
| AZ144 | L351L_F405S_Y407V | T366L_K392L_T394W |
| AZ145 | L351L_F405S_Y407V | T366L_K392M_T394W |
| AZ146 | L351L_F405S_Y407V | T366L_K392F_T394W |
| AZ147 | L351L_F405T_Y407I | T366L_K392L_T394W |
| AZ148 | L351L_F405T_Y407I | T366L_K392M_T394W |
| AZ149 | L351L_F405T_Y407I | T366L_K392F_T394W |
| AZ150 | L351L_F405T_Y407V | T366L_K392L_T394W |
| AZ151 | L351L_F405T_Y407V | T366L_K392M_T394W |
| AZ152 | L351L_F405T_Y407V | T366L_K392F_T394W |
| AZ153 | L351L_F405V_Y407I | T366L_K392L_T394W |
| AZ154 | L351L_F405V_Y407I | T366L_K392M_T394W |
| AZ155 | L351L_F405V_Y407I | T366L_K392F_T394W |
| AZ156 | L351L_F405V_Y407V | T366L_K392L_T394W |
| AZ157 | L351L_F405V_Y407V | T366L_K392M_T394W |
| AZ158 | L351L_F405V_Y407V | T366L_K392F_T394W |
| AZ159 | L351Y_F405A_Y407I | T366L_K392L_T394W |
| AZ160 | L351Y_F405A_Y407I | T366L_K392M_T394W |
| AZ161 | L351Y_F405A_Y407I | T366L_K392F_T394W |
| AZ162 | L351Y_F405A_Y407V | T366L_K392L_T394W |
| AZ163 | L351Y_F405A_Y407V | T366L_K392M_T394W |
| AZ164 | L351Y_F405A_Y407V | T366L_K392F_T394W |
| AZ165 | L351Y_F405S_Y407I | T366L_K392L_T394W |
| AZ166 | L351Y_F405S_Y407I | T366L_K392M_T394W |
| AZ167 | L351Y_F405S_Y407I | T366L_K392F_T394W |
| AZ168 | L351Y_F405S_Y407V | T366L_K392L_T394W |
| AZ169 | L351Y_F405S_Y407V | T366L_K392M_T394W |
| AZ170 | L351Y_F405S_Y407V | T366L_K392F_T394W |
| AZ171 | L351Y_F405T_Y407I | T366L_K392L_T394W |
| AZ172 | L351Y_F405T_Y407I | T366L_K392M_T394W |
| AZ173 | L351Y_F405T_Y407I | T366L_K392F_T394W |
| AZ174 | L351Y_F405T_Y407V | T366L_K392L_T394W |
| AZ175 | L351Y_F405T_Y407V | T366L_K392M_T394W |
| AZ176 | L351Y_F405T_Y407V | T366L_K392F_T394W |
| AZ177 | L351Y_F405V_Y407I | T366L_K392L_T394W |
| AZ178 | L351Y_F405V_Y407I | T366L_K392M_T394W |
| AZ179 | L351Y_F405V_Y407I | T366L_K392F_T394W |
| AZ180 | L351Y_F405V_Y407V | T366L_K392L_T394W |
| AZ181 | L351Y_F405V_Y407V | T366L_K392M_T394W |
| AZ182 | L351Y_F405V_Y407V | T366L_K392F_T394W |
| AZ183 | Q347E_L351L_F405A_Y407I | T366L_K392L_T394W |
| AZ184 | Q347E_L351L_F405A_Y407I | T366L_K392M_T394W |
| AZ185 | Q347E_L351L_F405A_Y407I | T366L_K392F_T394W |
| AZ186 | Q347E_L351L_F405A_Y407V | T366L_K392L_T394W |

FIG. 37A

| | | |
|---|---|---|
| AZ187 | Q347E_L351L_F405A_Y407V | T366L_K392L_T394W |
| AZ188 | Q347E_L351L_F405A_Y407V | T366L_K392F_T394W |
| AZ189 | Q347E_L351L_F405S_Y407I | T366L_K392L_T394W |
| AZ190 | Q347E_L351L_F405S_Y407I | T366L_K392M_T394W |
| AZ191 | Q347E_L351L_F405S_Y407I | T366L_K392F_T394W |
| AZ192 | Q347E_L351L_F405S_Y407V | T366L_K392L_T394W |
| AZ193 | Q347E_L351L_F405S_Y407V | T366L_K392M_T394W |
| AZ194 | Q347E_L351L_F405S_Y407V | T366L_K392F_T394W |
| AZ195 | Q347E_L351L_F405T_Y407I | T366L_K392L_T394W |
| AZ196 | Q347E_L351L_F405T_Y407I | T366L_K392M_T394W |
| AZ197 | Q347E_L351L_F405T_Y407I | T366L_K392F_T394W |
| AZ198 | Q347E_L351L_F405T_Y407V | T366L_K392L_T394W |
| AZ199 | Q347E_L351L_F405T_Y407V | T366L_K392M_T394W |
| AZ200 | Q347E_L351L_F405T_Y407V | T366L_K392F_T394W |
| AZ201 | Q347E_L351L_F405V_Y407I | T366L_K392L_T394W |
| AZ202 | Q347E_L351L_F405V_Y407I | T366L_K392M_T394W |
| AZ203 | Q347E_L351L_F405V_Y407I | T366L_K392F_T394W |
| AZ204 | Q347E_L351L_F405V_Y407V | T366L_K392L_T394W |
| AZ205 | Q347E_L351L_F405V_Y407V | T366L_K392M_T394W |
| AZ206 | Q347E_L351L_F405V_Y407V | T366L_K392F_T394W |
| AZ207 | Q347E_L351Y_F405A_Y407I | T366L_K392L_T394W |
| AZ208 | Q347E_L351Y_F405A_Y407I | T366L_K392M_T394W |
| AZ209 | Q347E_L351Y_F405A_Y407I | T366L_K392F_T394W |
| AZ210 | Q347E_L351Y_F405A_Y407V | T366L_K392L_T394W |
| AZ211 | Q347E_L351Y_F405A_Y407V | T366L_K392M_T394W |
| AZ212 | Q347E_L351Y_F405A_Y407V | T366L_K392F_T394W |
| AZ213 | Q347E_L351Y_F405S_Y407I | T366L_K392L_T394W |
| AZ214 | Q347E_L351Y_F405S_Y407I | T366L_K392M_T394W |
| AZ215 | Q347E_L351Y_F405S_Y407I | T366L_K392F_T394W |
| AZ216 | Q347E_L351Y_F405S_Y407V | T366L_K392L_T394W |
| AZ217 | Q347E_L351Y_F405S_Y407V | T366L_K392M_T394W |
| AZ218 | Q347E_L351Y_F405S_Y407V | T366L_K392F_T394W |
| AZ219 | Q347E_L351Y_F405T_Y407I | T366L_K392L_T394W |
| AZ220 | Q347E_L351Y_F405T_Y407I | T366L_K392M_T394W |
| AZ221 | Q347E_L351Y_F405T_Y407I | T366L_K392F_T394W |
| AZ222 | Q347E_L351Y_F405T_Y407V | T366L_K392L_T394W |
| AZ223 | Q347E_L351Y_F405T_Y407V | T366L_K392M_T394W |
| AZ224 | Q347E_L351Y_F405T_Y407V | T366L_K392F_T394W |
| AZ225 | Q347E_L351Y_F405V_Y407I | T366L_K392L_T394W |
| AZ226 | Q347E_L351Y_F405V_Y407I | T366L_K392M_T394W |
| AZ227 | Q347E_L351Y_F405V_Y407I | T366L_K392F_T394W |
| AZ228 | Q347E_L351Y_F405V_Y407V | T366L_K392L_T394W |
| AZ229 | Q347E_L351Y_F405V_Y407V | T366L_K392M_T394W |
| AZ230 | Q347E_L351Y_F405V_Y407V | T366L_K392F_T394W |
| AZ231 | Q347R_L351L_F405A_Y407I | K360D_T366L_K392L_T394W |
| AZ232 | Q347R_L351L_F405A_Y407I | K360D_T366L_K392M_T394W |
| AZ233 | Q347R_L351L_F405A_Y407I | K360D_T366L_K392F_T394W |
| AZ234 | Q347R_L351L_F405A_Y407I | K360E_T366L_K392L_T394W |
| AZ235 | Q347R_L351L_F405A_Y407I | K360E_T366L_K392M_T394W |
| AZ236 | Q347R_L351L_F405A_Y407I | K360E_T366L_K392F_T394W |
| AZ237 | Q347R_L351L_F405A_Y407V | K360D_T366L_K392L_T394W |
| AZ238 | Q347R_L351L_F405A_Y407V | K360D_T366L_K392M_T394W |
| AZ239 | Q347R_L351L_F405A_Y407V | K360D_T366L_K392F_T394W |
| AZ240 | Q347R_L351L_F405A_Y407V | K360E_T366L_K392L_T394W |
| AZ241 | Q347R_L351L_F405A_Y407V | K360E_T366L_K392M_T394W |
| AZ242 | Q347R_L351L_F405A_Y407V | K360E_T366L_K392F_T394W |
| AZ243 | Q347R_L351L_F405S_Y407I | K360D_T366L_K392L_T394W |
| AZ244 | Q347R_L351L_F405S_Y407I | K360D_T366L_K392M_T394W |

FIG. 37B

| | | |
|---|---|---|
| AZ245 | Q347R_L351L_F405S_Y407I | K360D_T366L_K392F_T394W |
| AZ246 | Q347R_L351L_F405S_Y407I | K360E_T366L_K392L_T394W |
| AZ247 | Q347R_L351L_F405S_Y407I | K360E_T366L_K392M_T394W |
| AZ248 | Q347R_L351L_F405S_Y407I | K360E_T366L_K392F_T394W |
| AZ249 | Q347R_L351L_F405S_Y407V | K360D_T366L_K392L_T394W |
| AZ250 | Q347R_L351L_F405S_Y407V | K360D_T366L_K392M_T394W |
| AZ251 | Q347R_L351L_F405S_Y407V | K360D_T366L_K392F_T394W |
| AZ252 | Q347R_L351L_F405S_Y407V | K360E_T366L_K392L_T394W |
| AZ253 | Q347R_L351L_F405S_Y407V | K360E_T366L_K392M_T394W |
| AZ254 | Q347R_L351L_F405S_Y407V | K360E_T366L_K392F_T394W |
| AZ255 | Q347R_L351L_F405T_Y407I | K360D_T366L_K392L_T394W |
| AZ256 | Q347R_L351L_F405T_Y407I | K360D_T366L_K392M_T394W |
| AZ257 | Q347R_L351L_F405T_Y407I | K360D_T366L_K392F_T394W |
| AZ258 | Q347R_L351L_F405T_Y407I | K360E_T366L_K392L_T394W |
| AZ259 | Q347R_L351L_F405T_Y407I | K360E_T366L_K392M_T394W |
| AZ260 | Q347R_L351L_F405T_Y407I | K360E_T366L_K392F_T394W |
| AZ261 | Q347R_L351L_F405T_Y407V | K360D_T366L_K392L_T394W |
| AZ262 | Q347R_L351L_F405T_Y407V | K360D_T366L_K392M_T394W |
| AZ263 | Q347R_L351L_F405T_Y407V | K360D_T366L_K392F_T394W |
| AZ264 | Q347R_L351L_F405T_Y407V | K360E_T366L_K392L_T394W |
| AZ265 | Q347R_L351L_F405T_Y407V | K360E_T366L_K392M_T394W |
| AZ266 | Q347R_L351L_F405T_Y407V | K360E_T366L_K392F_T394W |
| AZ267 | Q347R_L351L_F405V_Y407I | K360D_T366L_K392L_T394W |
| AZ268 | Q347R_L351L_F405V_Y407I | K360D_T366L_K392M_T394W |
| AZ269 | Q347R_L351L_F405V_Y407I | K360D_T366L_K392F_T394W |
| AZ270 | Q347R_L351L_F405V_Y407I | K360E_T366L_K392L_T394W |
| AZ271 | Q347R_L351L_F405V_Y407I | K360E_T366L_K392M_T394W |
| AZ272 | Q347R_L351L_F405V_Y407I | K360E_T366L_K392F_T394W |
| AZ273 | Q347R_L351L_F405V_Y407V | K360D_T366L_K392L_T394W |
| AZ274 | Q347R_L351L_F405V_Y407V | K360D_T366L_K392M_T394W |
| AZ275 | Q347R_L351L_F405V_Y407V | K360D_T366L_K392F_T394W |
| AZ276 | Q347R_L351L_F405V_Y407V | K360E_T366L_K392L_T394W |
| AZ277 | Q347R_L351L_F405V_Y407V | K360E_T366L_K392M_T394W |
| AZ278 | Q347R_L351L_F405V_Y407V | K360E_T366L_K392F_T394W |
| AZ279 | Q347R_L351Y_F405A_Y407I | K360D_T366L_K392L_T394W |
| AZ280 | Q347R_L351Y_F405A_Y407I | K360D_T366L_K392M_T394W |
| AZ281 | Q347R_L351Y_F405A_Y407I | K360D_T366L_K392F_T394W |
| AZ282 | Q347R_L351Y_F405A_Y407I | K360E_T366L_K392L_T394W |
| AZ283 | Q347R_L351Y_F405A_Y407I | K360E_T366L_K392M_T394W |
| AZ284 | Q347R_L351Y_F405A_Y407I | K360E_T366L_K392F_T394W |
| AZ285 | Q347R_L351Y_F405A_Y407V | K360D_T366L_K392L_T394W |
| AZ286 | Q347R_L351Y_F405A_Y407V | K360D_T366L_K392M_T394W |
| AZ287 | Q347R_L351Y_F405A_Y407V | K360D_T366L_K392F_T394W |
| AZ288 | Q347R_L351Y_F405A_Y407V | K360E_T366L_K392L_T394W |
| AZ289 | Q347R_L351Y_F405A_Y407V | K360E_T366L_K392M_T394W |
| AZ290 | Q347R_L351Y_F405A_Y407V | K360E_T366L_K392F_T394W |
| AZ291 | Q347R_L351Y_F405S_Y407I | K360D_T366L_K392L_T394W |
| AZ292 | Q347R_L351Y_F405S_Y407I | K360D_T366L_K392M_T394W |
| AZ293 | Q347R_L351Y_F405S_Y407I | K360D_T366L_K392F_T394W |
| AZ294 | Q347R_L351Y_F405S_Y407I | K360E_T366L_K392L_T394W |
| AZ295 | Q347R_L351Y_F405S_Y407I | K360E_T366L_K392M_T394W |
| AZ296 | Q347R_L351Y_F405S_Y407I | K360E_T366L_K392F_T394W |
| AZ297 | Q347R_L351Y_F405S_Y407V | K360D_T366L_K392L_T394W |
| AZ298 | Q347R_L351Y_F405S_Y407V | K360D_T366L_K392M_T394W |
| AZ299 | Q347R_L351Y_F405S_Y407V | K360D_T366L_K392F_T394W |
| AZ300 | Q347R_L351Y_F405S_Y407V | K360E_T366L_K392L_T394W |
| AZ301 | Q347R_L351Y_F405S_Y407V | K360E_T366L_K392M_T394W |
| AZ302 | Q347R_L351Y_F405S_Y407V | K360E_T366L_K392F_T394W |

FIG. 37C

| AZ303 | Q347R_L351Y_F405T_Y407I | K360D_T366L_K392L_T394W |
|---|---|---|
| AZ304 | Q347R_L351Y_F405T_Y407I | K360D_T366L_K392M_T394W |
| AZ305 | Q347R_L351Y_F405T_Y407I | K360D_T366L_K392F_T394W |
| AZ306 | Q347R_L351Y_F405T_Y407I | K360E_T366L_K392L_T394W |
| AZ307 | Q347R_L351Y_F405T_Y407I | K360E_T366L_K392M_T394W |
| AZ308 | Q347R_L351Y_F405T_Y407I | K360E_T366L_K392F_T394W |
| AZ309 | Q347R_L351Y_F405T_Y407V | K360D_T366L_K392L_T394W |
| AZ310 | Q347R_L351Y_F405T_Y407V | K360D_T366L_K392M_T394W |
| AZ311 | Q347R_L351Y_F405T_Y407V | K360D_T366L_K392F_T394W |
| AZ312 | Q347R_L351Y_F405T_Y407V | K360E_T366L_K392L_T394W |
| AZ313 | Q347R_L351Y_F405T_Y407V | K360E_T366L_K392M_T394W |
| AZ314 | Q347R_L351Y_F405T_Y407V | K360E_T366L_K392F_T394W |
| AZ315 | Q347R_L351Y_F405V_Y407I | K360D_T366L_K392L_T394W |
| AZ316 | Q347R_L351Y_F405V_Y407I | K360D_T366L_K392M_T394W |
| AZ317 | Q347R_L351Y_F405V_Y407I | K360D_T366L_K392F_T394W |
| AZ318 | Q347R_L351Y_F405V_Y407I | K360E_T366L_K392L_T394W |
| AZ319 | Q347R_L351Y_F405V_Y407I | K360E_T366L_K392M_T394W |
| AZ320 | Q347R_L351Y_F405V_Y407I | K360E_T366L_K392F_T394W |
| AZ321 | Q347R_L351Y_F405V_Y407V | K360D_T366L_K392L_T394W |
| AZ322 | Q347R_L351Y_F405V_Y407V | K360D_T366L_K392M_T394W |
| AZ323 | Q347R_L351Y_F405V_Y407V | K360D_T366L_K392F_T394W |
| AZ324 | Q347R_L351Y_F405V_Y407V | K360E_T366L_K392L_T394W |
| AZ325 | Q347R_L351Y_F405V_Y407V | K360E_T366L_K392M_T394W |
| AZ326 | Q347R_L351Y_F405V_Y407V | K360E_T366L_K392F_T394W |
| AZ327 | Q347K_L351L_F405A_Y407I | K360D_T366L_K392L_T394W |
| AZ328 | Q347K_L351L_F405A_Y407I | K360D_T366L_K392M_T394W |
| AZ329 | Q347K_L351L_F405A_Y407I | K360D_T366L_K392F_T394W |
| AZ330 | Q347K_L351L_F405A_Y407I | K360E_T366L_K392L_T394W |
| AZ331 | Q347K_L351L_F405A_Y407I | K360E_T366L_K392M_T394W |
| AZ332 | Q347K_L351L_F405A_Y407I | K360E_T366L_K392F_T394W |
| AZ333 | Q347K_L351L_F405A_Y407V | K360D_T366L_K392L_T394W |
| AZ334 | Q347K_L351L_F405A_Y407V | K360D_T366L_K392M_T394W |
| AZ335 | Q347K_L351L_F405A_Y407V | K360D_T366L_K392F_T394W |
| AZ336 | Q347K_L351L_F405A_Y407V | K360E_T366L_K392L_T394W |
| AZ337 | Q347K_L351L_F405A_Y407V | K360E_T366L_K392M_T394W |
| AZ338 | Q347K_L351L_F405A_Y407V | K360E_T366L_K392F_T394W |
| AZ339 | Q347K_L351L_F405S_Y407I | K360D_T366L_K392L_T394W |
| AZ340 | Q347K_L351L_F405S_Y407I | K360D_T366L_K392M_T394W |
| AZ341 | Q347K_L351L_F405S_Y407I | K360D_T366L_K392F_T394W |
| AZ342 | Q347K_L351L_F405S_Y407I | K360E_T366L_K392L_T394W |
| AZ343 | Q347K_L351L_F405S_Y407I | K360E_T366L_K392M_T394W |
| AZ344 | Q347K_L351L_F405S_Y407I | K360E_T366L_K392F_T394W |
| AZ345 | Q347K_L351L_F405S_Y407V | K360D_T366L_K392L_T394W |
| AZ346 | Q347K_L351L_F405S_Y407V | K360D_T366L_K392M_T394W |
| AZ347 | Q347K_L351L_F405S_Y407V | K360D_T366L_K392F_T394W |
| AZ348 | Q347K_L351L_F405S_Y407V | K360E_T366L_K392L_T394W |
| AZ349 | Q347K_L351L_F405S_Y407V | K360E_T366L_K392M_T394W |
| AZ350 | Q347K_L351L_F405S_Y407V | K360E_T366L_K392F_T394W |
| AZ351 | Q347K_L351L_F405T_Y407I | K360D_T366L_K392L_T394W |
| AZ352 | Q347K_L351L_F405T_Y407I | K360D_T366L_K392M_T394W |
| AZ353 | Q347K_L351L_F405T_Y407I | K360D_T366L_K392F_T394W |
| AZ354 | Q347K_L351L_F405T_Y407I | K360E_T366L_K392L_T394W |
| AZ355 | Q347K_L351L_F405T_Y407I | K360E_T366L_K392M_T394W |
| AZ356 | Q347K_L351L_F405T_Y407I | K360E_T366L_K392F_T394W |
| AZ357 | Q347K_L351L_F405T_Y407V | K360D_T366L_K392L_T394W |
| AZ358 | Q347K_L351L_F405T_Y407V | K360D_T366L_K392M_T394W |
| AZ359 | Q347K_L351L_F405T_Y407V | K360D_T366L_K392F_T394W |
| AZ360 | Q347K_L351L_F405T_Y407V | K360E_T366L_K392L_T394W |

FIG. 37D

| | | |
|---|---|---|
| AZ361 | Q347K_L351L_F405T_Y407V | K360E_T366L_K392M_T394W |
| AZ362 | Q347K_L351L_F405T_Y407V | K360E_T366L_K392F_T394W |
| AZ363 | Q347K_L351L_F405V_Y407I | K360D_T366L_K392L_T394W |
| AZ364 | Q347K_L351L_F405V_Y407I | K360D_T366L_K392M_T394W |
| AZ365 | Q347K_L351L_F405V_Y407I | K360D_T366L_K392F_T394W |
| AZ366 | Q347K_L351L_F405V_Y407I | K360E_T366L_K392L_T394W |
| AZ367 | Q347K_L351L_F405V_Y407I | K360E_T366L_K392M_T394W |
| AZ368 | Q347K_L351L_F405V_Y407I | K360E_T366L_K392F_T394W |
| AZ369 | Q347K_L351L_F405V_Y407V | K360D_T366L_K392L_T394W |
| AZ370 | Q347K_L351L_F405V_Y407V | K360D_T366L_K392M_T394W |
| AZ371 | Q347K_L351L_F405V_Y407V | K360D_T366L_K392F_T394W |
| AZ372 | Q347K_L351L_F405V_Y407V | K360E_T366L_K392L_T394W |
| AZ373 | Q347K_L351L_F405V_Y407V | K360E_T366L_K392M_T394W |
| AZ374 | Q347K_L351L_F405V_Y407V | K360E_T366L_K392F_T394W |
| AZ375 | Q347K_L351Y_F405A_Y407I | K360D_T366L_K392L_T394W |
| AZ376 | Q347K_L351Y_F405A_Y407I | K360D_T366L_K392M_T394W |
| AZ377 | Q347K_L351Y_F405A_Y407I | K360D_T366L_K392F_T394W |
| AZ378 | Q347K_L351Y_F405A_Y407I | K360E_T366L_K392L_T394W |
| AZ379 | Q347K_L351Y_F405A_Y407I | K360E_T366L_K392M_T394W |
| AZ380 | Q347K_L351Y_F405A_Y407I | K360E_T366L_K392F_T394W |
| AZ381 | Q347K_L351Y_F405A_Y407V | K360D_T366L_K392L_T394W |
| AZ382 | Q347K_L351Y_F405A_Y407V | K360D_T366L_K392M_T394W |
| AZ383 | Q347K_L351Y_F405A_Y407V | K360D_T366L_K392F_T394W |
| AZ384 | Q347K_L351Y_F405A_Y407V | K360E_T366L_K392L_T394W |
| AZ385 | Q347K_L351Y_F405A_Y407V | K360E_T366L_K392M_T394W |
| AZ386 | Q347K_L351Y_F405A_Y407V | K360E_T366L_K392F_T394W |
| AZ387 | Q347K_L351Y_F405S_Y407I | K360D_T366L_K392L_T394W |
| AZ388 | Q347K_L351Y_F405S_Y407I | K360D_T366L_K392M_T394W |
| AZ389 | Q347K_L351Y_F405S_Y407I | K360D_T366L_K392F_T394W |
| AZ390 | Q347K_L351Y_F405S_Y407I | K360E_T366L_K392L_T394W |
| AZ391 | Q347K_L351Y_F405S_Y407I | K360E_T366L_K392M_T394W |
| AZ392 | Q347K_L351Y_F405S_Y407I | K360E_T366L_K392F_T394W |
| AZ393 | Q347K_L351Y_F405S_Y407V | K360D_T366L_K392L_T394W |
| AZ394 | Q347K_L351Y_F405S_Y407V | K360D_T366L_K392M_T394W |
| AZ395 | Q347K_L351Y_F405S_Y407V | K360D_T366L_K392F_T394W |
| AZ396 | Q347K_L351Y_F405S_Y407V | K360E_T366L_K392L_T394W |
| AZ397 | Q347K_L351Y_F405S_Y407V | K360E_T366L_K392M_T394W |
| AZ398 | Q347K_L351Y_F405S_Y407V | K360E_T366L_K392F_T394W |
| AZ399 | Q347K_L351Y_F405T_Y407I | K360D_T366L_K392L_T394W |
| AZ400 | Q347K_L351Y_F405T_Y407I | K360D_T366L_K392M_T394W |
| AZ401 | Q347K_L351Y_F405T_Y407I | K360D_T366L_K392F_T394W |
| AZ402 | Q347K_L351Y_F405T_Y407I | K360E_T366L_K392L_T394W |
| AZ403 | Q347K_L351Y_F405T_Y407I | K360E_T366L_K392M_T394W |
| AZ404 | Q347K_L351Y_F405T_Y407I | K360E_T366L_K392F_T394W |
| AZ405 | Q347K_L351Y_F405T_Y407V | K360D_T366L_K392L_T394W |
| AZ406 | Q347K_L351Y_F405T_Y407V | K360D_T366L_K392M_T394W |
| AZ407 | Q347K_L351Y_F405T_Y407V | K360D_T366L_K392F_T394W |
| AZ408 | Q347K_L351Y_F405T_Y407V | K360E_T366L_K392L_T394W |
| AZ409 | Q347K_L351Y_F405T_Y407V | K360E_T366L_K392M_T394W |
| AZ410 | Q347K_L351Y_F405T_Y407V | K360E_T366L_K392F_T394W |
| AZ411 | Q347K_L351Y_F405V_Y407I | K360D_T366L_K392L_T394W |
| AZ412 | Q347K_L351Y_F405V_Y407I | K360D_T366L_K392M_T394W |
| AZ413 | Q347K_L351Y_F405V_Y407I | K360D_T366L_K392F_T394W |
| AZ414 | Q347K_L351Y_F405V_Y407I | K360E_T366L_K392L_T394W |
| AZ415 | Q347K_L351Y_F405V_Y407I | K360E_T366L_K392M_T394W |
| AZ416 | Q347K_L351Y_F405V_Y407I | K360E_T366L_K392F_T394W |
| AZ417 | Q347K_L351Y_F405V_Y407V | K360D_T366L_K392L_T394W |
| AZ418 | Q347K_L351Y_F405V_Y407V | K360D_T366L_K392M_T394W |

FIG. 37E

| | | |
|---|---|---|
| AZ419 | Q347K_L351Y_F405V_Y407V | K360D_T366L_K392F_T394W |
| AZ420 | Q347K_L351Y_F405V_Y407V | K360E_T366L_K392L_T394W |
| AZ421 | Q347K_L351Y_F405V_Y407V | K360E_T366L_K392M_T394W |
| AZ422 | Q347K_L351Y_F405V_Y407V | K360E_T366L_K392F_T394W |
| AZ423 | L351L_S400D_F405A_Y407I | T366L_N390R_K392L_T394W |
| AZ424 | L351L_S400D_F405A_Y407I | T366L_N390R_K392M_T394W |
| AZ425 | L351L_S400D_F405A_Y407I | T366L_N390R_K392F_T394W |
| AZ426 | L351L_S400D_F405A_Y407I | T366L_N390K_K392L_T394W |
| AZ427 | L351L_S400D_F405A_Y407I | T366L_N390K_K392M_T394W |
| AZ428 | L351L_S400D_F405A_Y407I | T366L_N390K_K392F_T394W |
| AZ429 | L351L_S400D_F405A_Y407V | T366L_N390R_K392L_T394W |
| AZ430 | L351L_S400D_F405A_Y407V | T366L_N390R_K392M_T394W |
| AZ431 | L351L_S400D_F405A_Y407V | T366L_N390R_K392F_T394W |
| AZ432 | L351L_S400D_F405A_Y407V | T366L_N390K_K392L_T394W |
| AZ433 | L351L_S400D_F405A_Y407V | T366L_N390K_K392M_T394W |
| AZ434 | L351L_S400D_F405A_Y407V | T366L_N390K_K392F_T394W |
| AZ435 | L351L_S400D_F405S_Y407I | T366L_N390R_K392L_T394W |
| AZ436 | L351L_S400D_F405S_Y407I | T366L_N390R_K392M_T394W |
| AZ437 | L351L_S400D_F405S_Y407I | T366L_N390R_K392F_T394W |
| AZ438 | L351L_S400D_F405S_Y407I | T366L_N390K_K392L_T394W |
| AZ439 | L351L_S400D_F405S_Y407I | T366L_N390K_K392M_T394W |
| AZ440 | L351L_S400D_F405S_Y407I | T366L_N390K_K392F_T394W |
| AZ441 | L351L_S400D_F405S_Y407V | T366L_N390R_K392L_T394W |
| AZ442 | L351L_S400D_F405S_Y407V | T366L_N390R_K392M_T394W |
| AZ443 | L351L_S400D_F405S_Y407V | T366L_N390R_K392F_T394W |
| AZ444 | L351L_S400D_F405S_Y407V | T366L_N390K_K392L_T394W |
| AZ445 | L351L_S400D_F405S_Y407V | T366L_N390K_K392M_T394W |
| AZ446 | L351L_S400D_F405S_Y407V | T366L_N390K_K392F_T394W |
| AZ447 | L351L_S400D_F405T_Y407I | T366L_N390R_K392L_T394W |
| AZ448 | L351L_S400D_F405T_Y407I | T366L_N390R_K392M_T394W |
| AZ449 | L351L_S400D_F405T_Y407I | T366L_N390R_K392F_T394W |
| AZ450 | L351L_S400D_F405T_Y407I | T366L_N390K_K392L_T394W |
| AZ451 | L351L_S400D_F405T_Y407I | T366L_N390K_K392M_T394W |
| AZ452 | L351L_S400D_F405T_Y407I | T366L_N390K_K392F_T394W |
| AZ453 | L351L_S400D_F405T_Y407V | T366L_N390R_K392L_T394W |
| AZ454 | L351L_S400D_F405T_Y407V | T366L_N390R_K392M_T394W |
| AZ455 | L351L_S400D_F405T_Y407V | T366L_N390R_K392F_T394W |
| AZ456 | L351L_S400D_F405T_Y407V | T366L_N390K_K392L_T394W |
| AZ457 | L351L_S400D_F405T_Y407V | T366L_N390K_K392M_T394W |
| AZ458 | L351L_S400D_F405T_Y407V | T366L_N390K_K392F_T394W |
| AZ459 | L351L_S400D_F405V_Y407I | T366L_N390R_K392L_T394W |
| AZ460 | L351L_S400D_F405V_Y407I | T366L_N390R_K392M_T394W |
| AZ461 | L351L_S400D_F405V_Y407I | T366L_N390R_K392F_T394W |
| AZ462 | L351L_S400D_F405V_Y407I | T366L_N390K_K392L_T394W |
| AZ463 | L351L_S400D_F405V_Y407I | T366L_N390K_K392M_T394W |
| AZ464 | L351L_S400D_F405V_Y407I | T366L_N390K_K392F_T394W |
| AZ465 | L351L_S400D_F405V_Y407V | T366L_N390R_K392L_T394W |
| AZ466 | L351L_S400D_F405V_Y407V | T366L_N390R_K392M_T394W |
| AZ467 | L351L_S400D_F405V_Y407V | T366L_N390R_K392F_T394W |
| AZ468 | L351L_S400D_F405V_Y407V | T366L_N390K_K392L_T394W |
| AZ469 | L351L_S400D_F405V_Y407V | T366L_N390K_K392M_T394W |
| AZ470 | L351L_S400D_F405V_Y407V | T366L_N390K_K392F_T394W |
| AZ471 | L351L_S400E_F405A_Y407I | T366L_N390R_K392L_T394W |
| AZ472 | L351L_S400E_F405A_Y407I | T366L_N390R_K392M_T394W |
| AZ473 | L351L_S400E_F405A_Y407I | T366L_N390R_K392F_T394W |
| AZ474 | L351L_S400E_F405A_Y407I | T366L_N390K_K392L_T394W |
| AZ475 | L351L_S400E_F405A_Y407I | T366L_N390K_K392M_T394W |
| AZ476 | L351L_S400E_F405A_Y407I | T366L_N390K_K392F_T394W |

FIG. 37F

| | | |
|---|---|---|
| AZ477 | L351L_S400E_F405A_Y407V | T366L_N390R_K392L_T394W |
| AZ478 | L351L_S400E_F405A_Y407V | T366L_N390R_K392M_T394W |
| AZ479 | L351L_S400E_F405A_Y407V | T366L_N390R_K392F_T394W |
| AZ480 | L351L_S400E_F405A_Y407V | T366L_N390K_K392L_T394W |
| AZ481 | L351L_S400E_F405A_Y407V | T366L_N390K_K392M_T394W |
| AZ482 | L351L_S400E_F405A_Y407V | T366L_N390K_K392F_T394W |
| AZ483 | L351L_S400E_F405S_Y407I | T366L_N390R_K392L_T394W |
| AZ484 | L351L_S400E_F405S_Y407I | T366L_N390R_K392M_T394W |
| AZ485 | L351L_S400E_F405S_Y407I | T366L_N390R_K392F_T394W |
| AZ486 | L351L_S400E_F405S_Y407I | T366L_N390K_K392L_T394W |
| AZ487 | L351L_S400E_F405S_Y407I | T366L_N390K_K392M_T394W |
| AZ488 | L351L_S400E_F405S_Y407I | T366L_N390K_K392F_T394W |
| AZ489 | L351L_S400E_F405S_Y407V | T366L_N390R_K392L_T394W |
| AZ490 | L351L_S400E_F405S_Y407V | T366L_N390R_K392M_T394W |
| AZ491 | L351L_S400E_F405S_Y407V | T366L_N390R_K392F_T394W |
| AZ492 | L351L_S400E_F405S_Y407V | T366L_N390K_K392L_T394W |
| AZ493 | L351L_S400E_F405S_Y407V | T366L_N390K_K392M_T394W |
| AZ494 | L351L_S400E_F405S_Y407V | T366L_N390K_K392F_T394W |
| AZ495 | L351L_S400E_F405T_Y407I | T366L_N390R_K392L_T394W |
| AZ496 | L351L_S400E_F405T_Y407I | T366L_N390R_K392M_T394W |
| AZ497 | L351L_S400E_F405T_Y407I | T366L_N390R_K392F_T394W |
| AZ498 | L351L_S400E_F405T_Y407I | T366L_N390K_K392L_T394W |
| AZ499 | L351L_S400E_F405T_Y407I | T366L_N390K_K392M_T394W |
| AZ500 | L351L_S400E_F405T_Y407I | T366L_N390K_K392F_T394W |
| AZ501 | L351L_S400E_F405T_Y407V | T366L_N390R_K392L_T394W |
| AZ502 | L351L_S400E_F405T_Y407V | T366L_N390R_K392M_T394W |
| AZ503 | L351L_S400E_F405T_Y407V | T366L_N390R_K392F_T394W |
| AZ504 | L351L_S400E_F405T_Y407V | T366L_N390K_K392L_T394W |
| AZ505 | L351L_S400E_F405T_Y407V | T366L_N390K_K392M_T394W |
| AZ506 | L351L_S400E_F405T_Y407V | T366L_N390K_K392F_T394W |
| AZ507 | L351L_S400E_F405V_Y407I | T366L_N390R_K392L_T394W |
| AZ508 | L351L_S400E_F405V_Y407I | T366L_N390R_K392M_T394W |
| AZ509 | L351L_S400E_F405V_Y407I | T366L_N390R_K392F_T394W |
| AZ510 | L351L_S400E_F405V_Y407I | T366L_N390K_K392L_T394W |
| AZ511 | L351L_S400E_F405V_Y407I | T366L_N390K_K392M_T394W |
| AZ512 | L351L_S400E_F405V_Y407I | T366L_N390K_K392F_T394W |
| AZ513 | L351L_S400E_F405V_Y407V | T366L_N390R_K392L_T394W |
| AZ514 | L351L_S400E_F405V_Y407V | T366L_N390R_K392M_T394W |
| AZ515 | L351L_S400E_F405V_Y407V | T366L_N390R_K392F_T394W |
| AZ516 | L351L_S400E_F405V_Y407V | T366L_N390K_K392L_T394W |
| AZ517 | L351L_S400E_F405V_Y407V | T366L_N390K_K392M_T394W |
| AZ518 | L351L_S400E_F405V_Y407V | T366L_N390K_K392F_T394W |
| AZ519 | L351L_F405A_Y407I | T366L_K392L_T394W_K409L_T411R |
| AZ520 | L351L_F405A_Y407I | T366L_K392L_T394W_K409L_T411K |
| AZ521 | L351L_F405A_Y407I | T366L_K392L_T394W_K409M_T411R |
| AZ522 | L351L_F405A_Y407I | T366L_K392L_T394W_K409M_T411K |
| AZ523 | L351L_F405A_Y407I | T366L_K392M_T394W_K409L_T411R |
| AZ524 | L351L_F405A_Y407I | T366L_K392M_T394W_K409L_T411K |
| AZ525 | L351L_F405A_Y407I | T366L_K392M_T394W_K409M_T411R |
| AZ526 | L351L_F405A_Y407I | T366L_K392M_T394W_K409M_T411K |
| AZ527 | L351L_F405A_Y407I | T366L_K392F_T394W_K409L_T411R |
| AZ528 | L351L_F405A_Y407I | T366L_K392F_T394W_K409L_T411K |
| AZ529 | L351L_F405A_Y407I | T366L_K392F_T394W_K409M_T411R |
| AZ530 | L351L_F405A_Y407I | T366L_K392F_T394W_K409M_T411K |
| AZ531 | L351L_F405A_Y407V | T366L_K392L_T394W_K409L_T411R |
| AZ532 | L351L_F405A_Y407V | T366L_K392L_T394W_K409L_T411K |
| AZ533 | L351L_F405A_Y407V | T366L_K392L_T394W_K409M_T411R |
| AZ534 | L351L_F405A_Y407V | T366L_K392L_T394W_K409M_T411K |

FIG. 37G

| | | |
|---|---|---|
| AZ535 | L351L_F405A_Y407V | T366L_K392M_T394W_K409L_T411R |
| AZ536 | L351L_F405A_Y407V | T366L_K392M_T394W_K409L_T411K |
| AZ537 | L351L_F405A_Y407V | T366L_K392M_T394W_K409M_T411R |
| AZ538 | L351L_F405A_Y407V | T366L_K392M_T394W_K409M_T411K |
| AZ539 | L351L_F405A_Y407V | T366L_K392F_T394W_K409L_T411R |
| AZ540 | L351L_F405A_Y407V | T366L_K392F_T394W_K409L_T411K |
| AZ541 | L351L_F405A_Y407V | T366L_K392F_T394W_K409M_T411R |
| AZ542 | L351L_F405A_Y407V | T366L_K392F_T394W_K409M_T411K |
| AZ543 | L351L_F405S_Y407I | T366L_K392L_T394W_K409L_T411R |
| AZ544 | L351L_F405S_Y407I | T366L_K392L_T394W_K409L_T411K |
| AZ545 | L351L_F405S_Y407I | T366L_K392L_T394W_K409M_T411R |
| AZ546 | L351L_F405S_Y407I | T366L_K392L_T394W_K409M_T411K |
| AZ547 | L351L_F405S_Y407I | T366L_K392M_T394W_K409L_T411R |
| AZ548 | L351L_F405S_Y407I | T366L_K392M_T394W_K409L_T411K |
| AZ549 | L351L_F405S_Y407I | T366L_K392M_T394W_K409M_T411R |
| AZ550 | L351L_F405S_Y407I | T366L_K392M_T394W_K409M_T411K |
| AZ551 | L351L_F405S_Y407I | T366L_K392F_T394W_K409L_T411R |
| AZ552 | L351L_F405S_Y407I | T366L_K392F_T394W_K409L_T411K |
| AZ553 | L351L_F405S_Y407I | T366L_K392F_T394W_K409M_T411R |
| AZ554 | L351L_F405S_Y407I | T366L_K392F_T394W_K409M_T411K |
| AZ555 | L351L_F405S_Y407V | T366L_K392L_T394W_K409L_T411R |
| AZ556 | L351L_F405S_Y407V | T366L_K392L_T394W_K409L_T411K |
| AZ557 | L351L_F405S_Y407V | T366L_K392L_T394W_K409M_T411R |
| AZ558 | L351L_F405S_Y407V | T366L_K392L_T394W_K409M_T411K |
| AZ559 | L351L_F405S_Y407V | T366L_K392M_T394W_K409L_T411R |
| AZ560 | L351L_F405S_Y407V | T366L_K392M_T394W_K409L_T411K |
| AZ561 | L351L_F405S_Y407V | T366L_K392M_T394W_K409M_T411R |
| AZ562 | L351L_F405S_Y407V | T366L_K392M_T394W_K409M_T411K |
| AZ563 | L351L_F405S_Y407V | T366L_K392F_T394W_K409L_T411R |
| AZ564 | L351L_F405S_Y407V | T366L_K392F_T394W_K409L_T411K |
| AZ565 | L351L_F405S_Y407V | T366L_K392F_T394W_K409M_T411R |
| AZ566 | L351L_F405S_Y407V | T366L_K392F_T394W_K409M_T411K |
| AZ567 | L351L_F405V_Y407I | T366L_K392L_T394W_K409L_T411R |
| AZ568 | L351L_F405V_Y407I | T366L_K392L_T394W_K409L_T411K |
| AZ569 | L351L_F405V_Y407I | T366L_K392L_T394W_K409M_T411R |
| AZ570 | L351L_F405V_Y407I | T366L_K392L_T394W_K409M_T411K |
| AZ571 | L351L_F405V_Y407I | T366L_K392M_T394W_K409L_T411R |
| AZ572 | L351L_F405V_Y407I | T366L_K392M_T394W_K409L_T411K |
| AZ573 | L351L_F405V_Y407I | T366L_K392M_T394W_K409M_T411R |
| AZ574 | L351L_F405V_Y407I | T366L_K392M_T394W_K409M_T411K |
| AZ575 | L351L_F405V_Y407I | T366L_K392F_T394W_K409L_T411R |
| AZ576 | L351L_F405V_Y407I | T366L_K392F_T394W_K409L_T411K |
| AZ577 | L351L_F405V_Y407I | T366L_K392F_T394W_K409M_T411R |
| AZ578 | L351L_F405V_Y407I | T366L_K392F_T394W_K409M_T411K |
| AZ579 | L351L_F405V_Y407V | T366L_K392L_T394W_K409L_T411R |
| AZ580 | L351L_F405V_Y407V | T366L_K392L_T394W_K409L_T411K |
| AZ581 | L351L_F405V_Y407V | T366L_K392L_T394W_K409M_T411R |
| AZ582 | L351L_F405V_Y407V | T366L_K392L_T394W_K409M_T411K |
| AZ583 | L351L_F405V_Y407V | T366L_K392M_T394W_K409L_T411R |
| AZ584 | L351L_F405V_Y407V | T366L_K392M_T394W_K409L_T411K |
| AZ585 | L351L_F405V_Y407V | T366L_K392M_T394W_K409M_T411R |
| AZ586 | L351L_F405V_Y407V | T366L_K392M_T394W_K409M_T411K |
| AZ587 | L351L_F405V_Y407V | T366L_K392F_T394W_K409L_T411R |
| AZ588 | L351L_F405V_Y407V | T366L_K392F_T394W_K409L_T411K |
| AZ589 | L351L_F405V_Y407V | T366L_K392F_T394W_K409M_T411R |
| AZ590 | L351L_F405V_Y407V | T366L_K392F_T394W_K409M_T411K |
| AZ591 | L351Y_S400D_F405A_Y407I | T366L_N390R_K392L_T394W |
| AZ592 | L351Y_S400D_F405A_Y407I | T366L_N390R_K392M_T394W |

FIG. 37H

| | | |
|---|---|---|
| AZ593 | L351Y_S400D_F405A_Y407I | T366L_N390R_K392F_T394W |
| AZ594 | L351Y_S400D_F405A_Y407I | T366L_N390K_K392L_T394W |
| AZ595 | L351Y_S400D_F405A_Y407I | T366L_N390K_K392M_T394W |
| AZ596 | L351Y_S400D_F405A_Y407I | T366L_N390K_K392F_T394W |
| AZ597 | L351Y_S400D_F405A_Y407V | T366L_N390R_K392L_T394W |
| AZ598 | L351Y_S400D_F405A_Y407V | T366L_N390R_K392M_T394W |
| AZ599 | L351Y_S400D_F405A_Y407V | T366L_N390R_K392F_T394W |
| AZ600 | L351Y_S400D_F405A_Y407V | T366L_N390K_K392L_T394W |
| AZ601 | L351Y_S400D_F405A_Y407V | T366L_N390K_K392M_T394W |
| AZ602 | L351Y_S400D_F405A_Y407V | T366L_N390K_K392F_T394W |
| AZ603 | L351Y_S400D_F405S_Y407I | T366L_N390R_K392L_T394W |
| AZ604 | L351Y_S400D_F405S_Y407I | T366L_N390R_K392M_T394W |
| AZ605 | L351Y_S400D_F405S_Y407I | T366L_N390R_K392F_T394W |
| AZ606 | L351Y_S400D_F405S_Y407I | T366L_N390K_K392L_T394W |
| AZ607 | L351Y_S400D_F405S_Y407I | T366L_N390K_K392M_T394W |
| AZ608 | L351Y_S400D_F405S_Y407I | T366L_N390K_K392F_T394W |
| AZ609 | L351Y_S400D_F405S_Y407V | T366L_N390R_K392L_T394W |
| AZ610 | L351Y_S400D_F405S_Y407V | T366L_N390R_K392M_T394W |
| AZ611 | L351Y_S400D_F405S_Y407V | T366L_N390R_K392F_T394W |
| AZ612 | L351Y_S400D_F405S_Y407V | T366L_N390K_K392L_T394W |
| AZ613 | L351Y_S400D_F405S_Y407V | T366L_N390K_K392M_T394W |
| AZ614 | L351Y_S400D_F405S_Y407V | T366L_N390K_K392F_T394W |
| AZ615 | L351Y_S400D_F405T_Y407I | T366L_N390R_K392L_T394W |
| AZ616 | L351Y_S400D_F405T_Y407I | T366L_N390R_K392M_T394W |
| AZ617 | L351Y_S400D_F405T_Y407I | T366L_N390R_K392F_T394W |
| AZ618 | L351Y_S400D_F405T_Y407I | T366L_N390K_K392L_T394W |
| AZ619 | L351Y_S400D_F405T_Y407I | T366L_N390K_K392M_T394W |
| AZ620 | L351Y_S400D_F405T_Y407I | T366L_N390K_K392F_T394W |
| AZ621 | L351Y_S400D_F405T_Y407V | T366L_N390R_K392L_T394W |
| AZ622 | L351Y_S400D_F405T_Y407V | T366L_N390R_K392M_T394W |
| AZ623 | L351Y_S400D_F405T_Y407V | T366L_N390R_K392F_T394W |
| AZ624 | L351Y_S400D_F405T_Y407V | T366L_N390K_K392L_T394W |
| AZ625 | L351Y_S400D_F405T_Y407V | T366L_N390K_K392M_T394W |
| AZ626 | L351Y_S400D_F405T_Y407V | T366L_N390K_K392F_T394W |
| AZ627 | L351Y_S400D_F405V_Y407I | T366L_N390R_K392L_T394W |
| AZ628 | L351Y_S400D_F405V_Y407I | T366L_N390R_K392M_T394W |
| AZ629 | L351Y_S400D_F405V_Y407I | T366L_N390R_K392F_T394W |
| AZ630 | L351Y_S400D_F405V_Y407I | T366L_N390K_K392L_T394W |
| AZ631 | L351Y_S400D_F405V_Y407I | T366L_N390K_K392M_T394W |
| AZ632 | L351Y_S400D_F405V_Y407I | T366L_N390K_K392F_T394W |
| AZ633 | L351Y_S400D_F405V_Y407V | T366L_N390R_K392L_T394W |
| AZ634 | L351Y_S400D_F405V_Y407V | T366L_N390R_K392M_T394W |
| AZ635 | L351Y_S400D_F405V_Y407V | T366L_N390R_K392F_T394W |
| AZ636 | L351Y_S400D_F405V_Y407V | T366L_N390K_K392L_T394W |
| AZ637 | L351Y_S400D_F405V_Y407V | T366L_N390K_K392M_T394W |
| AZ638 | L351Y_S400D_F405V_Y407V | T366L_N390K_K392F_T394W |
| AZ639 | L351Y_S400E_F405A_Y407I | T366L_N390R_K392L_T394W |
| AZ640 | L351Y_S400E_F405A_Y407I | T366L_N390R_K392M_T394W |
| AZ641 | L351Y_S400E_F405A_Y407I | T366L_N390R_K392F_T394W |
| AZ642 | L351Y_S400E_F405A_Y407I | T366L_N390K_K392L_T394W |
| AZ643 | L351Y_S400E_F405A_Y407I | T366L_N390K_K392M_T394W |
| AZ644 | L351Y_S400E_F405A_Y407I | T366L_N390K_K392F_T394W |
| AZ645 | L351Y_S400E_F405A_Y407V | T366L_N390R_K392L_T394W |
| AZ646 | L351Y_S400E_F405A_Y407V | T366L_N390R_K392M_T394W |
| AZ647 | L351Y_S400E_F405A_Y407V | T366L_N390R_K392F_T394W |
| AZ648 | L351Y_S400E_F405A_Y407V | T366L_N390K_K392L_T394W |
| AZ649 | L351Y_S400E_F405A_Y407V | T366L_N390K_K392M_T394W |
| AZ650 | L351Y_S400E_F405A_Y407V | T366L_N390K_K392F_T394W |

FIG. 37I

| | | |
|---|---|---|
| AZ651 | L351Y_S400E_F405S_Y407I | T366L_N390R_K392L_T394W |
| AZ652 | L351Y_S400E_F405S_Y407I | T366L_N390R_K392M_T394W |
| AZ653 | L351Y_S400E_F405S_Y407I | T366L_N390R_K392F_T394W |
| AZ654 | L351Y_S400E_F405S_Y407I | T366L_N390K_K392L_T394W |
| AZ655 | L351Y_S400E_F405S_Y407I | T366L_N390K_K392M_T394W |
| AZ656 | L351Y_S400E_F405S_Y407I | T366L_N390K_K392F_T394W |
| AZ657 | L351Y_S400E_F405S_Y407V | T366L_N390R_K392L_T394W |
| AZ658 | L351Y_S400E_F405S_Y407V | T366L_N390R_K392M_T394W |
| AZ659 | L351Y_S400E_F405S_Y407V | T366L_N390R_K392F_T394W |
| AZ660 | L351Y_S400E_F405S_Y407V | T366L_N390K_K392L_T394W |
| AZ661 | L351Y_S400E_F405S_Y407V | T366L_N390K_K392M_T394W |
| AZ662 | L351Y_S400E_F405S_Y407V | T366L_N390K_K392F_T394W |
| AZ663 | L351Y_S400E_F405T_Y407I | T366L_N390R_K392L_T394W |
| AZ664 | L351Y_S400E_F405T_Y407I | T366L_N390R_K392M_T394W |
| AZ665 | L351Y_S400E_F405T_Y407I | T366L_N390R_K392F_T394W |
| AZ666 | L351Y_S400E_F405T_Y407I | T366L_N390K_K392L_T394W |
| AZ667 | L351Y_S400E_F405T_Y407I | T366L_N390K_K392M_T394W |
| AZ668 | L351Y_S400E_F405T_Y407I | T366L_N390K_K392F_T394W |
| AZ669 | L351Y_S400E_F405T_Y407V | T366L_N390R_K392L_T394W |
| AZ670 | L351Y_S400E_F405T_Y407V | T366L_N390R_K392M_T394W |
| AZ671 | L351Y_S400E_F405T_Y407V | T366L_N390R_K392F_T394W |
| AZ672 | L351Y_S400E_F405T_Y407V | T366L_N390K_K392L_T394W |
| AZ673 | L351Y_S400E_F405T_Y407V | T366L_N390K_K392M_T394W |
| AZ674 | L351Y_S400E_F405T_Y407V | T366L_N390K_K392F_T394W |
| AZ675 | L351Y_S400E_F405V_Y407I | T366L_N390R_K392L_T394W |
| AZ676 | L351Y_S400E_F405V_Y407I | T366L_N390R_K392M_T394W |
| AZ677 | L351Y_S400E_F405V_Y407I | T366L_N390R_K392F_T394W |
| AZ678 | L351Y_S400E_F405V_Y407I | T366L_N390K_K392L_T394W |
| AZ679 | L351Y_S400E_F405V_Y407I | T366L_N390K_K392M_T394W |
| AZ680 | L351Y_S400E_F405V_Y407I | T366L_N390K_K392F_T394W |
| AZ681 | L351Y_S400E_F405V_Y407V | T366L_N390R_K392L_T394W |
| AZ682 | L351Y_S400E_F405V_Y407V | T366L_N390R_K392M_T394W |
| AZ683 | L351Y_S400E_F405V_Y407V | T366L_N390R_K392F_T394W |
| AZ684 | L351Y_S400E_F405V_Y407V | T366L_N390K_K392L_T394W |
| AZ685 | L351Y_S400E_F405V_Y407V | T366L_N390K_K392M_T394W |
| AZ686 | L351Y_S400E_F405V_Y407V | T366L_N390K_K392F_T394W |
| AZ687 | L351Y_F405A_Y407I | T366L_K392L_T394W_K409L_T411R |
| AZ688 | L351Y_F405A_Y407I | T366L_K392L_T394W_K409L_T411K |
| AZ689 | L351Y_F405A_Y407I | T366L_K392L_T394W_K409M_T411R |
| AZ690 | L351Y_F405A_Y407I | T366L_K392L_T394W_K409M_T411K |
| AZ691 | L351Y_F405A_Y407I | T366L_K392M_T394W_K409L_T411R |
| AZ692 | L351Y_F405A_Y407I | T366L_K392M_T394W_K409L_T411K |
| AZ693 | L351Y_F405A_Y407I | T366L_K392M_T394W_K409M_T411R |
| AZ694 | L351Y_F405A_Y407I | T366L_K392M_T394W_K409M_T411K |
| AZ695 | L351Y_F405A_Y407I | T366L_K392F_T394W_K409L_T411R |
| AZ696 | L351Y_F405A_Y407I | T366L_K392F_T394W_K409L_T411K |
| AZ697 | L351Y_F405A_Y407I | T366L_K392F_T394W_K409M_T411R |
| AZ698 | L351Y_F405A_Y407I | T366L_K392F_T394W_K409M_T411K |
| AZ699 | L351Y_F405A_Y407V | T366L_K392L_T394W_K409L_T411R |
| AZ700 | L351Y_F405A_Y407V | T366L_K392L_T394W_K409L_T411K |
| AZ701 | L351Y_F405A_Y407V | T366L_K392L_T394W_K409M_T411R |
| AZ702 | L351Y_F405A_Y407V | T366L_K392L_T394W_K409M_T411K |
| AZ703 | L351Y_F405A_Y407V | T366L_K392M_T394W_K409L_T411R |
| AZ704 | L351Y_F405A_Y407V | T366L_K392M_T394W_K409L_T411K |
| AZ705 | L351Y_F405A_Y407V | T366L_K392M_T394W_K409M_T411R |
| AZ706 | L351Y_F405A_Y407V | T366L_K392M_T394W_K409M_T411K |
| AZ707 | L351Y_F405A_Y407V | T366L_K392F_T394W_K409L_T411R |
| AZ708 | L351Y_F405A_Y407V | T366L_K392F_T394W_K409L_T411K |

FIG. 37J

| | | |
|---|---|---|
| AZ709 | L351Y_F405A_Y407V | T366L_K392F_T394W_K409M_T411R |
| AZ710 | L351Y_F405A_Y407V | T366L_K392F_T394W_K409M_T411K |
| AZ711 | L351Y_F405S_Y407I | T366L_K392L_T394W_K409L_T411R |
| AZ712 | L351Y_F405S_Y407I | T366L_K392L_T394W_K409L_T411K |
| AZ713 | L351Y_F405S_Y407I | T366L_K392L_T394W_K409M_T411R |
| AZ714 | L351Y_F405S_Y407I | T366L_K392L_T394W_K409M_T411K |
| AZ715 | L351Y_F405S_Y407I | T366L_K392M_T394W_K409L_T411R |
| AZ716 | L351Y_F405S_Y407I | T366L_K392M_T394W_K409L_T411K |
| AZ717 | L351Y_F405S_Y407I | T366L_K392M_T394W_K409M_T411R |
| AZ718 | L351Y_F405S_Y407I | T366L_K392M_T394W_K409M_T411K |
| AZ719 | L351Y_F405S_Y407I | T366L_K392F_T394W_K409L_T411R |
| AZ720 | L351Y_F405S_Y407I | T366L_K392F_T394W_K409L_T411K |
| AZ721 | L351Y_F405S_Y407I | T366L_K392F_T394W_K409M_T411R |
| AZ722 | L351Y_F405S_Y407I | T366L_K392F_T394W_K409M_T411K |
| AZ723 | L351Y_F405S_Y407V | T366L_K392L_T394W_K409L_T411R |
| AZ724 | L351Y_F405S_Y407V | T366L_K392L_T394W_K409L_T411K |
| AZ725 | L351Y_F405S_Y407V | T366L_K392L_T394W_K409M_T411R |
| AZ726 | L351Y_F405S_Y407V | T366L_K392L_T394W_K409M_T411K |
| AZ727 | L351Y_F405S_Y407V | T366L_K392M_T394W_K409L_T411R |
| AZ728 | L351Y_F405S_Y407V | T366L_K392M_T394W_K409L_T411K |
| AZ729 | L351Y_F405S_Y407V | T366L_K392M_T394W_K409M_T411R |
| AZ730 | L351Y_F405S_Y407V | T366L_K392M_T394W_K409M_T411K |
| AZ731 | L351Y_F405S_Y407V | T366L_K392F_T394W_K409L_T411R |
| AZ732 | L351Y_F405S_Y407V | T366L_K392F_T394W_K409L_T411K |
| AZ733 | L351Y_F405S_Y407V | T366L_K392F_T394W_K409M_T411R |
| AZ734 | L351Y_F405S_Y407V | T366L_K392F_T394W_K409M_T411K |
| AZ735 | L351Y_F405V_Y407I | T366L_K392L_T394W_K409L_T411R |
| AZ736 | L351Y_F405V_Y407I | T366L_K392L_T394W_K409L_T411K |
| AZ737 | L351Y_F405V_Y407I | T366L_K392L_T394W_K409M_T411R |
| AZ738 | L351Y_F405V_Y407I | T366L_K392L_T394W_K409M_T411K |
| AZ739 | L351Y_F405V_Y407I | T366L_K392M_T394W_K409L_T411R |
| AZ740 | L351Y_F405V_Y407I | T366L_K392M_T394W_K409L_T411K |
| AZ741 | L351Y_F405V_Y407I | T366L_K392M_T394W_K409M_T411R |
| AZ742 | L351Y_F405V_Y407I | T366L_K392M_T394W_K409M_T411K |
| AZ743 | L351Y_F405V_Y407I | T366L_K392F_T394W_K409L_T411R |
| AZ744 | L351Y_F405V_Y407I | T366L_K392F_T394W_K409L_T411K |
| AZ745 | L351Y_F405V_Y407I | T366L_K392F_T394W_K409M_T411R |
| AZ746 | L351Y_F405V_Y407I | T366L_K392F_T394W_K409M_T411K |
| AZ747 | L351Y_F405V_Y407V | T366L_K392L_T394W_K409L_T411R |
| AZ748 | L351Y_F405V_Y407V | T366L_K392L_T394W_K409L_T411K |
| AZ749 | L351Y_F405V_Y407V | T366L_K392L_T394W_K409M_T411R |
| AZ750 | L351Y_F405V_Y407V | T366L_K392L_T394W_K409M_T411K |
| AZ751 | L351Y_F405V_Y407V | T366L_K392M_T394W_K409L_T411R |
| AZ752 | L351Y_F405V_Y407V | T366L_K392M_T394W_K409L_T411K |
| AZ753 | L351Y_F405V_Y407V | T366L_K392M_T394W_K409M_T411R |
| AZ754 | L351Y_F405V_Y407V | T366L_K392M_T394W_K409M_T411K |
| AZ755 | L351Y_F405V_Y407V | T366L_K392F_T394W_K409L_T411R |
| AZ756 | L351Y_F405V_Y407V | T366L_K392F_T394W_K409L_T411K |
| AZ757 | L351Y_F405V_Y407V | T366L_K392F_T394W_K409M_T411R |
| AZ758 | L351Y_F405V_Y407V | T366L_K392F_T394W_K409M_T411K |
| AZ759 | D399C_F405A_Y407I | T366L_K392C_T394W_K409L_T411L |
| AZ760 | D399C_F405A_Y407I | T366L_K392C_T394W_K409L_T411T |
| AZ761 | D399C_F405A_Y407I | T366L_K392C_T394W_K409L_T411L |
| AZ762 | D399C_F405A_Y407I | T366L_K392C_T394W_K409L_T411T |
| AZ763 | D399C_F405A_Y407I | T366L_K392C_T394W_K409K_T411L |
| AZ764 | D399C_F405A_Y407I | T366L_K392C_T394W_K409K_T411T |
| AZ765 | D399C_F405A_Y407I | T366L_K392C_T394W_K409M_T411L |
| AZ766 | D399C_F405A_Y407I | T366L_K392C_T394W_K409M_T411T |

FIG. 37K

| | | |
|---|---|---|
| AZ767 | D399C_F405A_Y407V | T366L_K392C_T394W_K409L_T411L |
| AZ768 | D399C_F405A_Y407V | T366L_K392C_T394W_K409L_T411T |
| AZ769 | D399C_F405A_Y407V | T366L_K392C_T394W_K409L_T411L |
| AZ770 | D399C_F405A_Y407V | T366L_K392C_T394W_K409L_T411T |
| AZ771 | D399C_F405A_Y407V | T366L_K392C_T394W_K409K_T411L |
| AZ772 | D399C_F405A_Y407V | T366L_K392C_T394W_K409K_T411T |
| AZ773 | D399C_F405A_Y407V | T366L_K392C_T394W_K409M_T411L |
| AZ774 | D399C_F405A_Y407V | T366L_K392C_T394W_K409M_T411T |
| AZ775 | D399C_F405S_Y407I | T366L_K392C_T394W_K409L_T411L |
| AZ776 | D399C_F405S_Y407I | T366L_K392C_T394W_K409L_T411T |
| AZ777 | D399C_F405S_Y407I | T366L_K392C_T394W_K409L_T411L |
| AZ778 | D399C_F405S_Y407I | T366L_K392C_T394W_K409L_T411T |
| AZ779 | D399C_F405S_Y407I | T366L_K392C_T394W_K409K_T411L |
| AZ780 | D399C_F405S_Y407I | T366L_K392C_T394W_K409K_T411T |
| AZ781 | D399C_F405S_Y407I | T366L_K392C_T394W_K409M_T411L |
| AZ782 | D399C_F405S_Y407I | T366L_K392C_T394W_K409M_T411T |
| AZ783 | D399C_F405S_Y407V | T366L_K392C_T394W_K409L_T411L |
| AZ784 | D399C_F405S_Y407V | T366L_K392C_T394W_K409L_T411T |
| AZ785 | D399C_F405S_Y407V | T366L_K392C_T394W_K409L_T411L |
| AZ786 | D399C_F405S_Y407V | T366L_K392C_T394W_K409L_T411T |
| AZ787 | D399C_F405S_Y407V | T366L_K392C_T394W_K409K_T411L |
| AZ788 | D399C_F405S_Y407V | T366L_K392C_T394W_K409K_T411T |
| AZ789 | D399C_F405S_Y407V | T366L_K392C_T394W_K409M_T411L |
| AZ790 | D399C_F405S_Y407V | T366L_K392C_T394W_K409M_T411T |
| AZ791 | D399C_F405V_Y407I | T366L_K392C_T394W_K409L_T411L |
| AZ792 | D399C_F405V_Y407I | T366L_K392C_T394W_K409L_T411T |
| AZ793 | D399C_F405V_Y407I | T366L_K392C_T394W_K409L_T411L |
| AZ794 | D399C_F405V_Y407I | T366L_K392C_T394W_K409L_T411T |
| AZ795 | D399C_F405V_Y407I | T366L_K392C_T394W_K409K_T411L |
| AZ796 | D399C_F405V_Y407I | T366L_K392C_T394W_K409K_T411T |
| AZ797 | D399C_F405V_Y407I | T366L_K392C_T394W_K409M_T411L |
| AZ798 | D399C_F405V_Y407I | T366L_K392C_T394W_K409M_T411T |
| AZ799 | D399C_F405V_Y407V | T366L_K392C_T394W_K409L_T411L |
| AZ800 | D399C_F405V_Y407V | T366L_K392C_T394W_K409L_T411T |
| AZ801 | D399C_F405V_Y407V | T366L_K392C_T394W_K409L_T411L |
| AZ802 | D399C_F405V_Y407V | T366L_K392C_T394W_K409L_T411T |
| AZ803 | D399C_F405V_Y407V | T366L_K392C_T394W_K409K_T411L |
| AZ804 | D399C_F405V_Y407V | T366L_K392C_T394W_K409K_T411T |
| AZ805 | D399C_F405V_Y407V | T366L_K392C_T394W_K409M_T411L |
| AZ806 | D399C_F405V_Y407V | T366L_K392C_T394W_K409M_T411T |
| AZ807 | L351L_D399R_F405A_Y407I | T366L_K392L_T394W_K409L_T411E |
| AZ808 | L351L_D399R_F405A_Y407I | T366L_K392L_T394W_K409M_T411E |
| AZ809 | L351L_D399R_F405A_Y407I | T366L_K392M_T394W_K409L_T411E |
| AZ810 | L351L_D399R_F405A_Y407I | T366L_K392M_T394W_K409M_T411E |
| AZ811 | L351L_D399R_F405A_Y407I | T366L_K392F_T394W_K409L_T411E |
| AZ812 | L351L_D399R_F405A_Y407I | T366L_K392F_T394W_K409M_T411E |
| AZ813 | L351L_D399R_F405A_Y407V | T366L_K392L_T394W_K409L_T411E |
| AZ814 | L351L_D399R_F405A_Y407V | T366L_K392L_T394W_K409M_T411E |
| AZ815 | L351L_D399R_F405A_Y407V | T366L_K392M_T394W_K409L_T411E |
| AZ816 | L351L_D399R_F405A_Y407V | T366L_K392M_T394W_K409M_T411E |
| AZ817 | L351L_D399R_F405A_Y407V | T366L_K392F_T394W_K409L_T411E |
| AZ818 | L351L_D399R_F405A_Y407V | T366L_K392F_T394W_K409M_T411E |
| AZ819 | L351L_D399R_F405M_Y407I | T366L_K392L_T394W_K409V_T411E |
| AZ820 | L351L_D399R_F405M_Y407I | T366L_K392M_T394W_K409V_T411E |
| AZ821 | L351L_D399R_F405M_Y407I | T366L_K392L_T394W_K409V_T411E |
| AZ822 | L351L_D399R_F405M_Y407V | T366L_K392L_T394W_K409V_T411E |
| AZ823 | L351L_D399R_F405M_Y407V | T366L_K392M_T394W_K409V_T411E |
| AZ824 | L351L_D399R_F405M_Y407V | T366L_K392F_T394W_K409V_T411E |

FIG. 37L

| | | |
|---|---|---|
| AZ825 | L351L_D399R_F405S_Y407I | T366L_K392L_T394W_K409L_T411E |
| AZ826 | L351L_D399R_F405S_Y407I | T366L_K392L_T394W_K409M_T411E |
| AZ827 | L351L_D399R_F405S_Y407I | T366L_K392M_T394W_K409L_T411E |
| AZ828 | L351L_D399R_F405S_Y407I | T366L_K392M_T394W_K409M_T411E |
| AZ829 | L351L_D399R_F405S_Y407I | T366L_K392F_T394W_K409L_T411E |
| AZ830 | L351L_D399R_F405S_Y407I | T366L_K392F_T394W_K409M_T411E |
| AZ831 | L351L_D399R_F405S_Y407V | T366L_K392L_T394W_K409L_T411E |
| AZ832 | L351L_D399R_F405S_Y407V | T366L_K392L_T394W_K409M_T411E |
| AZ833 | L351L_D399R_F405S_Y407V | T366L_K392M_T394W_K409L_T411E |
| AZ834 | L351L_D399R_F405S_Y407V | T366L_K392M_T394W_K409M_T411E |
| AZ835 | L351L_D399R_F405S_Y407V | T366L_K392F_T394W_K409L_T411E |
| AZ836 | L351L_D399R_F405S_Y407V | T366L_K392F_T394W_K409M_T411E |
| AZ837 | L351L_D399R_F405V_Y407I | T366L_K392L_T394W_K409L_T411E |
| AZ838 | L351L_D399R_F405V_Y407I | T366L_K392L_T394W_K409M_T411E |
| AZ839 | L351L_D399R_F405V_Y407I | T366L_K392M_T394W_K409L_T411E |
| AZ840 | L351L_D399R_F405V_Y407I | T366L_K392M_T394W_K409M_T411E |
| AZ841 | L351L_D399R_F405V_Y407I | T366L_K392F_T394W_K409L_T411E |
| AZ842 | L351L_D399R_F405V_Y407I | T366L_K392F_T394W_K409M_T411E |
| AZ843 | L351L_D399R_F405V_Y407V | T366L_K392L_T394W_K409L_T411E |
| AZ844 | L351L_D399R_F405V_Y407V | T366L_K392L_T394W_K409M_T411E |
| AZ845 | L351L_D399R_F405V_Y407V | T366L_K392M_T394W_K409L_T411E |
| AZ846 | L351L_D399R_F405V_Y407V | T366L_K392M_T394W_K409M_T411E |
| AZ847 | L351L_D399R_F405V_Y407V | T366L_K392F_T394W_K409L_T411E |
| AZ848 | L351L_D399R_F405V_Y407V | T366L_K392F_T394W_K409M_T411E |
| AZ849 | L351L_S400R_F405A_Y407I | T366L_N390N_K392L_T394W_T411N |
| AZ850 | L351L_S400R_F405A_Y407I | T366L_N390N_K392L_T394W_T411S |
| AZ851 | L351L_S400R_F405A_Y407I | T366L_N390N_K392L_T394W_T411T |
| AZ852 | L351L_S400R_F405A_Y407I | T366L_N390N_K392M_T394W_T411N |
| AZ853 | L351L_S400R_F405A_Y407I | T366L_N390N_K392M_T394W_T411S |
| AZ854 | L351L_S400R_F405A_Y407I | T366L_N390N_K392M_T394W_T411T |
| AZ855 | L351L_S400R_F405A_Y407I | T366L_N390N_K392F_T394W_T411N |
| AZ856 | L351L_S400R_F405A_Y407I | T366L_N390N_K392F_T394W_T411S |
| AZ857 | L351L_S400R_F405A_Y407I | T366L_N390N_K392F_T394W_T411T |
| AZ858 | L351L_S400R_F405A_Y407I | T366L_N390D_K392L_T394W_T411N |
| AZ859 | L351L_S400R_F405A_Y407I | T366L_N390D_K392L_T394W_T411S |
| AZ860 | L351L_S400R_F405A_Y407I | T366L_N390D_K392L_T394W_T411T |
| AZ861 | L351L_S400R_F405A_Y407I | T366L_N390D_K392M_T394W_T411N |
| AZ862 | L351L_S400R_F405A_Y407I | T366L_N390D_K392M_T394W_T411S |
| AZ863 | L351L_S400R_F405A_Y407I | T366L_N390D_K392M_T394W_T411T |
| AZ864 | L351L_S400R_F405A_Y407I | T366L_N390D_K392F_T394W_T411N |
| AZ865 | L351L_S400R_F405A_Y407I | T366L_N390D_K392F_T394W_T411S |
| AZ866 | L351L_S400R_F405A_Y407I | T366L_N390D_K392F_T394W_T411T |
| AZ867 | L351L_S400R_F405A_Y407I | T366L_N390E_K392L_T394W_T411N |
| AZ868 | L351L_S400R_F405A_Y407I | T366L_N390E_K392L_T394W_T411L |
| AZ869 | L351L_S400R_F405A_Y407I | T366L_N390E_K392L_T394W_T411S |
| AZ870 | L351L_S400R_F405A_Y407I | T366L_N390E_K392L_T394W_T411T |
| AZ871 | L351L_S400R_F405A_Y407I | T366L_N390E_K392M_T394W_T411N |
| AZ872 | L351L_S400R_F405A_Y407I | T366L_N390E_K392M_T394W_T411L |
| AZ873 | L351L_S400R_F405A_Y407I | T366L_N390E_K392M_T394W_T411S |
| AZ874 | L351L_S400R_F405A_Y407I | T366L_N390E_K392M_T394W_T411T |
| AZ875 | L351L_S400R_F405A_Y407I | T366L_N390E_K392F_T394W_T411N |
| AZ876 | L351L_S400R_F405A_Y407I | T366L_N390E_K392F_T394W_T411L |
| AZ877 | L351L_S400R_F405A_Y407I | T366L_N390E_K392F_T394W_T411S |
| AZ878 | L351L_S400R_F405A_Y407I | T366L_N390E_K392F_T394W_T411T |
| AZ879 | L351L_S400R_F405A_Y407V | T366L_N390N_K392L_T394W_T411N |
| AZ880 | L351L_S400R_F405A_Y407V | T366L_N390N_K392L_T394W_T411S |
| AZ881 | L351L_S400R_F405A_Y407V | T366L_N390N_K392L_T394W_T411T |
| AZ882 | L351L_S400R_F405A_Y407V | T366L_N390N_K392M_T394W_T411N |

FIG. 37M

| | | |
|---|---|---|
| AZ883 | L351L_S400R_F405A_Y407V | T366L_N390N_K392M_T394W_T411S |
| AZ884 | L351L_S400R_F405A_Y407V | T366L_N390N_K392M_T394W_T411T |
| AZ885 | L351L_S400R_F405A_Y407V | T366L_N390N_K392F_T394W_T411N |
| AZ886 | L351L_S400R_F405A_Y407V | T366L_N390N_K392F_T394W_T411S |
| AZ887 | L351L_S400R_F405A_Y407V | T366L_N390N_K392F_T394W_T411T |
| AZ888 | L351L_S400R_F405A_Y407V | T366L_N390D_K392L_T394W_T411N |
| AZ889 | L351L_S400R_F405A_Y407V | T366L_N390D_K392L_T394W_T411S |
| AZ890 | L351L_S400R_F405A_Y407V | T366L_N390D_K392L_T394W_T411T |
| AZ891 | L351L_S400R_F405A_Y407V | T366L_N390D_K392M_T394W_T411N |
| AZ892 | L351L_S400R_F405A_Y407V | T366L_N390D_K392M_T394W_T411S |
| AZ893 | L351L_S400R_F405A_Y407V | T366L_N390D_K392M_T394W_T411T |
| AZ894 | L351L_S400R_F405A_Y407V | T366L_N390D_K392F_T394W_T411N |
| AZ895 | L351L_S400R_F405A_Y407V | T366L_N390D_K392F_T394W_T411S |
| AZ896 | L351L_S400R_F405A_Y407V | T366L_N390D_K392F_T394W_T411T |
| AZ897 | L351L_S400R_F405A_Y407V | T366L_N390E_K392L_T394W_T411N |
| AZ898 | L351L_S400R_F405A_Y407V | T366L_N390E_K392L_T394W_T411L |
| AZ899 | L351L_S400R_F405A_Y407V | T366L_N390E_K392L_T394W_T411S |
| AZ900 | L351L_S400R_F405A_Y407V | T366L_N390E_K392L_T394W_T411T |
| AZ901 | L351L_S400R_F405A_Y407V | T366L_N390E_K392M_T394W_T411N |
| AZ902 | L351L_S400R_F405A_Y407V | T366L_N390E_K392M_T394W_T411L |
| AZ903 | L351L_S400R_F405A_Y407V | T366L_N390E_K392M_T394W_T411S |
| AZ904 | L351L_S400R_F405A_Y407V | T366L_N390E_K392M_T394W_T411T |
| AZ905 | L351L_S400R_F405A_Y407V | T366L_N390E_K392F_T394W_T411N |
| AZ906 | L351L_S400R_F405A_Y407V | T366L_N390E_K392F_T394W_T411L |
| AZ907 | L351L_S400R_F405A_Y407V | T366L_N390E_K392F_T394W_T411S |
| AZ908 | L351L_S400R_F405A_Y407V | T366L_N390E_K392F_T394W_T411T |
| AZ909 | L351L_S400R_F405S_Y407I | T366L_N390N_K392L_T394W_T411N |
| AZ910 | L351L_S400R_F405S_Y407I | T366L_N390N_K392L_T394W_T411S |
| AZ911 | L351L_S400R_F405S_Y407I | T366L_N390N_K392L_T394W_T411T |
| AZ912 | L351L_S400R_F405S_Y407I | T366L_N390N_K392M_T394W_T411N |
| AZ913 | L351L_S400R_F405S_Y407I | T366L_N390N_K392M_T394W_T411S |
| AZ914 | L351L_S400R_F405S_Y407I | T366L_N390N_K392M_T394W_T411T |
| AZ915 | L351L_S400R_F405S_Y407I | T366L_N390N_K392F_T394W_T411N |
| AZ916 | L351L_S400R_F405S_Y407I | T366L_N390N_K392F_T394W_T411S |
| AZ917 | L351L_S400R_F405S_Y407I | T366L_N390N_K392F_T394W_T411T |
| AZ918 | L351L_S400R_F405S_Y407I | T366L_N390D_K392L_T394W_T411N |
| AZ919 | L351L_S400R_F405S_Y407I | T366L_N390D_K392L_T394W_T411S |
| AZ920 | L351L_S400R_F405S_Y407I | T366L_N390D_K392L_T394W_T411T |
| AZ921 | L351L_S400R_F405S_Y407I | T366L_N390D_K392M_T394W_T411N |
| AZ922 | L351L_S400R_F405S_Y407I | T366L_N390D_K392M_T394W_T411S |
| AZ923 | L351L_S400R_F405S_Y407I | T366L_N390D_K392M_T394W_T411T |
| AZ924 | L351L_S400R_F405S_Y407I | T366L_N390D_K392F_T394W_T411N |
| AZ925 | L351L_S400R_F405S_Y407I | T366L_N390D_K392F_T394W_T411S |
| AZ926 | L351L_S400R_F405S_Y407I | T366L_N390D_K392F_T394W_T411T |
| AZ927 | L351L_S400R_F405S_Y407I | T366L_N390E_K392L_T394W_T411N |
| AZ928 | L351L_S400R_F405S_Y407I | T366L_N390E_K392L_T394W_T411L |
| AZ929 | L351L_S400R_F405S_Y407I | T366L_N390E_K392L_T394W_T411S |
| AZ930 | L351L_S400R_F405S_Y407I | T366L_N390E_K392L_T394W_T411T |
| AZ931 | L351L_S400R_F405S_Y407I | T366L_N390E_K392M_T394W_T411N |
| AZ932 | L351L_S400R_F405S_Y407I | T366L_N390E_K392M_T394W_T411L |
| AZ933 | L351L_S400R_F405S_Y407I | T366L_N390E_K392M_T394W_T411S |
| AZ934 | L351L_S400R_F405S_Y407I | T366L_N390E_K392M_T394W_T411T |
| AZ935 | L351L_S400R_F405S_Y407I | T366L_N390E_K392F_T394W_T411N |
| AZ936 | L351L_S400R_F405S_Y407I | T366L_N390E_K392F_T394W_T411L |
| AZ937 | L351L_S400R_F405S_Y407I | T366L_N390E_K392F_T394W_T411S |
| AZ938 | L351L_S400R_F405S_Y407I | T366L_N390E_K392F_T394W_T411T |
| AZ939 | L351L_S400R_F405S_Y407V | T366L_N390N_K392L_T394W_T411N |
| AZ940 | L351L_S400R_F405S_Y407V | T366L_N390N_K392L_T394W_T411S |

FIG. 37N

| | | |
|---|---|---|
| AZ941 | L351L_S400R_F405S_Y407V | T366L_N390N_K392L_T394W_T411T |
| AZ942 | L351L_S400R_F405S_Y407V | T366L_N390N_K392M_T394W_T411N |
| AZ943 | L351L_S400R_F405S_Y407V | T366L_N390N_K392M_T394W_T411S |
| AZ944 | L351L_S400R_F405S_Y407V | T366L_N390N_K392M_T394W_T411T |
| AZ945 | L351L_S400R_F405S_Y407V | T366L_N390N_K392F_T394W_T411N |
| AZ946 | L351L_S400R_F405S_Y407V | T366L_N390N_K392F_T394W_T411S |
| AZ947 | L351L_S400R_F405S_Y407V | T366L_N390N_K392F_T394W_T411T |
| AZ948 | L351L_S400R_F405S_Y407V | T366L_N390D_K392L_T394W_T411N |
| AZ949 | L351L_S400R_F405S_Y407V | T366L_N390D_K392L_T394W_T411S |
| AZ950 | L351L_S400R_F405S_Y407V | T366L_N390D_K392L_T394W_T411T |
| AZ951 | L351L_S400R_F405S_Y407V | T366L_N390D_K392M_T394W_T411N |
| AZ952 | L351L_S400R_F405S_Y407V | T366L_N390D_K392M_T394W_T411S |
| AZ953 | L351L_S400R_F405S_Y407V | T366L_N390D_K392M_T394W_T411T |
| AZ954 | L351L_S400R_F405S_Y407V | T366L_N390D_K392F_T394W_T411N |
| AZ955 | L351L_S400R_F405S_Y407V | T366L_N390D_K392F_T394W_T411S |
| AZ956 | L351L_S400R_F405S_Y407V | T366L_N390D_K392F_T394W_T411T |
| AZ957 | L351L_S400R_F405S_Y407V | T366L_N390E_K392L_T394W_T411N |
| AZ958 | L351L_S400R_F405S_Y407V | T366L_N390E_K392L_T394W_T411L |
| AZ959 | L351L_S400R_F405S_Y407V | T366L_N390E_K392L_T394W_T411S |
| AZ960 | L351L_S400R_F405S_Y407V | T366L_N390E_K392L_T394W_T411T |
| AZ961 | L351L_S400R_F405S_Y407V | T366L_N390E_K392M_T394W_T411N |
| AZ962 | L351L_S400R_F405S_Y407V | T366L_N390E_K392M_T394W_T411L |
| AZ963 | L351L_S400R_F405S_Y407V | T366L_N390E_K392M_T394W_T411S |
| AZ964 | L351L_S400R_F405S_Y407V | T366L_N390E_K392M_T394W_T411T |
| AZ965 | L351L_S400R_F405S_Y407V | T366L_N390E_K392F_T394W_T411N |
| AZ966 | L351L_S400R_F405S_Y407V | T366L_N390E_K392F_T394W_T411L |
| AZ967 | L351L_S400R_F405S_Y407V | T366L_N390E_K392F_T394W_T411S |
| AZ968 | L351L_S400R_F405S_Y407V | T366L_N390E_K392F_T394W_T411T |
| AZ969 | L351L_S400R_F405T_Y407I | T366L_N390N_K392L_T394W_T411N |
| AZ970 | L351L_S400R_F405T_Y407I | T366L_N390N_K392L_T394W_T411S |
| AZ971 | L351L_S400R_F405T_Y407I | T366L_N390N_K392L_T394W_T411T |
| AZ972 | L351L_S400R_F405T_Y407I | T366L_N390N_K392M_T394W_T411N |
| AZ973 | L351L_S400R_F405T_Y407I | T366L_N390N_K392M_T394W_T411S |
| AZ974 | L351L_S400R_F405T_Y407I | T366L_N390N_K392M_T394W_T411T |
| AZ975 | L351L_S400R_F405T_Y407I | T366L_N390N_K392F_T394W_T411N |
| AZ976 | L351L_S400R_F405T_Y407I | T366L_N390N_K392F_T394W_T411S |
| AZ977 | L351L_S400R_F405T_Y407I | T366L_N390N_K392F_T394W_T411T |
| AZ978 | L351L_S400R_F405T_Y407I | T366L_N390D_K392L_T394W_T411N |
| AZ979 | L351L_S400R_F405T_Y407I | T366L_N390D_K392L_T394W_T411S |
| AZ980 | L351L_S400R_F405T_Y407I | T366L_N390D_K392L_T394W_T411T |
| AZ981 | L351L_S400R_F405T_Y407I | T366L_N390D_K392M_T394W_T411N |
| AZ982 | L351L_S400R_F405T_Y407I | T366L_N390D_K392M_T394W_T411S |
| AZ983 | L351L_S400R_F405T_Y407I | T366L_N390D_K392M_T394W_T411T |
| AZ984 | L351L_S400R_F405T_Y407I | T366L_N390D_K392F_T394W_T411N |
| AZ985 | L351L_S400R_F405T_Y407I | T366L_N390D_K392F_T394W_T411S |
| AZ986 | L351L_S400R_F405T_Y407I | T366L_N390D_K392F_T394W_T411T |
| AZ987 | L351L_S400R_F405T_Y407I | T366L_N390E_K392L_T394W_T411N |
| AZ988 | L351L_S400R_F405T_Y407I | T366L_N390E_K392L_T394W_T411L |
| AZ989 | L351L_S400R_F405T_Y407I | T366L_N390E_K392L_T394W_T411S |
| AZ990 | L351L_S400R_F405T_Y407I | T366L_N390E_K392L_T394W_T411T |
| AZ991 | L351L_S400R_F405T_Y407I | T366L_N390E_K392M_T394W_T411N |
| AZ992 | L351L_S400R_F405T_Y407I | T366L_N390E_K392M_T394W_T411L |
| AZ993 | L351L_S400R_F405T_Y407I | T366L_N390E_K392M_T394W_T411S |
| AZ994 | L351L_S400R_F405T_Y407I | T366L_N390E_K392M_T394W_T411T |
| AZ995 | L351L_S400R_F405T_Y407I | T366L_N390E_K392F_T394W_T411N |
| AZ996 | L351L_S400R_F405T_Y407I | T366L_N390E_K392F_T394W_T411L |
| AZ997 | L351L_S400R_F405T_Y407I | T366L_N390E_K392F_T394W_T411S |
| AZ998 | L351L_S400R_F405T_Y407I | T366L_N390E_K392F_T394W_T411T |

FIG. 37O

| | | |
|---|---|---|
| AZ999 | L351L_S400R_F405T_Y407V | T366L_N390N_K392L_T394W_T411N |
| AZ1000 | L351L_S400R_F405T_Y407V | T366L_N390N_K392L_T394W_T411S |
| AZ1001 | L351L_S400R_F405T_Y407V | T366L_N390N_K392L_T394W_T411T |
| AZ1002 | L351L_S400R_F405T_Y407V | T366L_N390N_K392M_T394W_T411N |
| AZ1003 | L351L_S400R_F405T_Y407V | T366L_N390N_K392M_T394W_T411S |
| AZ1004 | L351L_S400R_F405T_Y407V | T366L_N390N_K392M_T394W_T411T |
| AZ1005 | L351L_S400R_F405T_Y407V | T366L_N390N_K392F_T394W_T411N |
| AZ1006 | L351L_S400R_F405T_Y407V | T366L_N390N_K392F_T394W_T411S |
| AZ1007 | L351L_S400R_F405T_Y407V | T366L_N390N_K392F_T394W_T411T |
| AZ1008 | L351L_S400R_F405T_Y407V | T366L_N390D_K392L_T394W_T411N |
| AZ1009 | L351L_S400R_F405T_Y407V | T366L_N390D_K392L_T394W_T411S |
| AZ1010 | L351L_S400R_F405T_Y407V | T366L_N390D_K392L_T394W_T411T |
| AZ1011 | L351L_S400R_F405T_Y407V | T366L_N390D_K392M_T394W_T411N |
| AZ1012 | L351L_S400R_F405T_Y407V | T366L_N390D_K392M_T394W_T411S |
| AZ1013 | L351L_S400R_F405T_Y407V | T366L_N390D_K392M_T394W_T411T |
| AZ1014 | L351L_S400R_F405T_Y407V | T366L_N390D_K392F_T394W_T411N |
| AZ1015 | L351L_S400R_F405T_Y407V | T366L_N390D_K392F_T394W_T411S |
| AZ1016 | L351L_S400R_F405T_Y407V | T366L_N390D_K392F_T394W_T411T |
| AZ1017 | L351L_S400R_F405T_Y407V | T366L_N390E_K392L_T394W_T411N |
| AZ1018 | L351L_S400R_F405T_Y407V | T366L_N390E_K392L_T394W_T411L |
| AZ1019 | L351L_S400R_F405T_Y407V | T366L_N390E_K392L_T394W_T411S |
| AZ1020 | L351L_S400R_F405T_Y407V | T366L_N390E_K392L_T394W_T411T |
| AZ1021 | L351L_S400R_F405T_Y407V | T366L_N390E_K392M_T394W_T411N |
| AZ1022 | L351L_S400R_F405T_Y407V | T366L_N390E_K392M_T394W_T411L |
| AZ1023 | L351L_S400R_F405T_Y407V | T366L_N390E_K392M_T394W_T411S |
| AZ1024 | L351L_S400R_F405T_Y407V | T366L_N390E_K392M_T394W_T411T |
| AZ1025 | L351L_S400R_F405T_Y407V | T366L_N390E_K392F_T394W_T411N |
| AZ1026 | L351L_S400R_F405T_Y407V | T366L_N390E_K392F_T394W_T411L |
| AZ1027 | L351L_S400R_F405T_Y407V | T366L_N390E_K392F_T394W_T411S |
| AZ1028 | L351L_S400R_F405T_Y407V | T366L_N390E_K392F_T394W_T411T |
| AZ1029 | L351L_S400R_F405V_Y407I | T366L_N390N_K392L_T394W_T411N |
| AZ1030 | L351L_S400R_F405V_Y407I | T366L_N390N_K392L_T394W_T411S |
| AZ1031 | L351L_S400R_F405V_Y407I | T366L_N390N_K392L_T394W_T411T |
| AZ1032 | L351L_S400R_F405V_Y407I | T366L_N390N_K392M_T394W_T411N |
| AZ1033 | L351L_S400R_F405V_Y407I | T366L_N390N_K392M_T394W_T411S |
| AZ1034 | L351L_S400R_F405V_Y407I | T366L_N390N_K392M_T394W_T411T |
| AZ1035 | L351L_S400R_F405V_Y407I | T366L_N390N_K392F_T394W_T411N |
| AZ1036 | L351L_S400R_F405V_Y407I | T366L_N390N_K392F_T394W_T411S |
| AZ1037 | L351L_S400R_F405V_Y407I | T366L_N390N_K392F_T394W_T411T |
| AZ1038 | L351L_S400R_F405V_Y407I | T366L_N390D_K392L_T394W_T411N |
| AZ1039 | L351L_S400R_F405V_Y407I | T366L_N390D_K392L_T394W_T411S |
| AZ1040 | L351L_S400R_F405V_Y407I | T366L_N390D_K392L_T394W_T411T |
| AZ1041 | L351L_S400R_F405V_Y407I | T366L_N390D_K392M_T394W_T411N |
| AZ1042 | L351L_S400R_F405V_Y407I | T366L_N390D_K392M_T394W_T411S |
| AZ1043 | L351L_S400R_F405V_Y407I | T366L_N390D_K392M_T394W_T411T |
| AZ1044 | L351L_S400R_F405V_Y407I | T366L_N390D_K392F_T394W_T411N |
| AZ1045 | L351L_S400R_F405V_Y407I | T366L_N390D_K392F_T394W_T411S |
| AZ1046 | L351L_S400R_F405V_Y407I | T366L_N390D_K392F_T394W_T411T |
| AZ1047 | L351L_S400R_F405V_Y407I | T366L_N390E_K392L_T394W_T411N |
| AZ1048 | L351L_S400R_F405V_Y407I | T366L_N390E_K392L_T394W_T411L |
| AZ1049 | L351L_S400R_F405V_Y407I | T366L_N390E_K392L_T394W_T411S |
| AZ1050 | L351L_S400R_F405V_Y407I | T366L_N390E_K392L_T394W_T411T |
| AZ1051 | L351L_S400R_F405V_Y407I | T366L_N390E_K392M_T394W_T411N |
| AZ1052 | L351L_S400R_F405V_Y407I | T366L_N390E_K392M_T394W_T411L |
| AZ1053 | L351L_S400R_F405V_Y407I | T366L_N390E_K392M_T394W_T411S |
| AZ1054 | L351L_S400R_F405V_Y407I | T366L_N390E_K392M_T394W_T411T |
| AZ1055 | L351L_S400R_F405V_Y407I | T366L_N390E_K392F_T394W_T411N |
| AZ1056 | L351L_S400R_F405V_Y407I | T366L_N390E_K392F_T394W_T411L |

FIG. 37P

| | | |
|---|---|---|
| AZ1057 | L351L_S400R_F405V_Y407I | T366L_N390E_K392F_T394W_T411S |
| AZ1058 | L351L_S400R_F405V_Y407I | T366L_N390E_K392F_T394W_T411T |
| AZ1059 | L351L_S400R_F405V_Y407V | T366L_N390N_K392L_T394W_T411N |
| AZ1060 | L351L_S400R_F405V_Y407V | T366L_N390N_K392L_T394W_T411S |
| AZ1061 | L351L_S400R_F405V_Y407V | T366L_N390N_K392L_T394W_T411T |
| AZ1062 | L351L_S400R_F405V_Y407V | T366L_N390N_K392M_T394W_T411N |
| AZ1063 | L351L_S400R_F405V_Y407V | T366L_N390N_K392M_T394W_T411S |
| AZ1064 | L351L_S400R_F405V_Y407V | T366L_N390N_K392M_T394W_T411T |
| AZ1065 | L351L_S400R_F405V_Y407V | T366L_N390N_K392F_T394W_T411N |
| AZ1066 | L351L_S400R_F405V_Y407V | T366L_N390N_K392F_T394W_T411S |
| AZ1067 | L351L_S400R_F405V_Y407V | T366L_N390N_K392F_T394W_T411T |
| AZ1068 | L351L_S400R_F405V_Y407V | T366L_N390D_K392L_T394W_T411N |
| AZ1069 | L351L_S400R_F405V_Y407V | T366L_N390D_K392L_T394W_T411S |
| AZ1070 | L351L_S400R_F405V_Y407V | T366L_N390D_K392L_T394W_T411T |
| AZ1071 | L351L_S400R_F405V_Y407V | T366L_N390D_K392M_T394W_T411N |
| AZ1072 | L351L_S400R_F405V_Y407V | T366L_N390D_K392M_T394W_T411S |
| AZ1073 | L351L_S400R_F405V_Y407V | T366L_N390D_K392M_T394W_T411T |
| AZ1074 | L351L_S400R_F405V_Y407V | T366L_N390D_K392F_T394W_T411N |
| AZ1075 | L351L_S400R_F405V_Y407V | T366L_N390D_K392F_T394W_T411S |
| AZ1076 | L351L_S400R_F405V_Y407V | T366L_N390D_K392F_T394W_T411T |
| AZ1077 | L351L_S400R_F405V_Y407V | T366L_N390E_K392L_T394W_T411N |
| AZ1078 | L351L_S400R_F405V_Y407V | T366L_N390E_K392L_T394W_T411L |
| AZ1079 | L351L_S400R_F405V_Y407V | T366L_N390E_K392L_T394W_T411S |
| AZ1080 | L351L_S400R_F405V_Y407V | T366L_N390E_K392L_T394W_T411T |
| AZ1081 | L351L_S400R_F405V_Y407V | T366L_N390E_K392M_T394W_T411N |
| AZ1082 | L351L_S400R_F405V_Y407V | T366L_N390E_K392M_T394W_T411L |
| AZ1083 | L351L_S400R_F405V_Y407V | T366L_N390E_K392M_T394W_T411S |
| AZ1084 | L351L_S400R_F405V_Y407V | T366L_N390E_K392M_T394W_T411T |
| AZ1085 | L351L_S400R_F405V_Y407V | T366L_N390E_K392F_T394W_T411N |
| AZ1086 | L351L_S400R_F405V_Y407V | T366L_N390E_K392F_T394W_T411L |
| AZ1087 | L351L_S400R_F405V_Y407V | T366L_N390E_K392F_T394W_T411S |
| AZ1088 | L351L_S400R_F405V_Y407V | T366L_N390E_K392F_T394W_T411T |
| AZ1089 | L351L_S400E_F405A_Y407I | T366L_N390R_K392L_T394W_T411N |
| AZ1090 | L351L_S400E_F405A_Y407I | T366L_N390R_K392L_T394W_T411L |
| AZ1091 | L351L_S400E_F405A_Y407I | T366L_N390R_K392L_T394W_T411S |
| AZ1092 | L351L_S400E_F405A_Y407I | T366L_N390R_K392M_T394W_T411N |
| AZ1093 | L351L_S400E_F405A_Y407I | T366L_N390R_K392M_T394W_T411L |
| AZ1094 | L351L_S400E_F405A_Y407I | T366L_N390R_K392M_T394W_T411S |
| AZ1095 | L351L_S400E_F405A_Y407I | T366L_N390R_K392F_T394W_T411N |
| AZ1096 | L351L_S400E_F405A_Y407I | T366L_N390R_K392F_T394W_T411L |
| AZ1097 | L351L_S400E_F405A_Y407I | T366L_N390R_K392F_T394W_T411S |
| AZ1098 | L351L_S400E_F405A_Y407I | T366L_N390N_K392L_T394W_T411N |
| AZ1099 | L351L_S400E_F405A_Y407I | T366L_N390N_K392L_T394W_T411L |
| AZ1100 | L351L_S400E_F405A_Y407I | T366L_N390N_K392L_T394W_T411S |
| AZ1101 | L351L_S400E_F405A_Y407I | T366L_N390N_K392M_T394W_T411N |
| AZ1102 | L351L_S400E_F405A_Y407I | T366L_N390N_K392M_T394W_T411L |
| AZ1103 | L351L_S400E_F405A_Y407I | T366L_N390N_K392M_T394W_T411S |
| AZ1104 | L351L_S400E_F405A_Y407I | T366L_N390N_K392F_T394W_T411N |
| AZ1105 | L351L_S400E_F405A_Y407I | T366L_N390N_K392F_T394W_T411L |
| AZ1106 | L351L_S400E_F405A_Y407I | T366L_N390N_K392F_T394W_T411S |
| AZ1107 | L351L_S400E_F405A_Y407I | T366L_N390K_K392L_T394W_T411N |
| AZ1108 | L351L_S400E_F405A_Y407I | T366L_N390K_K392L_T394W_T411L |
| AZ1109 | L351L_S400E_F405A_Y407I | T366L_N390K_K392L_T394W_T411S |
| AZ1110 | L351L_S400E_F405A_Y407I | T366L_N390K_K392M_T394W_T411N |
| AZ1111 | L351L_S400E_F405A_Y407I | T366L_N390K_K392M_T394W_T411L |
| AZ1112 | L351L_S400E_F405A_Y407I | T366L_N390K_K392M_T394W_T411S |
| AZ1113 | L351L_S400E_F405A_Y407I | T366L_N390K_K392F_T394W_T411N |
| AZ1114 | L351L_S400E_F405A_Y407I | T366L_N390K_K392F_T394W_T411L |

FIG. 37Q

| | | |
|---|---|---|
| AZ1115 | L351L_S400E_F405A_Y407I | T366L_N390K_K392F_T394W_T411S |
| AZ1116 | L351L_S400E_F405A_Y407V | T366L_N390R_K392L_T394W_T411N |
| AZ1117 | L351L_S400E_F405A_Y407V | T366L_N390R_K392L_T394W_T411L |
| AZ1118 | L351L_S400E_F405A_Y407V | T366L_N390R_K392L_T394W_T411S |
| AZ1119 | L351L_S400E_F405A_Y407V | T366L_N390R_K392M_T394W_T411N |
| AZ1120 | L351L_S400E_F405A_Y407V | T366L_N390R_K392M_T394W_T411L |
| AZ1121 | L351L_S400E_F405A_Y407V | T366L_N390R_K392M_T394W_T411S |
| AZ1122 | L351L_S400E_F405A_Y407V | T366L_N390R_K392F_T394W_T411N |
| AZ1123 | L351L_S400E_F405A_Y407V | T366L_N390R_K392F_T394W_T411L |
| AZ1124 | L351L_S400E_F405A_Y407V | T366L_N390R_K392F_T394W_T411S |
| AZ1125 | L351L_S400E_F405A_Y407V | T366L_N390N_K392L_T394W_T411N |
| AZ1126 | L351L_S400E_F405A_Y407V | T366L_N390N_K392L_T394W_T411L |
| AZ1127 | L351L_S400E_F405A_Y407V | T366L_N390N_K392L_T394W_T411S |
| AZ1128 | L351L_S400E_F405A_Y407V | T366L_N390N_K392M_T394W_T411N |
| AZ1129 | L351L_S400E_F405A_Y407V | T366L_N390N_K392M_T394W_T411L |
| AZ1130 | L351L_S400E_F405A_Y407V | T366L_N390N_K392M_T394W_T411S |
| AZ1131 | L351L_S400E_F405A_Y407V | T366L_N390N_K392F_T394W_T411N |
| AZ1132 | L351L_S400E_F405A_Y407V | T366L_N390N_K392F_T394W_T411L |
| AZ1133 | L351L_S400E_F405A_Y407V | T366L_N390N_K392F_T394W_T411S |
| AZ1134 | L351L_S400E_F405A_Y407V | T366L_N390K_K392L_T394W_T411N |
| AZ1135 | L351L_S400E_F405A_Y407V | T366L_N390K_K392L_T394W_T411L |
| AZ1136 | L351L_S400E_F405A_Y407V | T366L_N390K_K392L_T394W_T411S |
| AZ1137 | L351L_S400E_F405A_Y407V | T366L_N390K_K392M_T394W_T411N |
| AZ1138 | L351L_S400E_F405A_Y407V | T366L_N390K_K392M_T394W_T411L |
| AZ1139 | L351L_S400E_F405A_Y407V | T366L_N390K_K392M_T394W_T411S |
| AZ1140 | L351L_S400E_F405A_Y407V | T366L_N390K_K392F_T394W_T411N |
| AZ1141 | L351L_S400E_F405A_Y407V | T366L_N390K_K392F_T394W_T411L |
| AZ1142 | L351L_S400E_F405A_Y407V | T366L_N390K_K392F_T394W_T411S |
| AZ1143 | L351L_S400E_F405S_Y407I | T366L_N390R_K392L_T394W_T411N |
| AZ1144 | L351L_S400E_F405S_Y407I | T366L_N390R_K392L_T394W_T411L |
| AZ1145 | L351L_S400E_F405S_Y407I | T366L_N390R_K392L_T394W_T411S |
| AZ1146 | L351L_S400E_F405S_Y407I | T366L_N390R_K392M_T394W_T411N |
| AZ1147 | L351L_S400E_F405S_Y407I | T366L_N390R_K392M_T394W_T411L |
| AZ1148 | L351L_S400E_F405S_Y407I | T366L_N390R_K392M_T394W_T411S |
| AZ1149 | L351L_S400E_F405S_Y407I | T366L_N390R_K392F_T394W_T411N |
| AZ1150 | L351L_S400E_F405S_Y407I | T366L_N390R_K392F_T394W_T411L |
| AZ1151 | L351L_S400E_F405S_Y407I | T366L_N390R_K392F_T394W_T411S |
| AZ1152 | L351L_S400E_F405S_Y407I | T366L_N390N_K392L_T394W_T411N |
| AZ1153 | L351L_S400E_F405S_Y407I | T366L_N390N_K392L_T394W_T411L |
| AZ1154 | L351L_S400E_F405S_Y407I | T366L_N390N_K392L_T394W_T411S |
| AZ1155 | L351L_S400E_F405S_Y407I | T366L_N390N_K392M_T394W_T411N |
| AZ1156 | L351L_S400E_F405S_Y407I | T366L_N390N_K392M_T394W_T411L |
| AZ1157 | L351L_S400E_F405S_Y407I | T366L_N390N_K392M_T394W_T411S |
| AZ1158 | L351L_S400E_F405S_Y407I | T366L_N390N_K392F_T394W_T411N |
| AZ1159 | L351L_S400E_F405S_Y407I | T366L_N390N_K392F_T394W_T411L |
| AZ1160 | L351L_S400E_F405S_Y407I | T366L_N390N_K392F_T394W_T411S |
| AZ1161 | L351L_S400E_F405S_Y407I | T366L_N390K_K392L_T394W_T411N |
| AZ1162 | L351L_S400E_F405S_Y407I | T366L_N390K_K392L_T394W_T411L |
| AZ1163 | L351L_S400E_F405S_Y407I | T366L_N390K_K392L_T394W_T411S |
| AZ1164 | L351L_S400E_F405S_Y407I | T366L_N390K_K392M_T394W_T411N |
| AZ1165 | L351L_S400E_F405S_Y407I | T366L_N390K_K392M_T394W_T411L |
| AZ1166 | L351L_S400E_F405S_Y407I | T366L_N390K_K392M_T394W_T411S |
| AZ1167 | L351L_S400E_F405S_Y407I | T366L_N390K_K392F_T394W_T411N |
| AZ1168 | L351L_S400E_F405S_Y407I | T366L_N390K_K392F_T394W_T411L |
| AZ1169 | L351L_S400E_F405S_Y407I | T366L_N390K_K392F_T394W_T411S |
| AZ1170 | L351L_S400E_F405S_Y407V | T366L_N390R_K392L_T394W_T411N |
| AZ1171 | L351L_S400E_F405S_Y407V | T366L_N390R_K392L_T394W_T411L |
| AZ1172 | L351L_S400E_F405S_Y407V | T366L_N390R_K392L_T394W_T411S |

FIG. 37R

| | | |
|---|---|---|
| AZ1173 | L351L_S400E_F405S_Y407V | T366L_N390R_K392M_T394W_T411N |
| AZ1174 | L351L_S400E_F405S_Y407V | T366L_N390R_K392M_T394W_T411L |
| AZ1175 | L351L_S400E_F405S_Y407V | T366L_N390R_K392M_T394W_T411S |
| AZ1176 | L351L_S400E_F405S_Y407V | T366L_N390R_K392F_T394W_T411N |
| AZ1177 | L351L_S400E_F405S_Y407V | T366L_N390R_K392F_T394W_T411L |
| AZ1178 | L351L_S400E_F405S_Y407V | T366L_N390R_K392F_T394W_T411S |
| AZ1179 | L351L_S400E_F405S_Y407V | T366L_N390N_K392L_T394W_T411N |
| AZ1180 | L351L_S400E_F405S_Y407V | T366L_N390N_K392L_T394W_T411L |
| AZ1181 | L351L_S400E_F405S_Y407V | T366L_N390N_K392L_T394W_T411S |
| AZ1182 | L351L_S400E_F405S_Y407V | T366L_N390N_K392M_T394W_T411N |
| AZ1183 | L351L_S400E_F405S_Y407V | T366L_N390N_K392M_T394W_T411L |
| AZ1184 | L351L_S400E_F405S_Y407V | T366L_N390N_K392M_T394W_T411S |
| AZ1185 | L351L_S400E_F405S_Y407V | T366L_N390N_K392F_T394W_T411N |
| AZ1186 | L351L_S400E_F405S_Y407V | T366L_N390N_K392F_T394W_T411L |
| AZ1187 | L351L_S400E_F405S_Y407V | T366L_N390N_K392F_T394W_T411S |
| AZ1188 | L351L_S400E_F405S_Y407V | T366L_N390K_K392L_T394W_T411N |
| AZ1189 | L351L_S400E_F405S_Y407V | T366L_N390K_K392L_T394W_T411L |
| AZ1190 | L351L_S400E_F405S_Y407V | T366L_N390K_K392L_T394W_T411S |
| AZ1191 | L351L_S400E_F405S_Y407V | T366L_N390K_K392M_T394W_T411N |
| AZ1192 | L351L_S400E_F405S_Y407V | T366L_N390K_K392M_T394W_T411L |
| AZ1193 | L351L_S400E_F405S_Y407V | T366L_N390K_K392M_T394W_T411S |
| AZ1194 | L351L_S400E_F405S_Y407V | T366L_N390K_K392F_T394W_T411N |
| AZ1195 | L351L_S400E_F405S_Y407V | T366L_N390K_K392F_T394W_T411L |
| AZ1196 | L351L_S400E_F405S_Y407V | T366L_N390K_K392F_T394W_T411S |
| AZ1197 | L351L_S400E_F405T_Y407I | T366L_N390R_K392L_T394W_T411N |
| AZ1198 | L351L_S400E_F405T_Y407I | T366L_N390R_K392L_T394W_T411L |
| AZ1199 | L351L_S400E_F405T_Y407I | T366L_N390R_K392L_T394W_T411S |
| AZ1200 | L351L_S400E_F405T_Y407I | T366L_N390R_K392M_T394W_T411N |
| AZ1201 | L351L_S400E_F405T_Y407I | T366L_N390R_K392M_T394W_T411L |
| AZ1202 | L351L_S400E_F405T_Y407I | T366L_N390R_K392M_T394W_T411S |
| AZ1203 | L351L_S400E_F405T_Y407I | T366L_N390R_K392F_T394W_T411N |
| AZ1204 | L351L_S400E_F405T_Y407I | T366L_N390R_K392F_T394W_T411L |
| AZ1205 | L351L_S400E_F405T_Y407I | T366L_N390R_K392F_T394W_T411S |
| AZ1206 | L351L_S400E_F405T_Y407I | T366L_N390N_K392L_T394W_T411N |
| AZ1207 | L351L_S400E_F405T_Y407I | T366L_N390N_K392L_T394W_T411L |
| AZ1208 | L351L_S400E_F405T_Y407I | T366L_N390N_K392L_T394W_T411S |
| AZ1209 | L351L_S400E_F405T_Y407I | T366L_N390N_K392M_T394W_T411N |
| AZ1210 | L351L_S400E_F405T_Y407I | T366L_N390N_K392M_T394W_T411L |
| AZ1211 | L351L_S400E_F405T_Y407I | T366L_N390N_K392M_T394W_T411S |
| AZ1212 | L351L_S400E_F405T_Y407I | T366L_N390N_K392F_T394W_T411N |
| AZ1213 | L351L_S400E_F405T_Y407I | T366L_N390N_K392F_T394W_T411L |
| AZ1214 | L351L_S400E_F405T_Y407I | T366L_N390N_K392F_T394W_T411S |
| AZ1215 | L351L_S400E_F405T_Y407I | T366L_N390K_K392L_T394W_T411N |
| AZ1216 | L351L_S400E_F405T_Y407I | T366L_N390K_K392L_T394W_T411L |
| AZ1217 | L351L_S400E_F405T_Y407I | T366L_N390K_K392L_T394W_T411S |
| AZ1218 | L351L_S400E_F405T_Y407I | T366L_N390K_K392M_T394W_T411N |
| AZ1219 | L351L_S400E_F405T_Y407I | T366L_N390K_K392M_T394W_T411L |
| AZ1220 | L351L_S400E_F405T_Y407I | T366L_N390K_K392M_T394W_T411S |
| AZ1221 | L351L_S400E_F405T_Y407I | T366L_N390K_K392F_T394W_T411N |
| AZ1222 | L351L_S400E_F405T_Y407I | T366L_N390K_K392F_T394W_T411L |
| AZ1223 | L351L_S400E_F405T_Y407I | T366L_N390K_K392F_T394W_T411S |
| AZ1224 | L351L_S400E_F405T_Y407V | T366L_N390R_K392L_T394W_T411N |
| AZ1225 | L351L_S400E_F405T_Y407V | T366L_N390R_K392L_T394W_T411L |
| AZ1226 | L351L_S400E_F405T_Y407V | T366L_N390R_K392L_T394W_T411S |
| AZ1227 | L351L_S400E_F405T_Y407V | T366L_N390R_K392M_T394W_T411N |
| AZ1228 | L351L_S400E_F405T_Y407V | T366L_N390R_K392M_T394W_T411L |
| AZ1229 | L351L_S400E_F405T_Y407V | T366L_N390R_K392M_T394W_T411S |
| AZ1230 | L351L_S400E_F405T_Y407V | T366L_N390R_K392F_T394W_T411N |

FIG. 37S

| | | |
|---|---|---|
| AZ1231 | L351I_S400E_F405T_Y407V | T366L_N390R_K392F_T394W_T411N |
| AZ1232 | L351I_S400E_F405T_Y407V | T366L_N390R_K392F_T394W_T411S |
| AZ1233 | L351I_S400E_F405T_Y407V | T366L_N390N_K392L_T394W_T411N |
| AZ1234 | L351I_S400E_F405T_Y407V | T366L_N390N_K392L_T394W_T411L |
| AZ1235 | L351I_S400E_F405T_Y407V | T366L_N390N_K392L_T394W_T411S |
| AZ1236 | L351I_S400E_F405T_Y407V | T366L_N390N_K392M_T394W_T411N |
| AZ1237 | L351I_S400E_F405T_Y407V | T366L_N390N_K392M_T394W_T411L |
| AZ1238 | L351I_S400E_F405T_Y407V | T366L_N390N_K392M_T394W_T411S |
| AZ1239 | L351I_S400E_F405T_Y407V | T366L_N390N_K392F_T394W_T411N |
| AZ1240 | L351I_S400E_F405T_Y407V | T366L_N390N_K392F_T394W_T411L |
| AZ1241 | L351I_S400E_F405T_Y407V | T366L_N390N_K392F_T394W_T411S |
| AZ1242 | L351I_S400E_F405T_Y407V | T366L_N390K_K392L_T394W_T411N |
| AZ1243 | L351I_S400E_F405T_Y407V | T366L_N390K_K392L_T394W_T411L |
| AZ1244 | L351I_S400E_F405T_Y407V | T366L_N390K_K392L_T394W_T411S |
| AZ1245 | L351I_S400E_F405T_Y407V | T366L_N390K_K392M_T394W_T411N |
| AZ1246 | L351I_S400E_F405T_Y407V | T366L_N390K_K392M_T394W_T411L |
| AZ1247 | L351I_S400E_F405T_Y407V | T366L_N390K_K392M_T394W_T411S |
| AZ1248 | L351I_S400E_F405T_Y407V | T366L_N390K_K392F_T394W_T411N |
| AZ1249 | L351I_S400E_F405T_Y407V | T366L_N390K_K392F_T394W_T411L |
| AZ1250 | L351I_S400E_F405T_Y407V | T366L_N390K_K392F_T394W_T411S |
| AZ1251 | L351I_S400E_F405V_Y407I | T366L_N390R_K392L_T394W_T411N |
| AZ1252 | L351I_S400E_F405V_Y407I | T366L_N390R_K392L_T394W_T411L |
| AZ1253 | L351I_S400E_F405V_Y407I | T366L_N390R_K392L_T394W_T411S |
| AZ1254 | L351I_S400E_F405V_Y407I | T366L_N390R_K392M_T394W_T411N |
| AZ1255 | L351I_S400E_F405V_Y407I | T366L_N390R_K392M_T394W_T411L |
| AZ1256 | L351I_S400E_F405V_Y407I | T366L_N390R_K392M_T394W_T411S |
| AZ1257 | L351I_S400E_F405V_Y407I | T366L_N390R_K392F_T394W_T411N |
| AZ1258 | L351I_S400E_F405V_Y407I | T366L_N390R_K392F_T394W_T411L |
| AZ1259 | L351I_S400E_F405V_Y407I | T366L_N390R_K392F_T394W_T411S |
| AZ1260 | L351I_S400E_F405V_Y407I | T366L_N390N_K392L_T394W_T411N |
| AZ1261 | L351I_S400E_F405V_Y407I | T366L_N390N_K392L_T394W_T411L |
| AZ1262 | L351I_S400E_F405V_Y407I | T366L_N390N_K392L_T394W_T411S |
| AZ1263 | L351I_S400E_F405V_Y407I | T366L_N390N_K392M_T394W_T411N |
| AZ1264 | L351I_S400E_F405V_Y407I | T366L_N390N_K392M_T394W_T411L |
| AZ1265 | L351I_S400E_F405V_Y407I | T366L_N390N_K392M_T394W_T411S |
| AZ1266 | L351I_S400E_F405V_Y407I | T366L_N390N_K392F_T394W_T411N |
| AZ1267 | L351I_S400E_F405V_Y407I | T366L_N390N_K392F_T394W_T411L |
| AZ1268 | L351I_S400E_F405V_Y407I | T366L_N390N_K392F_T394W_T411S |
| AZ1269 | L351I_S400E_F405V_Y407I | T366L_N390K_K392L_T394W_T411N |
| AZ1270 | L351I_S400E_F405V_Y407I | T366L_N390K_K392L_T394W_T411L |
| AZ1271 | L351I_S400E_F405V_Y407I | T366L_N390K_K392L_T394W_T411S |
| AZ1272 | L351I_S400E_F405V_Y407I | T366L_N390K_K392M_T394W_T411N |
| AZ1273 | L351I_S400E_F405V_Y407I | T366L_N390K_K392M_T394W_T411L |
| AZ1274 | L351I_S400E_F405V_Y407I | T366L_N390K_K392M_T394W_T411S |
| AZ1275 | L351I_S400E_F405V_Y407I | T366L_N390K_K392F_T394W_T411N |
| AZ1276 | L351I_S400E_F405V_Y407I | T366L_N390K_K392F_T394W_T411L |
| AZ1277 | L351I_S400E_F405V_Y407I | T366L_N390K_K392F_T394W_T411S |
| AZ1278 | L351I_S400E_F405V_Y407V | T366L_N390R_K392L_T394W_T411N |
| AZ1279 | L351I_S400E_F405V_Y407V | T366L_N390R_K392L_T394W_T411L |
| AZ1280 | L351I_S400E_F405V_Y407V | T366L_N390R_K392L_T394W_T411S |
| AZ1281 | L351I_S400E_F405V_Y407V | T366L_N390R_K392M_T394W_T411N |
| AZ1282 | L351I_S400E_F405V_Y407V | T366L_N390R_K392M_T394W_T411L |
| AZ1283 | L351I_S400E_F405V_Y407V | T366L_N390R_K392M_T394W_T411S |
| AZ1284 | L351I_S400E_F405V_Y407V | T366L_N390R_K392F_T394W_T411N |
| AZ1285 | L351I_S400E_F405V_Y407V | T366L_N390R_K392F_T394W_T411L |
| AZ1286 | L351I_S400E_F405V_Y407V | T366L_N390R_K392F_T394W_T411S |
| AZ1287 | L351I_S400E_F405V_Y407V | T366L_N390N_K392L_T394W_T411N |
| AZ1288 | L351I_S400E_F405V_Y407V | T366L_N390N_K392L_T394W_T411L |

FIG. 37T

| | | |
|---|---|---|
| AZ1289 | L351L_S400E_F405V_Y407V | T366L_N390N_K392L_T394W_T411S |
| AZ1290 | L351L_S400E_F405V_Y407V | T366L_N390N_K392M_T394W_T411N |
| AZ1291 | L351L_S400E_F405V_Y407V | T366L_N390N_K392M_T394W_T411L |
| AZ1292 | L351L_S400E_F405V_Y407V | T366L_N390N_K392M_T394W_T411S |
| AZ1293 | L351L_S400E_F405V_Y407V | T366L_N390N_K392F_T394W_T411N |
| AZ1294 | L351L_S400E_F405V_Y407V | T366L_N390N_K392F_T394W_T411L |
| AZ1295 | L351L_S400E_F405V_Y407V | T366L_N390N_K392F_T394W_T411S |
| AZ1296 | L351L_S400E_F405V_Y407V | T366L_N390K_K392L_T394W_T411N |
| AZ1297 | L351L_S400E_F405V_Y407V | T366L_N390K_K392L_T394W_T411L |
| AZ1298 | L351L_S400E_F405V_Y407V | T366L_N390K_K392L_T394W_T411S |
| AZ1299 | L351L_S400E_F405V_Y407V | T366L_N390K_K392M_T394W_T411N |
| AZ1300 | L351L_S400E_F405V_Y407V | T366L_N390K_K392M_T394W_T411L |
| AZ1301 | L351L_S400E_F405V_Y407V | T366L_N390K_K392M_T394W_T411S |
| AZ1302 | L351L_S400E_F405V_Y407V | T366L_N390K_K392F_T394W_T411N |
| AZ1303 | L351L_S400E_F405V_Y407V | T366L_N390K_K392F_T394W_T411L |
| AZ1304 | L351L_S400E_F405V_Y407V | T366L_N390K_K392F_T394W_T411S |
| AZ1305 | L351L_S400K_F405A_Y407I | T366L_N390N_K392L_T394W_T411N |
| AZ1306 | L351L_S400K_F405A_Y407I | T366L_N390N_K392L_T394W_T411S |
| AZ1307 | L351L_S400K_F405A_Y407I | T366L_N390N_K392L_T394W_T411T |
| AZ1308 | L351L_S400K_F405A_Y407I | T366L_N390N_K392M_T394W_T411N |
| AZ1309 | L351L_S400K_F405A_Y407I | T366L_N390N_K392M_T394W_T411S |
| AZ1310 | L351L_S400K_F405A_Y407I | T366L_N390N_K392M_T394W_T411T |
| AZ1311 | L351L_S400K_F405A_Y407I | T366L_N390N_K392F_T394W_T411N |
| AZ1312 | L351L_S400K_F405A_Y407I | T366L_N390N_K392F_T394W_T411S |
| AZ1313 | L351L_S400K_F405A_Y407I | T366L_N390N_K392F_T394W_T411T |
| AZ1314 | L351L_S400K_F405A_Y407I | T366L_N390D_K392L_T394W_T411N |
| AZ1315 | L351L_S400K_F405A_Y407I | T366L_N390D_K392L_T394W_T411S |
| AZ1316 | L351L_S400K_F405A_Y407I | T366L_N390D_K392L_T394W_T411T |
| AZ1317 | L351L_S400K_F405A_Y407I | T366L_N390D_K392M_T394W_T411N |
| AZ1318 | L351L_S400K_F405A_Y407I | T366L_N390D_K392M_T394W_T411S |
| AZ1319 | L351L_S400K_F405A_Y407I | T366L_N390D_K392M_T394W_T411T |
| AZ1320 | L351L_S400K_F405A_Y407I | T366L_N390D_K392F_T394W_T411N |
| AZ1321 | L351L_S400K_F405A_Y407I | T366L_N390D_K392F_T394W_T411S |
| AZ1322 | L351L_S400K_F405A_Y407I | T366L_N390D_K392F_T394W_T411T |
| AZ1323 | L351L_S400K_F405A_Y407I | T366L_N390E_K392L_T394W_T411N |
| AZ1324 | L351L_S400K_F405A_Y407I | T366L_N390E_K392L_T394W_T411L |
| AZ1325 | L351L_S400K_F405A_Y407I | T366L_N390E_K392L_T394W_T411S |
| AZ1326 | L351L_S400K_F405A_Y407I | T366L_N390E_K392L_T394W_T411T |
| AZ1327 | L351L_S400K_F405A_Y407I | T366L_N390E_K392M_T394W_T411N |
| AZ1328 | L351L_S400K_F405A_Y407I | T366L_N390E_K392M_T394W_T411L |
| AZ1329 | L351L_S400K_F405A_Y407I | T366L_N390E_K392M_T394W_T411S |
| AZ1330 | L351L_S400K_F405A_Y407I | T366L_N390E_K392M_T394W_T411T |
| AZ1331 | L351L_S400K_F405A_Y407I | T366L_N390E_K392F_T394W_T411N |
| AZ1332 | L351L_S400K_F405A_Y407I | T366L_N390E_K392F_T394W_T411L |
| AZ1333 | L351L_S400K_F405A_Y407I | T366L_N390E_K392F_T394W_T411S |
| AZ1334 | L351L_S400K_F405A_Y407I | T366L_N390E_K392F_T394W_T411T |
| AZ1335 | L351L_S400K_F405A_Y407V | T366L_N390N_K392L_T394W_T411N |
| AZ1336 | L351L_S400K_F405A_Y407V | T366L_N390N_K392L_T394W_T411S |
| AZ1337 | L351L_S400K_F405A_Y407V | T366L_N390N_K392L_T394W_T411T |
| AZ1338 | L351L_S400K_F405A_Y407V | T366L_N390N_K392M_T394W_T411N |
| AZ1339 | L351L_S400K_F405A_Y407V | T366L_N390N_K392M_T394W_T411S |
| AZ1340 | L351L_S400K_F405A_Y407V | T366L_N390N_K392M_T394W_T411T |
| AZ1341 | L351L_S400K_F405A_Y407V | T366L_N390N_K392F_T394W_T411N |
| AZ1342 | L351L_S400K_F405A_Y407V | T366L_N390N_K392F_T394W_T411S |
| AZ1343 | L351L_S400K_F405A_Y407V | T366L_N390N_K392F_T394W_T411T |
| AZ1344 | L351L_S400K_F405A_Y407V | T366L_N390D_K392L_T394W_T411N |
| AZ1345 | L351L_S400K_F405A_Y407V | T366L_N390D_K392L_T394W_T411S |
| AZ1346 | L351L_S400K_F405A_Y407V | T366L_N390D_K392L_T394W_T411T |

FIG. 37U

| AZ1347 | L351L_S400K_F405A_Y407V | T366L_N390D_K392M_T394W_T411N |
|---|---|---|
| AZ1348 | L351L_S400K_F405A_Y407V | T366L_N390D_K392M_T394W_T411S |
| AZ1349 | L351L_S400K_F405A_Y407V | T366L_N390D_K392M_T394W_T411T |
| AZ1350 | L351L_S400K_F405A_Y407V | T366L_N390D_K392F_T394W_T411N |
| AZ1351 | L351L_S400K_F405A_Y407V | T366L_N390D_K392F_T394W_T411S |
| AZ1352 | L351L_S400K_F405A_Y407V | T366L_N390D_K392F_T394W_T411T |
| AZ1353 | L351L_S400K_F405A_Y407V | T366L_N390E_K392L_T394W_T411N |
| AZ1354 | L351L_S400K_F405A_Y407V | T366L_N390E_K392L_T394W_T411L |
| AZ1355 | L351L_S400K_F405A_Y407V | T366L_N390E_K392L_T394W_T411S |
| AZ1356 | L351L_S400K_F405A_Y407V | T366L_N390E_K392L_T394W_T411T |
| AZ1357 | L351L_S400K_F405A_Y407V | T366L_N390E_K392M_T394W_T411N |
| AZ1358 | L351L_S400K_F405A_Y407V | T366L_N390E_K392M_T394W_T411L |
| AZ1359 | L351L_S400K_F405A_Y407V | T366L_N390E_K392M_T394W_T411S |
| AZ1360 | L351L_S400K_F405A_Y407V | T366L_N390E_K392M_T394W_T411T |
| AZ1361 | L351L_S400K_F405A_Y407V | T366L_N390E_K392F_T394W_T411N |
| AZ1362 | L351L_S400K_F405A_Y407V | T366L_N390E_K392F_T394W_T411L |
| AZ1363 | L351L_S400K_F405A_Y407V | T366L_N390E_K392F_T394W_T411S |
| AZ1364 | L351L_S400K_F405A_Y407V | T366L_N390E_K392F_T394W_T411T |
| AZ1365 | L351L_S400K_F405S_Y407I | T366L_N390N_K392L_T394W_T411N |
| AZ1366 | L351L_S400K_F405S_Y407I | T366L_N390N_K392L_T394W_T411S |
| AZ1367 | L351L_S400K_F405S_Y407I | T366L_N390N_K392L_T394W_T411T |
| AZ1368 | L351L_S400K_F405S_Y407I | T366L_N390N_K392M_T394W_T411N |
| AZ1369 | L351L_S400K_F405S_Y407I | T366L_N390N_K392M_T394W_T411S |
| AZ1370 | L351L_S400K_F405S_Y407I | T366L_N390N_K392M_T394W_T411T |
| AZ1371 | L351L_S400K_F405S_Y407I | T366L_N390N_K392F_T394W_T411N |
| AZ1372 | L351L_S400K_F405S_Y407I | T366L_N390N_K392F_T394W_T411S |
| AZ1373 | L351L_S400K_F405S_Y407I | T366L_N390N_K392F_T394W_T411T |
| AZ1374 | L351L_S400K_F405S_Y407I | T366L_N390D_K392L_T394W_T411N |
| AZ1375 | L351L_S400K_F405S_Y407I | T366L_N390D_K392L_T394W_T411S |
| AZ1376 | L351L_S400K_F405S_Y407I | T366L_N390D_K392L_T394W_T411T |
| AZ1377 | L351L_S400K_F405S_Y407I | T366L_N390D_K392M_T394W_T411N |
| AZ1378 | L351L_S400K_F405S_Y407I | T366L_N390D_K392M_T394W_T411S |
| AZ1379 | L351L_S400K_F405S_Y407I | T366L_N390D_K392M_T394W_T411T |
| AZ1380 | L351L_S400K_F405S_Y407I | T366L_N390D_K392F_T394W_T411N |
| AZ1381 | L351L_S400K_F405S_Y407I | T366L_N390D_K392F_T394W_T411S |
| AZ1382 | L351L_S400K_F405S_Y407I | T366L_N390D_K392F_T394W_T411T |
| AZ1383 | L351L_S400K_F405S_Y407I | T366L_N390E_K392L_T394W_T411N |
| AZ1384 | L351L_S400K_F405S_Y407I | T366L_N390E_K392L_T394W_T411L |
| AZ1385 | L351L_S400K_F405S_Y407I | T366L_N390E_K392L_T394W_T411S |
| AZ1386 | L351L_S400K_F405S_Y407I | T366L_N390E_K392L_T394W_T411T |
| AZ1387 | L351L_S400K_F405S_Y407I | T366L_N390E_K392M_T394W_T411N |
| AZ1388 | L351L_S400K_F405S_Y407I | T366L_N390E_K392M_T394W_T411L |
| AZ1389 | L351L_S400K_F405S_Y407I | T366L_N390E_K392M_T394W_T411S |
| AZ1390 | L351L_S400K_F405S_Y407I | T366L_N390E_K392M_T394W_T411T |
| AZ1391 | L351L_S400K_F405S_Y407I | T366L_N390E_K392F_T394W_T411N |
| AZ1392 | L351L_S400K_F405S_Y407I | T366L_N390E_K392F_T394W_T411L |
| AZ1393 | L351L_S400K_F405S_Y407I | T366L_N390E_K392F_T394W_T411S |
| AZ1394 | L351L_S400K_F405S_Y407I | T366L_N390E_K392F_T394W_T411T |
| AZ1395 | L351L_S400K_F405S_Y407V | T366L_N390N_K392L_T394W_T411N |
| AZ1396 | L351L_S400K_F405S_Y407V | T366L_N390N_K392L_T394W_T411S |
| AZ1397 | L351L_S400K_F405S_Y407V | T366L_N390N_K392L_T394W_T411T |
| AZ1398 | L351L_S400K_F405S_Y407V | T366L_N390N_K392M_T394W_T411N |
| AZ1399 | L351L_S400K_F405S_Y407V | T366L_N390N_K392M_T394W_T411S |
| AZ1400 | L351L_S400K_F405S_Y407V | T366L_N390N_K392M_T394W_T411T |
| AZ1401 | L351L_S400K_F405S_Y407V | T366L_N390N_K392F_T394W_T411N |
| AZ1402 | L351L_S400K_F405S_Y407V | T366L_N390N_K392F_T394W_T411S |
| AZ1403 | L351L_S400K_F405S_Y407V | T366L_N390N_K392F_T394W_T411T |
| AZ1404 | L351L_S400K_F405S_Y407V | T366L_N390D_K392L_T394W_T411N |

FIG. 37V

| | | |
|---|---|---|
| AZ1405 | L351L_S400K_F405S_Y407V | T366L_N390D_K392L_T394W_T411S |
| AZ1406 | L351L_S400K_F405S_Y407V | T366L_N390D_K392L_T394W_T411T |
| AZ1407 | L351L_S400K_F405S_Y407V | T366L_N390D_K392M_T394W_T411N |
| AZ1408 | L351L_S400K_F405S_Y407V | T366L_N390D_K392M_T394W_T411S |
| AZ1409 | L351L_S400K_F405S_Y407V | T366L_N390D_K392M_T394W_T411T |
| AZ1410 | L351L_S400K_F405S_Y407V | T366L_N390D_K392F_T394W_T411N |
| AZ1411 | L351L_S400K_F405S_Y407V | T366L_N390D_K392F_T394W_T411S |
| AZ1412 | L351L_S400K_F405S_Y407V | T366L_N390D_K392F_T394W_T411T |
| AZ1413 | L351L_S400K_F405S_Y407V | T366L_N390E_K392L_T394W_T411N |
| AZ1414 | L351L_S400K_F405S_Y407V | T366L_N390E_K392L_T394W_T411L |
| AZ1415 | L351L_S400K_F405S_Y407V | T366L_N390E_K392L_T394W_T411S |
| AZ1416 | L351L_S400K_F405S_Y407V | T366L_N390E_K392L_T394W_T411T |
| AZ1417 | L351L_S400K_F405S_Y407V | T366L_N390E_K392M_T394W_T411N |
| AZ1418 | L351L_S400K_F405S_Y407V | T366L_N390E_K392M_T394W_T411L |
| AZ1419 | L351L_S400K_F405S_Y407V | T366L_N390E_K392M_T394W_T411S |
| AZ1420 | L351L_S400K_F405S_Y407V | T366L_N390E_K392M_T394W_T411T |
| AZ1421 | L351L_S400K_F405S_Y407V | T366L_N390E_K392F_T394W_T411N |
| AZ1422 | L351L_S400K_F405S_Y407V | T366L_N390E_K392F_T394W_T411L |
| AZ1423 | L351L_S400K_F405S_Y407V | T366L_N390E_K392F_T394W_T411S |
| AZ1424 | L351L_S400K_F405S_Y407V | T366L_N390E_K392F_T394W_T411T |
| AZ1425 | L351L_S400K_F405T_Y407I | T366L_N390N_K392L_T394W_T411N |
| AZ1426 | L351L_S400K_F405T_Y407I | T366L_N390N_K392L_T394W_T411S |
| AZ1427 | L351L_S400K_F405T_Y407I | T366L_N390N_K392L_T394W_T411T |
| AZ1428 | L351L_S400K_F405T_Y407I | T366L_N390N_K392M_T394W_T411N |
| AZ1429 | L351L_S400K_F405T_Y407I | T366L_N390N_K392M_T394W_T411S |
| AZ1430 | L351L_S400K_F405T_Y407I | T366L_N390N_K392M_T394W_T411T |
| AZ1431 | L351L_S400K_F405T_Y407I | T366L_N390N_K392F_T394W_T411N |
| AZ1432 | L351L_S400K_F405T_Y407I | T366L_N390N_K392F_T394W_T411S |
| AZ1433 | L351L_S400K_F405T_Y407I | T366L_N390N_K392F_T394W_T411T |
| AZ1434 | L351L_S400K_F405T_Y407I | T366L_N390D_K392L_T394W_T411N |
| AZ1435 | L351L_S400K_F405T_Y407I | T366L_N390D_K392L_T394W_T411S |
| AZ1436 | L351L_S400K_F405T_Y407I | T366L_N390D_K392L_T394W_T411T |
| AZ1437 | L351L_S400K_F405T_Y407I | T366L_N390D_K392M_T394W_T411N |
| AZ1438 | L351L_S400K_F405T_Y407I | T366L_N390D_K392M_T394W_T411S |
| AZ1439 | L351L_S400K_F405T_Y407I | T366L_N390D_K392M_T394W_T411T |
| AZ1440 | L351L_S400K_F405T_Y407I | T366L_N390D_K392F_T394W_T411N |
| AZ1441 | L351L_S400K_F405T_Y407I | T366L_N390D_K392F_T394W_T411S |
| AZ1442 | L351L_S400K_F405T_Y407I | T366L_N390D_K392F_T394W_T411T |
| AZ1443 | L351L_S400K_F405T_Y407I | T366L_N390E_K392L_T394W_T411N |
| AZ1444 | L351L_S400K_F405T_Y407I | T366L_N390E_K392L_T394W_T411L |
| AZ1445 | L351L_S400K_F405T_Y407I | T366L_N390E_K392L_T394W_T411S |
| AZ1446 | L351L_S400K_F405T_Y407I | T366L_N390E_K392L_T394W_T411T |
| AZ1447 | L351L_S400K_F405T_Y407I | T366L_N390E_K392M_T394W_T411N |
| AZ1448 | L351L_S400K_F405T_Y407I | T366L_N390E_K392M_T394W_T411L |
| AZ1449 | L351L_S400K_F405T_Y407I | T366L_N390E_K392M_T394W_T411S |
| AZ1450 | L351L_S400K_F405T_Y407I | T366L_N390E_K392M_T394W_T411T |
| AZ1451 | L351L_S400K_F405T_Y407I | T366L_N390E_K392F_T394W_T411N |
| AZ1452 | L351L_S400K_F405T_Y407I | T366L_N390E_K392F_T394W_T411L |
| AZ1453 | L351L_S400K_F405T_Y407I | T366L_N390E_K392F_T394W_T411S |
| AZ1454 | L351L_S400K_F405T_Y407I | T366L_N390E_K392F_T394W_T411T |
| AZ1455 | L351L_S400K_F405T_Y407V | T366L_N390N_K392L_T394W_T411N |
| AZ1456 | L351L_S400K_F405T_Y407V | T366L_N390N_K392L_T394W_T411S |
| AZ1457 | L351L_S400K_F405T_Y407V | T366L_N390N_K392L_T394W_T411T |
| AZ1458 | L351L_S400K_F405T_Y407V | T366L_N390N_K392M_T394W_T411N |
| AZ1459 | L351L_S400K_F405T_Y407V | T366L_N390N_K392M_T394W_T411S |
| AZ1460 | L351L_S400K_F405T_Y407V | T366L_N390N_K392M_T394W_T411T |
| AZ1461 | L351L_S400K_F405T_Y407V | T366L_N390N_K392F_T394W_T411N |
| AZ1462 | L351L_S400K_F405T_Y407V | T366L_N390N_K392F_T394W_T411S |

FIG. 37W

| AZ1463 | L351L_S400K_F405T_Y407V | T366L_N390N_K392F_T394W_T411T |
|---|---|---|
| AZ1464 | L351L_S400K_F405T_Y407V | T366L_N390D_K392L_T394W_T411N |
| AZ1465 | L351L_S400K_F405T_Y407V | T366L_N390D_K392L_T394W_T411S |
| AZ1466 | L351L_S400K_F405T_Y407V | T366L_N390D_K392L_T394W_T411T |
| AZ1467 | L351L_S400K_F405T_Y407V | T366L_N390D_K392M_T394W_T411N |
| AZ1468 | L351L_S400K_F405T_Y407V | T366L_N390D_K392M_T394W_T411S |
| AZ1469 | L351L_S400K_F405T_Y407V | T366L_N390D_K392M_T394W_T411T |
| AZ1470 | L351L_S400K_F405T_Y407V | T366L_N390D_K392F_T394W_T411N |
| AZ1471 | L351L_S400K_F405T_Y407V | T366L_N390D_K392F_T394W_T411S |
| AZ1472 | L351L_S400K_F405T_Y407V | T366L_N390D_K392F_T394W_T411T |
| AZ1473 | L351L_S400K_F405T_Y407V | T366L_N390E_K392L_T394W_T411N |
| AZ1474 | L351L_S400K_F405T_Y407V | T366L_N390E_K392L_T394W_T411L |
| AZ1475 | L351L_S400K_F405T_Y407V | T366L_N390E_K392L_T394W_T411S |
| AZ1476 | L351L_S400K_F405T_Y407V | T366L_N390E_K392L_T394W_T411T |
| AZ1477 | L351L_S400K_F405T_Y407V | T366L_N390E_K392M_T394W_T411N |
| AZ1478 | L351L_S400K_F405T_Y407V | T366L_N390E_K392M_T394W_T411L |
| AZ1479 | L351L_S400K_F405T_Y407V | T366L_N390E_K392M_T394W_T411S |
| AZ1480 | L351L_S400K_F405T_Y407V | T366L_N390E_K392M_T394W_T411T |
| AZ1481 | L351L_S400K_F405T_Y407V | T366L_N390E_K392F_T394W_T411N |
| AZ1482 | L351L_S400K_F405T_Y407V | T366L_N390E_K392F_T394W_T411L |
| AZ1483 | L351L_S400K_F405T_Y407V | T366L_N390E_K392F_T394W_T411S |
| AZ1484 | L351L_S400K_F405T_Y407V | T366L_N390E_K392F_T394W_T411T |
| AZ1485 | L351L_S400K_F405V_Y407I | T366L_N390N_K392L_T394W_T411N |
| AZ1486 | L351L_S400K_F405V_Y407I | T366L_N390N_K392L_T394W_T411S |
| AZ1487 | L351L_S400K_F405V_Y407I | T366L_N390N_K392L_T394W_T411T |
| AZ1488 | L351L_S400K_F405V_Y407I | T366L_N390N_K392M_T394W_T411N |
| AZ1489 | L351L_S400K_F405V_Y407I | T366L_N390N_K392M_T394W_T411S |
| AZ1490 | L351L_S400K_F405V_Y407I | T366L_N390N_K392M_T394W_T411T |
| AZ1491 | L351L_S400K_F405V_Y407I | T366L_N390N_K392F_T394W_T411N |
| AZ1492 | L351L_S400K_F405V_Y407I | T366L_N390N_K392F_T394W_T411S |
| AZ1493 | L351L_S400K_F405V_Y407I | T366L_N390N_K392F_T394W_T411T |
| AZ1494 | L351L_S400K_F405V_Y407I | T366L_N390D_K392L_T394W_T411N |
| AZ1495 | L351L_S400K_F405V_Y407I | T366L_N390D_K392L_T394W_T411S |
| AZ1496 | L351L_S400K_F405V_Y407I | T366L_N390D_K392L_T394W_T411T |
| AZ1497 | L351L_S400K_F405V_Y407I | T366L_N390D_K392M_T394W_T411N |
| AZ1498 | L351L_S400K_F405V_Y407I | T366L_N390D_K392M_T394W_T411S |
| AZ1499 | L351L_S400K_F405V_Y407I | T366L_N390D_K392M_T394W_T411T |
| AZ1500 | L351L_S400K_F405V_Y407I | T366L_N390D_K392F_T394W_T411N |
| AZ1501 | L351L_S400K_F405V_Y407I | T366L_N390D_K392F_T394W_T411S |
| AZ1502 | L351L_S400K_F405V_Y407I | T366L_N390D_K392F_T394W_T411T |
| AZ1503 | L351L_S400K_F405V_Y407I | T366L_N390E_K392L_T394W_T411N |
| AZ1504 | L351L_S400K_F405V_Y407I | T366L_N390E_K392L_T394W_T411L |
| AZ1505 | L351L_S400K_F405V_Y407I | T366L_N390E_K392L_T394W_T411S |
| AZ1506 | L351L_S400K_F405V_Y407I | T366L_N390E_K392L_T394W_T411T |
| AZ1507 | L351L_S400K_F405V_Y407I | T366L_N390E_K392M_T394W_T411N |
| AZ1508 | L351L_S400K_F405V_Y407I | T366L_N390E_K392M_T394W_T411L |
| AZ1509 | L351L_S400K_F405V_Y407I | T366L_N390E_K392M_T394W_T411S |
| AZ1510 | L351L_S400K_F405V_Y407I | T366L_N390E_K392M_T394W_T411T |
| AZ1511 | L351L_S400K_F405V_Y407I | T366L_N390E_K392F_T394W_T411N |
| AZ1512 | L351L_S400K_F405V_Y407I | T366L_N390E_K392F_T394W_T411L |
| AZ1513 | L351L_S400K_F405V_Y407I | T366L_N390E_K392F_T394W_T411S |
| AZ1514 | L351L_S400K_F405V_Y407I | T366L_N390E_K392F_T394W_T411T |
| AZ1515 | L351L_S400K_F405V_Y407V | T366L_N390N_K392L_T394W_T411N |
| AZ1516 | L351L_S400K_F405V_Y407V | T366L_N390N_K392L_T394W_T411S |
| AZ1517 | L351L_S400K_F405V_Y407V | T366L_N390N_K392L_T394W_T411T |
| AZ1518 | L351L_S400K_F405V_Y407V | T366L_N390N_K392M_T394W_T411N |
| AZ1519 | L351L_S400K_F405V_Y407V | T366L_N390N_K392M_T394W_T411S |
| AZ1520 | L351L_S400K_F405V_Y407V | T366L_N390N_K392M_T394W_T411T |

FIG. 37X

| | | |
|---|---|---|
| AZ1521 | L351L_S400K_F405V_Y407V | T366L_N390N_K392F_T394W_T411N |
| AZ1522 | L351L_S400K_F405V_Y407V | T366L_N390N_K392F_T394W_T411S |
| AZ1523 | L351L_S400K_F405V_Y407V | T366L_N390N_K392F_T394W_T411T |
| AZ1524 | L351L_S400K_F405V_Y407V | T366L_N390D_K392L_T394W_T411N |
| AZ1525 | L351L_S400K_F405V_Y407V | T366L_N390D_K392L_T394W_T411S |
| AZ1526 | L351L_S400K_F405V_Y407V | T366L_N390D_K392L_T394W_T411T |
| AZ1527 | L351L_S400K_F405V_Y407V | T366L_N390D_K392M_T394W_T411N |
| AZ1528 | L351L_S400K_F405V_Y407V | T366L_N390D_K392M_T394W_T411S |
| AZ1529 | L351L_S400K_F405V_Y407V | T366L_N390D_K392M_T394W_T411T |
| AZ1530 | L351L_S400K_F405V_Y407V | T366L_N390D_K392F_T394W_T411N |
| AZ1531 | L351L_S400K_F405V_Y407V | T366L_N390D_K392F_T394W_T411S |
| AZ1532 | L351L_S400K_F405V_Y407V | T366L_N390D_K392F_T394W_T411T |
| AZ1533 | L351L_S400K_F405V_Y407V | T366L_N390E_K392L_T394W_T411N |
| AZ1534 | L351L_S400K_F405V_Y407V | T366L_N390E_K392L_T394W_T411L |
| AZ1535 | L351L_S400K_F405V_Y407V | T366L_N390E_K392L_T394W_T411S |
| AZ1536 | L351L_S400K_F405V_Y407V | T366L_N390E_K392L_T394W_T411T |
| AZ1537 | L351L_S400K_F405V_Y407V | T366L_N390E_K392M_T394W_T411N |
| AZ1538 | L351L_S400K_F405V_Y407V | T366L_N390E_K392M_T394W_T411L |
| AZ1539 | L351L_S400K_F405V_Y407V | T366L_N390E_K392M_T394W_T411S |
| AZ1540 | L351L_S400K_F405V_Y407V | T366L_N390E_K392M_T394W_T411T |
| AZ1541 | L351L_S400K_F405V_Y407V | T366L_N390E_K392F_T394W_T411N |
| AZ1542 | L351L_S400K_F405V_Y407V | T366L_N390E_K392F_T394W_T411L |
| AZ1543 | L351L_S400K_F405V_Y407V | T366L_N390E_K392F_T394W_T411S |
| AZ1544 | L351L_S400K_F405V_Y407V | T366L_N390E_K392F_T394W_T411T |
| AZ1545 | L351Y_D399R_F405A_Y407I | T366L_K392L_T394W_K409L_T411E |
| AZ1546 | L351Y_D399R_F405A_Y407I | T366L_K392L_T394W_K409M_T411E |
| AZ1547 | L351Y_D399R_F405A_Y407I | T366L_K392M_T394W_K409L_T411E |
| AZ1548 | L351Y_D399R_F405A_Y407I | T366L_K392M_T394W_K409M_T411E |
| AZ1549 | L351Y_D399R_F405A_Y407I | T366L_K392F_T394W_K409L_T411E |
| AZ1550 | L351Y_D399R_F405A_Y407I | T366L_K392F_T394W_K409M_T411E |
| AZ1551 | L351Y_D399R_F405A_Y407V | T366L_K392L_T394W_K409L_T411E |
| AZ1552 | L351Y_D399R_F405A_Y407V | T366L_K392L_T394W_K409M_T411E |
| AZ1553 | L351Y_D399R_F405A_Y407V | T366L_K392M_T394W_K409L_T411E |
| AZ1554 | L351Y_D399R_F405A_Y407V | T366L_K392M_T394W_K409M_T411E |
| AZ1555 | L351Y_D399R_F405A_Y407V | T366L_K392F_T394W_K409L_T411E |
| AZ1556 | L351Y_D399R_F405A_Y407V | T366L_K392F_T394W_K409M_T411E |
| AZ1557 | L351Y_D399R_F405M_Y407I | T366L_K392L_T394W_K409V_T411E |
| AZ1558 | L351Y_D399R_F405M_Y407I | T366L_K392M_T394W_K409V_T411E |
| AZ1559 | L351Y_D399R_F405M_Y407I | T366L_K392F_T394W_K409V_T411E |
| AZ1560 | L351Y_D399R_F405M_Y407V | T366L_K392L_T394W_K409V_T411E |
| AZ1561 | L351Y_D399R_F405M_Y407V | T366L_K392M_T394W_K409V_T411E |
| AZ1562 | L351Y_D399R_F405M_Y407V | T366L_K392F_T394W_K409V_T411E |
| AZ1563 | L351Y_D399R_F405S_Y407I | T366L_K392L_T394W_K409L_T411E |
| AZ1564 | L351Y_D399R_F405S_Y407I | T366L_K392L_T394W_K409M_T411E |
| AZ1565 | L351Y_D399R_F405S_Y407I | T366L_K392M_T394W_K409L_T411E |
| AZ1566 | L351Y_D399R_F405S_Y407I | T366L_K392M_T394W_K409M_T411E |
| AZ1567 | L351Y_D399R_F405S_Y407I | T366L_K392F_T394W_K409L_T411E |
| AZ1568 | L351Y_D399R_F405S_Y407I | T366L_K392F_T394W_K409M_T411E |
| AZ1569 | L351Y_D399R_F405S_Y407V | T366L_K392L_T394W_K409L_T411E |
| AZ1570 | L351Y_D399R_F405S_Y407V | T366L_K392L_T394W_K409M_T411E |
| AZ1571 | L351Y_D399R_F405S_Y407V | T366L_K392M_T394W_K409L_T411E |
| AZ1572 | L351Y_D399R_F405S_Y407V | T366L_K392M_T394W_K409M_T411E |
| AZ1573 | L351Y_D399R_F405S_Y407V | T366L_K392F_T394W_K409L_T411E |
| AZ1574 | L351Y_D399R_F405S_Y407V | T366L_K392F_T394W_K409M_T411E |
| AZ1575 | L351Y_D399R_F405V_Y407I | T366L_K392L_T394W_K409L_T411E |
| AZ1576 | L351Y_D399R_F405V_Y407I | T366L_K392L_T394W_K409M_T411E |
| AZ1577 | L351Y_D399R_F405V_Y407I | T366L_K392M_T394W_K409L_T411E |
| AZ1578 | L351Y_D399R_F405V_Y407I | T366L_K392M_T394W_K409M_T411E |

FIG. 37Y

| | | |
|---|---|---|
| AZ1579 | L351Y_D399R_F405V_Y407I | T366L_K392F_T394W_K409L_T411E |
| AZ1580 | L351Y_D399R_F405V_Y407I | T366L_K392F_T394W_K409M_T411E |
| AZ1581 | L351Y_D399R_F405V_Y407V | T366L_K392L_T394W_K409L_T411E |
| AZ1582 | L351Y_D399R_F405V_Y407V | T366L_K392L_T394W_K409M_T411E |
| AZ1583 | L351Y_D399R_F405V_Y407V | T366L_K392M_T394W_K409L_T411E |
| AZ1584 | L351Y_D399R_F405V_Y407V | T366L_K392M_T394W_K409M_T411E |
| AZ1585 | L351Y_D399R_F405V_Y407V | T366L_K392F_T394W_K409L_T411E |
| AZ1586 | L351Y_D399R_F405V_Y407V | T366L_K392F_T394W_K409M_T411E |
| AZ1587 | L351Y_S400R_F405A_Y407I | T366L_N390N_K392L_T394W_T411N |
| AZ1588 | L351Y_S400R_F405A_Y407I | T366L_N390N_K392L_T394W_T411S |
| AZ1589 | L351Y_S400R_F405A_Y407I | T366L_N390N_K392L_T394W_T411T |
| AZ1590 | L351Y_S400R_F405A_Y407I | T366L_N390N_K392M_T394W_T411N |
| AZ1591 | L351Y_S400R_F405A_Y407I | T366L_N390N_K392M_T394W_T411S |
| AZ1592 | L351Y_S400R_F405A_Y407I | T366L_N390N_K392M_T394W_T411T |
| AZ1593 | L351Y_S400R_F405A_Y407I | T366L_N390N_K392F_T394W_T411N |
| AZ1594 | L351Y_S400R_F405A_Y407I | T366L_N390N_K392F_T394W_T411S |
| AZ1595 | L351Y_S400R_F405A_Y407I | T366L_N390N_K392F_T394W_T411T |
| AZ1596 | L351Y_S400R_F405A_Y407I | T366L_N390D_K392L_T394W_T411N |
| AZ1597 | L351Y_S400R_F405A_Y407I | T366L_N390D_K392L_T394W_T411S |
| AZ1598 | L351Y_S400R_F405A_Y407I | T366L_N390D_K392L_T394W_T411T |
| AZ1599 | L351Y_S400R_F405A_Y407I | T366L_N390D_K392M_T394W_T411N |
| AZ1600 | L351Y_S400R_F405A_Y407I | T366L_N390D_K392M_T394W_T411S |
| AZ1601 | L351Y_S400R_F405A_Y407I | T366L_N390D_K392M_T394W_T411T |
| AZ1602 | L351Y_S400R_F405A_Y407I | T366L_N390D_K392F_T394W_T411N |
| AZ1603 | L351Y_S400R_F405A_Y407I | T366L_N390D_K392F_T394W_T411S |
| AZ1604 | L351Y_S400R_F405A_Y407I | T366L_N390D_K392F_T394W_T411T |
| AZ1605 | L351Y_S400R_F405A_Y407I | T366L_N390E_K392L_T394W_T411N |
| AZ1606 | L351Y_S400R_F405A_Y407I | T366L_N390E_K392L_T394W_T411L |
| AZ1607 | L351Y_S400R_F405A_Y407I | T366L_N390E_K392L_T394W_T411S |
| AZ1608 | L351Y_S400R_F405A_Y407I | T366L_N390E_K392L_T394W_T411T |
| AZ1609 | L351Y_S400R_F405A_Y407I | T366L_N390E_K392M_T394W_T411N |
| AZ1610 | L351Y_S400R_F405A_Y407I | T366L_N390E_K392M_T394W_T411L |
| AZ1611 | L351Y_S400R_F405A_Y407I | T366L_N390E_K392M_T394W_T411S |
| AZ1612 | L351Y_S400R_F405A_Y407I | T366L_N390E_K392M_T394W_T411T |
| AZ1613 | L351Y_S400R_F405A_Y407I | T366L_N390E_K392F_T394W_T411N |
| AZ1614 | L351Y_S400R_F405A_Y407I | T366L_N390E_K392F_T394W_T411L |
| AZ1615 | L351Y_S400R_F405A_Y407I | T366L_N390E_K392F_T394W_T411S |
| AZ1616 | L351Y_S400R_F405A_Y407I | T366L_N390E_K392F_T394W_T411T |
| AZ1617 | L351Y_S400R_F405A_Y407V | T366L_N390N_K392L_T394W_T411N |
| AZ1618 | L351Y_S400R_F405A_Y407V | T366L_N390N_K392L_T394W_T411S |
| AZ1619 | L351Y_S400R_F405A_Y407V | T366L_N390N_K392L_T394W_T411T |
| AZ1620 | L351Y_S400R_F405A_Y407V | T366L_N390N_K392M_T394W_T411N |
| AZ1621 | L351Y_S400R_F405A_Y407V | T366L_N390N_K392M_T394W_T411S |
| AZ1622 | L351Y_S400R_F405A_Y407V | T366L_N390N_K392M_T394W_T411T |
| AZ1623 | L351Y_S400R_F405A_Y407V | T366L_N390N_K392F_T394W_T411N |
| AZ1624 | L351Y_S400R_F405A_Y407V | T366L_N390N_K392F_T394W_T411S |
| AZ1625 | L351Y_S400R_F405A_Y407V | T366L_N390N_K392F_T394W_T411T |
| AZ1626 | L351Y_S400R_F405A_Y407V | T366L_N390D_K392L_T394W_T411N |
| AZ1627 | L351Y_S400R_F405A_Y407V | T366L_N390D_K392L_T394W_T411S |
| AZ1628 | L351Y_S400R_F405A_Y407V | T366L_N390D_K392L_T394W_T411T |
| AZ1629 | L351Y_S400R_F405A_Y407V | T366L_N390D_K392M_T394W_T411N |
| AZ1630 | L351Y_S400R_F405A_Y407V | T366L_N390D_K392M_T394W_T411S |
| AZ1631 | L351Y_S400R_F405A_Y407V | T366L_N390D_K392M_T394W_T411T |
| AZ1632 | L351Y_S400R_F405A_Y407V | T366L_N390D_K392F_T394W_T411N |
| AZ1633 | L351Y_S400R_F405A_Y407V | T366L_N390D_K392F_T394W_T411S |
| AZ1634 | L351Y_S400R_F405A_Y407V | T366L_N390D_K392F_T394W_T411T |
| AZ1635 | L351Y_S400R_F405A_Y407V | T366L_N390E_K392L_T394W_T411N |
| AZ1636 | L351Y_S400R_F405A_Y407V | T366L_N390E_K392L_T394W_T411L |

FIG. 37Z

| | | |
|---|---|---|
| AZ1637 | L351Y_S400R_F405A_Y407V | T366L_N390E_K392L_T394W_T411S |
| AZ1638 | L351Y_S400R_F405A_Y407V | T366L_N390E_K392L_T394W_T411T |
| AZ1639 | L351Y_S400R_F405A_Y407V | T366L_N390E_K392M_T394W_T411N |
| AZ1640 | L351Y_S400R_F405A_Y407V | T366L_N390E_K392M_T394W_T411L |
| AZ1641 | L351Y_S400R_F405A_Y407V | T366L_N390E_K392M_T394W_T411S |
| AZ1642 | L351Y_S400R_F405A_Y407V | T366L_N390E_K392M_T394W_T411T |
| AZ1643 | L351Y_S400R_F405A_Y407V | T366L_N390E_K392F_T394W_T411N |
| AZ1644 | L351Y_S400R_F405A_Y407V | T366L_N390E_K392F_T394W_T411L |
| AZ1645 | L351Y_S400R_F405A_Y407V | T366L_N390E_K392F_T394W_T411S |
| AZ1646 | L351Y_S400R_F405A_Y407V | T366L_N390E_K392F_T394W_T411T |
| AZ1647 | L351Y_S400R_F405S_Y407I | T366L_N390N_K392L_T394W_T411N |
| AZ1648 | L351Y_S400R_F405S_Y407I | T366L_N390N_K392L_T394W_T411S |
| AZ1649 | L351Y_S400R_F405S_Y407I | T366L_N390N_K392L_T394W_T411T |
| AZ1650 | L351Y_S400R_F405S_Y407I | T366L_N390N_K392M_T394W_T411N |
| AZ1651 | L351Y_S400R_F405S_Y407I | T366L_N390N_K392M_T394W_T411S |
| AZ1652 | L351Y_S400R_F405S_Y407I | T366L_N390N_K392M_T394W_T411T |
| AZ1653 | L351Y_S400R_F405S_Y407I | T366L_N390N_K392F_T394W_T411N |
| AZ1654 | L351Y_S400R_F405S_Y407I | T366L_N390N_K392F_T394W_T411S |
| AZ1655 | L351Y_S400R_F405S_Y407I | T366L_N390N_K392F_T394W_T411T |
| AZ1656 | L351Y_S400R_F405S_Y407I | T366L_N390D_K392L_T394W_T411N |
| AZ1657 | L351Y_S400R_F405S_Y407I | T366L_N390D_K392L_T394W_T411S |
| AZ1658 | L351Y_S400R_F405S_Y407I | T366L_N390D_K392L_T394W_T411T |
| AZ1659 | L351Y_S400R_F405S_Y407I | T366L_N390D_K392M_T394W_T411N |
| AZ1660 | L351Y_S400R_F405S_Y407I | T366L_N390D_K392M_T394W_T411S |
| AZ1661 | L351Y_S400R_F405S_Y407I | T366L_N390D_K392M_T394W_T411T |
| AZ1662 | L351Y_S400R_F405S_Y407I | T366L_N390D_K392F_T394W_T411N |
| AZ1663 | L351Y_S400R_F405S_Y407I | T366L_N390D_K392F_T394W_T411S |
| AZ1664 | L351Y_S400R_F405S_Y407I | T366L_N390D_K392F_T394W_T411T |
| AZ1665 | L351Y_S400R_F405S_Y407I | T366L_N390E_K392L_T394W_T411N |
| AZ1666 | L351Y_S400R_F405S_Y407I | T366L_N390E_K392L_T394W_T411L |
| AZ1667 | L351Y_S400R_F405S_Y407I | T366L_N390E_K392L_T394W_T411S |
| AZ1668 | L351Y_S400R_F405S_Y407I | T366L_N390E_K392L_T394W_T411T |
| AZ1669 | L351Y_S400R_F405S_Y407I | T366L_N390E_K392M_T394W_T411N |
| AZ1670 | L351Y_S400R_F405S_Y407I | T366L_N390E_K392M_T394W_T411L |
| AZ1671 | L351Y_S400R_F405S_Y407I | T366L_N390E_K392M_T394W_T411S |
| AZ1672 | L351Y_S400R_F405S_Y407I | T366L_N390E_K392M_T394W_T411T |
| AZ1673 | L351Y_S400R_F405S_Y407I | T366L_N390E_K392F_T394W_T411N |
| AZ1674 | L351Y_S400R_F405S_Y407I | T366L_N390E_K392F_T394W_T411L |
| AZ1675 | L351Y_S400R_F405S_Y407I | T366L_N390E_K392F_T394W_T411S |
| AZ1676 | L351Y_S400R_F405S_Y407I | T366L_N390E_K392F_T394W_T411T |
| AZ1677 | L351Y_S400R_F405S_Y407V | T366L_N390N_K392L_T394W_T411N |
| AZ1678 | L351Y_S400R_F405S_Y407V | T366L_N390N_K392L_T394W_T411S |
| AZ1679 | L351Y_S400R_F405S_Y407V | T366L_N390N_K392L_T394W_T411T |
| AZ1680 | L351Y_S400R_F405S_Y407V | T366L_N390N_K392M_T394W_T411N |
| AZ1681 | L351Y_S400R_F405S_Y407V | T366L_N390N_K392M_T394W_T411S |
| AZ1682 | L351Y_S400R_F405S_Y407V | T366L_N390N_K392M_T394W_T411T |
| AZ1683 | L351Y_S400R_F405S_Y407V | T366L_N390N_K392F_T394W_T411N |
| AZ1684 | L351Y_S400R_F405S_Y407V | T366L_N390N_K392F_T394W_T411S |
| AZ1685 | L351Y_S400R_F405S_Y407V | T366L_N390N_K392F_T394W_T411T |
| AZ1686 | L351Y_S400R_F405S_Y407V | T366L_N390D_K392L_T394W_T411N |
| AZ1687 | L351Y_S400R_F405S_Y407V | T366L_N390D_K392L_T394W_T411S |
| AZ1688 | L351Y_S400R_F405S_Y407V | T366L_N390D_K392L_T394W_T411T |
| AZ1689 | L351Y_S400R_F405S_Y407V | T366L_N390D_K392M_T394W_T411N |
| AZ1690 | L351Y_S400R_F405S_Y407V | T366L_N390D_K392M_T394W_T411S |
| AZ1691 | L351Y_S400R_F405S_Y407V | T366L_N390D_K392M_T394W_T411T |
| AZ1692 | L351Y_S400R_F405S_Y407V | T366L_N390D_K392F_T394W_T411N |
| AZ1693 | L351Y_S400R_F405S_Y407V | T366L_N390D_K392F_T394W_T411S |
| AZ1694 | L351Y_S400R_F405S_Y407V | T366L_N390D_K392F_T394W_T411T |

FIG. 37Z1

| | | |
|---|---|---|
| AZ1695 | L351Y_S400R_F405S_Y407V | T366L_N390E_K392L_T394W_T411N |
| AZ1696 | L351Y_S400R_F405S_Y407V | T366L_N390E_K392L_T394W_T411L |
| AZ1697 | L351Y_S400R_F405S_Y407V | T366L_N390E_K392L_T394W_T411S |
| AZ1698 | L351Y_S400R_F405S_Y407V | T366L_N390E_K392L_T394W_T411T |
| AZ1699 | L351Y_S400R_F405S_Y407V | T366L_N390E_K392M_T394W_T411N |
| AZ1700 | L351Y_S400R_F405S_Y407V | T366L_N390E_K392M_T394W_T411L |
| AZ1701 | L351Y_S400R_F405S_Y407V | T366L_N390E_K392M_T394W_T411S |
| AZ1702 | L351Y_S400R_F405S_Y407V | T366L_N390E_K392M_T394W_T411T |
| AZ1703 | L351Y_S400R_F405S_Y407V | T366L_N390E_K392F_T394W_T411N |
| AZ1704 | L351Y_S400R_F405S_Y407V | T366L_N390E_K392F_T394W_T411L |
| AZ1705 | L351Y_S400R_F405S_Y407V | T366L_N390E_K392F_T394W_T411S |
| AZ1706 | L351Y_S400R_F405S_Y407V | T366L_N390E_K392F_T394W_T411T |
| AZ1707 | L351Y_S400R_F405T_Y407I | T366L_N390N_K392L_T394W_T411N |
| AZ1708 | L351Y_S400R_F405T_Y407I | T366L_N390N_K392L_T394W_T411S |
| AZ1709 | L351Y_S400R_F405T_Y407I | T366L_N390N_K392L_T394W_T411T |
| AZ1710 | L351Y_S400R_F405T_Y407I | T366L_N390N_K392M_T394W_T411N |
| AZ1711 | L351Y_S400R_F405T_Y407I | T366L_N390N_K392M_T394W_T411S |
| AZ1712 | L351Y_S400R_F405T_Y407I | T366L_N390N_K392M_T394W_T411T |
| AZ1713 | L351Y_S400R_F405T_Y407I | T366L_N390N_K392F_T394W_T411N |
| AZ1714 | L351Y_S400R_F405T_Y407I | T366L_N390N_K392F_T394W_T411S |
| AZ1715 | L351Y_S400R_F405T_Y407I | T366L_N390N_K392F_T394W_T411T |
| AZ1716 | L351Y_S400R_F405T_Y407I | T366L_N390D_K392L_T394W_T411N |
| AZ1717 | L351Y_S400R_F405T_Y407I | T366L_N390D_K392L_T394W_T411S |
| AZ1718 | L351Y_S400R_F405T_Y407I | T366L_N390D_K392L_T394W_T411T |
| AZ1719 | L351Y_S400R_F405T_Y407I | T366L_N390D_K392M_T394W_T411N |
| AZ1720 | L351Y_S400R_F405T_Y407I | T366L_N390D_K392M_T394W_T411S |
| AZ1721 | L351Y_S400R_F405T_Y407I | T366L_N390D_K392M_T394W_T411T |
| AZ1722 | L351Y_S400R_F405T_Y407I | T366L_N390D_K392F_T394W_T411N |
| AZ1723 | L351Y_S400R_F405T_Y407I | T366L_N390D_K392F_T394W_T411S |
| AZ1724 | L351Y_S400R_F405T_Y407I | T366L_N390D_K392F_T394W_T411T |
| AZ1725 | L351Y_S400R_F405T_Y407I | T366L_N390E_K392L_T394W_T411N |
| AZ1726 | L351Y_S400R_F405T_Y407I | T366L_N390E_K392L_T394W_T411L |
| AZ1727 | L351Y_S400R_F405T_Y407I | T366L_N390E_K392L_T394W_T411S |
| AZ1728 | L351Y_S400R_F405T_Y407I | T366L_N390E_K392L_T394W_T411T |
| AZ1729 | L351Y_S400R_F405T_Y407I | T366L_N390E_K392M_T394W_T411N |
| AZ1730 | L351Y_S400R_F405T_Y407I | T366L_N390E_K392M_T394W_T411L |
| AZ1731 | L351Y_S400R_F405T_Y407I | T366L_N390E_K392M_T394W_T411S |
| AZ1732 | L351Y_S400R_F405T_Y407I | T366L_N390E_K392M_T394W_T411T |
| AZ1733 | L351Y_S400R_F405T_Y407I | T366L_N390E_K392F_T394W_T411N |
| AZ1734 | L351Y_S400R_F405T_Y407I | T366L_N390E_K392F_T394W_T411L |
| AZ1735 | L351Y_S400R_F405T_Y407I | T366L_N390E_K392F_T394W_T411S |
| AZ1736 | L351Y_S400R_F405T_Y407I | T366L_N390E_K392F_T394W_T411T |
| AZ1737 | L351Y_S400R_F405T_Y407V | T366L_N390N_K392L_T394W_T411N |
| AZ1738 | L351Y_S400R_F405T_Y407V | T366L_N390N_K392L_T394W_T411S |
| AZ1739 | L351Y_S400R_F405T_Y407V | T366L_N390N_K392L_T394W_T411T |
| AZ1740 | L351Y_S400R_F405T_Y407V | T366L_N390N_K392M_T394W_T411N |
| AZ1741 | L351Y_S400R_F405T_Y407V | T366L_N390N_K392M_T394W_T411S |
| AZ1742 | L351Y_S400R_F405T_Y407V | T366L_N390N_K392M_T394W_T411T |
| AZ1743 | L351Y_S400R_F405T_Y407V | T366L_N390N_K392F_T394W_T411N |
| AZ1744 | L351Y_S400R_F405T_Y407V | T366L_N390N_K392F_T394W_T411S |
| AZ1745 | L351Y_S400R_F405T_Y407V | T366L_N390N_K392F_T394W_T411T |
| AZ1746 | L351Y_S400R_F405T_Y407V | T366L_N390D_K392L_T394W_T411N |
| AZ1747 | L351Y_S400R_F405T_Y407V | T366L_N390D_K392L_T394W_T411S |
| AZ1748 | L351Y_S400R_F405T_Y407V | T366L_N390D_K392L_T394W_T411T |
| AZ1749 | L351Y_S400R_F405T_Y407V | T366L_N390D_K392M_T394W_T411N |
| AZ1750 | L351Y_S400R_F405T_Y407V | T366L_N390D_K392M_T394W_T411S |
| AZ1751 | L351Y_S400R_F405T_Y407V | T366L_N390D_K392M_T394W_T411T |
| AZ1752 | L351Y_S400R_F405T_Y407V | T366L_N390D_K392F_T394W_T411N |

FIG. 37Z2

| | | |
|---|---|---|
| AZ1753 | L351Y_S400R_F405T_Y407V | T366L_N390D_K392F_T394W_T411S |
| AZ1754 | L351Y_S400R_F405T_Y407V | T366L_N390D_K392F_T394W_T411T |
| AZ1755 | L351Y_S400R_F405T_Y407V | T366L_N390E_K392L_T394W_T411N |
| AZ1756 | L351Y_S400R_F405T_Y407V | T366L_N390E_K392L_T394W_T411L |
| AZ1757 | L351Y_S400R_F405T_Y407V | T366L_N390E_K392L_T394W_T411S |
| AZ1758 | L351Y_S400R_F405T_Y407V | T366L_N390E_K392L_T394W_T411T |
| AZ1759 | L351Y_S400R_F405T_Y407V | T366L_N390E_K392M_T394W_T411N |
| AZ1760 | L351Y_S400R_F405T_Y407V | T366L_N390E_K392M_T394W_T411L |
| AZ1761 | L351Y_S400R_F405T_Y407V | T366L_N390E_K392M_T394W_T411S |
| AZ1762 | L351Y_S400R_F405T_Y407V | T366L_N390E_K392M_T394W_T411T |
| AZ1763 | L351Y_S400R_F405T_Y407V | T366L_N390E_K392F_T394W_T411N |
| AZ1764 | L351Y_S400R_F405T_Y407V | T366L_N390E_K392F_T394W_T411L |
| AZ1765 | L351Y_S400R_F405T_Y407V | T366L_N390E_K392F_T394W_T411S |
| AZ1766 | L351Y_S400R_F405T_Y407V | T366L_N390E_K392F_T394W_T411T |
| AZ1767 | L351Y_S400R_F405V_Y407I | T366L_N390N_K392L_T394W_T411N |
| AZ1768 | L351Y_S400R_F405V_Y407I | T366L_N390N_K392L_T394W_T411S |
| AZ1769 | L351Y_S400R_F405V_Y407I | T366L_N390N_K392L_T394W_T411T |
| AZ1770 | L351Y_S400R_F405V_Y407I | T366L_N390N_K392M_T394W_T411N |
| AZ1771 | L351Y_S400R_F405V_Y407I | T366L_N390N_K392M_T394W_T411S |
| AZ1772 | L351Y_S400R_F405V_Y407I | T366L_N390N_K392M_T394W_T411T |
| AZ1773 | L351Y_S400R_F405V_Y407I | T366L_N390N_K392F_T394W_T411N |
| AZ1774 | L351Y_S400R_F405V_Y407I | T366L_N390N_K392F_T394W_T411S |
| AZ1775 | L351Y_S400R_F405V_Y407I | T366L_N390N_K392F_T394W_T411T |
| AZ1776 | L351Y_S400R_F405V_Y407I | T366L_N390D_K392L_T394W_T411N |
| AZ1777 | L351Y_S400R_F405V_Y407I | T366L_N390D_K392L_T394W_T411S |
| AZ1778 | L351Y_S400R_F405V_Y407I | T366L_N390D_K392L_T394W_T411T |
| AZ1779 | L351Y_S400R_F405V_Y407I | T366L_N390D_K392M_T394W_T411N |
| AZ1780 | L351Y_S400R_F405V_Y407I | T366L_N390D_K392M_T394W_T411S |
| AZ1781 | L351Y_S400R_F405V_Y407I | T366L_N390D_K392M_T394W_T411T |
| AZ1782 | L351Y_S400R_F405V_Y407I | T366L_N390D_K392F_T394W_T411N |
| AZ1783 | L351Y_S400R_F405V_Y407I | T366L_N390D_K392F_T394W_T411S |
| AZ1784 | L351Y_S400R_F405V_Y407I | T366L_N390D_K392F_T394W_T411T |
| AZ1785 | L351Y_S400R_F405V_Y407I | T366L_N390E_K392L_T394W_T411N |
| AZ1786 | L351Y_S400R_F405V_Y407I | T366L_N390E_K392L_T394W_T411L |
| AZ1787 | L351Y_S400R_F405V_Y407I | T366L_N390E_K392L_T394W_T411S |
| AZ1788 | L351Y_S400R_F405V_Y407I | T366L_N390E_K392L_T394W_T411T |
| AZ1789 | L351Y_S400R_F405V_Y407I | T366L_N390E_K392M_T394W_T411N |
| AZ1790 | L351Y_S400R_F405V_Y407I | T366L_N390E_K392M_T394W_T411L |
| AZ1791 | L351Y_S400R_F405V_Y407I | T366L_N390E_K392M_T394W_T411S |
| AZ1792 | L351Y_S400R_F405V_Y407I | T366L_N390E_K392M_T394W_T411T |
| AZ1793 | L351Y_S400R_F405V_Y407I | T366L_N390E_K392F_T394W_T411N |
| AZ1794 | L351Y_S400R_F405V_Y407I | T366L_N390E_K392F_T394W_T411L |
| AZ1795 | L351Y_S400R_F405V_Y407I | T366L_N390E_K392F_T394W_T411S |
| AZ1796 | L351Y_S400R_F405V_Y407I | T366L_N390E_K392F_T394W_T411T |
| AZ1797 | L351Y_S400R_F405V_Y407V | T366L_N390N_K392L_T394W_T411N |
| AZ1798 | L351Y_S400R_F405V_Y407V | T366L_N390N_K392L_T394W_T411S |
| AZ1799 | L351Y_S400R_F405V_Y407V | T366L_N390N_K392L_T394W_T411T |
| AZ1800 | L351Y_S400R_F405V_Y407V | T366L_N390N_K392M_T394W_T411N |
| AZ1801 | L351Y_S400R_F405V_Y407V | T366L_N390N_K392M_T394W_T411S |
| AZ1802 | L351Y_S400R_F405V_Y407V | T366L_N390N_K392M_T394W_T411T |
| AZ1803 | L351Y_S400R_F405V_Y407V | T366L_N390N_K392F_T394W_T411N |
| AZ1804 | L351Y_S400R_F405V_Y407V | T366L_N390N_K392F_T394W_T411S |
| AZ1805 | L351Y_S400R_F405V_Y407V | T366L_N390N_K392F_T394W_T411T |
| AZ1806 | L351Y_S400R_F405V_Y407V | T366L_N390D_K392L_T394W_T411N |
| AZ1807 | L351Y_S400R_F405V_Y407V | T366L_N390D_K392L_T394W_T411S |
| AZ1808 | L351Y_S400R_F405V_Y407V | T366L_N390D_K392L_T394W_T411T |
| AZ1809 | L351Y_S400R_F405V_Y407V | T366L_N390D_K392M_T394W_T411N |
| AZ1810 | L351Y_S400R_F405V_Y407V | T366L_N390D_K392M_T394W_T411S |

FIG. 37Z3

| | | |
|---|---|---|
| AZ1811 | L351Y_S400R_F405V_Y407V | T366L_N390D_K392M_T394W_T411T |
| AZ1812 | L351Y_S400R_F405V_Y407V | T366L_N390D_K392F_T394W_T411N |
| AZ1813 | L351Y_S400R_F405V_Y407V | T366L_N390D_K392F_T394W_T411S |
| AZ1814 | L351Y_S400R_F405V_Y407V | T366L_N390D_K392F_T394W_T411T |
| AZ1815 | L351Y_S400R_F405V_Y407V | T366L_N390E_K392L_T394W_T411N |
| AZ1816 | L351Y_S400R_F405V_Y407V | T366L_N390E_K392L_T394W_T411L |
| AZ1817 | L351Y_S400R_F405V_Y407V | T366L_N390E_K392L_T394W_T411S |
| AZ1818 | L351Y_S400R_F405V_Y407V | T366L_N390E_K392L_T394W_T411T |
| AZ1819 | L351Y_S400R_F405V_Y407V | T366L_N390E_K392M_T394W_T411N |
| AZ1820 | L351Y_S400R_F405V_Y407V | T366L_N390E_K392M_T394W_T411L |
| AZ1821 | L351Y_S400R_F405V_Y407V | T366L_N390E_K392M_T394W_T411S |
| AZ1822 | L351Y_S400R_F405V_Y407V | T366L_N390E_K392M_T394W_T411T |
| AZ1823 | L351Y_S400R_F405V_Y407V | T366L_N390E_K392F_T394W_T411N |
| AZ1824 | L351Y_S400R_F405V_Y407V | T366L_N390E_K392F_T394W_T411L |
| AZ1825 | L351Y_S400R_F405V_Y407V | T366L_N390E_K392F_T394W_T411S |
| AZ1826 | L351Y_S400R_F405V_Y407V | T366L_N390E_K392F_T394W_T411T |
| AZ1827 | L351Y_S400E_F405A_Y407I | T366L_N390R_K392L_T394W_T411N |
| AZ1828 | L351Y_S400E_F405A_Y407I | T366L_N390R_K392L_T394W_T411L |
| AZ1829 | L351Y_S400E_F405A_Y407I | T366L_N390R_K392L_T394W_T411S |
| AZ1830 | L351Y_S400E_F405A_Y407I | T366L_N390R_K392M_T394W_T411N |
| AZ1831 | L351Y_S400E_F405A_Y407I | T366L_N390R_K392M_T394W_T411L |
| AZ1832 | L351Y_S400E_F405A_Y407I | T366L_N390R_K392M_T394W_T411S |
| AZ1833 | L351Y_S400E_F405A_Y407I | T366L_N390R_K392F_T394W_T411N |
| AZ1834 | L351Y_S400E_F405A_Y407I | T366L_N390R_K392F_T394W_T411L |
| AZ1835 | L351Y_S400E_F405A_Y407I | T366L_N390R_K392F_T394W_T411S |
| AZ1836 | L351Y_S400E_F405A_Y407I | T366L_N390N_K392L_T394W_T411N |
| AZ1837 | L351Y_S400E_F405A_Y407I | T366L_N390N_K392L_T394W_T411L |
| AZ1838 | L351Y_S400E_F405A_Y407I | T366L_N390N_K392L_T394W_T411S |
| AZ1839 | L351Y_S400E_F405A_Y407I | T366L_N390N_K392M_T394W_T411N |
| AZ1840 | L351Y_S400E_F405A_Y407I | T366L_N390N_K392M_T394W_T411L |
| AZ1841 | L351Y_S400E_F405A_Y407I | T366L_N390N_K392M_T394W_T411S |
| AZ1842 | L351Y_S400E_F405A_Y407I | T366L_N390N_K392F_T394W_T411N |
| AZ1843 | L351Y_S400E_F405A_Y407I | T366L_N390N_K392F_T394W_T411L |
| AZ1844 | L351Y_S400E_F405A_Y407I | T366L_N390N_K392F_T394W_T411S |
| AZ1845 | L351Y_S400E_F405A_Y407I | T366L_N390K_K392L_T394W_T411N |
| AZ1846 | L351Y_S400E_F405A_Y407I | T366L_N390K_K392L_T394W_T411L |
| AZ1847 | L351Y_S400E_F405A_Y407I | T366L_N390K_K392L_T394W_T411S |
| AZ1848 | L351Y_S400E_F405A_Y407I | T366L_N390K_K392M_T394W_T411N |
| AZ1849 | L351Y_S400E_F405A_Y407I | T366L_N390K_K392M_T394W_T411L |
| AZ1850 | L351Y_S400E_F405A_Y407I | T366L_N390K_K392M_T394W_T411S |
| AZ1851 | L351Y_S400E_F405A_Y407I | T366L_N390K_K392F_T394W_T411N |
| AZ1852 | L351Y_S400E_F405A_Y407I | T366L_N390K_K392F_T394W_T411L |
| AZ1853 | L351Y_S400E_F405A_Y407I | T366L_N390K_K392F_T394W_T411S |
| AZ1854 | L351Y_S400E_F405A_Y407V | T366L_N390R_K392L_T394W_T411N |
| AZ1855 | L351Y_S400E_F405A_Y407V | T366L_N390R_K392L_T394W_T411L |
| AZ1856 | L351Y_S400E_F405A_Y407V | T366L_N390R_K392L_T394W_T411S |
| AZ1857 | L351Y_S400E_F405A_Y407V | T366L_N390R_K392M_T394W_T411N |
| AZ1858 | L351Y_S400E_F405A_Y407V | T366L_N390R_K392M_T394W_T411L |
| AZ1859 | L351Y_S400E_F405A_Y407V | T366L_N390R_K392M_T394W_T411S |
| AZ1860 | L351Y_S400E_F405A_Y407V | T366L_N390R_K392F_T394W_T411N |
| AZ1861 | L351Y_S400E_F405A_Y407V | T366L_N390R_K392F_T394W_T411L |
| AZ1862 | L351Y_S400E_F405A_Y407V | T366L_N390R_K392F_T394W_T411S |
| AZ1863 | L351Y_S400E_F405A_Y407V | T366L_N390N_K392L_T394W_T411N |
| AZ1864 | L351Y_S400E_F405A_Y407V | T366L_N390N_K392L_T394W_T411L |
| AZ1865 | L351Y_S400E_F405A_Y407V | T366L_N390N_K392L_T394W_T411S |
| AZ1866 | L351Y_S400E_F405A_Y407V | T366L_N390N_K392M_T394W_T411N |
| AZ1867 | L351Y_S400E_F405A_Y407V | T366L_N390N_K392M_T394W_T411L |
| AZ1868 | L351Y_S400E_F405A_Y407V | T366L_N390N_K392M_T394W_T411S |

FIG. 37Z4

| | | |
|---|---|---|
| AZ1869 | L351Y_S400E_F405A_Y407V | T366L_N390N_K392F_T394W_T411N |
| AZ1870 | L351Y_S400E_F405A_Y407V | T366L_N390N_K392F_T394W_T411L |
| AZ1871 | L351Y_S400E_F405A_Y407V | T366L_N390N_K392F_T394W_T411S |
| AZ1872 | L351Y_S400E_F405A_Y407V | T366L_N390K_K392L_T394W_T411N |
| AZ1873 | L351Y_S400E_F405A_Y407V | T366L_N390K_K392L_T394W_T411L |
| AZ1874 | L351Y_S400E_F405A_Y407V | T366L_N390K_K392L_T394W_T411S |
| AZ1875 | L351Y_S400E_F405A_Y407V | T366L_N390K_K392M_T394W_T411N |
| AZ1876 | L351Y_S400E_F405A_Y407V | T366L_N390K_K392M_T394W_T411L |
| AZ1877 | L351Y_S400E_F405A_Y407V | T366L_N390K_K392M_T394W_T411S |
| AZ1878 | L351Y_S400E_F405A_Y407V | T366L_N390K_K392F_T394W_T411N |
| AZ1879 | L351Y_S400E_F405A_Y407V | T366L_N390K_K392F_T394W_T411L |
| AZ1880 | L351Y_S400E_F405A_Y407V | T366L_N390K_K392F_T394W_T411S |
| AZ1881 | L351Y_S400E_F405S_Y407I | T366L_N390K_K392L_T394W_T411N |
| AZ1882 | L351Y_S400E_F405S_Y407I | T366L_N390K_K392L_T394W_T411L |
| AZ1883 | L351Y_S400E_F405S_Y407I | T366L_N390K_K392L_T394W_T411S |
| AZ1884 | L351Y_S400E_F405S_Y407I | T366L_N390R_K392M_T394W_T411N |
| AZ1885 | L351Y_S400E_F405S_Y407I | T366L_N390R_K392M_T394W_T411L |
| AZ1886 | L351Y_S400E_F405S_Y407I | T366L_N390R_K392M_T394W_T411S |
| AZ1887 | L351Y_S400E_F405S_Y407I | T366L_N390R_K392F_T394W_T411N |
| AZ1888 | L351Y_S400E_F405S_Y407I | T366L_N390R_K392F_T394W_T411L |
| AZ1889 | L351Y_S400E_F405S_Y407I | T366L_N390R_K392F_T394W_T411S |
| AZ1890 | L351Y_S400E_F405S_Y407I | T366L_N390N_K392L_T394W_T411N |
| AZ1891 | L351Y_S400E_F405S_Y407I | T366L_N390N_K392L_T394W_T411L |
| AZ1892 | L351Y_S400E_F405S_Y407I | T366L_N390N_K392L_T394W_T411S |
| AZ1893 | L351Y_S400E_F405S_Y407I | T366L_N390N_K392M_T394W_T411N |
| AZ1894 | L351Y_S400E_F405S_Y407I | T366L_N390N_K392M_T394W_T411L |
| AZ1895 | L351Y_S400E_F405S_Y407I | T366L_N390N_K392M_T394W_T411S |
| AZ1896 | L351Y_S400E_F405S_Y407I | T366L_N390N_K392F_T394W_T411N |
| AZ1897 | L351Y_S400E_F405S_Y407I | T366L_N390N_K392F_T394W_T411L |
| AZ1898 | L351Y_S400E_F405S_Y407I | T366L_N390N_K392F_T394W_T411S |
| AZ1899 | L351Y_S400E_F405S_Y407I | T366L_N390K_K392L_T394W_T411N |
| AZ1900 | L351Y_S400E_F405S_Y407I | T366L_N390K_K392L_T394W_T411L |
| AZ1901 | L351Y_S400E_F405S_Y407I | T366L_N390K_K392L_T394W_T411S |
| AZ1902 | L351Y_S400E_F405S_Y407I | T366L_N390K_K392M_T394W_T411N |
| AZ1903 | L351Y_S400E_F405S_Y407I | T366L_N390K_K392M_T394W_T411L |
| AZ1904 | L351Y_S400E_F405S_Y407I | T366L_N390K_K392M_T394W_T411S |
| AZ1905 | L351Y_S400E_F405S_Y407I | T366L_N390K_K392F_T394W_T411N |
| AZ1906 | L351Y_S400E_F405S_Y407I | T366L_N390K_K392F_T394W_T411L |
| AZ1907 | L351Y_S400E_F405S_Y407I | T366L_N390K_K392F_T394W_T411S |
| AZ1908 | L351Y_S400E_F405S_Y407V | T366L_N390R_K392L_T394W_T411N |
| AZ1909 | L351Y_S400E_F405S_Y407V | T366L_N390R_K392L_T394W_T411L |
| AZ1910 | L351Y_S400E_F405S_Y407V | T366L_N390R_K392L_T394W_T411S |
| AZ1911 | L351Y_S400E_F405S_Y407V | T366L_N390R_K392M_T394W_T411N |
| AZ1912 | L351Y_S400E_F405S_Y407V | T366L_N390R_K392M_T394W_T411L |
| AZ1913 | L351Y_S400E_F405S_Y407V | T366L_N390R_K392M_T394W_T411S |
| AZ1914 | L351Y_S400E_F405S_Y407V | T366L_N390R_K392F_T394W_T411N |
| AZ1915 | L351Y_S400E_F405S_Y407V | T366L_N390R_K392F_T394W_T411L |
| AZ1916 | L351Y_S400E_F405S_Y407V | T366L_N390R_K392F_T394W_T411S |
| AZ1917 | L351Y_S400E_F405S_Y407V | T366L_N390N_K392L_T394W_T411N |
| AZ1918 | L351Y_S400E_F405S_Y407V | T366L_N390N_K392L_T394W_T411L |
| AZ1919 | L351Y_S400E_F405S_Y407V | T366L_N390N_K392L_T394W_T411S |
| AZ1920 | L351Y_S400E_F405S_Y407V | T366L_N390N_K392M_T394W_T411N |
| AZ1921 | L351Y_S400E_F405S_Y407V | T366L_N390N_K392M_T394W_T411L |
| AZ1922 | L351Y_S400E_F405S_Y407V | T366L_N390N_K392M_T394W_T411S |
| AZ1923 | L351Y_S400E_F405S_Y407V | T366L_N390N_K392F_T394W_T411N |
| AZ1924 | L351Y_S400E_F405S_Y407V | T366L_N390N_K392F_T394W_T411L |
| AZ1925 | L351Y_S400E_F405S_Y407V | T366L_N390N_K392F_T394W_T411S |
| AZ1926 | L351Y_S400E_F405S_Y407V | T366L_N390K_K392L_T394W_T411N |

FIG. 37Z5

| | | |
|---|---|---|
| AZ1927 | L351Y_S400E_F405S_Y407V | T366L_N390K_K392L_T394W_T411L |
| AZ1928 | L351Y_S400E_F405S_Y407V | T366L_N390K_K392L_T394W_T411S |
| AZ1929 | L351Y_S400E_F405S_Y407V | T366L_N390K_K392M_T394W_T411N |
| AZ1930 | L351Y_S400E_F405S_Y407V | T366L_N390K_K392M_T394W_T411L |
| AZ1931 | L351Y_S400E_F405S_Y407V | T366L_N390K_K392M_T394W_T411S |
| AZ1932 | L351Y_S400E_F405S_Y407V | T366L_N390K_K392F_T394W_T411N |
| AZ1933 | L351Y_S400E_F405S_Y407V | T366L_N390K_K392F_T394W_T411L |
| AZ1934 | L351Y_S400E_F405S_Y407V | T366L_N390K_K392F_T394W_T411S |
| AZ1935 | L351Y_S400E_F405T_Y407I | T366L_N390R_K392L_T394W_T411N |
| AZ1936 | L351Y_S400E_F405T_Y407I | T366L_N390R_K392L_T394W_T411L |
| AZ1937 | L351Y_S400E_F405T_Y407I | T366L_N390R_K392L_T394W_T411S |
| AZ1938 | L351Y_S400E_F405T_Y407I | T366L_N390R_K392M_T394W_T411N |
| AZ1939 | L351Y_S400E_F405T_Y407I | T366L_N390R_K392M_T394W_T411L |
| AZ1940 | L351Y_S400E_F405T_Y407I | T366L_N390R_K392M_T394W_T411S |
| AZ1941 | L351Y_S400E_F405T_Y407I | T366L_N390R_K392F_T394W_T411N |
| AZ1942 | L351Y_S400E_F405T_Y407I | T366L_N390R_K392F_T394W_T411L |
| AZ1943 | L351Y_S400E_F405T_Y407I | T366L_N390R_K392F_T394W_T411S |
| AZ1944 | L351Y_S400E_F405T_Y407I | T366L_N390N_K392L_T394W_T411N |
| AZ1945 | L351Y_S400E_F405T_Y407I | T366L_N390N_K392L_T394W_T411L |
| AZ1946 | L351Y_S400E_F405T_Y407I | T366L_N390N_K392L_T394W_T411S |
| AZ1947 | L351Y_S400E_F405T_Y407I | T366L_N390N_K392M_T394W_T411N |
| AZ1948 | L351Y_S400E_F405T_Y407I | T366L_N390N_K392M_T394W_T411L |
| AZ1949 | L351Y_S400E_F405T_Y407I | T366L_N390N_K392M_T394W_T411S |
| AZ1950 | L351Y_S400E_F405T_Y407I | T366L_N390N_K392F_T394W_T411N |
| AZ1951 | L351Y_S400E_F405T_Y407I | T366L_N390N_K392F_T394W_T411L |
| AZ1952 | L351Y_S400E_F405T_Y407I | T366L_N390N_K392F_T394W_T411S |
| AZ1953 | L351Y_S400E_F405T_Y407I | T366L_N390K_K392L_T394W_T411N |
| AZ1954 | L351Y_S400E_F405T_Y407I | T366L_N390K_K392L_T394W_T411L |
| AZ1955 | L351Y_S400E_F405T_Y407I | T366L_N390K_K392L_T394W_T411S |
| AZ1956 | L351Y_S400E_F405T_Y407I | T366L_N390K_K392M_T394W_T411N |
| AZ1957 | L351Y_S400E_F405T_Y407I | T366L_N390K_K392M_T394W_T411L |
| AZ1958 | L351Y_S400E_F405T_Y407I | T366L_N390K_K392M_T394W_T411S |
| AZ1959 | L351Y_S400E_F405T_Y407I | T366L_N390K_K392F_T394W_T411N |
| AZ1960 | L351Y_S400E_F405T_Y407I | T366L_N390K_K392F_T394W_T411L |
| AZ1961 | L351Y_S400E_F405T_Y407I | T366L_N390K_K392F_T394W_T411S |
| AZ1962 | L351Y_S400E_F405T_Y407V | T366L_N390R_K392L_T394W_T411N |
| AZ1963 | L351Y_S400E_F405T_Y407V | T366L_N390R_K392L_T394W_T411L |
| AZ1964 | L351Y_S400E_F405T_Y407V | T366L_N390R_K392L_T394W_T411S |
| AZ1965 | L351Y_S400E_F405T_Y407V | T366L_N390R_K392M_T394W_T411N |
| AZ1966 | L351Y_S400E_F405T_Y407V | T366L_N390R_K392M_T394W_T411L |
| AZ1967 | L351Y_S400E_F405T_Y407V | T366L_N390R_K392M_T394W_T411S |
| AZ1968 | L351Y_S400E_F405T_Y407V | T366L_N390R_K392F_T394W_T411N |
| AZ1969 | L351Y_S400E_F405T_Y407V | T366L_N390R_K392F_T394W_T411L |
| AZ1970 | L351Y_S400E_F405T_Y407V | T366L_N390R_K392F_T394W_T411S |
| AZ1971 | L351Y_S400E_F405T_Y407V | T366L_N390N_K392L_T394W_T411N |
| AZ1972 | L351Y_S400E_F405T_Y407V | T366L_N390N_K392L_T394W_T411L |
| AZ1973 | L351Y_S400E_F405T_Y407V | T366L_N390N_K392L_T394W_T411S |
| AZ1974 | L351Y_S400E_F405T_Y407V | T366L_N390N_K392M_T394W_T411N |
| AZ1975 | L351Y_S400E_F405T_Y407V | T366L_N390N_K392M_T394W_T411L |
| AZ1976 | L351Y_S400E_F405T_Y407V | T366L_N390N_K392M_T394W_T411S |
| AZ1977 | L351Y_S400E_F405T_Y407V | T366L_N390N_K392F_T394W_T411N |
| AZ1978 | L351Y_S400E_F405T_Y407V | T366L_N390N_K392F_T394W_T411L |
| AZ1979 | L351Y_S400E_F405T_Y407V | T366L_N390N_K392F_T394W_T411S |
| AZ1980 | L351Y_S400E_F405T_Y407V | T366L_N390K_K392L_T394W_T411N |
| AZ1981 | L351Y_S400E_F405T_Y407V | T366L_N390K_K392L_T394W_T411L |
| AZ1982 | L351Y_S400E_F405T_Y407V | T366L_N390K_K392L_T394W_T411S |
| AZ1983 | L351Y_S400E_F405T_Y407V | T366L_N390K_K392M_T394W_T411N |
| AZ1984 | L351Y_S400E_F405T_Y407V | T366L_N390K_K392M_T394W_T411L |

FIG. 37Z6

| | | |
|---|---|---|
| AZ1985 | L351Y_S400E_F405T_Y407V | T366L_N390K_K392M_T394W_T411S |
| AZ1986 | L351Y_S400E_F405T_Y407V | T366L_N390K_K392F_T394W_T411N |
| AZ1987 | L351Y_S400E_F405T_Y407V | T366L_N390K_K392F_T394W_T411L |
| AZ1988 | L351Y_S400E_F405T_Y407V | T366L_N390K_K392F_T394W_T411S |
| AZ1989 | L351Y_S400E_F405V_Y407I | T366L_N390K_K392L_T394W_T411N |
| AZ1990 | L351Y_S400E_F405V_Y407I | T366L_N390R_K392L_T394W_T411L |
| AZ1991 | L351Y_S400E_F405V_Y407I | T366L_N390R_K392L_T394W_T411S |
| AZ1992 | L351Y_S400E_F405V_Y407I | T366L_N390R_K392M_T394W_T411N |
| AZ1993 | L351Y_S400E_F405V_Y407I | T366L_N390R_K392M_T394W_T411L |
| AZ1994 | L351Y_S400E_F405V_Y407I | T366L_N390R_K392M_T394W_T411S |
| AZ1995 | L351Y_S400E_F405V_Y407I | T366L_N390R_K392F_T394W_T411N |
| AZ1996 | L351Y_S400E_F405V_Y407I | T366L_N390R_K392F_T394W_T411L |
| AZ1997 | L351Y_S400E_F405V_Y407I | T366L_N390R_K392F_T394W_T411S |
| AZ1998 | L351Y_S400E_F405V_Y407I | T366L_N390N_K392L_T394W_T411N |
| AZ1999 | L351Y_S400E_F405V_Y407I | T366L_N390N_K392L_T394W_T411L |
| AZ2000 | L351Y_S400E_F405V_Y407I | T366L_N390N_K392L_T394W_T411S |
| AZ2001 | L351Y_S400E_F405V_Y407I | T366L_N390N_K392M_T394W_T411N |
| AZ2002 | L351Y_S400E_F405V_Y407I | T366L_N390N_K392M_T394W_T411L |
| AZ2003 | L351Y_S400E_F405V_Y407I | T366L_N390N_K392M_T394W_T411S |
| AZ2004 | L351Y_S400E_F405V_Y407I | T366L_N390N_K392F_T394W_T411N |
| AZ2005 | L351Y_S400E_F405V_Y407I | T366L_N390N_K392F_T394W_T411L |
| AZ2006 | L351Y_S400E_F405V_Y407I | T366L_N390N_K392F_T394W_T411S |
| AZ2007 | L351Y_S400E_F405V_Y407I | T366L_N390K_K392L_T394W_T411N |
| AZ2008 | L351Y_S400E_F405V_Y407I | T366L_N390K_K392L_T394W_T411L |
| AZ2009 | L351Y_S400E_F405V_Y407I | T366L_N390K_K392L_T394W_T411S |
| AZ2010 | L351Y_S400E_F405V_Y407I | T366L_N390K_K392M_T394W_T411N |
| AZ2011 | L351Y_S400E_F405V_Y407I | T366L_N390K_K392M_T394W_T411L |
| AZ2012 | L351Y_S400E_F405V_Y407I | T366L_N390K_K392M_T394W_T411S |
| AZ2013 | L351Y_S400E_F405V_Y407I | T366L_N390K_K392F_T394W_T411N |
| AZ2014 | L351Y_S400E_F405V_Y407I | T366L_N390K_K392F_T394W_T411L |
| AZ2015 | L351Y_S400E_F405V_Y407I | T366L_N390K_K392F_T394W_T411S |
| AZ2016 | L351Y_S400E_F405V_Y407V | T366L_N390R_K392L_T394W_T411N |
| AZ2017 | L351Y_S400E_F405V_Y407V | T366L_N390R_K392L_T394W_T411L |
| AZ2018 | L351Y_S400E_F405V_Y407V | T366L_N390R_K392L_T394W_T411S |
| AZ2019 | L351Y_S400E_F405V_Y407V | T366L_N390R_K392M_T394W_T411N |
| AZ2020 | L351Y_S400E_F405V_Y407V | T366L_N390R_K392M_T394W_T411L |
| AZ2021 | L351Y_S400E_F405V_Y407V | T366L_N390R_K392M_T394W_T411S |
| AZ2022 | L351Y_S400E_F405V_Y407V | T366L_N390R_K392F_T394W_T411N |
| AZ2023 | L351Y_S400E_F405V_Y407V | T366L_N390R_K392F_T394W_T411L |
| AZ2024 | L351Y_S400E_F405V_Y407V | T366L_N390R_K392F_T394W_T411S |
| AZ2025 | L351Y_S400E_F405V_Y407V | T366L_N390N_K392L_T394W_T411N |
| AZ2026 | L351Y_S400E_F405V_Y407V | T366L_N390N_K392L_T394W_T411L |
| AZ2027 | L351Y_S400E_F405V_Y407V | T366L_N390N_K392L_T394W_T411S |
| AZ2028 | L351Y_S400E_F405V_Y407V | T366L_N390N_K392M_T394W_T411N |
| AZ2029 | L351Y_S400E_F405V_Y407V | T366L_N390N_K392M_T394W_T411L |
| AZ2030 | L351Y_S400E_F405V_Y407V | T366L_N390N_K392M_T394W_T411S |
| AZ2031 | L351Y_S400E_F405V_Y407V | T366L_N390N_K392F_T394W_T411N |
| AZ2032 | L351Y_S400E_F405V_Y407V | T366L_N390N_K392F_T394W_T411L |
| AZ2033 | L351Y_S400E_F405V_Y407V | T366L_N390N_K392F_T394W_T411S |
| AZ2034 | L351Y_S400E_F405V_Y407V | T366L_N390K_K392L_T394W_T411N |
| AZ2035 | L351Y_S400E_F405V_Y407V | T366L_N390K_K392L_T394W_T411L |
| AZ2036 | L351Y_S400E_F405V_Y407V | T366L_N390K_K392L_T394W_T411S |
| AZ2037 | L351Y_S400E_F405V_Y407V | T366L_N390K_K392M_T394W_T411N |
| AZ2038 | L351Y_S400E_F405V_Y407V | T366L_N390K_K392M_T394W_T411L |
| AZ2039 | L351Y_S400E_F405V_Y407V | T366L_N390K_K392M_T394W_T411S |
| AZ2040 | L351Y_S400E_F405V_Y407V | T366L_N390K_K392F_T394W_T411N |
| AZ2041 | L351Y_S400E_F405V_Y407V | T366L_N390K_K392F_T394W_T411L |
| AZ2042 | L351Y_S400E_F405V_Y407V | T366L_N390K_K392F_T394W_T411S |

FIG. 37Z7

| | | |
|---|---|---|
| AZ2043 | L351Y_S400K_F405A_Y407I | T366L_N390N_K392L_T394W_T411N |
| AZ2044 | L351Y_S400K_F405A_Y407I | T366L_N390N_K392L_T394W_T411S |
| AZ2045 | L351Y_S400K_F405A_Y407I | T366L_N390N_K392L_T394W_T411T |
| AZ2046 | L351Y_S400K_F405A_Y407I | T366L_N390N_K392M_T394W_T411N |
| AZ2047 | L351Y_S400K_F405A_Y407I | T366L_N390N_K392M_T394W_T411S |
| AZ2048 | L351Y_S400K_F405A_Y407I | T366L_N390N_K392M_T394W_T411T |
| AZ2049 | L351Y_S400K_F405A_Y407I | T366L_N390N_K392F_T394W_T411N |
| AZ2050 | L351Y_S400K_F405A_Y407I | T366L_N390N_K392F_T394W_T411S |
| AZ2051 | L351Y_S400K_F405A_Y407I | T366L_N390N_K392F_T394W_T411T |
| AZ2052 | L351Y_S400K_F405A_Y407I | T366L_N390Q_K392L_T394W_T411N |
| AZ2053 | L351Y_S400K_F405A_Y407I | T366L_N390Q_K392L_T394W_T411S |
| AZ2054 | L351Y_S400K_F405A_Y407I | T366L_N390Q_K392L_T394W_T411T |
| AZ2055 | L351Y_S400K_F405A_Y407I | T366L_N390Q_K392M_T394W_T411N |
| AZ2056 | L351Y_S400K_F405A_Y407I | T366L_N390Q_K392M_T394W_T411S |
| AZ2057 | L351Y_S400K_F405A_Y407I | T366L_N390Q_K392M_T394W_T411T |
| AZ2058 | L351Y_S400K_F405A_Y407I | T366L_N390Q_K392F_T394W_T411N |
| AZ2059 | L351Y_S400K_F405A_Y407I | T366L_N390Q_K392F_T394W_T411S |
| AZ2060 | L351Y_S400K_F405A_Y407I | T366L_N390Q_K392F_T394W_T411T |
| AZ2061 | L351Y_S400K_F405A_Y407I | T366L_N390E_K392L_T394W_T411N |
| AZ2062 | L351Y_S400K_F405A_Y407I | T366L_N390E_K392L_T394W_T411L |
| AZ2063 | L351Y_S400K_F405A_Y407I | T366L_N390E_K392L_T394W_T411S |
| AZ2064 | L351Y_S400K_F405A_Y407I | T366L_N390E_K392L_T394W_T411T |
| AZ2065 | L351Y_S400K_F405A_Y407I | T366L_N390E_K392M_T394W_T411N |
| AZ2066 | L351Y_S400K_F405A_Y407I | T366L_N390E_K392M_T394W_T411L |
| AZ2067 | L351Y_S400K_F405A_Y407I | T366L_N390E_K392M_T394W_T411S |
| AZ2068 | L351Y_S400K_F405A_Y407I | T366L_N390E_K392M_T394W_T411T |
| AZ2069 | L351Y_S400K_F405A_Y407I | T366L_N390E_K392F_T394W_T411N |
| AZ2070 | L351Y_S400K_F405A_Y407I | T366L_N390E_K392F_T394W_T411L |
| AZ2071 | L351Y_S400K_F405A_Y407I | T366L_N390E_K392F_T394W_T411S |
| AZ2072 | L351Y_S400K_F405A_Y407I | T366L_N390E_K392F_T394W_T411T |
| AZ2073 | L351Y_S400K_F405A_Y407V | T366L_N390N_K392L_T394W_T411N |
| AZ2074 | L351Y_S400K_F405A_Y407V | T366L_N390N_K392L_T394W_T411S |
| AZ2075 | L351Y_S400K_F405A_Y407V | T366L_N390N_K392L_T394W_T411T |
| AZ2076 | L351Y_S400K_F405A_Y407V | T366L_N390N_K392M_T394W_T411N |
| AZ2077 | L351Y_S400K_F405A_Y407V | T366L_N390N_K392M_T394W_T411S |
| AZ2078 | L351Y_S400K_F405A_Y407V | T366L_N390N_K392M_T394W_T411T |
| AZ2079 | L351Y_S400K_F405A_Y407V | T366L_N390N_K392F_T394W_T411N |
| AZ2080 | L351Y_S400K_F405A_Y407V | T366L_N390N_K392F_T394W_T411S |
| AZ2081 | L351Y_S400K_F405A_Y407V | T366L_N390N_K392F_T394W_T411T |
| AZ2082 | L351Y_S400K_F405A_Y407V | T366L_N390D_K392L_T394W_T411N |
| AZ2083 | L351Y_S400K_F405A_Y407V | T366L_N390D_K392L_T394W_T411S |
| AZ2084 | L351Y_S400K_F405A_Y407V | T366L_N390D_K392L_T394W_T411T |
| AZ2085 | L351Y_S400K_F405A_Y407V | T366L_N390D_K392M_T394W_T411N |
| AZ2086 | L351Y_S400K_F405A_Y407V | T366L_N390D_K392M_T394W_T411S |
| AZ2087 | L351Y_S400K_F405A_Y407V | T366L_N390D_K392M_T394W_T411T |
| AZ2088 | L351Y_S400K_F405A_Y407V | T366L_N390D_K392F_T394W_T411N |
| AZ2089 | L351Y_S400K_F405A_Y407V | T366L_N390D_K392F_T394W_T411S |
| AZ2090 | L351Y_S400K_F405A_Y407V | T366L_N390D_K392F_T394W_T411T |
| AZ2091 | L351Y_S400K_F405A_Y407V | T366L_N390E_K392L_T394W_T411N |
| AZ2092 | L351Y_S400K_F405A_Y407V | T366L_N390E_K392L_T394W_T411L |
| AZ2093 | L351Y_S400K_F405A_Y407V | T366L_N390E_K392L_T394W_T411S |
| AZ2094 | L351Y_S400K_F405A_Y407V | T366L_N390E_K392L_T394W_T411T |
| AZ2095 | L351Y_S400K_F405A_Y407V | T366L_N390E_K392M_T394W_T411N |
| AZ2096 | L351Y_S400K_F405A_Y407V | T366L_N390E_K392M_T394W_T411L |
| AZ2097 | L351Y_S400K_F405A_Y407V | T366L_N390E_K392M_T394W_T411S |
| AZ2098 | L351Y_S400K_F405A_Y407V | T366L_N390E_K392M_T394W_T411T |
| AZ2099 | L351Y_S400K_F405A_Y407V | T366L_N390E_K392F_T394W_T411N |
| AZ2100 | L351Y_S400K_F405A_Y407V | T366L_N390E_K392F_T394W_T411L |

FIG. 37Z8

| | | |
|---|---|---|
| AZ2101 | L351Y_S400K_F405A_Y407V | T366L_N390E_K392F_T394W_T411S |
| AZ2102 | L351Y_S400K_F405A_Y407V | T366L_N390E_K392F_T394W_T411T |
| AZ2103 | L351Y_S400K_F405S_Y407I | T366L_N390N_K392L_T394W_T411N |
| AZ2104 | L351Y_S400K_F405S_Y407I | T366L_N390N_K392L_T394W_T411S |
| AZ2105 | L351Y_S400K_F405S_Y407I | T366L_N390N_K392L_T394W_T411T |
| AZ2106 | L351Y_S400K_F405S_Y407I | T366L_N390N_K392M_T394W_T411N |
| AZ2107 | L351Y_S400K_F405S_Y407I | T366L_N390N_K392M_T394W_T411S |
| AZ2108 | L351Y_S400K_F405S_Y407I | T366L_N390N_K392M_T394W_T411T |
| AZ2109 | L351Y_S400K_F405S_Y407I | T366L_N390N_K392F_T394W_T411N |
| AZ2110 | L351Y_S400K_F405S_Y407I | T366L_N390N_K392F_T394W_T411S |
| AZ2111 | L351Y_S400K_F405S_Y407I | T366L_N390N_K392F_T394W_T411T |
| AZ2112 | L351Y_S400K_F405S_Y407I | T366L_N390D_K392L_T394W_T411N |
| AZ2113 | L351Y_S400K_F405S_Y407I | T366L_N390D_K392L_T394W_T411S |
| AZ2114 | L351Y_S400K_F405S_Y407I | T366L_N390D_K392L_T394W_T411T |
| AZ2115 | L351Y_S400K_F405S_Y407I | T366L_N390D_K392M_T394W_T411N |
| AZ2116 | L351Y_S400K_F405S_Y407I | T366L_N390D_K392M_T394W_T411S |
| AZ2117 | L351Y_S400K_F405S_Y407I | T366L_N390D_K392M_T394W_T411T |
| AZ2118 | L351Y_S400K_F405S_Y407I | T366L_N390D_K392F_T394W_T411N |
| AZ2119 | L351Y_S400K_F405S_Y407I | T366L_N390D_K392F_T394W_T411S |
| AZ2120 | L351Y_S400K_F405S_Y407I | T366L_N390D_K392F_T394W_T411T |
| AZ2121 | L351Y_S400K_F405S_Y407I | T366L_N390E_K392L_T394W_T411N |
| AZ2122 | L351Y_S400K_F405S_Y407I | T366L_N390E_K392L_T394W_T411L |
| AZ2123 | L351Y_S400K_F405S_Y407I | T366L_N390E_K392L_T394W_T411S |
| AZ2124 | L351Y_S400K_F405S_Y407I | T366L_N390E_K392L_T394W_T411T |
| AZ2125 | L351Y_S400K_F405S_Y407I | T366L_N390E_K392M_T394W_T411N |
| AZ2126 | L351Y_S400K_F405S_Y407I | T366L_N390E_K392M_T394W_T411L |
| AZ2127 | L351Y_S400K_F405S_Y407I | T366L_N390E_K392M_T394W_T411S |
| AZ2128 | L351Y_S400K_F405S_Y407I | T366L_N390E_K392M_T394W_T411T |
| AZ2129 | L351Y_S400K_F405S_Y407I | T366L_N390E_K392F_T394W_T411N |
| AZ2130 | L351Y_S400K_F405S_Y407I | T366L_N390E_K392F_T394W_T411L |
| AZ2131 | L351Y_S400K_F405S_Y407I | T366L_N390E_K392F_T394W_T411S |
| AZ2132 | L351Y_S400K_F405S_Y407I | T366L_N390E_K392F_T394W_T411T |
| AZ2133 | L351Y_S400K_F405S_Y407V | T366L_N390N_K392L_T394W_T411N |
| AZ2134 | L351Y_S400K_F405S_Y407V | T366L_N390N_K392L_T394W_T411S |
| AZ2135 | L351Y_S400K_F405S_Y407V | T366L_N390N_K392L_T394W_T411T |
| AZ2136 | L351Y_S400K_F405S_Y407V | T366L_N390N_K392M_T394W_T411N |
| AZ2137 | L351Y_S400K_F405S_Y407V | T366L_N390N_K392M_T394W_T411S |
| AZ2138 | L351Y_S400K_F405S_Y407V | T366L_N390N_K392M_T394W_T411T |
| AZ2139 | L351Y_S400K_F405S_Y407V | T366L_N390N_K392F_T394W_T411N |
| AZ2140 | L351Y_S400K_F405S_Y407V | T366L_N390N_K392F_T394W_T411S |
| AZ2141 | L351Y_S400K_F405S_Y407V | T366L_N390N_K392F_T394W_T411T |
| AZ2142 | L351Y_S400K_F405S_Y407V | T366L_N390D_K392L_T394W_T411N |
| AZ2143 | L351Y_S400K_F405S_Y407V | T366L_N390D_K392L_T394W_T411S |
| AZ2144 | L351Y_S400K_F405S_Y407V | T366L_N390D_K392L_T394W_T411T |
| AZ2145 | L351Y_S400K_F405S_Y407V | T366L_N390D_K392M_T394W_T411N |
| AZ2146 | L351Y_S400K_F405S_Y407V | T366L_N390D_K392M_T394W_T411S |
| AZ2147 | L351Y_S400K_F405S_Y407V | T366L_N390D_K392M_T394W_T411T |
| AZ2148 | L351Y_S400K_F405S_Y407V | T366L_N390D_K392F_T394W_T411N |
| AZ2149 | L351Y_S400K_F405S_Y407V | T366L_N390D_K392F_T394W_T411S |
| AZ2150 | L351Y_S400K_F405S_Y407V | T366L_N390D_K392F_T394W_T411T |
| AZ2151 | L351Y_S400K_F405S_Y407V | T366L_N390E_K392L_T394W_T411N |
| AZ2152 | L351Y_S400K_F405S_Y407V | T366L_N390E_K392L_T394W_T411L |
| AZ2153 | L351Y_S400K_F405S_Y407V | T366L_N390E_K392L_T394W_T411S |
| AZ2154 | L351Y_S400K_F405S_Y407V | T366L_N390E_K392L_T394W_T411T |
| AZ2155 | L351Y_S400K_F405S_Y407V | T366L_N390E_K392M_T394W_T411N |
| AZ2156 | L351Y_S400K_F405S_Y407V | T366L_N390E_K392M_T394W_T411L |
| AZ2157 | L351Y_S400K_F405S_Y407V | T366L_N390E_K392M_T394W_T411S |
| AZ2158 | L351Y_S400K_F405S_Y407V | T366L_N390E_K392M_T394W_T411T |

FIG. 37Z9

| | | |
|---|---|---|
| AZ2159 | L351Y_S400K_F405S_Y407V | T366L_N390E_K392F_T394W_T411N |
| AZ2160 | L351Y_S400K_F405S_Y407V | T366L_N390E_K392F_T394W_T411L |
| AZ2161 | L351Y_S400K_F405S_Y407V | T366L_N390E_K392F_T394W_T411S |
| AZ2162 | L351Y_S400K_F405S_Y407V | T366L_N390E_K392F_T394W_T411T |
| AZ2163 | L351Y_S400K_F405T_Y407I | T366L_N390N_K392L_T394W_T411N |
| AZ2164 | L351Y_S400K_F405T_Y407I | T366L_N390N_K392L_T394W_T411S |
| AZ2165 | L351Y_S400K_F405T_Y407I | T366L_N390N_K392L_T394W_T411T |
| AZ2166 | L351Y_S400K_F405T_Y407I | T366L_N390N_K392M_T394W_T411N |
| AZ2167 | L351Y_S400K_F405T_Y407I | T366L_N390N_K392M_T394W_T411S |
| AZ2168 | L351Y_S400K_F405T_Y407I | T366L_N390N_K392M_T394W_T411T |
| AZ2169 | L351Y_S400K_F405T_Y407I | T366L_N390N_K392F_T394W_T411N |
| AZ2170 | L351Y_S400K_F405T_Y407I | T366L_N390N_K392F_T394W_T411S |
| AZ2171 | L351Y_S400K_F405T_Y407I | T366L_N390N_K392F_T394W_T411T |
| AZ2172 | L351Y_S400K_F405T_Y407I | T366L_N390D_K392L_T394W_T411N |
| AZ2173 | L351Y_S400K_F405T_Y407I | T366L_N390D_K392L_T394W_T411S |
| AZ2174 | L351Y_S400K_F405T_Y407I | T366L_N390D_K392L_T394W_T411T |
| AZ2175 | L351Y_S400K_F405T_Y407I | T366L_N390D_K392M_T394W_T411N |
| AZ2176 | L351Y_S400K_F405T_Y407I | T366L_N390D_K392M_T394W_T411S |
| AZ2177 | L351Y_S400K_F405T_Y407I | T366L_N390D_K392M_T394W_T411T |
| AZ2178 | L351Y_S400K_F405T_Y407I | T366L_N390D_K392F_T394W_T411N |
| AZ2179 | L351Y_S400K_F405T_Y407I | T366L_N390D_K392F_T394W_T411S |
| AZ2180 | L351Y_S400K_F405T_Y407I | T366L_N390D_K392F_T394W_T411T |
| AZ2181 | L351Y_S400K_F405T_Y407I | T366L_N390E_K392L_T394W_T411N |
| AZ2182 | L351Y_S400K_F405T_Y407I | T366L_N390E_K392L_T394W_T411L |
| AZ2183 | L351Y_S400K_F405T_Y407I | T366L_N390E_K392L_T394W_T411S |
| AZ2184 | L351Y_S400K_F405T_Y407I | T366L_N390E_K392L_T394W_T411T |
| AZ2185 | L351Y_S400K_F405T_Y407I | T366L_N390E_K392M_T394W_T411N |
| AZ2186 | L351Y_S400K_F405T_Y407I | T366L_N390E_K392M_T394W_T411L |
| AZ2187 | L351Y_S400K_F405T_Y407I | T366L_N390E_K392M_T394W_T411S |
| AZ2188 | L351Y_S400K_F405T_Y407I | T366L_N390E_K392M_T394W_T411T |
| AZ2189 | L351Y_S400K_F405T_Y407I | T366L_N390E_K392F_T394W_T411N |
| AZ2190 | L351Y_S400K_F405T_Y407I | T366L_N390E_K392F_T394W_T411L |
| AZ2191 | L351Y_S400K_F405T_Y407I | T366L_N390E_K392F_T394W_T411S |
| AZ2192 | L351Y_S400K_F405T_Y407I | T366L_N390E_K392F_T394W_T411T |
| AZ2193 | L351Y_S400K_F405T_Y407V | T366L_N390N_K392L_T394W_T411N |
| AZ2194 | L351Y_S400K_F405T_Y407V | T366L_N390N_K392L_T394W_T411S |
| AZ2195 | L351Y_S400K_F405T_Y407V | T366L_N390N_K392L_T394W_T411T |
| AZ2196 | L351Y_S400K_F405T_Y407V | T366L_N390N_K392M_T394W_T411N |
| AZ2197 | L351Y_S400K_F405T_Y407V | T366L_N390N_K392M_T394W_T411S |
| AZ2198 | L351Y_S400K_F405T_Y407V | T366L_N390N_K392M_T394W_T411T |
| AZ2199 | L351Y_S400K_F405T_Y407V | T366L_N390N_K392F_T394W_T411N |
| AZ2200 | L351Y_S400K_F405T_Y407V | T366L_N390N_K392F_T394W_T411S |
| AZ2201 | L351Y_S400K_F405T_Y407V | T366L_N390N_K392F_T394W_T411T |
| AZ2202 | L351Y_S400K_F405T_Y407V | T366L_N390D_K392L_T394W_T411N |
| AZ2203 | L351Y_S400K_F405T_Y407V | T366L_N390D_K392L_T394W_T411S |
| AZ2204 | L351Y_S400K_F405T_Y407V | T366L_N390D_K392L_T394W_T411T |
| AZ2205 | L351Y_S400K_F405T_Y407V | T366L_N390D_K392M_T394W_T411N |
| AZ2206 | L351Y_S400K_F405T_Y407V | T366L_N390D_K392M_T394W_T411S |
| AZ2207 | L351Y_S400K_F405T_Y407V | T366L_N390D_K392M_T394W_T411T |
| AZ2208 | L351Y_S400K_F405T_Y407V | T366L_N390D_K392F_T394W_T411N |
| AZ2209 | L351Y_S400K_F405T_Y407V | T366L_N390D_K392F_T394W_T411S |
| AZ2210 | L351Y_S400K_F405T_Y407V | T366L_N390D_K392F_T394W_T411T |
| AZ2211 | L351Y_S400K_F405T_Y407V | T366L_N390E_K392L_T394W_T411N |
| AZ2212 | L351Y_S400K_F405T_Y407V | T366L_N390E_K392L_T394W_T411L |
| AZ2213 | L351Y_S400K_F405T_Y407V | T366L_N390E_K392L_T394W_T411S |
| AZ2214 | L351Y_S400K_F405T_Y407V | T366L_N390E_K392L_T394W_T411T |
| AZ2215 | L351Y_S400K_F405T_Y407V | T366L_N390E_K392M_T394W_T411N |
| AZ2216 | L351Y_S400K_F405T_Y407V | T366L_N390E_K392M_T394W_T411L |

FIG. 37Z10

| | | |
|---|---|---|
| AZ2217 | L351Y_S400K_F405T_Y407V | T366L_N390E_K392M_T394W_T411S |
| AZ2218 | L351Y_S400K_F405T_Y407V | T366L_N390E_K392M_T394W_T411T |
| AZ2219 | L351Y_S400K_F405T_Y407V | T366L_N390E_K392F_T394W_T411N |
| AZ2220 | L351Y_S400K_F405T_Y407V | T366L_N390E_K392F_T394W_T411L |
| AZ2221 | L351Y_S400K_F405T_Y407V | T366L_N390E_K392F_T394W_T411S |
| AZ2222 | L351Y_S400K_F405T_Y407V | T366L_N390E_K392F_T394W_T411T |
| AZ2223 | L351Y_S400K_F405V_Y407I | T366L_N390N_K392L_T394W_T411N |
| AZ2224 | L351Y_S400K_F405V_Y407I | T366L_N390N_K392L_T394W_T411S |
| AZ2225 | L351Y_S400K_F405V_Y407I | T366L_N390N_K392L_T394W_T411T |
| AZ2226 | L351Y_S400K_F405V_Y407I | T366L_N390N_K392M_T394W_T411N |
| AZ2227 | L351Y_S400K_F405V_Y407I | T366L_N390N_K392M_T394W_T411S |
| AZ2228 | L351Y_S400K_F405V_Y407I | T366L_N390N_K392M_T394W_T411T |
| AZ2229 | L351Y_S400K_F405V_Y407I | T366L_N390N_K392F_T394W_T411N |
| AZ2230 | L351Y_S400K_F405V_Y407I | T366L_N390N_K392F_T394W_T411S |
| AZ2231 | L351Y_S400K_F405V_Y407I | T366L_N390N_K392F_T394W_T411T |
| AZ2232 | L351Y_S400K_F405V_Y407I | T366L_N390D_K392L_T394W_T411N |
| AZ2233 | L351Y_S400K_F405V_Y407I | T366L_N390D_K392L_T394W_T411S |
| AZ2234 | L351Y_S400K_F405V_Y407I | T366L_N390D_K392L_T394W_T411T |
| AZ2235 | L351Y_S400K_F405V_Y407I | T366L_N390D_K392M_T394W_T411N |
| AZ2236 | L351Y_S400K_F405V_Y407I | T366L_N390D_K392M_T394W_T411S |
| AZ2237 | L351Y_S400K_F405V_Y407I | T366L_N390D_K392M_T394W_T411T |
| AZ2238 | L351Y_S400K_F405V_Y407I | T366L_N390D_K392F_T394W_T411N |
| AZ2239 | L351Y_S400K_F405V_Y407I | T366L_N390D_K392F_T394W_T411S |
| AZ2240 | L351Y_S400K_F405V_Y407I | T366L_N390D_K392F_T394W_T411T |
| AZ2241 | L351Y_S400K_F405V_Y407I | T366L_N390E_K392L_T394W_T411N |
| AZ2242 | L351Y_S400K_F405V_Y407I | T366L_N390E_K392L_T394W_T411L |
| AZ2243 | L351Y_S400K_F405V_Y407I | T366L_N390E_K392L_T394W_T411S |
| AZ2244 | L351Y_S400K_F405V_Y407I | T366L_N390E_K392L_T394W_T411T |
| AZ2245 | L351Y_S400K_F405V_Y407I | T366L_N390E_K392M_T394W_T411N |
| AZ2246 | L351Y_S400K_F405V_Y407I | T366L_N390E_K392M_T394W_T411L |
| AZ2247 | L351Y_S400K_F405V_Y407I | T366L_N390E_K392M_T394W_T411S |
| AZ2248 | L351Y_S400K_F405V_Y407I | T366L_N390E_K392M_T394W_T411T |
| AZ2249 | L351Y_S400K_F405V_Y407I | T366L_N390E_K392F_T394W_T411N |
| AZ2250 | L351Y_S400K_F405V_Y407I | T366L_N390E_K392F_T394W_T411L |
| AZ2251 | L351Y_S400K_F405V_Y407I | T366L_N390E_K392F_T394W_T411S |
| AZ2252 | L351Y_S400K_F405V_Y407I | T366L_N390E_K392F_T394W_T411T |
| AZ2253 | L351Y_S400K_F405V_Y407V | T366L_N390N_K392L_T394W_T411N |
| AZ2254 | L351Y_S400K_F405V_Y407V | T366L_N390N_K392L_T394W_T411S |
| AZ2255 | L351Y_S400K_F405V_Y407V | T366L_N390N_K392L_T394W_T411T |
| AZ2256 | L351Y_S400K_F405V_Y407V | T366L_N390N_K392M_T394W_T411N |
| AZ2257 | L351Y_S400K_F405V_Y407V | T366L_N390N_K392M_T394W_T411S |
| AZ2258 | L351Y_S400K_F405V_Y407V | T366L_N390N_K392M_T394W_T411T |
| AZ2259 | L351Y_S400K_F405V_Y407V | T366L_N390N_K392F_T394W_T411N |
| AZ2260 | L351Y_S400K_F405V_Y407V | T366L_N390N_K392F_T394W_T411S |
| AZ2261 | L351Y_S400K_F405V_Y407V | T366L_N390N_K392F_T394W_T411T |
| AZ2262 | L351Y_S400K_F405V_Y407V | T366L_N390D_K392L_T394W_T411N |
| AZ2263 | L351Y_S400K_F405V_Y407V | T366L_N390D_K392L_T394W_T411S |
| AZ2264 | L351Y_S400K_F405V_Y407V | T366L_N390D_K392L_T394W_T411T |
| AZ2265 | L351Y_S400K_F405V_Y407V | T366L_N390D_K392M_T394W_T411N |
| AZ2266 | L351Y_S400K_F405V_Y407V | T366L_N390D_K392M_T394W_T411S |
| AZ2267 | L351Y_S400K_F405V_Y407V | T366L_N390D_K392M_T394W_T411T |
| AZ2268 | L351Y_S400K_F405V_Y407V | T366L_N390D_K392F_T394W_T411N |
| AZ2269 | L351Y_S400K_F405V_Y407V | T366L_N390D_K392F_T394W_T411S |
| AZ2270 | L351Y_S400K_F405V_Y407V | T366L_N390D_K392F_T394W_T411T |
| AZ2271 | L351Y_S400K_F405V_Y407V | T366L_N390E_K392L_T394W_T411N |
| AZ2272 | L351Y_S400K_F405V_Y407V | T366L_N390E_K392L_T394W_T411L |
| AZ2273 | L351Y_S400K_F405V_Y407V | T366L_N390E_K392L_T394W_T411S |
| AZ2274 | L351Y_S400K_F405V_Y407V | T366L_N390E_K392L_T394W_T411T |

FIG. 37Z11

| | | |
|---|---|---|
| AZ2275 | L351Y_S400K_F405V_Y407V | T366L_N390E_K392M_T394W_T411N |
| AZ2276 | L351Y_S400K_F405V_Y407V | T366L_N390E_K392M_T394W_T411L |
| AZ2277 | L351Y_S400K_F405V_Y407V | T366L_N390E_K392M_T394W_T411S |
| AZ2278 | L351Y_S400K_F405V_Y407V | T366L_N390E_K392M_T394W_T411T |
| AZ2279 | L351Y_S400K_F405V_Y407V | T366L_N390E_K392F_T394W_T411N |
| AZ2280 | L351Y_S400K_F405V_Y407V | T366L_N390E_K392F_T394W_T411L |
| AZ2281 | L351Y_S400K_F405V_Y407V | T366L_N390E_K392F_T394W_T411S |
| AZ2282 | L351Y_S400K_F405V_Y407V | T366L_N390E_K392F_T394W_T411T |
| AZ2283 | Y349C_D399C_F405A_Y407I | S354C_T366L_K392C_T394W_K409L_T411L |
| AZ2284 | Y349C_D399C_F405A_Y407I | S354C_T366L_K392C_T394W_K409L_T411T |
| AZ2285 | Y349C_D399C_F405A_Y407I | S354C_T366L_K392C_T394W_K409L_T411L |
| AZ2286 | Y349C_D399C_F405A_Y407I | S354C_T366L_K392C_T394W_K409L_T411T |
| AZ2287 | Y349C_D399C_F405A_Y407I | S354C_T366L_K392C_T394W_K409K_T411L |
| AZ2288 | Y349C_D399C_F405A_Y407I | S354C_T366L_K392C_T394W_K409K_T411T |
| AZ2289 | Y349C_D399C_F405A_Y407I | S354C_T366L_K392C_T394W_K409M_T411L |
| AZ2290 | Y349C_D399C_F405A_Y407I | S354C_T366L_K392C_T394W_K409M_T411T |
| AZ2291 | Y349C_D399C_F405A_Y407V | S354C_T366L_K392C_T394W_K409L_T411L |
| AZ2292 | Y349C_D399C_F405A_Y407V | S354C_T366L_K392C_T394W_K409L_T411T |
| AZ2293 | Y349C_D399C_F405A_Y407V | S354C_T366L_K392C_T394W_K409L_T411L |
| AZ2294 | Y349C_D399C_F405A_Y407V | S354C_T366L_K392C_T394W_K409L_T411T |
| AZ2295 | Y349C_D399C_F405A_Y407V | S354C_T366L_K392C_T394W_K409K_T411L |
| AZ2296 | Y349C_D399C_F405A_Y407V | S354C_T366L_K392C_T394W_K409K_T411T |
| AZ2297 | Y349C_D399C_F405A_Y407V | S354C_T366L_K392C_T394W_K409M_T411L |
| AZ2298 | Y349C_D399C_F405A_Y407V | S354C_T366L_K392C_T394W_K409M_T411T |
| AZ2299 | Y349C_D399C_F405S_Y407I | S354C_T366L_K392C_T394W_K409L_T411L |
| AZ2300 | Y349C_D399C_F405S_Y407I | S354C_T366L_K392C_T394W_K409L_T411T |
| AZ2301 | Y349C_D399C_F405S_Y407I | S354C_T366L_K392C_T394W_K409L_T411L |
| AZ2302 | Y349C_D399C_F405S_Y407I | S354C_T366L_K392C_T394W_K409L_T411T |
| AZ2303 | Y349C_D399C_F405S_Y407I | S354C_T366L_K392C_T394W_K409K_T411L |
| AZ2304 | Y349C_D399C_F405S_Y407I | S354C_T366L_K392C_T394W_K409K_T411T |
| AZ2305 | Y349C_D399C_F405S_Y407I | S354C_T366L_K392C_T394W_K409M_T411L |
| AZ2306 | Y349C_D399C_F405S_Y407I | S354C_T366L_K392C_T394W_K409M_T411T |
| AZ2307 | Y349C_D399C_F405S_Y407V | S354C_T366L_K392C_T394W_K409L_T411L |
| AZ2308 | Y349C_D399C_F405S_Y407V | S354C_T366L_K392C_T394W_K409L_T411T |
| AZ2309 | Y349C_D399C_F405S_Y407V | S354C_T366L_K392C_T394W_K409L_T411L |
| AZ2310 | Y349C_D399C_F405S_Y407V | S354C_T366L_K392C_T394W_K409L_T411T |
| AZ2311 | Y349C_D399C_F405S_Y407V | S354C_T366L_K392C_T394W_K409K_T411L |
| AZ2312 | Y349C_D399C_F405S_Y407V | S354C_T366L_K392C_T394W_K409K_T411T |
| AZ2313 | Y349C_D399C_F405S_Y407V | S354C_T366L_K392C_T394W_K409M_T411L |
| AZ2314 | Y349C_D399C_F405S_Y407V | S354C_T366L_K392C_T394W_K409M_T411T |
| AZ2315 | Y349C_D399C_F405V_Y407I | S354C_T366L_K392C_T394W_K409L_T411L |
| AZ2316 | Y349C_D399C_F405V_Y407I | S354C_T366L_K392C_T394W_K409L_T411T |
| AZ2317 | Y349C_D399C_F405V_Y407I | S354C_T366L_K392C_T394W_K409L_T411L |
| AZ2318 | Y349C_D399C_F405V_Y407I | S354C_T366L_K392C_T394W_K409L_T411T |
| AZ2319 | Y349C_D399C_F405V_Y407I | S354C_T366L_K392C_T394W_K409K_T411L |
| AZ2320 | Y349C_D399C_F405V_Y407I | S354C_T366L_K392C_T394W_K409K_T411T |
| AZ2321 | Y349C_D399C_F405V_Y407I | S354C_T366L_K392C_T394W_K409M_T411L |
| AZ2322 | Y349C_D399C_F405V_Y407I | S354C_T366L_K392C_T394W_K409M_T411T |
| AZ2323 | Y349C_D399C_F405V_Y407V | S354C_T366L_K392C_T394W_K409L_T411L |
| AZ2324 | Y349C_D399C_F405V_Y407V | S354C_T366L_K392C_T394W_K409L_T411T |
| AZ2325 | Y349C_D399C_F405V_Y407V | S354C_T366L_K392C_T394W_K409L_T411L |
| AZ2326 | Y349C_D399C_F405V_Y407V | S354C_T366L_K392C_T394W_K409L_T411T |
| AZ2327 | Y349C_D399C_F405V_Y407V | S354C_T366L_K392C_T394W_K409K_T411L |
| AZ2328 | Y349C_D399C_F405V_Y407V | S354C_T366L_K392C_T394W_K409K_T411T |
| AZ2329 | Y349C_D399C_F405V_Y407V | S354C_T366L_K392C_T394W_K409M_T411L |
| AZ2330 | Y349C_D399C_F405V_Y407V | S354C_T366L_K392C_T394W_K409M_T411T |
| AZ2331 | L351L_K370T_G371D_F405A_Y407I | T366L_K392L_T394W_K409M_T411R |
| AZ2332 | L351L_K370T_G371D_F405A_Y407I | T366L_K392M_T394W_K409M_T411R |

FIG. 37Z12

| AZ2333 | L351L_K370T_G371D_F405A_Y407I | T366L_K392F_T394W_K409M_T411R |
|---|---|---|
| AZ2334 | L351L_K370T_G371D_F405A_Y407V | T366L_K392L_T394W_K409M_T411R |
| AZ2335 | L351L_K370T_G371D_F405A_Y407V | T366L_K392M_T394W_K409M_T411R |
| AZ2336 | L351L_K370T_G371D_F405A_Y407V | T366L_K392F_T394W_K409M_T411R |
| AZ2337 | L351L_K370T_G371D_F405S_Y407I | T366L_K392L_T394W_K409M_T411R |
| AZ2338 | L351L_K370T_G371D_F405S_Y407I | T366L_K392M_T394W_K409M_T411R |
| AZ2339 | L351L_K370T_G371D_F405S_Y407I | T366L_K392F_T394W_K409M_T411R |
| AZ2340 | L351L_K370T_G371D_F405S_Y407V | T366L_K392L_T394W_K409M_T411R |
| AZ2341 | L351L_K370T_G371D_F405S_Y407V | T366L_K392M_T394W_K409M_T411R |
| AZ2342 | L351L_K370T_G371D_F405S_Y407V | T366L_K392F_T394W_K409M_T411R |
| AZ2343 | L351L_K370T_G371D_F405V_Y407I | T366L_K392L_T394W_K409M_T411R |
| AZ2344 | L351L_K370T_G371D_F405V_Y407I | T366L_K392M_T394W_K409M_T411R |
| AZ2345 | L351L_K370T_G371D_F405V_Y407I | T366L_K392F_T394W_K409M_T411R |
| AZ2346 | L351L_K370T_G371D_F405V_Y407V | T366L_K392L_T394W_K409M_T411R |
| AZ2347 | L351L_K370T_G371D_F405V_Y407V | T366L_K392M_T394W_K409M_T411R |
| AZ2348 | L351L_K370T_G371D_F405V_Y407V | T366L_K392F_T394W_K409M_T411R |
| AZ2349 | L351Y_K370T_G371D_F405A_Y407I | T366L_K392L_T394W_K409M_T411R |
| AZ2350 | L351Y_K370T_G371D_F405A_Y407I | T366L_K392M_T394W_K409M_T411R |
| AZ2351 | L351Y_K370T_G371D_F405A_Y407I | T366L_K392F_T394W_K409M_T411R |
| AZ2352 | L351Y_K370T_G371D_F405A_Y407V | T366L_K392L_T394W_K409M_T411R |
| AZ2353 | L351Y_K370T_G371D_F405A_Y407V | T366L_K392M_T394W_K409M_T411R |
| AZ2354 | L351Y_K370T_G371D_F405A_Y407V | T366L_K392F_T394W_K409M_T411R |
| AZ2355 | L351Y_K370T_G371D_F405S_Y407I | T366L_K392L_T394W_K409M_T411R |
| AZ2356 | L351Y_K370T_G371D_F405S_Y407I | T366L_K392M_T394W_K409M_T411R |
| AZ2357 | L351Y_K370T_G371D_F405S_Y407I | T366L_K392F_T394W_K409M_T411R |
| AZ2358 | L351Y_K370T_G371D_F405S_Y407V | T366L_K392L_T394W_K409M_T411R |
| AZ2359 | L351Y_K370T_G371D_F405S_Y407V | T366L_K392M_T394W_K409M_T411R |
| AZ2360 | L351Y_K370T_G371D_F405S_Y407V | T366L_K392F_T394W_K409M_T411R |
| AZ2361 | L351Y_K370T_G371D_F405V_Y407I | T366L_K392L_T394W_K409M_T411R |
| AZ2362 | L351Y_K370T_G371D_F405V_Y407I | T366L_K392M_T394W_K409M_T411R |
| AZ2363 | L351Y_K370T_G371D_F405V_Y407I | T366L_K392F_T394W_K409M_T411R |
| AZ2364 | L351Y_K370T_G371D_F405V_Y407V | T366L_K392L_T394W_K409M_T411R |
| AZ2365 | L351Y_K370T_G371D_F405V_Y407V | T366L_K392M_T394W_K409M_T411R |
| AZ2366 | L351Y_K370T_G371D_F405V_Y407V | T366L_K392F_T394W_K409M_T411R |
| AZ2367 | L351L_K370T_G371D_F405A_Y407I | E357Q_S364R_T366L_K392L_T394W_K409L_T411R |
| AZ2368 | L351L_K370T_G371D_F405A_Y407I | E357Q_S364R_T366L_K392L_T394W_K409M_T411R |
| AZ2369 | L351L_K370T_G371D_F405A_Y407I | E357Q_S364R_T366L_K392M_T394W_K409L_T411R |
| AZ2370 | L351L_K370T_G371D_F405A_Y407I | E357Q_S364R_T366L_K392M_T394W_K409M_T411R |
| AZ2371 | L351L_K370T_G371D_F405A_Y407I | E357Q_S364R_T366L_K392F_T394W_K409L_T411R |
| AZ2372 | L351L_K370T_G371D_F405A_Y407I | E357Q_S364R_T366L_K392F_T394W_K409M_T411R |
| AZ2373 | L351L_K370T_G371D_F405A_Y407V | E357Q_S364R_T366L_K392L_T394W_K409L_T411R |
| AZ2374 | L351L_K370T_G371D_F405A_Y407V | E357Q_S364R_T366L_K392L_T394W_K409M_T411R |
| AZ2375 | L351L_K370T_G371D_F405A_Y407V | E357Q_S364R_T366L_K392M_T394W_K409L_T411R |
| AZ2376 | L351L_K370T_G371D_F405A_Y407V | E357Q_S364R_T366L_K392M_T394W_K409M_T411R |
| AZ2377 | L351L_K370T_G371D_F405A_Y407V | E357Q_S364R_T366L_K392F_T394W_K409L_T411R |
| AZ2378 | L351L_K370T_G371D_F405A_Y407V | E357Q_S364R_T366L_K392F_T394W_K409M_T411R |
| AZ2379 | L351L_K370T_G371D_F405S_Y407I | E357Q_S364R_T366L_K392L_T394W_K409L_T411R |
| AZ2380 | L351L_K370T_G371D_F405S_Y407I | E357Q_S364R_T366L_K392L_T394W_K409M_T411R |
| AZ2381 | L351L_K370T_G371D_F405S_Y407I | E357Q_S364R_T366L_K392M_T394W_K409L_T411R |
| AZ2382 | L351L_K370T_G371D_F405S_Y407I | E357Q_S364R_T366L_K392M_T394W_K409M_T411R |
| AZ2383 | L351L_K370T_G371D_F405S_Y407I | E357Q_S364R_T366L_K392F_T394W_K409L_T411R |
| AZ2384 | L351L_K370T_G371D_F405S_Y407I | E357Q_S364R_T366L_K392F_T394W_K409M_T411R |
| AZ2385 | L351L_K370T_G371D_F405S_Y407V | E357Q_S364R_T366L_K392L_T394W_K409L_T411R |
| AZ2386 | L351L_K370T_G371D_F405S_Y407V | E357Q_S364R_T366L_K392L_T394W_K409M_T411R |
| AZ2387 | L351L_K370T_G371D_F405S_Y407V | E357Q_S364R_T366L_K392M_T394W_K409L_T411R |
| AZ2388 | L351L_K370T_G371D_F405S_Y407V | E357Q_S364R_T366L_K392M_T394W_K409M_T411R |
| AZ2389 | L351L_K370T_G371D_F405S_Y407V | E357Q_S364R_T366L_K392F_T394W_K409L_T411R |
| AZ2390 | L351L_K370T_G371D_F405S_Y407V | E357Q_S364R_T366L_K392F_T394W_K409M_T411R |

FIG. 37Z13

| | | |
|---|---|---|
| AZ2391 | L351L_K370T_G371D_F405V_Y407I | E357Q_S364R_T366L_K392L_T394W_K409L_T411R |
| AZ2392 | L351L_K370T_G371D_F405V_Y407I | E357Q_S364R_T366L_K392L_T394W_K409M_T411R |
| AZ2393 | L351L_K370T_G371D_F405V_Y407I | E357Q_S364R_T366L_K392M_T394W_K409L_T411R |
| AZ2394 | L351L_K370T_G371D_F405V_Y407I | E357Q_S364R_T366L_K392M_T394W_K409M_T411R |
| AZ2395 | L351L_K370T_G371D_F405V_Y407I | E357Q_S364R_T366L_K392F_T394W_K409L_T411R |
| AZ2396 | L351L_K370T_G371D_F405V_Y407I | E357Q_S364R_T366L_K392F_T394W_K409M_T411R |
| AZ2397 | L351L_K370T_G371D_F405V_Y407V | E357Q_S364R_T366L_K392L_T394W_K409L_T411R |
| AZ2398 | L351L_K370T_G371D_F405V_Y407V | E357Q_S364R_T366L_K392L_T394W_K409M_T411R |
| AZ2399 | L351L_K370T_G371D_F405V_Y407V | E357Q_S364R_T366L_K392M_T394W_K409L_T411R |
| AZ2400 | L351L_K370T_G371D_F405V_Y407V | E357Q_S364R_T366L_K392M_T394W_K409M_T411R |
| AZ2401 | L351L_K370T_G371D_F405V_Y407V | E357Q_S364R_T366L_K392F_T394W_K409L_T411R |
| AZ2402 | L351L_K370T_G371D_F405V_Y407V | E357Q_S364R_T366L_K392F_T394W_K409M_T411R |
| AZ2403 | L351Y_K370T_G371D_F405A_Y407I | E357Q_S364R_T366L_K392L_T394W_K409L_T411R |
| AZ2404 | L351Y_K370T_G371D_F405A_Y407I | E357Q_S364R_T366L_K392L_T394W_K409M_T411R |
| AZ2405 | L351Y_K370T_G371D_F405A_Y407I | E357Q_S364R_T366L_K392M_T394W_K409L_T411R |
| AZ2406 | L351Y_K370T_G371D_F405A_Y407I | E357Q_S364R_T366L_K392M_T394W_K409M_T411R |
| AZ2407 | L351Y_K370T_G371D_F405A_Y407I | E357Q_S364R_T366L_K392F_T394W_K409L_T411R |
| AZ2408 | L351Y_K370T_G371D_F405A_Y407I | E357Q_S364R_T366L_K392F_T394W_K409M_T411R |
| AZ2409 | L351Y_K370T_G371D_F405A_Y407V | E357Q_S364R_T366L_K392L_T394W_K409L_T411R |
| AZ2410 | L351Y_K370T_G371D_F405A_Y407V | E357Q_S364R_T366L_K392L_T394W_K409M_T411R |
| AZ2411 | L351Y_K370T_G371D_F405A_Y407V | E357Q_S364R_T366L_K392M_T394W_K409L_T411R |
| AZ2412 | L351Y_K370T_G371D_F405A_Y407V | E357Q_S364R_T366L_K392M_T394W_K409M_T411R |
| AZ2413 | L351Y_K370T_G371D_F405A_Y407V | E357Q_S364R_T366L_K392F_T394W_K409L_T411R |
| AZ2414 | L351Y_K370T_G371D_F405A_Y407V | E357Q_S364R_T366L_K392F_T394W_K409M_T411R |
| AZ2415 | L351Y_K370T_G371D_F405S_Y407I | E357Q_S364R_T366L_K392L_T394W_K409L_T411R |
| AZ2416 | L351Y_K370T_G371D_F405S_Y407I | E357Q_S364R_T366L_K392L_T394W_K409M_T411R |
| AZ2417 | L351Y_K370T_G371D_F405S_Y407I | E357Q_S364R_T366L_K392M_T394W_K409L_T411R |
| AZ2418 | L351Y_K370T_G371D_F405S_Y407I | E357Q_S364R_T366L_K392M_T394W_K409M_T411R |
| AZ2419 | L351Y_K370T_G371D_F405S_Y407I | E357Q_S364R_T366L_K392F_T394W_K409L_T411R |
| AZ2420 | L351Y_K370T_G371D_F405S_Y407I | E357Q_S364R_T366L_K392F_T394W_K409M_T411R |
| AZ2421 | L351Y_K370T_G371D_F405S_Y407V | E357Q_S364R_T366L_K392L_T394W_K409L_T411R |
| AZ2422 | L351Y_K370T_G371D_F405S_Y407V | E357Q_S364R_T366L_K392L_T394W_K409M_T411R |
| AZ2423 | L351Y_K370T_G371D_F405S_Y407V | E357Q_S364R_T366L_K392M_T394W_K409L_T411R |
| AZ2424 | L351Y_K370T_G371D_F405S_Y407V | E357Q_S364R_T366L_K392M_T394W_K409M_T411R |
| AZ2425 | L351Y_K370T_G371D_F405S_Y407V | E357Q_S364R_T366L_K392F_T394W_K409L_T411R |
| AZ2426 | L351Y_K370T_G371D_F405S_Y407V | E357Q_S364R_T366L_K392F_T394W_K409M_T411R |
| AZ2427 | L351Y_K370T_G371D_F405V_Y407I | E357Q_S364R_T366L_K392L_T394W_K409L_T411R |
| AZ2428 | L351Y_K370T_G371D_F405V_Y407I | E357Q_S364R_T366L_K392L_T394W_K409M_T411R |
| AZ2429 | L351Y_K370T_G371D_F405V_Y407I | E357Q_S364R_T366L_K392M_T394W_K409L_T411R |
| AZ2430 | L351Y_K370T_G371D_F405V_Y407I | E357Q_S364R_T366L_K392M_T394W_K409M_T411R |
| AZ2431 | L351Y_K370T_G371D_F405V_Y407I | E357Q_S364R_T366L_K392F_T394W_K409L_T411R |
| AZ2432 | L351Y_K370T_G371D_F405V_Y407I | E357Q_S364R_T366L_K392F_T394W_K409M_T411R |
| AZ2433 | L351Y_K370T_G371D_F405V_Y407V | E357Q_S364R_T366L_K392L_T394W_K409L_T411R |
| AZ2434 | L351Y_K370T_G371D_F405V_Y407V | E357Q_S364R_T366L_K392L_T394W_K409M_T411R |
| AZ2435 | L351Y_K370T_G371D_F405V_Y407V | E357Q_S364R_T366L_K392M_T394W_K409L_T411R |
| AZ2436 | L351Y_K370T_G371D_F405V_Y407V | E357Q_S364R_T366L_K392M_T394W_K409M_T411R |
| AZ2437 | L351Y_K370T_G371D_F405V_Y407V | E357Q_S364R_T366L_K392F_T394W_K409L_T411R |
| AZ2438 | L351Y_K370T_G371D_F405V_Y407V | E357Q_S364R_T366L_K392F_T394W_K409M_T411R |

FIG. 38A

Table 7

| Variant | Fc mutations chain A | Fc mutations chain B |
|---|---|---|
| AZ2439 | T366V_K392L_K409F_T411E | L351Y_D399R_Y407A |
| AZ2440 | T366V_K392E_K409F_T411E | L351Y_D399R_S400R_Y407A |
| AZ2441 | T366I_K409F | L351Y_Y407A |
| AZ2442 | T366I_K409F | L351Y_Y407I |
| AZ2443 | T366I_K409F | L351Y_Y407V |
| AZ2444 | T366M_K409F | L351Y_Y407A |
| AZ2445 | T366M_K409F | L351Y_Y407I |
| AZ2446 | T366M_K409F | L351Y_Y407V |
| AZ2447 | T366V_K409F | L351Y_Y407A |
| AZ2448 | T366V_K409F | L351Y_Y407I |
| AZ2449 | T366V_K409F | L351Y_Y407V |
| AZ2450 | T366I_T394S_K409W | L351Y_F405L_Y407A |
| AZ2451 | T366I_T394S_K409W | L351Y_F405L_Y407I |
| AZ2452 | T366I_T394S_K409W | L351Y_F405L_Y407L |
| AZ2453 | T366I_T394S_K409W | L351Y_F405L_Y407M |
| AZ2454 | T366I_T394S_K409W | L351Y_F405L_Y407V |
| AZ2455 | T366I_T394S_K409W | L351Y_F405M_Y407A |
| AZ2456 | T366I_T394S_K409W | L351Y_F405M_Y407I |
| AZ2457 | T366I_T394S_K409W | L351Y_F405M_Y407L |
| AZ2458 | T366I_T394S_K409W | L351Y_F405M_Y407M |
| AZ2459 | T366I_T394S_K409W | L351Y_F405M_Y407V |
| AZ2460 | T366I_T394S_K409W | L351Y_F405F_Y407A |
| AZ2461 | T366I_T394S_K409W | L351Y_F405F_Y407I |
| AZ2462 | T366I_T394S_K409W | L351Y_F405F_Y407L |
| AZ2463 | T366I_T394S_K409W | L351Y_F405F_Y407M |
| AZ2464 | T366I_T394S_K409W | L351Y_F405F_Y407V |
| AZ2465 | T366I_T394V_K409W | L351Y_F405L_Y407A |
| AZ2466 | T366I_T394V_K409W | L351Y_F405L_Y407I |
| AZ2467 | T366I_T394V_K409W | L351Y_F405L_Y407L |
| AZ2468 | T366I_T394V_K409W | L351Y_F405L_Y407M |
| AZ2469 | T366I_T394V_K409W | L351Y_F405L_Y407V |
| AZ2470 | T366I_T394V_K409W | L351Y_F405M_Y407A |
| AZ2471 | T366I_T394V_K409W | L351Y_F405M_Y407I |
| AZ2472 | T366I_T394V_K409W | L351Y_F405M_Y407L |
| AZ2473 | T366I_T394V_K409W | L351Y_F405M_Y407M |
| AZ2474 | T366I_T394V_K409W | L351Y_F405M_Y407V |
| AZ2475 | T366I_T394V_K409W | L351Y_F405F_Y407A |
| AZ2476 | T366I_T394V_K409W | L351Y_F405F_Y407I |
| AZ2477 | T366I_T394V_K409W | L351Y_F405F_Y407L |
| AZ2478 | T366I_T394V_K409W | L351Y_F405F_Y407M |
| AZ2479 | T366I_T394V_K409W | L351Y_F405F_Y407V |
| AZ2480 | T366M_T394S_K409W | L351Y_F405L_Y407A |
| AZ2481 | T366M_T394S_K409W | L351Y_F405L_Y407I |
| AZ2482 | T366M_T394S_K409W | L351Y_F405L_Y407L |
| AZ2483 | T366M_T394S_K409W | L351Y_F405L_Y407M |
| AZ2484 | T366M_T394S_K409W | L351Y_F405L_Y407V |
| AZ2485 | T366M_T394S_K409W | L351Y_F405M_Y407A |
| AZ2486 | T366M_T394S_K409W | L351Y_F405M_Y407I |
| AZ2487 | T366M_T394S_K409W | L351Y_F405M_Y407L |
| AZ2488 | T366M_T394S_K409W | L351Y_F405M_Y407M |
| AZ2489 | T366M_T394S_K409W | L351Y_F405M_Y407V |
| AZ2490 | T366M_T394S_K409W | L351Y_F405F_Y407A |
| AZ2491 | T366M_T394S_K409W | L351Y_F405F_Y407I |
| AZ2492 | T366M_T394S_K409W | L351Y_F405F_Y407L |

FIG. 38B

| | | |
|---|---|---|
| AZ2493 | T366M_T394S_K409W | L351Y_F405F_Y407M |
| AZ2494 | T366M_T394S_K409W | L351Y_F405F_Y407V |
| AZ2495 | T366M_T394V_K409W | L351Y_F405L_Y407A |
| AZ2496 | T366M_T394V_K409W | L351Y_F405L_Y407I |
| AZ2497 | T366M_T394V_K409W | L351Y_F405L_Y407L |
| AZ2498 | T366M_T394V_K409W | L351Y_F405L_Y407M |
| AZ2499 | T366M_T394V_K409W | L351Y_F405L_Y407V |
| AZ2500 | T366M_T394V_K409W | L351Y_F405M_Y407A |
| AZ2501 | T366M_T394V_K409W | L351Y_F405M_Y407I |
| AZ2502 | T366M_T394V_K409W | L351Y_F405M_Y407L |
| AZ2503 | T366M_T394V_K409W | L351Y_F405M_Y407M |
| AZ2504 | T366M_T394V_K409W | L351Y_F405M_Y407V |
| AZ2505 | T366M_T394V_K409W | L351Y_F405F_Y407A |
| AZ2506 | T366M_T394V_K409W | L351Y_F405F_Y407I |
| AZ2507 | T366M_T394V_K409W | L351Y_F405F_Y407L |
| AZ2508 | T366M_T394V_K409W | L351Y_F405F_Y407M |
| AZ2509 | T366M_T394V_K409W | L351Y_F405F_Y407V |
| AZ2510 | T366V_T394S_K409W | L351Y_F405L_Y407A |
| AZ2511 | T366V_T394S_K409W | L351Y_F405L_Y407I |
| AZ2512 | T366V_T394S_K409W | L351Y_F405L_Y407L |
| AZ2513 | T366V_T394S_K409W | L351Y_F405L_Y407M |
| AZ2514 | T366V_T394S_K409W | L351Y_F405L_Y407V |
| AZ2515 | T366V_T394S_K409W | L351Y_F405M_Y407A |
| AZ2516 | T366V_T394S_K409W | L351Y_F405M_Y407I |
| AZ2517 | T366V_T394S_K409W | L351Y_F405M_Y407L |
| AZ2518 | T366V_T394S_K409W | L351Y_F405M_Y407M |
| AZ2519 | T366V_T394S_K409W | L351Y_F405M_Y407V |
| AZ2520 | T366V_T394S_K409W | L351Y_F405F_Y407A |
| AZ2521 | T366V_T394S_K409W | L351Y_F405F_Y407I |
| AZ2522 | T366V_T394S_K409W | L351Y_F405F_Y407L |
| AZ2523 | T366V_T394S_K409W | L351Y_F405F_Y407M |
| AZ2524 | T366V_T394S_K409W | L351Y_F405F_Y407V |
| AZ2525 | T366V_T394V_K409W | L351Y_F405L_Y407A |
| AZ2526 | T366V_T394V_K409W | L351Y_F405L_Y407I |
| AZ2527 | T366V_T394V_K409W | L351Y_F405L_Y407L |
| AZ2528 | T366V_T394V_K409W | L351Y_F405L_Y407M |
| AZ2529 | T366V_T394V_K409W | L351Y_F405L_Y407V |
| AZ2530 | T366V_T394V_K409W | L351Y_F405M_Y407A |
| AZ2531 | T366V_T394V_K409W | L351Y_F405M_Y407I |
| AZ2532 | T366V_T394V_K409W | L351Y_F405M_Y407L |
| AZ2533 | T366V_T394V_K409W | L351Y_F405M_Y407M |
| AZ2534 | T366V_T394V_K409W | L351Y_F405M_Y407V |
| AZ2535 | T366V_T394V_K409W | L351Y_F405F_Y407A |
| AZ2536 | T366V_T394V_K409W | L351Y_F405F_Y407I |
| AZ2537 | T366V_T394V_K409W | L351Y_F405F_Y407L |
| AZ2538 | T366V_T394V_K409W | L351Y_F405F_Y407M |
| AZ2539 | T366V_T394V_K409W | L351Y_F405F_Y407V |
| AZ2540 | T366I_K392C_K409F_T411I | L351Y_D399C_Y407A |
| AZ2541 | T366I_K392C_K409F_T411I | L351Y_D399C_Y407I |
| AZ2542 | T366I_K392C_K409F_T411I | L351Y_D399C_Y407V |
| AZ2543 | T366I_K392C_K409F_T411L | L351Y_D399C_Y407A |
| AZ2544 | T366I_K392C_K409F_T411L | L351Y_D399C_Y407I |
| AZ2545 | T366I_K392C_K409F_T411L | L351Y_D399C_Y407V |
| AZ2546 | T366I_K392C_K409F_T411T | L351Y_D399C_Y407A |
| AZ2547 | T366I_K392C_K409F_T411T | L351Y_D399C_Y407I |
| AZ2548 | T366I_K392C_K409F_T411T | L351Y_D399C_Y407V |
| AZ2549 | T366I_K392L_K409F_T411E | L351Y_D399R_Y407A |
| AZ2550 | T366I_K392L_K409F_T411E | L351Y_D399R_Y407I |

FIG. 38C

| | | |
|---|---|---|
| AZ2551 | T366I_K392L_K409F_T411E | L351Y_D399R_Y407V |
| AZ2552 | T366M_K392C_K409F_T411I | L351Y_D399C_Y407A |
| AZ2553 | T366M_K392C_K409F_T411I | L351Y_D399C_Y407I |
| AZ2554 | T366M_K392C_K409F_T411I | L351Y_D399C_Y407V |
| AZ2555 | T366M_K392C_K409F_T411L | L351Y_D399C_Y407A |
| AZ2556 | T366M_K392C_K409F_T411L | L351Y_D399C_Y407I |
| AZ2557 | T366M_K392C_K409F_T411L | L351Y_D399C_Y407V |
| AZ2558 | T366M_K392C_K409F_T411T | L351Y_D399C_Y407A |
| AZ2559 | T366M_K392C_K409F_T411T | L351Y_D399C_Y407I |
| AZ2560 | T366M_K392C_K409F_T411T | L351Y_D399C_Y407V |
| AZ2561 | T366M_K392L_K409F_T411E | L351Y_D399R_Y407A |
| AZ2562 | T366M_K392L_K409F_T411E | L351Y_D399R_Y407I |
| AZ2563 | T366M_K392L_K409F_T411E | L351Y_D399R_Y407V |
| AZ2564 | T366V_K392C_K409F_T411I | L351Y_D399C_Y407A |
| AZ2565 | T366V_K392C_K409F_T411I | L351Y_D399C_Y407I |
| AZ2566 | T366V_K392C_K409F_T411I | L351Y_D399C_Y407V |
| AZ2567 | T366V_K392C_K409F_T411L | L351Y_D399C_Y407A |
| AZ2568 | T366V_K392C_K409F_T411L | L351Y_D399C_Y407I |
| AZ2569 | T366V_K392C_K409F_T411L | L351Y_D399C_Y407V |
| AZ2570 | T366V_K392C_K409F_T411T | L351Y_D399C_Y407A |
| AZ2571 | T366V_K392C_K409F_T411T | L351Y_D399C_Y407I |
| AZ2572 | T366V_K392C_K409F_T411T | L351Y_D399C_Y407V |
| AZ2573 | T366V_K392L_K409F_T411E | L351Y_D399R_Y407A |
| AZ2574 | T366V_K392L_K409F_T411E | L351Y_D399R_Y407I |
| AZ2575 | T366V_K392L_K409F_T411E | L351Y_D399R_Y407V |
| AZ2576 | T366I_K392D_K409F_T411D | L351Y_D399R_S400S_Y407A |
| AZ2577 | T366I_K392D_K409F_T411D | L351Y_D399R_S400S_Y407I |
| AZ2578 | T366I_K392D_K409F_T411D | L351Y_D399R_S400S_Y407V |
| AZ2579 | T366I_K392D_K409F_T411D | L351Y_D399K_S400S_Y407A |
| AZ2580 | T366I_K392D_K409F_T411D | L351Y_D399K_S400S_Y407I |
| AZ2581 | T366I_K392D_K409F_T411D | L351Y_D399K_S400S_Y407V |
| AZ2582 | T366I_K392D_K409F_T411E | L351Y_D399R_S400R_Y407A |
| AZ2583 | T366I_K392D_K409F_T411E | L351Y_D399R_S400R_Y407I |
| AZ2584 | T366I_K392D_K409F_T411E | L351Y_D399R_S400R_Y407V |
| AZ2585 | T366I_K392D_K409F_T411E | L351Y_D399R_S400K_Y407A |
| AZ2586 | T366I_K392D_K409F_T411E | L351Y_D399R_S400K_Y407I |
| AZ2587 | T366I_K392D_K409F_T411E | L351Y_D399R_S400K_Y407V |
| AZ2588 | T366I_K392D_K409F_T411E | L351Y_D399R_S400S_Y407A |
| AZ2589 | T366I_K392D_K409F_T411E | L351Y_D399R_S400S_Y407I |
| AZ2590 | T366I_K392D_K409F_T411E | L351Y_D399R_S400S_Y407V |
| AZ2591 | T366I_K392D_K409F_T411E | L351Y_D399K_S400S_Y407A |
| AZ2592 | T366I_K392D_K409F_T411E | L351Y_D399K_S400S_Y407I |
| AZ2593 | T366I_K392D_K409F_T411E | L351Y_D399K_S400S_Y407V |
| AZ2594 | T366I_K392E_K409F_T411D | L351Y_D399R_S400S_Y407A |
| AZ2595 | T366I_K392E_K409F_T411D | L351Y_D399R_S400S_Y407I |
| AZ2596 | T366I_K392E_K409F_T411D | L351Y_D399R_S400S_Y407V |
| AZ2597 | T366I_K392E_K409F_T411D | L351Y_D399K_S400S_Y407A |
| AZ2598 | T366I_K392E_K409F_T411D | L351Y_D399K_S400S_Y407I |
| AZ2599 | T366I_K392E_K409F_T411D | L351Y_D399K_S400S_Y407V |
| AZ2600 | T366I_K392E_K409F_T411E | L351Y_D399R_S400R_Y407A |
| AZ2601 | T366I_K392E_K409F_T411E | L351Y_D399R_S400R_Y407I |
| AZ2602 | T366I_K392E_K409F_T411E | L351Y_D399R_S400R_Y407V |
| AZ2603 | T366I_K392E_K409F_T411E | L351Y_D399R_S400K_Y407A |
| AZ2604 | T366I_K392E_K409F_T411E | L351Y_D399R_S400K_Y407I |
| AZ2605 | T366I_K392E_K409F_T411E | L351Y_D399R_S400K_Y407V |
| AZ2606 | T366I_K392E_K409F_T411E | L351Y_D399R_S400S_Y407A |
| AZ2607 | T366I_K392E_K409F_T411E | L351Y_D399R_S400S_Y407I |
| AZ2608 | T366I_K392E_K409F_T411E | L351Y_D399R_S400S_Y407V |

FIG. 38D

| | | |
|---|---|---|
| AZ2609 | T366I_K392E_K409F_T411E | L351Y_D399K_S400S_Y407A |
| AZ2610 | T366I_K392E_K409F_T411E | L351Y_D399K_S400S_Y407I |
| AZ2611 | T366I_K392E_K409F_T411E | L351Y_D399K_S400S_Y407V |
| AZ2612 | T366M_K392D_K409F_T411D | L351Y_D399R_S400S_Y407A |
| AZ2613 | T366M_K392D_K409F_T411D | L351Y_D399R_S400S_Y407I |
| AZ2614 | T366M_K392D_K409F_T411D | L351Y_D399R_S400S_Y407V |
| AZ2615 | T366M_K392D_K409F_T411D | L351Y_D399K_S400S_Y407A |
| AZ2616 | T366M_K392D_K409F_T411D | L351Y_D399K_S400S_Y407I |
| AZ2617 | T366M_K392D_K409F_T411D | L351Y_D399K_S400S_Y407V |
| AZ2618 | T366M_K392D_K409F_T411E | L351Y_D399R_S400R_Y407A |
| AZ2619 | T366M_K392D_K409F_T411E | L351Y_D399R_S400R_Y407I |
| AZ2620 | T366M_K392D_K409F_T411E | L351Y_D399R_S400R_Y407V |
| AZ2621 | T366M_K392D_K409F_T411E | L351Y_D399R_S400K_Y407A |
| AZ2622 | T366M_K392D_K409F_T411E | L351Y_D399R_S400K_Y407I |
| AZ2623 | T366M_K392D_K409F_T411E | L351Y_D399R_S400K_Y407V |
| AZ2624 | T366M_K392D_K409F_T411E | L351Y_D399R_S400S_Y407A |
| AZ2625 | T366M_K392D_K409F_T411E | L351Y_D399R_S400S_Y407I |
| AZ2626 | T366M_K392D_K409F_T411E | L351Y_D399R_S400S_Y407V |
| AZ2627 | T366M_K392D_K409F_T411E | L351Y_D399K_S400S_Y407A |
| AZ2628 | T366M_K392D_K409F_T411E | L351Y_D399K_S400S_Y407I |
| AZ2629 | T366M_K392D_K409F_T411E | L351Y_D399K_S400S_Y407V |
| AZ2630 | T366M_K392E_K409F_T411D | L351Y_D399R_S400S_Y407A |
| AZ2631 | T366M_K392E_K409F_T411D | L351Y_D399R_S400S_Y407I |
| AZ2632 | T366M_K392E_K409F_T411D | L351Y_D399R_S400S_Y407V |
| AZ2633 | T366M_K392E_K409F_T411D | L351Y_D399K_S400S_Y407A |
| AZ2634 | T366M_K392E_K409F_T411D | L351Y_D399K_S400S_Y407I |
| AZ2635 | T366M_K392E_K409F_T411D | L351Y_D399K_S400S_Y407V |
| AZ2636 | T366M_K392E_K409F_T411E | L351Y_D399R_S400R_Y407A |
| AZ2637 | T366M_K392E_K409F_T411E | L351Y_D399R_S400R_Y407I |
| AZ2638 | T366M_K392E_K409F_T411E | L351Y_D399R_S400R_Y407V |
| AZ2639 | T366M_K392E_K409F_T411E | L351Y_D399R_S400K_Y407A |
| AZ2640 | T366M_K392E_K409F_T411E | L351Y_D399R_S400K_Y407I |
| AZ2641 | T366M_K392E_K409F_T411E | L351Y_D399R_S400K_Y407V |
| AZ2642 | T366M_K392E_K409F_T411E | L351Y_D399R_S400S_Y407A |
| AZ2643 | T366M_K392E_K409F_T411E | L351Y_D399R_S400S_Y407I |
| AZ2644 | T366M_K392E_K409F_T411E | L351Y_D399R_S400S_Y407V |
| AZ2645 | T366M_K392E_K409F_T411E | L351Y_D399K_S400S_Y407A |
| AZ2646 | T366M_K392E_K409F_T411E | L351Y_D399K_S400S_Y407I |
| AZ2647 | T366M_K392E_K409F_T411E | L351Y_D399K_S400S_Y407V |
| AZ2648 | T366V_K392D_K409F_T411D | L351Y_D399R_S400S_Y407A |
| AZ2649 | T366V_K392D_K409F_T411D | L351Y_D399R_S400S_Y407I |
| AZ2650 | T366V_K392D_K409F_T411D | L351Y_D399R_S400S_Y407V |
| AZ2651 | T366V_K392D_K409F_T411D | L351Y_D399K_S400S_Y407A |
| AZ2652 | T366V_K392D_K409F_T411D | L351Y_D399K_S400S_Y407I |
| AZ2653 | T366V_K392D_K409F_T411D | L351Y_D399K_S400S_Y407V |
| AZ2654 | T366V_K392D_K409F_T411E | L351Y_D399R_S400R_Y407A |
| AZ2655 | T366V_K392D_K409F_T411E | L351Y_D399R_S400R_Y407I |
| AZ2656 | T366V_K392D_K409F_T411E | L351Y_D399R_S400R_Y407V |
| AZ2657 | T366V_K392D_K409F_T411E | L351Y_D399R_S400K_Y407A |
| AZ2658 | T366V_K392D_K409F_T411E | L351Y_D399R_S400K_Y407I |
| AZ2659 | T366V_K392D_K409F_T411E | L351Y_D399R_S400K_Y407V |
| AZ2660 | T366V_K392D_K409F_T411E | L351Y_D399R_S400S_Y407A |
| AZ2661 | T366V_K392D_K409F_T411E | L351Y_D399R_S400S_Y407I |
| AZ2662 | T366V_K392D_K409F_T411E | L351Y_D399R_S400S_Y407V |
| AZ2663 | T366V_K392D_K409F_T411E | L351Y_D399K_S400S_Y407A |
| AZ2664 | T366V_K392D_K409F_T411E | L351Y_D399K_S400S_Y407I |
| AZ2665 | T366V_K392D_K409F_T411E | L351Y_D399K_S400S_Y407V |
| AZ2666 | T366V_K392E_K409F_T411D | L351Y_D399R_S400S_Y407A |

FIG. 38E

| | | |
|---|---|---|
| AZ2667 | T366V_K392E_K409F_T411D | L351Y_D399R_S400S_Y407I |
| AZ2668 | T366V_K392E_K409F_T411D | L351Y_D399R_S400S_Y407V |
| AZ2669 | T366V_K392E_K409F_T411D | L351Y_D399K_S400S_Y407A |
| AZ2670 | T366V_K392E_K409F_T411D | L351Y_D399K_S400S_Y407I |
| AZ2671 | T366V_K392E_K409F_T411D | L351Y_D399K_S400S_Y407V |
| AZ2672 | T366V_K392E_K409F_T411E | L351Y_D399R_S400R_Y407A |
| AZ2673 | T366V_K392E_K409F_T411E | L351Y_D399R_S400R_Y407I |
| AZ2674 | T366V_K392E_K409F_T411E | L351Y_D399R_S400R_Y407V |
| AZ2675 | T366V_K392E_K409F_T411E | L351Y_D399R_S400K_Y407A |
| AZ2676 | T366V_K392E_K409F_T411E | L351Y_D399R_S400K_Y407I |
| AZ2677 | T366V_K392E_K409F_T411E | L351Y_D399R_S400K_Y407V |
| AZ2678 | T366V_K392E_K409F_T411E | L351Y_D399R_S400S_Y407A |
| AZ2679 | T366V_K392E_K409F_T411E | L351Y_D399R_S400S_Y407I |
| AZ2680 | T366V_K392E_K409F_T411E | L351Y_D399R_S400S_Y407V |
| AZ2681 | T366V_K392E_K409F_T411E | L351Y_D399K_S400S_Y407A |
| AZ2682 | T366V_K392E_K409F_T411E | L351Y_D399K_S400S_Y407I |
| AZ2683 | T366V_K392E_K409F_T411E | L351Y_D399K_S400S_Y407V |
| AZ2684 | S354C_T366I_K392C_K409F_T411I | Y349C_L351Y_D399C_Y407A |
| AZ2685 | S354C_T366I_K392C_K409F_T411I | Y349C_L351Y_D399C_Y407I |
| AZ2686 | S354C_T366I_K392C_K409F_T411I | Y349C_L351Y_D399C_Y407V |
| AZ2687 | S354C_T366I_K392C_K409F_T411L | Y349C_L351Y_D399C_Y407A |
| AZ2688 | S354C_T366I_K392C_K409F_T411L | Y349C_L351Y_D399C_Y407I |
| AZ2689 | S354C_T366I_K392C_K409F_T411L | Y349C_L351Y_D399C_Y407V |
| AZ2690 | S354C_T366I_K392C_K409F_T411T | Y349C_L351Y_D399C_Y407A |
| AZ2691 | S354C_T366I_K392C_K409F_T411T | Y349C_L351Y_D399C_Y407I |
| AZ2692 | S354C_T366I_K392C_K409F_T411T | Y349C_L351Y_D399C_Y407V |
| AZ2693 | S354C_T366M_K392C_K409F_T411I | Y349C_L351Y_D399C_Y407A |
| AZ2694 | S354C_T366M_K392C_K409F_T411I | Y349C_L351Y_D399C_Y407I |
| AZ2695 | S354C_T366M_K392C_K409F_T411I | Y349C_L351Y_D399C_Y407V |
| AZ2696 | S354C_T366M_K392C_K409F_T411L | Y349C_L351Y_D399C_Y407A |
| AZ2697 | S354C_T366M_K392C_K409F_T411L | Y349C_L351Y_D399C_Y407I |
| AZ2698 | S354C_T366M_K392C_K409F_T411L | Y349C_L351Y_D399C_Y407V |
| AZ2699 | S354C_T366M_K392C_K409F_T411T | Y349C_L351Y_D399C_Y407A |
| AZ2700 | S354C_T366M_K392C_K409F_T411T | Y349C_L351Y_D399C_Y407I |
| AZ2701 | S354C_T366M_K392C_K409F_T411T | Y349C_L351Y_D399C_Y407V |
| AZ2702 | S354C_T366V_K392C_K409F_T411I | Y349C_L351Y_D399C_Y407A |
| AZ2703 | S354C_T366V_K392C_K409F_T411I | Y349C_L351Y_D399C_Y407I |
| AZ2704 | S354C_T366V_K392C_K409F_T411I | Y349C_L351Y_D399C_Y407V |
| AZ2705 | S354C_T366V_K392C_K409F_T411L | Y349C_L351Y_D399C_Y407A |
| AZ2706 | S354C_T366V_K392C_K409F_T411L | Y349C_L351Y_D399C_Y407I |
| AZ2707 | S354C_T366V_K392C_K409F_T411L | Y349C_L351Y_D399C_Y407V |
| AZ2708 | S354C_T366V_K392C_K409F_T411T | Y349C_L351Y_D399C_Y407A |
| AZ2709 | S354C_T366V_K392C_K409F_T411T | Y349C_L351Y_D399C_Y407I |
| AZ2710 | S354C_T366V_K392C_K409F_T411T | Y349C_L351Y_D399C_Y407V |
| AZ2711 | Q362E_T366I_K392L_K409F_T411E | L351Y_G371G_D399R_Y407A |
| AZ2712 | Q362E_T366I_K392L_K409F_T411E | L351Y_G371G_D399R_Y407I |
| AZ2713 | Q362E_T366I_K392L_K409F_T411E | L351Y_G371G_D399R_Y407V |
| AZ2714 | Q362E_T366I_K392L_K409F_T411E | L351Y_G371S_D399R_Y407A |
| AZ2715 | Q362E_T366I_K392L_K409F_T411E | L351Y_G371S_D399R_Y407I |
| AZ2716 | Q362E_T366I_K392L_K409F_T411E | L351Y_G371S_D399R_Y407V |
| AZ2717 | Q362E_T366M_K392L_K409F_T411E | L351Y_G371G_D399R_Y407A |
| AZ2718 | Q362E_T366M_K392L_K409F_T411E | L351Y_G371G_D399R_Y407I |
| AZ2719 | Q362E_T366M_K392L_K409F_T411E | L351Y_G371G_D399R_Y407V |
| AZ2720 | Q362E_T366M_K392L_K409F_T411E | L351Y_G371S_D399R_Y407A |
| AZ2721 | Q362E_T366M_K392L_K409F_T411E | L351Y_G371S_D399R_Y407I |
| AZ2722 | Q362E_T366M_K392L_K409F_T411E | L351Y_G371S_D399R_Y407V |
| AZ2723 | Q362E_T366V_K392L_K409F_T411E | L351Y_G371G_D399R_Y407A |
| AZ2724 | Q362E_T366V_K392L_K409F_T411E | L351Y_G371G_D399R_Y407I |

FIG. 38F

| | | |
|---|---|---|
| AZ2725 | Q362E_T366V_K392L_K409F_T411E | L351Y_G371G_D399R_Y407V |
| AZ2726 | Q362E_T366V_K392L_K409F_T411E | L351Y_G371S_D399R_Y407A |
| AZ2727 | Q362E_T366V_K392L_K409F_T411E | L351Y_G371S_D399R_Y407I |
| AZ2728 | Q362E_T366V_K392L_K409F_T411E | L351Y_G371S_D399R_Y407V |
| AZ2729 | T366I_N390R_K392L_K409F_T411E | L351Y_D399R_S400D_Y407A |
| AZ2730 | T366I_N390R_K392L_K409F_T411E | L351Y_D399R_S400D_Y407I |
| AZ2731 | T366I_N390R_K392L_K409F_T411E | L351Y_D399R_S400D_Y407V |
| AZ2732 | T366I_N390R_K392L_K409F_T411E | L351Y_D399R_S400E_Y407A |
| AZ2733 | T366I_N390R_K392L_K409F_T411E | L351Y_D399R_S400E_Y407I |
| AZ2734 | T366I_N390R_K392L_K409F_T411E | L351Y_D399R_S400E_Y407V |
| AZ2735 | T366I_N390R_K392K_K409F_T411E | L351Y_D399R_S400D_Y407A |
| AZ2736 | T366I_N390R_K392K_K409F_T411E | L351Y_D399R_S400D_Y407I |
| AZ2737 | T366I_N390R_K392K_K409F_T411E | L351Y_D399R_S400D_Y407V |
| AZ2738 | T366I_N390R_K392K_K409F_T411E | L351Y_D399R_S400E_Y407A |
| AZ2739 | T366I_N390R_K392K_K409F_T411E | L351Y_D399R_S400E_Y407I |
| AZ2740 | T366I_N390R_K392K_K409F_T411E | L351Y_D399R_S400E_Y407V |
| AZ2741 | T366I_N390N_K392I_K409F_T411E | L351Y_D399R_S400R_Y407A |
| AZ2742 | T366I_N390N_K392I_K409F_T411E | L351Y_D399R_S400R_Y407I |
| AZ2743 | T366I_N390N_K392I_K409F_T411E | L351Y_D399R_S400R_Y407V |
| AZ2744 | T366I_N390N_K392I_K409F_T411E | L351Y_D399R_S400K_Y407A |
| AZ2745 | T366I_N390N_K392I_K409F_T411E | L351Y_D399R_S400K_Y407I |
| AZ2746 | T366I_N390N_K392I_K409F_T411E | L351Y_D399R_S400K_Y407V |
| AZ2747 | T366I_N390N_K392I_K409F_T411E | L351Y_D399R_S400S_Y407A |
| AZ2748 | T366I_N390N_K392I_K409F_T411E | L351Y_D399R_S400S_Y407I |
| AZ2749 | T366I_N390N_K392I_K409F_T411E | L351Y_D399R_S400S_Y407V |
| AZ2750 | T366I_N390N_K392L_K409F_T411E | L351Y_D399R_S400R_Y407A |
| AZ2751 | T366I_N390N_K392L_K409F_T411E | L351Y_D399R_S400R_Y407I |
| AZ2752 | T366I_N390N_K392L_K409F_T411E | L351Y_D399R_S400R_Y407V |
| AZ2753 | T366I_N390N_K392L_K409F_T411E | L351Y_D399R_S400D_Y407A |
| AZ2754 | T366I_N390N_K392L_K409F_T411E | L351Y_D399R_S400D_Y407I |
| AZ2755 | T366I_N390N_K392L_K409F_T411E | L351Y_D399R_S400D_Y407V |
| AZ2756 | T366I_N390N_K392L_K409F_T411E | L351Y_D399R_S400E_Y407A |
| AZ2757 | T366I_N390N_K392L_K409F_T411E | L351Y_D399R_S400E_Y407I |
| AZ2758 | T366I_N390N_K392L_K409F_T411E | L351Y_D399R_S400E_Y407V |
| AZ2759 | T366I_N390N_K392L_K409F_T411E | L351Y_D399R_S400K_Y407A |
| AZ2760 | T366I_N390N_K392L_K409F_T411E | L351Y_D399R_S400K_Y407I |
| AZ2761 | T366I_N390N_K392L_K409F_T411E | L351Y_D399R_S400K_Y407V |
| AZ2762 | T366I_N390N_K392L_K409F_T411E | L351Y_D399R_S400S_Y407A |
| AZ2763 | T366I_N390N_K392L_K409F_T411E | L351Y_D399R_S400S_Y407I |
| AZ2764 | T366I_N390N_K392L_K409F_T411E | L351Y_D399R_S400S_Y407V |
| AZ2765 | T366I_N390N_K392K_K409F_T411E | L351Y_D399R_S400D_Y407A |
| AZ2766 | T366I_N390N_K392K_K409F_T411E | L351Y_D399R_S400D_Y407I |
| AZ2767 | T366I_N390N_K392K_K409F_T411E | L351Y_D399R_S400D_Y407V |
| AZ2768 | T366I_N390N_K392K_K409F_T411E | L351Y_D399R_S400E_Y407A |
| AZ2769 | T366I_N390N_K392K_K409F_T411E | L351Y_D399R_S400E_Y407I |
| AZ2770 | T366I_N390N_K392K_K409F_T411E | L351Y_D399R_S400E_Y407V |
| AZ2771 | T366I_N390D_K392I_K409F_T411E | L351Y_D399R_S400R_Y407A |
| AZ2772 | T366I_N390D_K392I_K409F_T411E | L351Y_D399R_S400R_Y407I |
| AZ2773 | T366I_N390D_K392I_K409F_T411E | L351Y_D399R_S400R_Y407V |
| AZ2774 | T366I_N390D_K392I_K409F_T411E | L351Y_D399R_S400K_Y407A |
| AZ2775 | T366I_N390D_K392I_K409F_T411E | L351Y_D399R_S400K_Y407I |
| AZ2776 | T366I_N390D_K392I_K409F_T411E | L351Y_D399R_S400K_Y407V |
| AZ2777 | T366I_N390D_K392I_K409F_T411E | L351Y_D399R_S400S_Y407A |
| AZ2778 | T366I_N390D_K392I_K409F_T411E | L351Y_D399R_S400S_Y407I |
| AZ2779 | T366I_N390D_K392I_K409F_T411E | L351Y_D399R_S400S_Y407V |
| AZ2780 | T366I_N390D_K392I_K409F_T411E | L351Y_D399R_S400R_Y407A |
| AZ2781 | T366I_N390D_K392I_K409F_T411E | L351Y_D399R_S400R_Y407I |
| AZ2782 | T366I_N390D_K392I_K409F_T411E | L351Y_D399R_S400R_Y407V |

FIG. 38G

| | | |
|---|---|---|
| AZ2783 | T366I_N390D_K392L_K409F_T411E | L351Y_D399R_S400K_Y407A |
| AZ2784 | T366I_N390D_K392L_K409F_T411E | L351Y_D399R_S400K_Y407I |
| AZ2785 | T366I_N390D_K392L_K409F_T411E | L351Y_D399R_S400K_Y407V |
| AZ2786 | T366I_N390D_K392L_K409F_T411E | L351Y_D399R_S400S_Y407A |
| AZ2787 | T366I_N390D_K392L_K409F_T411E | L351Y_D399R_S400S_Y407I |
| AZ2788 | T366I_N390D_K392L_K409F_T411E | L351Y_D399R_S400S_Y407V |
| AZ2789 | T366I_N390K_K392L_K409F_T411E | L351Y_D399R_S400D_Y407A |
| AZ2790 | T366I_N390K_K392L_K409F_T411E | L351Y_D399R_S400D_Y407I |
| AZ2791 | T366I_N390K_K392L_K409F_T411E | L351Y_D399R_S400D_Y407V |
| AZ2792 | T366I_N390K_K392L_K409F_T411E | L351Y_D399R_S400E_Y407A |
| AZ2793 | T366I_N390K_K392L_K409F_T411E | L351Y_D399R_S400E_Y407I |
| AZ2794 | T366I_N390K_K392L_K409F_T411E | L351Y_D399R_S400E_Y407V |
| AZ2795 | T366I_N390K_K392K_K409F_T411E | L351Y_D399R_S400D_Y407A |
| AZ2796 | T366I_N390K_K392K_K409F_T411E | L351Y_D399R_S400D_Y407I |
| AZ2797 | T366I_N390K_K392K_K409F_T411E | L351Y_D399R_S400D_Y407V |
| AZ2798 | T366I_N390K_K392K_K409F_T411E | L351Y_D399R_S400E_Y407A |
| AZ2799 | T366I_N390K_K392K_K409F_T411E | L351Y_D399R_S400E_Y407I |
| AZ2800 | T366I_N390K_K392K_K409F_T411E | L351Y_D399R_S400E_Y407V |
| AZ2801 | T366M_N390R_K392L_K409F_T411E | L351Y_D399R_S400D_Y407A |
| AZ2802 | T366M_N390R_K392L_K409F_T411E | L351Y_D399R_S400D_Y407I |
| AZ2803 | T366M_N390R_K392L_K409F_T411E | L351Y_D399R_S400D_Y407V |
| AZ2804 | T366M_N390R_K392L_K409F_T411E | L351Y_D399R_S400E_Y407A |
| AZ2805 | T366M_N390R_K392L_K409F_T411E | L351Y_D399R_S400E_Y407I |
| AZ2806 | T366M_N390R_K392L_K409F_T411E | L351Y_D399R_S400E_Y407V |
| AZ2807 | T366M_N390R_K392K_K409F_T411E | L351Y_D399R_S400D_Y407A |
| AZ2808 | T366M_N390R_K392K_K409F_T411E | L351Y_D399R_S400D_Y407I |
| AZ2809 | T366M_N390R_K392K_K409F_T411E | L351Y_D399R_S400D_Y407V |
| AZ2810 | T366M_N390R_K392K_K409F_T411E | L351Y_D399R_S400E_Y407A |
| AZ2811 | T366M_N390R_K392K_K409F_T411E | L351Y_D399R_S400E_Y407I |
| AZ2812 | T366M_N390R_K392K_K409F_T411E | L351Y_D399R_S400E_Y407V |
| AZ2813 | T366M_N390N_K392I_K409F_T411E | L351Y_D399R_S400R_Y407A |
| AZ2814 | T366M_N390N_K392I_K409F_T411E | L351Y_D399R_S400R_Y407I |
| AZ2815 | T366M_N390N_K392I_K409F_T411E | L351Y_D399R_S400R_Y407V |
| AZ2816 | T366M_N390N_K392I_K409F_T411E | L351Y_D399R_S400K_Y407A |
| AZ2817 | T366M_N390N_K392I_K409F_T411E | L351Y_D399R_S400K_Y407I |
| AZ2818 | T366M_N390N_K392I_K409F_T411E | L351Y_D399R_S400K_Y407V |
| AZ2819 | T366M_N390N_K392I_K409F_T411E | L351Y_D399R_S400S_Y407A |
| AZ2820 | T366M_N390N_K392I_K409F_T411E | L351Y_D399R_S400S_Y407I |
| AZ2821 | T366M_N390N_K392I_K409F_T411E | L351Y_D399R_S400S_Y407V |
| AZ2822 | T366M_N390N_K392I_K409F_T411E | L351Y_D399R_S400R_Y407A |
| AZ2823 | T366M_N390N_K392I_K409F_T411E | L351Y_D399R_S400R_Y407I |
| AZ2824 | T366M_N390N_K392I_K409F_T411E | L351Y_D399R_S400R_Y407V |
| AZ2825 | T366M_N390N_K392I_K409F_T411E | L351Y_D399R_S400D_Y407A |
| AZ2826 | T366M_N390N_K392I_K409F_T411E | L351Y_D399R_S400D_Y407I |
| AZ2827 | T366M_N390N_K392I_K409F_T411E | L351Y_D399R_S400D_Y407V |
| AZ2828 | T366M_N390N_K392I_K409F_T411E | L351Y_D399R_S400E_Y407A |
| AZ2829 | T366M_N390N_K392I_K409F_T411E | L351Y_D399R_S400E_Y407I |
| AZ2830 | T366M_N390N_K392I_K409F_T411E | L351Y_D399R_S400E_Y407V |
| AZ2831 | T366M_N390N_K392I_K409F_T411E | L351Y_D399R_S400K_Y407A |
| AZ2832 | T366M_N390N_K392I_K409F_T411E | L351Y_D399R_S400K_Y407I |
| AZ2833 | T366M_N390N_K392I_K409F_T411E | L351Y_D399R_S400K_Y407V |
| AZ2834 | T366M_N390N_K392I_K409F_T411E | L351Y_D399R_S400S_Y407A |
| AZ2835 | T366M_N390N_K392I_K409F_T411E | L351Y_D399R_S400S_Y407I |
| AZ2836 | T366M_N390N_K392I_K409F_T411E | L351Y_D399R_S400S_Y407V |
| AZ2837 | T366M_N390N_K392K_K409F_T411E | L351Y_D399R_S400D_Y407A |
| AZ2838 | T366M_N390N_K392K_K409F_T411E | L351Y_D399R_S400D_Y407I |
| AZ2839 | T366M_N390N_K392K_K409F_T411E | L351Y_D399R_S400D_Y407V |
| AZ2840 | T366M_N390N_K392K_K409F_T411E | L351Y_D399R_S400E_Y407A |

FIG. 38H

| | | |
|---|---|---|
| AZ2841 | T366M_N390N_K392K_K409F_T411E | L351Y_D399R_S400E_Y407I |
| AZ2842 | T366M_N390N_K392K_K409F_T411E | L351Y_D399R_S400E_Y407V |
| AZ2843 | T366M_N390D_K392I_K409F_T411E | L351Y_D399R_S400R_Y407A |
| AZ2844 | T366M_N390D_K392I_K409F_T411E | L351Y_D399R_S400R_Y407I |
| AZ2845 | T366M_N390D_K392I_K409F_T411E | L351Y_D399R_S400R_Y407V |
| AZ2846 | T366M_N390D_K392I_K409F_T411E | L351Y_D399R_S400K_Y407A |
| AZ2847 | T366M_N390D_K392I_K409F_T411E | L351Y_D399R_S400K_Y407I |
| AZ2848 | T366M_N390D_K392I_K409F_T411E | L351Y_D399R_S400K_Y407V |
| AZ2849 | T366M_N390D_K392I_K409F_T411E | L351Y_D399R_S400S_Y407A |
| AZ2850 | T366M_N390D_K392I_K409F_T411E | L351Y_D399R_S400S_Y407I |
| AZ2851 | T366M_N390D_K392I_K409F_T411E | L351Y_D399R_S400S_Y407V |
| AZ2852 | T366M_N390D_K392L_K409F_T411E | L351Y_D399R_S400R_Y407A |
| AZ2853 | T366M_N390D_K392L_K409F_T411E | L351Y_D399R_S400R_Y407I |
| AZ2854 | T366M_N390D_K392L_K409F_T411E | L351Y_D399R_S400R_Y407V |
| AZ2855 | T366M_N390D_K392L_K409F_T411E | L351Y_D399R_S400K_Y407A |
| AZ2856 | T366M_N390D_K392L_K409F_T411E | L351Y_D399R_S400K_Y407I |
| AZ2857 | T366M_N390D_K392L_K409F_T411E | L351Y_D399R_S400K_Y407V |
| AZ2858 | T366M_N390D_K392L_K409F_T411E | L351Y_D399R_S400S_Y407A |
| AZ2859 | T366M_N390D_K392L_K409F_T411E | L351Y_D399R_S400S_Y407I |
| AZ2860 | T366M_N390D_K392L_K409F_T411E | L351Y_D399R_S400S_Y407V |
| AZ2861 | T366M_N390K_K392I_K409F_T411E | L351Y_D399R_S400D_Y407A |
| AZ2862 | T366M_N390K_K392I_K409F_T411E | L351Y_D399R_S400D_Y407I |
| AZ2863 | T366M_N390K_K392I_K409F_T411E | L351Y_D399R_S400D_Y407V |
| AZ2864 | T366M_N390K_K392I_K409F_T411E | L351Y_D399R_S400E_Y407A |
| AZ2865 | T366M_N390K_K392I_K409F_T411E | L351Y_D399R_S400E_Y407I |
| AZ2866 | T366M_N390K_K392I_K409F_T411E | L351Y_D399R_S400E_Y407V |
| AZ2867 | T366M_N390K_K392L_K409F_T411E | L351Y_D399R_S400D_Y407A |
| AZ2868 | T366M_N390K_K392L_K409F_T411E | L351Y_D399R_S400D_Y407I |
| AZ2869 | T366M_N390K_K392L_K409F_T411E | L351Y_D399R_S400D_Y407V |
| AZ2870 | T366M_N390K_K392K_K409F_T411E | L351Y_D399R_S400E_Y407A |
| AZ2871 | T366M_N390K_K392K_K409F_T411E | L351Y_D399R_S400E_Y407I |
| AZ2872 | T366M_N390K_K392K_K409F_T411E | L351Y_D399R_S400E_Y407V |
| AZ2873 | T366V_N390R_K392I_K409F_T411E | L351Y_D399R_S400D_Y407A |
| AZ2874 | T366V_N390R_K392I_K409F_T411E | L351Y_D399R_S400D_Y407I |
| AZ2875 | T366V_N390R_K392I_K409F_T411E | L351Y_D399R_S400D_Y407V |
| AZ2876 | T366V_N390R_K392I_K409F_T411E | L351Y_D399R_S400E_Y407A |
| AZ2877 | T366V_N390R_K392I_K409F_T411E | L351Y_D399R_S400E_Y407I |
| AZ2878 | T366V_N390R_K392I_K409F_T411E | L351Y_D399R_S400E_Y407V |
| AZ2879 | T366V_N390R_K392K_K409F_T411E | L351Y_D399R_S400D_Y407A |
| AZ2880 | T366V_N390R_K392K_K409F_T411E | L351Y_D399R_S400D_Y407I |
| AZ2881 | T366V_N390R_K392K_K409F_T411E | L351Y_D399R_S400D_Y407V |
| AZ2882 | T366V_N390R_K392K_K409F_T411E | L351Y_D399R_S400E_Y407A |
| AZ2883 | T366V_N390R_K392K_K409F_T411E | L351Y_D399R_S400E_Y407I |
| AZ2884 | T366V_N390R_K392K_K409F_T411E | L351Y_D399R_S400E_Y407V |
| AZ2885 | T366V_N390N_K392I_K409F_T411E | L351Y_D399R_S400R_Y407A |
| AZ2886 | T366V_N390N_K392I_K409F_T411E | L351Y_D399R_S400R_Y407I |
| AZ2887 | T366V_N390N_K392I_K409F_T411E | L351Y_D399R_S400R_Y407V |
| AZ2888 | T366V_N390N_K392I_K409F_T411E | L351Y_D399R_S400K_Y407A |
| AZ2889 | T366V_N390N_K392I_K409F_T411E | L351Y_D399R_S400K_Y407I |
| AZ2890 | T366V_N390N_K392I_K409F_T411E | L351Y_D399R_S400K_Y407V |
| AZ2891 | T366V_N390N_K392I_K409F_T411E | L351Y_D399R_S400S_Y407A |
| AZ2892 | T366V_N390N_K392I_K409F_T411E | L351Y_D399R_S400S_Y407I |
| AZ2893 | T366V_N390N_K392I_K409F_T411E | L351Y_D399R_S400S_Y407V |
| AZ2894 | T366V_N390N_K392L_K409F_T411E | L351Y_D399R_S400R_Y407A |
| AZ2895 | T366V_N390N_K392L_K409F_T411E | L351Y_D399R_S400R_Y407I |
| AZ2896 | T366V_N390N_K392L_K409F_T411E | L351Y_D399R_S400R_Y407V |
| AZ2897 | T366V_N390N_K392L_K409F_T411E | L351Y_D399R_S400D_Y407A |
| AZ2898 | T366V_N390N_K392L_K409F_T411E | L351Y_D399R_S400D_Y407I |

FIG. 38I

| | | |
|---|---|---|
| AZ2899 | T366V_N390N_K392L_K409F_T411E | L351Y_D399R_S400D_Y407V |
| AZ2900 | T366V_N390N_K392L_K409F_T411E | L351Y_D399R_S400D_Y407A |
| AZ2901 | T366V_N390N_K392L_K409F_T411E | L351Y_D399R_S400E_Y407I |
| AZ2902 | T366V_N390N_K392L_K409F_T411E | L351Y_D399R_S400D_Y407V |
| AZ2903 | T366V_N390N_K392L_K409F_T411E | L351Y_D399R_S400D_Y407A |
| AZ2904 | T366V_N390N_K392L_K409F_T411E | L351Y_D399R_S400D_Y407I |
| AZ2905 | T366V_N390N_K392L_K409F_T411E | L351Y_D399R_S400D_Y407V |
| AZ2906 | T366V_N390N_K392L_K409F_T411E | L351Y_D399R_S400S_Y407A |
| AZ2907 | T366V_N390N_K392L_K409F_T411E | L351Y_D399R_S400S_Y407I |
| AZ2908 | T366V_N390N_K392L_K409F_T411E | L351Y_D399R_S400S_Y407V |
| AZ2909 | T366V_N390N_K392K_K409F_T411E | L351Y_D399R_S400D_Y407A |
| AZ2910 | T366V_N390N_K392K_K409F_T411E | L351Y_D399R_S400D_Y407I |
| AZ2911 | T366V_N390N_K392K_K409F_T411E | L351Y_D399R_S400D_Y407V |
| AZ2912 | T366V_N390N_K392K_K409F_T411E | L351Y_D399R_S400E_Y407A |
| AZ2913 | T366V_N390N_K392K_K409F_T411E | L351Y_D399R_S400E_Y407I |
| AZ2914 | T366V_N390N_K392K_K409F_T411E | L351Y_D399R_S400E_Y407V |
| AZ2915 | T366V_N390D_K392L_K409F_T411E | L351Y_D399R_S400K_Y407A |
| AZ2916 | T366V_N390D_K392L_K409F_T411E | L351Y_D399R_S400K_Y407I |
| AZ2917 | T366V_N390D_K392L_K409F_T411E | L351Y_D399R_S400K_Y407V |
| AZ2918 | T366V_N390D_K392L_K409F_T411E | L351Y_D399R_S400K_Y407A |
| AZ2919 | T366V_N390D_K392L_K409F_T411E | L351Y_D399R_S400K_Y407I |
| AZ2920 | T366V_N390D_K392L_K409F_T411E | L351Y_D399R_S400K_Y407V |
| AZ2921 | T366V_N390D_K392L_K409F_T411E | L351Y_D399R_S400S_Y407A |
| AZ2922 | T366V_N390D_K392L_K409F_T411E | L351Y_D399R_S400S_Y407I |
| AZ2923 | T366V_N390D_K392L_K409F_T411E | L351Y_D399R_S400S_Y407V |
| AZ2924 | T366V_N390D_K392L_K409F_T411E | L351Y_D399R_S400K_Y407A |
| AZ2925 | T366V_N390D_K392L_K409F_T411E | L351Y_D399R_S400K_Y407I |
| AZ2926 | T366V_N390D_K392L_K409F_T411E | L351Y_D399R_S400K_Y407V |
| AZ2927 | T366V_N390D_K392L_K409F_T411E | L351Y_D399R_S400K_Y407A |
| AZ2928 | T366V_N390D_K392L_K409F_T411E | L351Y_D399R_S400K_Y407I |
| AZ2929 | T366V_N390D_K392L_K409F_T411E | L351Y_D399R_S400K_Y407V |
| AZ2930 | T366V_N390D_K392L_K409F_T411E | L351Y_D399R_S400S_Y407A |
| AZ2931 | T366V_N390D_K392L_K409F_T411E | L351Y_D399R_S400S_Y407I |
| AZ2932 | T366V_N390D_K392L_K409F_T411E | L351Y_D399R_S400S_Y407V |
| AZ2933 | T366V_N390K_K392L_K409F_T411E | L351Y_D399R_S400D_Y407A |
| AZ2934 | T366V_N390K_K392L_K409F_T411E | L351Y_D399R_S400D_Y407I |
| AZ2935 | T366V_N390K_K392L_K409F_T411E | L351Y_D399R_S400D_Y407V |
| AZ2936 | T366V_N390K_K392L_K409F_T411E | L351Y_D399R_S400E_Y407A |
| AZ2937 | T366V_N390K_K392L_K409F_T411E | L351Y_D399R_S400E_Y407I |
| AZ2938 | T366V_N390K_K392L_K409F_T411E | L351Y_D399R_S400E_Y407V |
| AZ2939 | T366V_N390K_K392K_K409F_T411E | L351Y_D399R_S400D_Y407A |
| AZ2940 | T366V_N390K_K392K_K409F_T411E | L351Y_D399R_S400D_Y407I |
| AZ2941 | T366V_N390K_K392K_K409F_T411E | L351Y_D399R_S400D_Y407V |
| AZ2942 | T366V_N390K_K392K_K409F_T411E | L351Y_D399R_S400E_Y407A |
| AZ2943 | T366V_N390K_K392K_K409F_T411E | L351Y_D399R_S400E_Y407I |
| AZ2944 | T366V_N390K_K392K_K409F_T411E | L351Y_D399R_S400E_Y407V |

STABLE HETERODIMERIC ANTIBODY DESIGN WITH MUTATIONS IN THE FC DOMAIN

CROSS REFERENCE TO RELATED APPLICATIONS

This application is a continuation of U.S. application Ser. No. 13/289,934. Filed Nov. 4, 2011, which claims the benefit under 35 U.S.C. § 119(e) of U.S. Provisional Patent Application No. 61/410,746, filed Nov. 5, 2010; U.S. Provisional Patent Application No. 61/425,375, filed Dec. 21, 2010; U.S. Provisional Patent Application No. 61/439,341, filed Feb. 3, 2011; U.S. Provisional Patent Application No. 61/475,614, filed Apr. 14, 2011; U.S. Provisional Patent Application No. 61/491,846, filed May 31, 2011 and U.S. Provisional Patent Application No. 61/497,861, filed Jun. 16, 2011, each of which is herein incorporated by reference in its entirety.

STATEMENT REGARDING SEQUENCE LISTING

This application incorporates by reference a Sequence Listing submitted with this application as text file Zymeworks V84467WO.txt created on Nov. 4, 2011 and having a size of 15 kilobytes.

FIELD OF THE INVENTION

The present disclosure generally provides polypeptide heterodimers, compositions thereof, and methods for making and using such polypeptide heterodimers. More specifically, the present invention relates to thermo-stable multi-specific, including bispecific, antibodies comprising a heterodimeric Fc domain.

BACKGROUND OF THE INVENTION

Bispecific antibodies are antibody-based molecules that can simultaneously bind two separate and distinct antigens (or different epitopes of the same antigen). One use of bispecific antibodies has been to redirect cytotoxic immune effector cells for enhanced killing of tumor cells, such as by antibody dependent cellular cytotoxicity (ADCC). In this context, one arm of the bispecific antibody binds an antigen on the tumor cell, and the other binds a determinant expressed on effector cells. By cross-linking tumor and effector cells, the bispecific antibody not only brings the effector cells within the proximity of the tumor cells but also simultaneously triggers their activation, leading to effective tumor cell-killing. Bispecific antibodies have also been used to enrich chemo- or radiotherapeutic agents in tumor tissues to minimize detrimental effects to normal tissue. In this setting, one arm of the bispecific antibody binds an antigen expressed on the cell targeted for destruction, and the other arm delivers a chemotherapeutic drug, radioisotope, or toxin.

A major obstacle in the general development of bispecific antibodies has been the difficulty of producing materials of sufficient quality and quantity for both preclinical and clinical studies.

Traditional production of full-length bispecific antibodies is based on the co-expression of two immunoglobulin heavy chain-light chain pairs, where the two chains have different specificities (Millstein et al., 1983, Nature, 305:537-539). The intrinsic tendency of the Fc portion of the antibody molecule to dimerize leads to the formation of complex mixtures of up to 10 different IgG molecules consisting of various combinations of heavy and light chains, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., 1991, EMBO J., 10:3655-3659. Thus, the production of a bispecific antibody molecule with the two Fab arms selected to bind two different targets using traditional hybridoma techniques is challenging [Segal D M et al. (2001) J Immunol Methods. 248, 1-6.]. The trifunctional antibody, Catumaxomab, is a rat/mouse quadroma derived bispecific mAb and the purification of this molecule is achieved on the basis of a pH dependent elution in protein A column based chromatographic separation [Lindhofer H. et al. (1995) J Immunol 155, 219-225].

Another traditional method for bispecific antibody production is chemical conjugation of two antibodies or their fragments having different specificities. However, this method is also complicated, and the chemical modification process may inactivate the antibody or promote aggregation. Because purification from undesired products remains difficult, the resulting low yield and poor quality of bispecific antibody make this process unsuitable for the large scale production required for clinical development. In addition, these molecules may not maintain the traditional antibody conformation.

Recently, various heterodimerization techniques have been used to improve the production of bispecific antibodies. However, fusion of simple heterodimerization domains like the Jun/Fos coiled-coil to scFv domains lead to a mixture of homo- and heterodimers and need to be assembled by refolding (de Kruif and Logtenberg, J. Biol. Chem. 271: 7630-4, 1996). Fusion of scFv fragments to whole antibodies was also used as a dimerization device (Coloma and Morrison, Nat. Biotechnol. 15: 159-63, 1997). However, such fusion results in a large molecule with poor solid tissue penetration capabilities. Fusion of two scFv fragments together has also been used to generate bispecific proteins (e.g., BITE® antibodies by Micromet Inc., Bethesda, Md., U.S. Pat. No. 7,635,472). However, such proteins do not contain Fc regions, and thus do not allow manipulation of their activities via Fc regions. In addition, these proteins are small (~55 kDa) and thus have a relatively short half-live in serum.

In other heterodimerization techniques, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., 1986, Methods in Enzymology, 121:210.

According to another approach described in WO96/27011, a pair of antibody molecules can be engineered to maximize the percentage of heterodimers that are recovered from recombinant cell culture. In this method, one or more small amino acid side chains from the CH3 interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers [US005731168A, US007183076B2, Ridgway J B, Presta L G, Carter P. *Protein Eng* 1996 July; 9(7): 617-21; Atwell S, Ridgway J B, Wells J A, Carter P. *J Mol Biol* 1997 Jul. 4; 270(1): 26-35.]. Gunasekaran and coworkers [Gunasekaran K. et al. (2010) *J Biol Chem.* 285, 19637-46] have recently employed a complementary electrostatic design strategy to achieve the selective heterodimerization goal. Davis and coworkers [Davis, J H. et al. (2010) Prot Eng Des Sel; 23(4):195-202] have designed CH3 domains using a strand exchange engineered domain (SEED), which comprises of alternating segments of human IgA and IgG CH3 sequences, and these preferentially associate in the form of heterodimers. However, all of these technologies result in antibodies comprising heterodimer Fc regions that are significantly less stable than the parent or wildtype molecule.

Therefore, there remains a need in the art for alternative multispecific variant Fc heterodimers, specifically variant CH3 domains, which have been modified to select for heterodimers with an increased stability and purity.

SUMMARY OF THE INVENTION

There is provided according to one aspect of the invention an isolated heteromultimer comprising a heterodimer Fc region, wherein the heterodimer Fc region comprises a variant CH3 domain comprising amino acid mutations to promote heterodimer formation, wherein the heterodimer Fc region further comprises a variant CH2 domain comprising asymmetric amino acid modifications to promote selective binding of a Fcgamma receptor. In one embodiment the variant CH2 domain selectively binds Fcgamma IIIa receptor as compared to wild-type CH2 domain. In one embodiment, the variant CH3 domain has a melting temperature (Tm) of about 70° C. or greater.

There is provided in another aspect an isolated heteromultimer comprising a heterodimer Fc region, wherein the heterodimer Fc region comprises a variant CH3 domain comprising amino acid mutations to promote heterodimer formation with increased stability, wherein the variant CH3 domain has a melting temperature (Tm) of about 70° C. or greater. In one embodiment, heterodimer Fc region does not comprise an additional disulfide bond in the CH3 domain relative to a wild type Fc region, more specifically the heterodimer Fc region does not comprise an additional disulfide bond in the CH3 domain relative to a wild type Fc region. In an alternative embodiment, the heterodimer Fc region comprises an additional disulfide bond in the variant CH3 domain relative to a wild type Fc region, with the proviso that the melting temperature (Tm) of about 70° C. or greater is in the absence of the additional disulfide bond. In yet another embodiment, the heterodimer Fc region comprises an additional disulfide bond in the variant CH3 domain relative to a wild type Fc region, and wherein the variant CH3 domain has a melting temperature (Tm) of about 77.5° C. or greater.

Provided in one embodiment, an isolated heteromultimer comprising a heterodimer Fc region, wherein the heterodimer Fc region comprises a variant CH3 domain comprising amino acid mutations to promote heterodimer formation with increased stability, wherein the variant CH3 domain has a melting temperature (Tm) of about 70° C. or greater and the heterodimer Fc region has a purity greater than about 90%, or the heterodimer Fc region has a purity of about 95% or greater or the heterodimer Fc region has a purity of about 98% or greater.

Also provided in one embodiment is an isolated heteromultimer comprising a heterodimer Fc region, wherein the heterodimer Fc region comprises a variant CH3 domain comprising amino acid mutations to promote heterodimer formation with increased stability, wherein the variant CH3 domain has a melting temperature (Tm) of about 70° C. or greater or the Tm is about 71° C. or greater or the Tm is about 74° C. or greater. In another embodiment, the heterodimer Fc region has a purity of about 98% or greater and the Tm is about 73° C. or wherein the heterodimer Fc region has a purity of about 90% or greater and the Tm is about 75° C.

Provided in certain embodiments is an isolated heteromultimer comprising a heterodimer Fc region, wherein the heterodimer Fc region comprises a first CH3 domain polypeptide comprising amino acid modifications L351Y and Y407A and a second CH3 domain polypeptide comprising amino acid modifications T366A and K409F. In one aspect, the first CH3 domain polypeptide or the second CH3 domain polypeptide comprises a further amino acid modification at position T411, D399, S400, F405, N390, or K392. The amino acid modification at position T411 is selected from T411N, T411R, T411Q, T411K, T411D, T411E or T411W. The amino acid modification at position D399 is selected from D399R, D399W, D399Y or D399K. The amino acid modification at position S400 is selected from S400E, S400D, S400R, or S400K. The amino acid modification at position F405 is selected from F405I, F405M, F405T, F405S, F405V or F405W. The amino acid modification at position N390 is selected from N390R, N390K or N390D. The amino acid modification at position K392 is selected from K392V, K392M, K392R, K392L, K392F or K392E.

In certain embodiments is provided an isolated heteromultimer comprising a heterodimer Fc region, wherein the heterodimer Fc region comprises a first CH3 domain polypeptide comprising amino acid modifications L351Y and Y407A and a second CH3 domain polypeptide comprising amino acid modifications T366V and K409F.

In another embodiment is provided an isolated heteromultimer comprising a heterodimer Fc region, wherein the heterodimer Fc region comprises a first CH3 domain polypeptide comprising amino acid modification Y407A and a second CH3 domain polypeptide comprising amino acid modifications T366A and K409F. In one aspect the first CH3 domain polypeptide or the second CH3 domain polypeptide comprises further amino acid modifications K392E, T411E, D399R and S400R. In another aspect, the first CH3 domain polypeptide comprises amino acid modification D399R, S400R and Y407A and the second CH3 domain polypeptide comprises amino acid modification T366A, K409F, K392E and T411E. In a further embodiment the variant CH3 domain has a melting temperature (Tm) of about 74° C. or greater and the heterodimer has a purity of about 95% or greater.

Provided in another embodiment is an isolated heteromultimer comprising a heterodimer Fc region, wherein the heterodimer Fc region comprises a first CH3 domain polypeptide comprising an amino acid modification at positions L351 and amino acid modification Y407A and a second CH3 domain polypeptide comprises an amino acid modification at position T366 and amino acid modification K409F. In one aspect the amino acid modification at position L351 is selected from L351Y, L351I, L351D, L351R or L351F. In another aspect, the amino acid modification at position Y407 is selected from Y407A, Y407V or Y407S. In yet another aspect the amino acid modification at position T366 is selected from T366A, T366I, T366L, T366M, T366Y, T366S, T366C, T366V or T366W. In one embodiment the variant CH3 domain has a melting temperature (Tm) of about 75° C. or greater and the heterodimer has a purity of about 90% or greater.

Provided in another embodiment is an isolated heteromultimer comprising a heterodimer Fc region, wherein the heterodimer Fc region comprises a first CH3 domain polypeptide comprising an amino acid modification at position F405 and amino acid modifications L351Y and Y407V and a second CH3 domain polypeptide comprises amino acid modification T394W. In one aspect the first CH3 domain polypeptide or the second CH3 domain polypeptide comprise an amino acid modification at positions K392, T411, T366, L368 or S400. The amino acid modification at position F405 is F405A, F405I, F405M, F405T, F405S, F405V or F405W. The amino acid modification at position K392 is K392V, K392M, K392R, K392L, K392F or K392E. The amino acid modification at position T411 is T411N, T411R, T411Q, T411K, T411D, T411E or T411W. The amino acid modification at position S400 is S400E, S400D, S400R or S400K. The amino acid modification at position T366 is T366A, T366I, T366L, T366M, T366Y, T366S, T366C, T366V or T366W. The amino acid modification at position L368 is L368D, L368R, L368T, L368M, L368V, L368F, L368S and L368A.

In another embodiment is provided an isolated heteromultimer comprising a heterodimer Fc region, wherein the heterodimer Fc region comprises a first CH3 domain polypeptide comprising an amino acid modifications L351Y, F405A and Y407V and a second CH3 domain polypeptide comprises amino acid modification T394W. In one aspect, the second CH3 domain polypeptide comprises amino acid modification T366L or T366I.

In yet another embodiment is provided an isolated heteromultimer comprising a heterodimer Fc region, wherein the heterodimer Fc region comprises a first CH3 domain polypeptide comprising an amino acid modifications F405A and Y407V and a second CH3 domain polypeptide comprises amino acid modifications T366I, K392M and T394W.

In certain embodiments are provided an isolated heteromultimer comprising a heterodimer Fc region, wherein the heterodimer Fc region comprises a first CH3 domain polypeptide comprising an amino acid modifications F405A and Y407V and a second CH3 domain polypeptide comprises amino acid modifications T366L, K392M and T394W.

In another embodiment is provided an isolated heteromultimer comprising a heterodimer Fc region, wherein the heterodimer Fc region comprises a first CH3 domain polypeptide comprising an amino acid modifications F405A and Y407V and a second CH3 domain polypeptide comprises amino acid modifications T366L and T394W.

In another embodiment is provided an isolated heteromultimer comprising a heterodimer Fc region, wherein the heterodimer Fc region comprises a first CH3 domain polypeptide comprising an amino acid modifications F405A and Y407V and a second CH3 domain polypeptide comprises amino acid modifications T366I and T394W.

In certain embodiments of the heteromultimer is provided bispecific antibody or a multispecific antibody.

In another embodiment is provided a composition comprising a heteromultimer of the invention and a pharmaceutically acceptable carrier.

In another embodiment is provided a host cell comprising nucleic acid encoding the heteromultimer of the invention.

In certain embodiments is provided heteromultimer, wherein the heteromultimer comprises at least one therapeutic antibody. In one aspect the therapeutic antibody is selected from the group consisting of abagovomab, adalimumab, alemtuzumab, aurograb, bapineuzumab, basiliximab, belimumab, bevacizumab, briakinumab, canakinumab, catumaxomab, certolizumab pegol, cetuximab, daclizumab, denosumab, efalizumab, galiximab, gemtuzumab ozogamicin, golimumab, ibritumomab tiuxetan, infliximab, ipilimumab, lumiliximab, mepolizumab, motavizumab, muromonab, mycograb, natalizumab, nimotuzumab, ocrelizumab, ofatumumab, omalizumab, palivizumab, panitumumab, pertuzumab, ranibizumab, reslizumab, rituximab, teplizumab, tocilizumab/atlizumab, tositumomab, trastuzumab, Proxinium™, Rencarex™, ustekinumab, and zalutumumab.

In another embodiment of the heteromultimer of the invention is provided a method of treating cancer in a patient having a cancer characterized by a cancer antigen, said method comprising administering to said patient a therapeutically effective amount of a heteromultimer.

In another embodiment of the heteromultimer of the invention is provided a method of treating immune disorders in a patient having an immune disorder characterized by an immune antigen, said method comprising administering to said patient a therapeutically effective amount of a heteromultimer.

In yet another embodiment is provided an isolated heteromultimer comprising a heterodimer Fc region, wherein the heterodimer Fc region comprises a variant CH3 domain comprising amino acid mutations to promote heterodimer formation with increased stability and wherein the variant CH3 domains are selected from the variants listed in Table 1, Table 6 or Table 7.

BRIEF DESCRIPTION OF THE FIGURES

FIG. 4 is a graphical 3-D representation of additional mutations in Region 2;

FIG. 7 show graphical 3-D representations of AZ2 and AZ3 variants;

FIG. 12 is a table as described for FIG. 5 showing in silico data for AZ4, AZ5 and AZ6;

Figure 16:
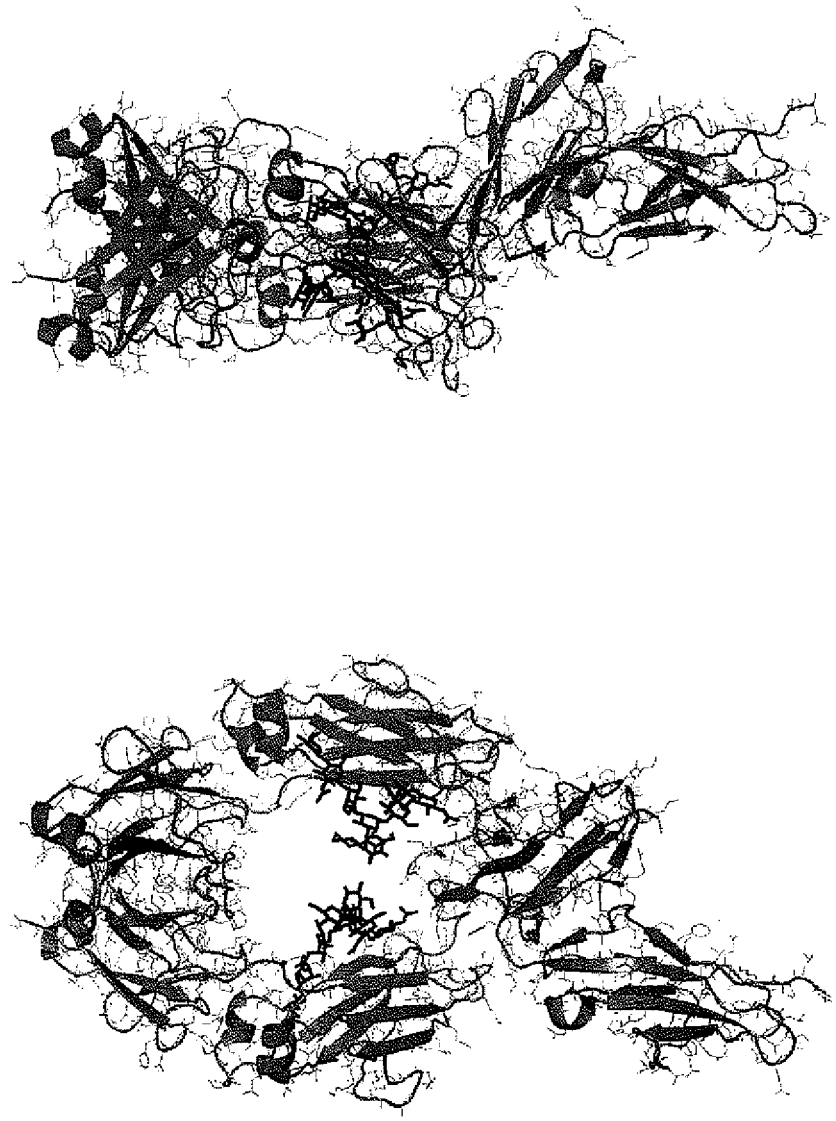
Figure 17:
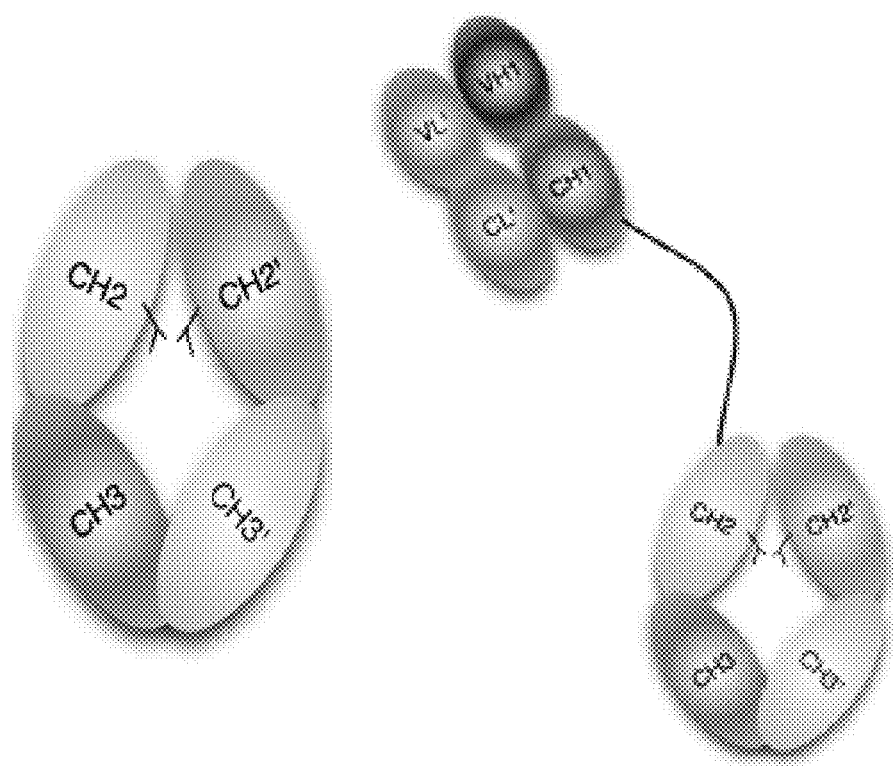

FcγRIIA (sp P12318), FcγRIIB (sp P31994), FcγRIIC (gi 126116592), FcγRIIIA (sp P08637), FcγRIIIB (sp O75015);

FIG. 16 is a schematic of the crystal structure of Fc-FcγRIIIb Complex [PDB ID: 1T83, Radaev & Sun]. A 1:1 complex of the Fc and Fcγ receptor is observed with an asymmetric contact between the two chains of Fc and the FcγR;

FIG. 17 shows a schematic of alternative multifunctional molecules based on the asymmetric Fc scaffold:

Asymetric Fc Scaffold and Asymetric Fc-Monomeric IgG Arm;

FIG. 18 shows a schematic of alternative multifunctional molecules based on the asymmetric Fc scaffold:

Asymmetric Fc-Monospecific IgG arms and Asymmetric Fc-Bispecific IgG Arms (Common Light Chain);

FIG. 19 shows an illustration of alternative multifunctional molecules based on the asymmetric Fc scaffold. Asymmetric Fc-Bispecific IgG Arms and a functional molecule such as toxin;

FIG. 20 illustrates alternative multifunctional molecules based on the asymmetric Fc scaffold:

Asymmetric Fc-Single scFv arm and Asymmetric Fc-bispecific scFv Arms;

FIG. 21 illustrations of alternative multifunctional molecules based on the assymetric Fc scaffold:

Asymmetric Fc-Trispecific scFv Arms and Asymmetric Fc-tetraspecific scFv arms.

Figure 22:
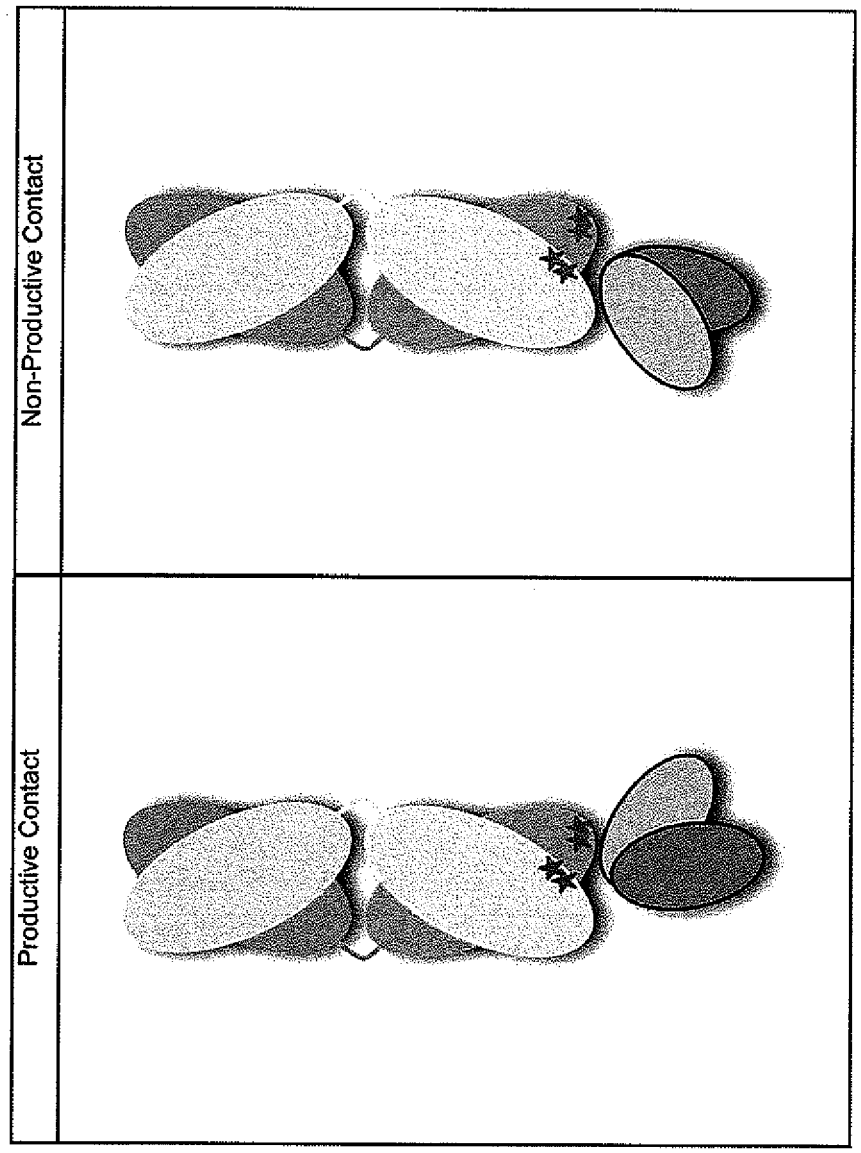

FIG. 22 displays asymmetric design of mutations on one face of the Fc for better FcγR selectivity introduces a productive side for FcγR interactions and a non-productive face with wild type like interactions. Mutations on the non-productive face of the Fc can be introduced to block interactions with FcR and bias polarity of the Fc so as to interact on the productive face only.

Figure 23:
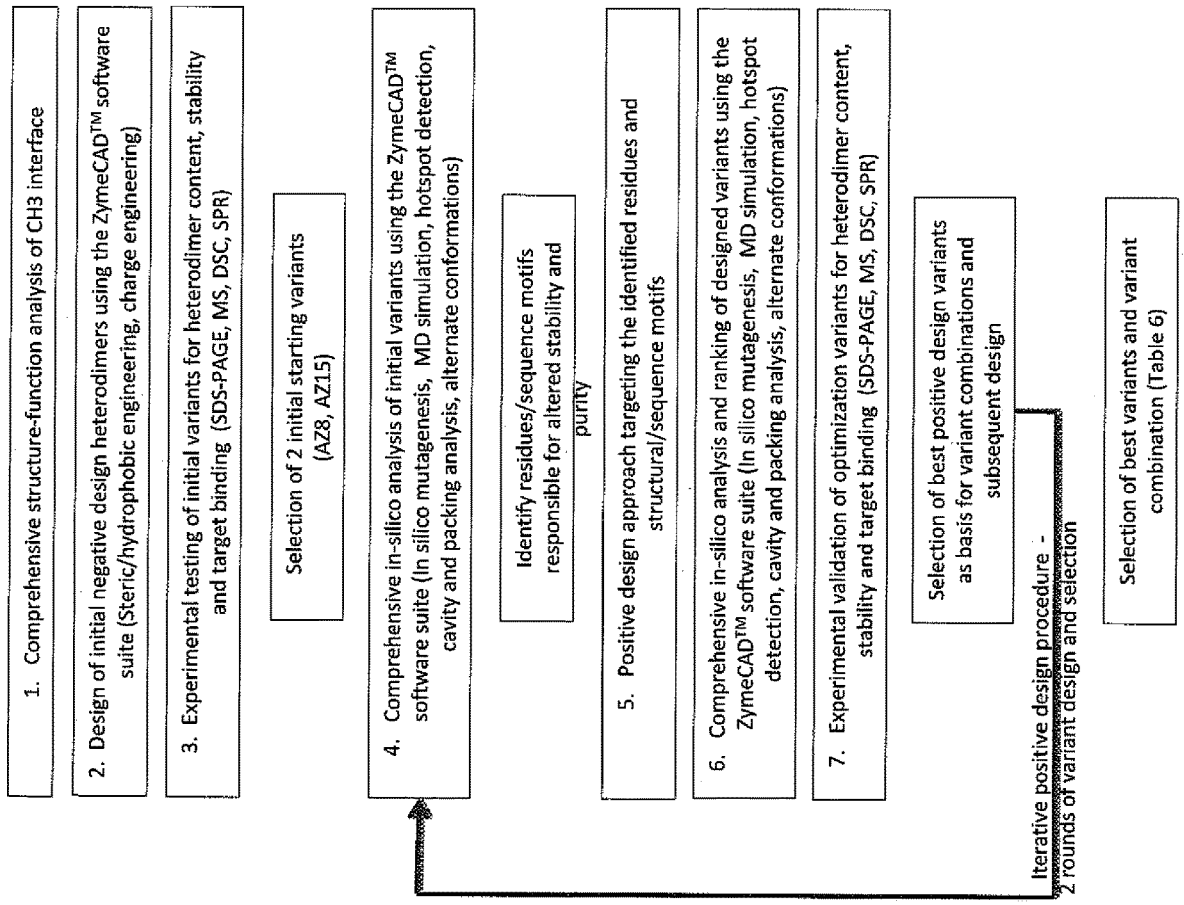

FIG. 23 shows the amino acid sequence for wild-type human IgG1.

Figure 24:
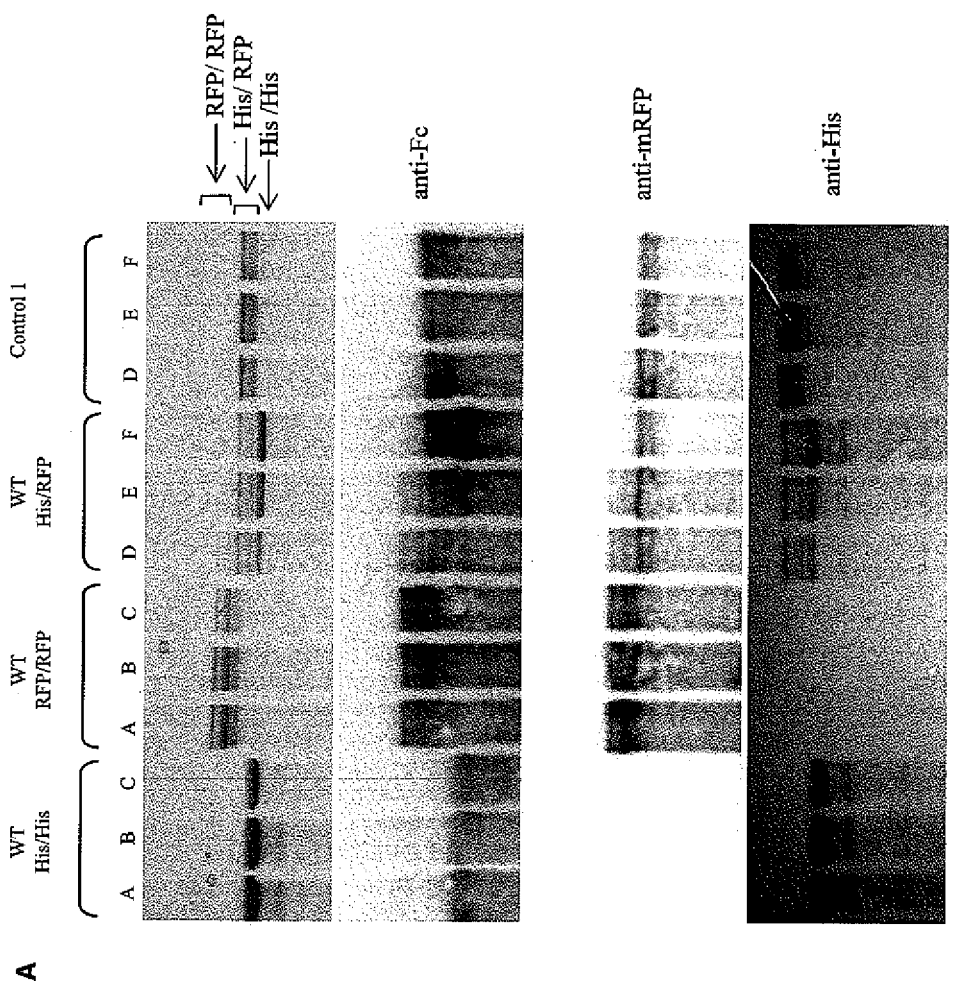

FIG. 24 Shows the iterative process of the Fc heterodimer design, combining positive and negative design strategies as described in detail below.

Figure 25:
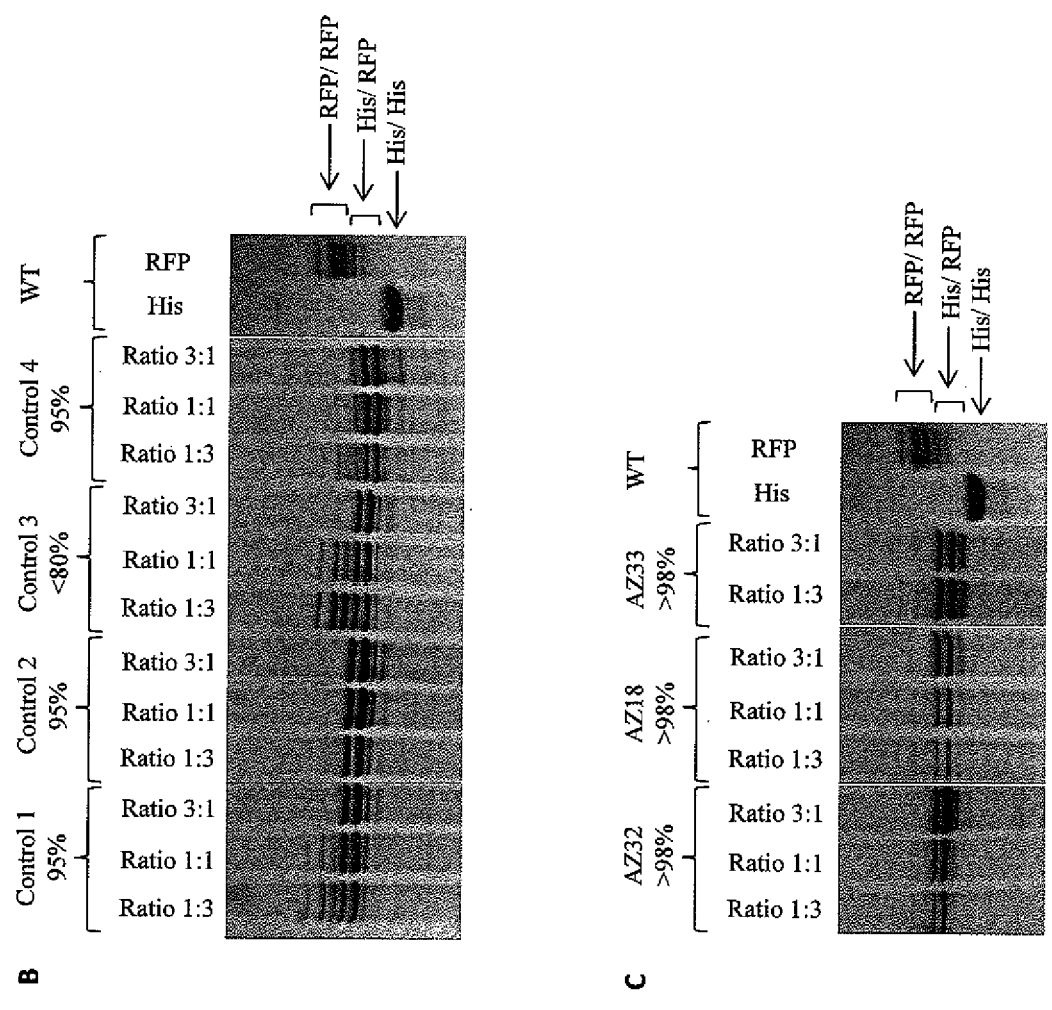

FIG. 25 Shows the in vitro assay used to determine heterodimer purity. The assay is based on a full length monospecific antibody scaffold with two Fc heavy chains of different molecular weight; Heavy chain A has a C-terminal HisTag (His) and heavy chain B a C-terminal, cleavable mRFP Tag (RFP). The two heavy chains A (His) and B (RFP) are expressed in different relative ratios together with a fixed amount of light chain, giving rise to 3 possible dimer species with different molecular weight:

a) Homodimer Chain A (His)/Chain A (His) (~150 kDa);
b) Heterodimer Chain A (His)/Chain B (RFP) (~175 kDa);
c) Homodimer Chain B (RFP)/Chain B (RFP) (~200 kDa). After expression, as described in Example 2, the ratio of heterodimer vs. the two homodimers was determined by non-reducing SDS-PAGE, which allows separation of the 3 dimer species by molecular weight. SDS-PAGE gels were stained with Coomassie Brilliant Blue.

FIG. 25A. The variants tested were WT Chain A (His) only; WT chain B (RFP) only; WT chain A (His) plus chain B (RFP); Control 1 chain A (His) plus chain B (RFP), which has a reported heterodimer purity of >95%. The composition of the dimer bands was verified by Western Blot with antibodies directed against the IgG-Fc (anti-Fc), the mRFP Tag (anti-mRFP) and the HisTag (anti-His), as illustrated above. The SDS-PAGE shows a single band for the His/His homodimer, a double band for the His/RFP heterodimer and multiple bands for the RFP homodimer. The multiple bands are an artifact of the mRFP Tag and have been confirmed not to influence the physical properties of the Fc heterodimer.

FIG. 25B. The SDS-PAGE assay was validated with the published Fc heterodimer variants Controls 1-4 as controls, See, Table A. The variants were expressed with different relative ratios of chain A (His) vs chain B (RFP):

Specifically, Ratio 1:3 is equivalent to a LC,HC_His, HC_mRFP ratio of 25%,10%,65%; Ratio 1:1 of 25%,20%, 55% and Ratio 3:1 of 25%,40%,35% respectively (the apparent 1:1 expression of chain A (His) to chain B (RFP) has been determined to be close to 20%/55% (His/RFP) for WT Fc).

Figure 1:
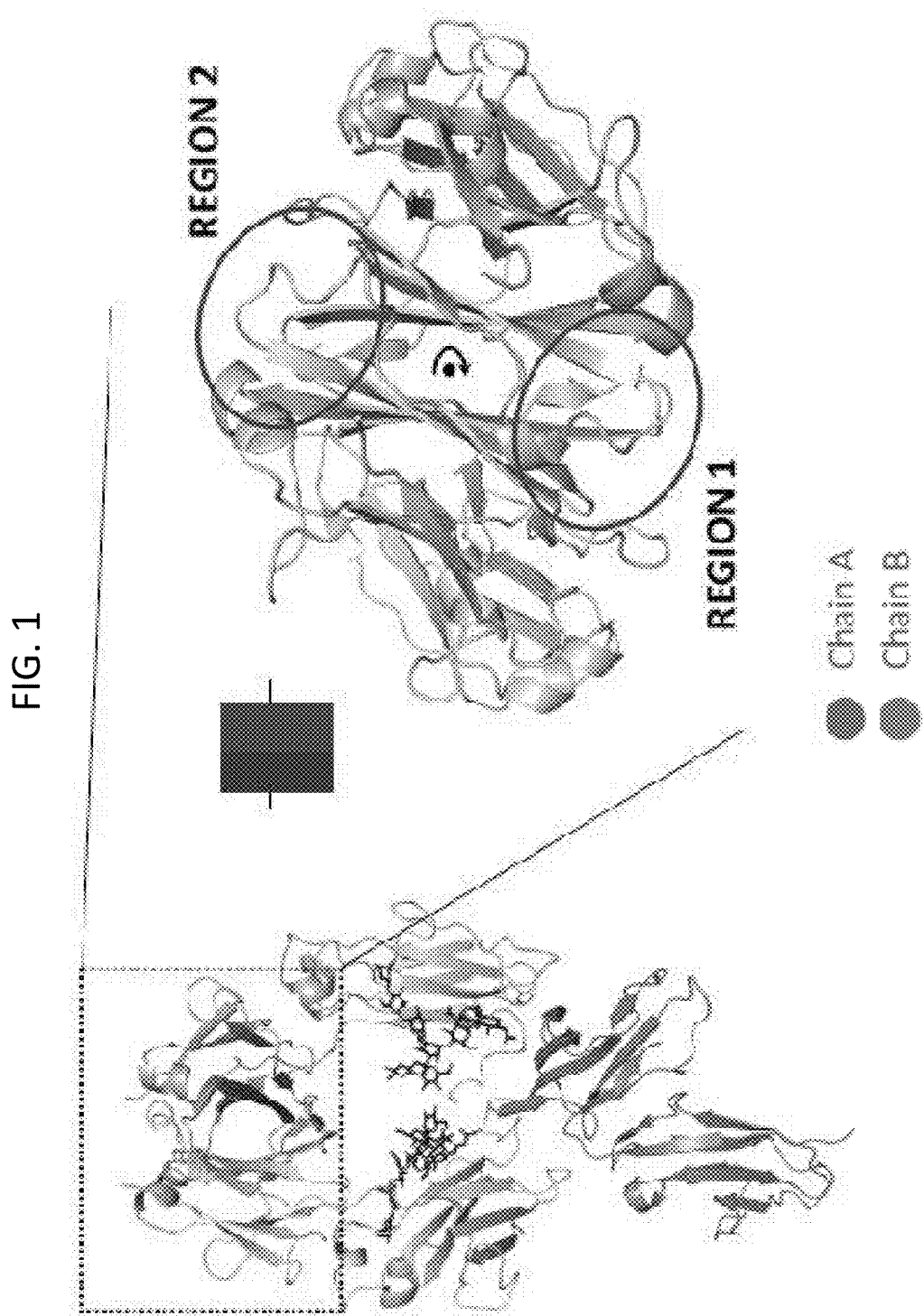
FIG. 1 is a graphical 3-D structure of a wild type antibody showing the CH3 (top), CH2 (middle) and receptor regions. The dotted line rectangle on the left hand side is expanded to the right hand side showing two regions, Region 1 and Region 2, of the target area of CH3.
Figure 2:
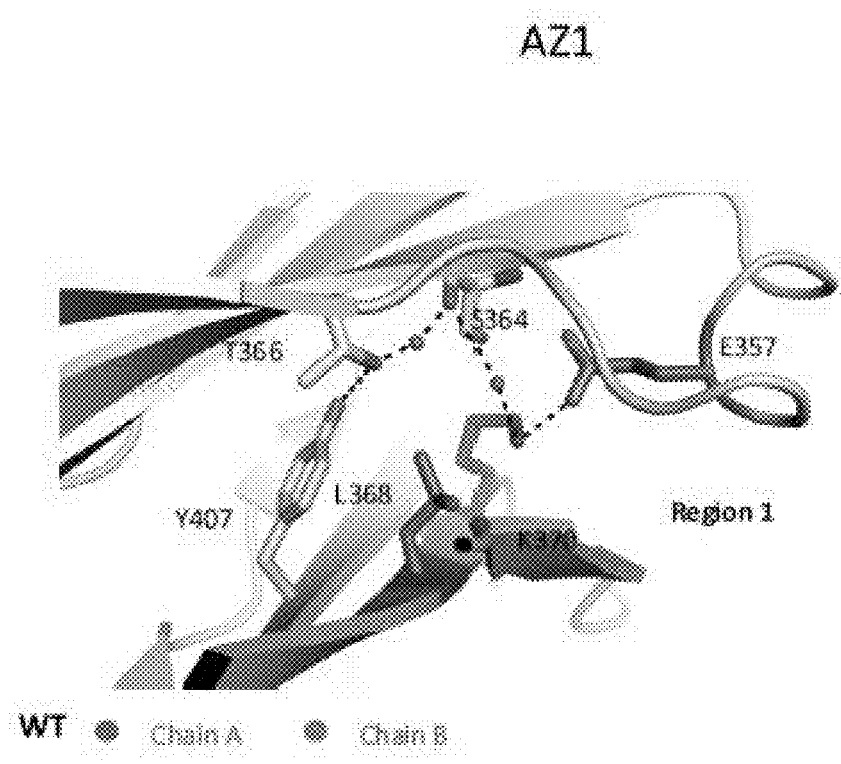
FIG. 2 is a graphical 3-D representation of showing the wild type residue at position 368.
Figure 3:
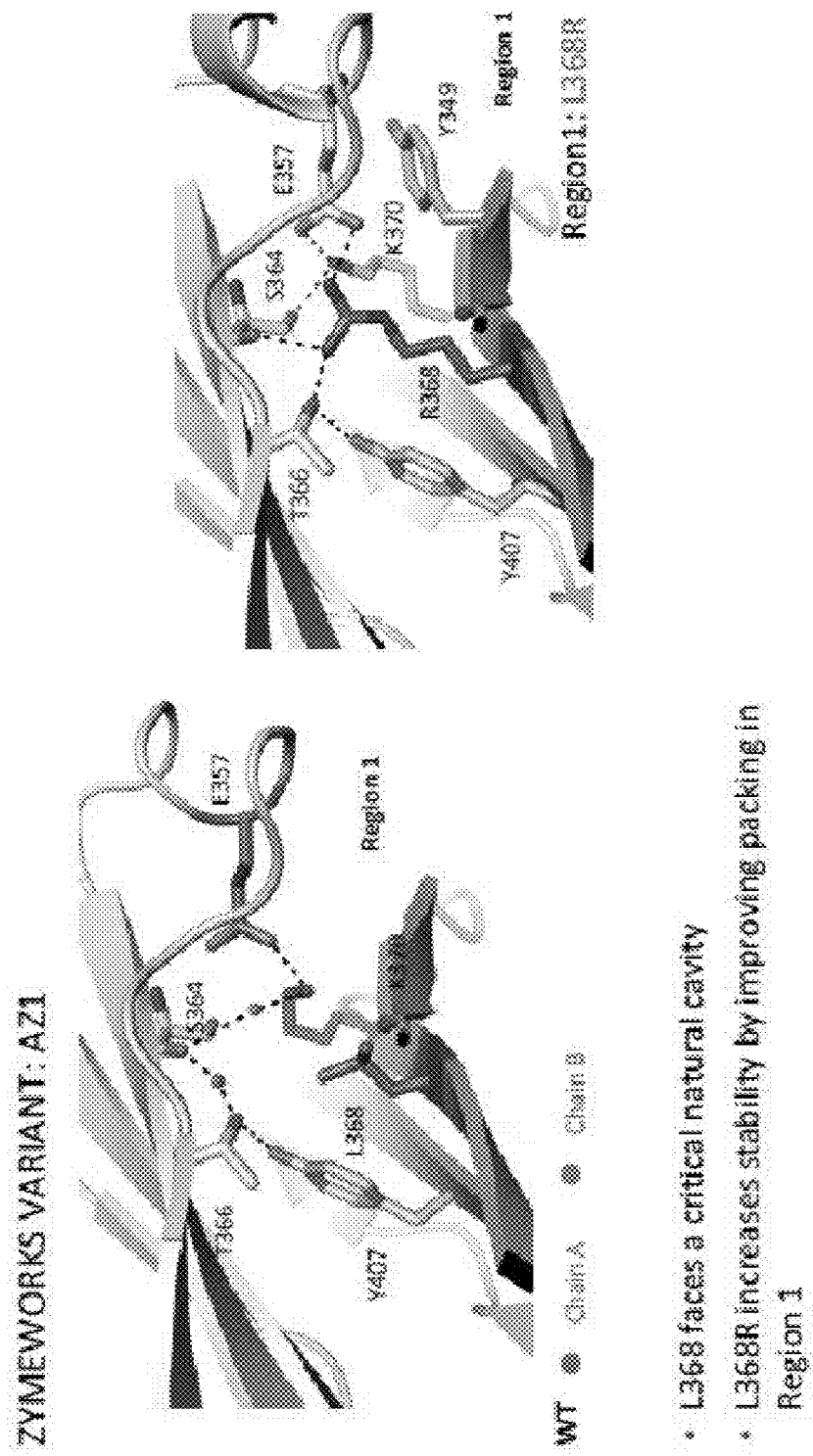
FIG. 3 is a graphical 3-D representation of Region 1 showing mutated position 368.
Figure 5:
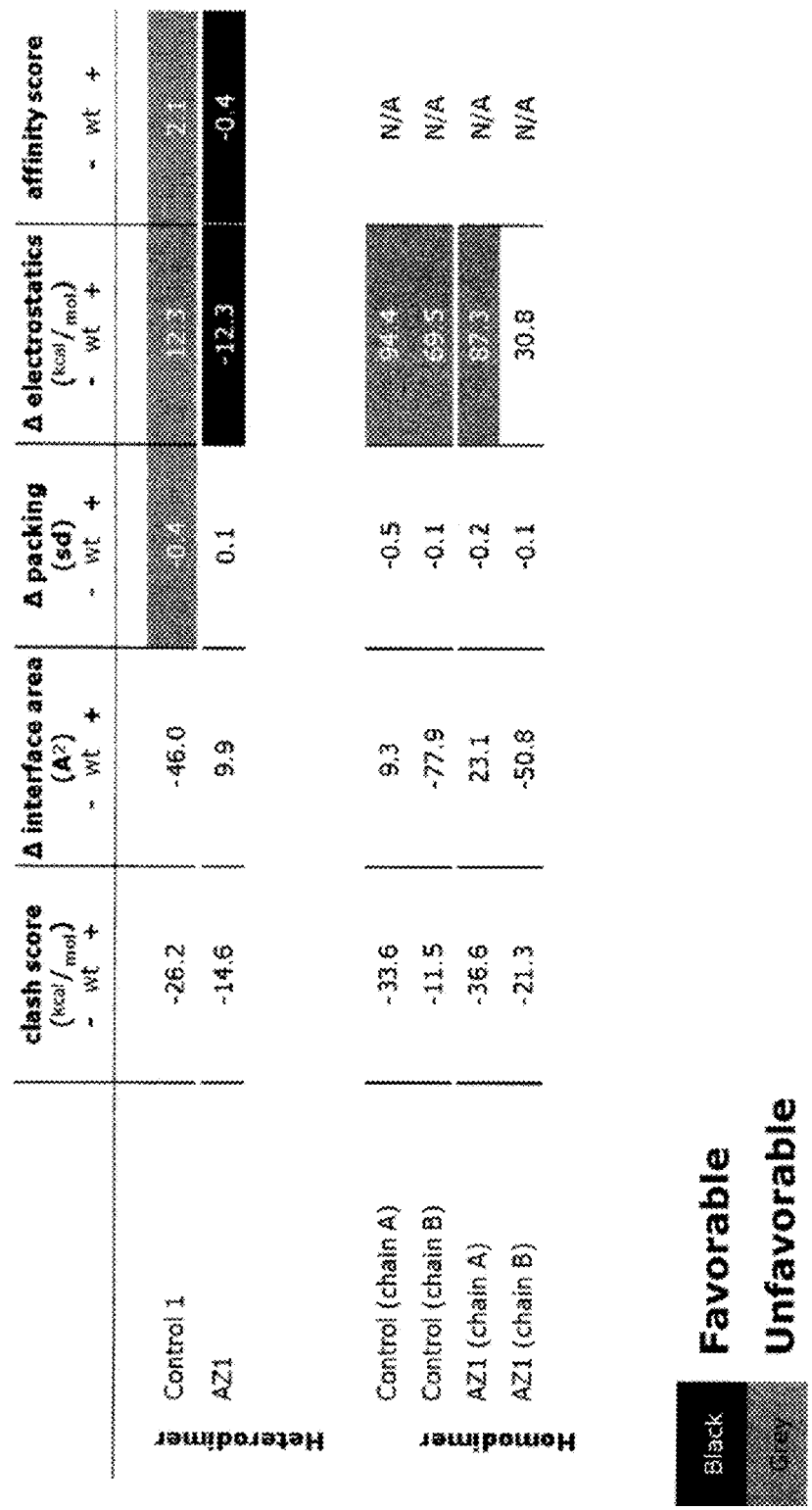
FIG. 5 is a table of in silico calculations for clash score, interface area difference, packing different, electrostatic energy difference and overall "affinity score" for the first three variants AZ1, AZ2 and AZ3.
Figure 6:
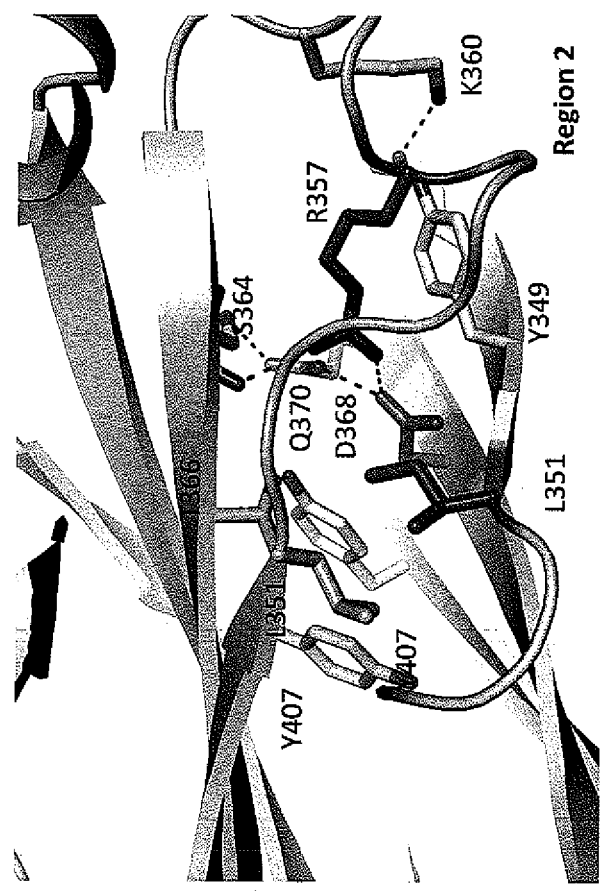
FIG. 6 shows a graphical 3-D image showing variants AZ2 and AZ3, which are "built onto" variant AZ1.
Figure 8:
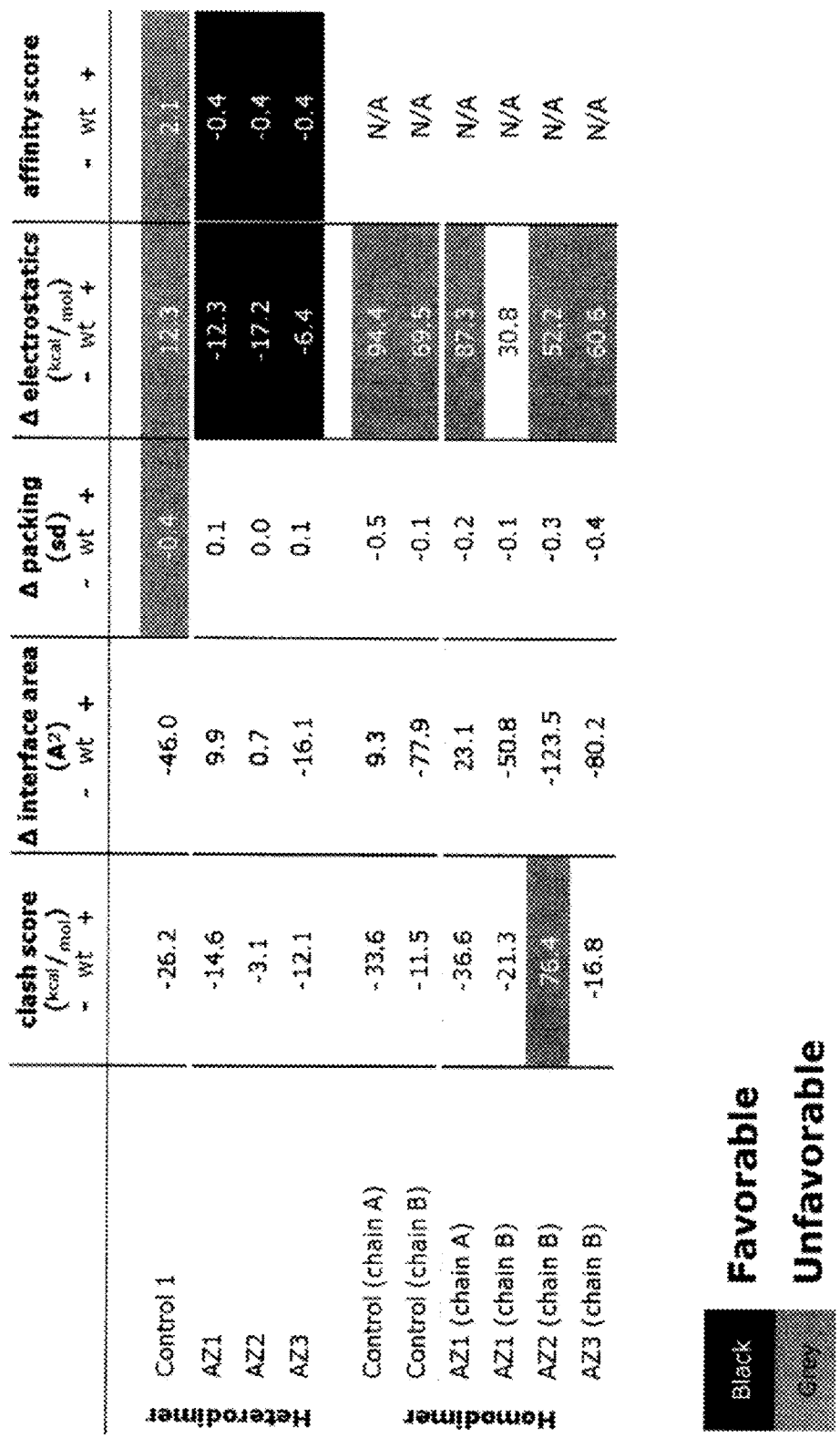
FIG. 8 shows a table as in FIG. 5 but for AZ1, AZ2 and AZ3 heterodimers, and homodimers. Affinity score is not relevant for homodimers so there is no score showing for that aspect for the homodimers.
Figure 9:
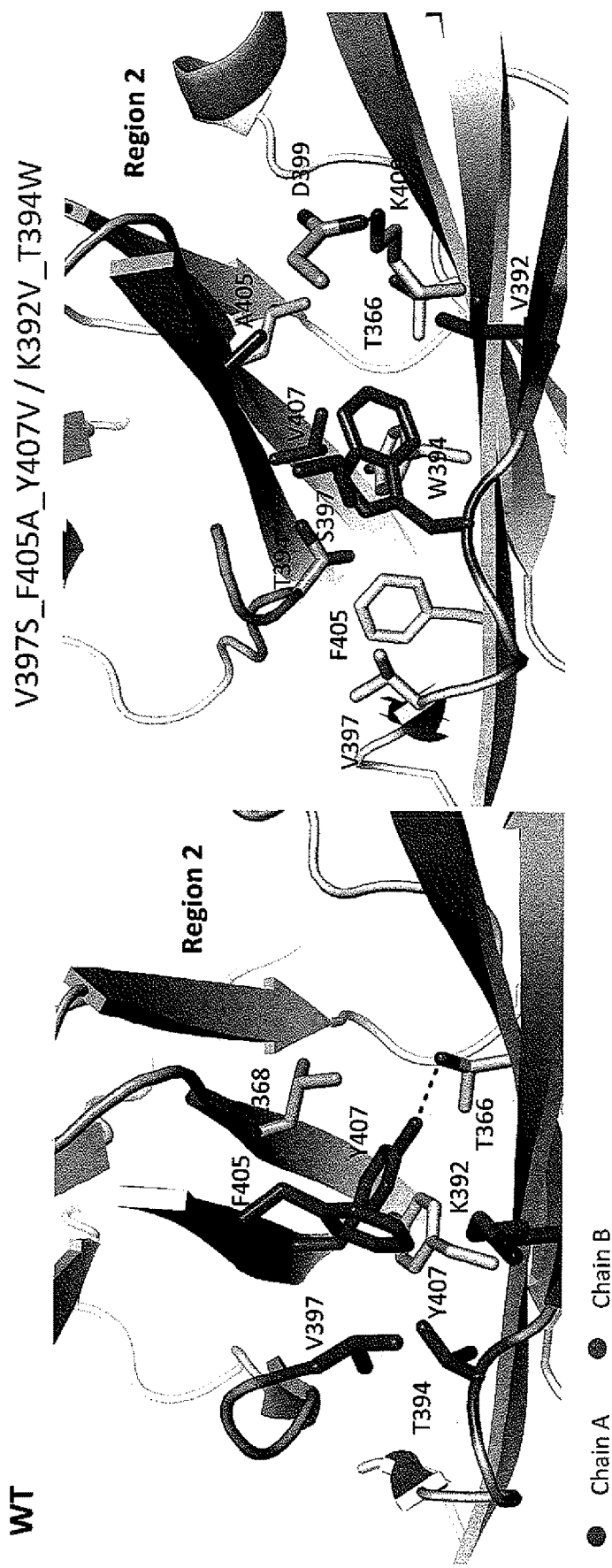
FIG. 9 is a graphical representation of a 3-D representation of wild type (left) and mutated AZ4 (right)
Figure 10:
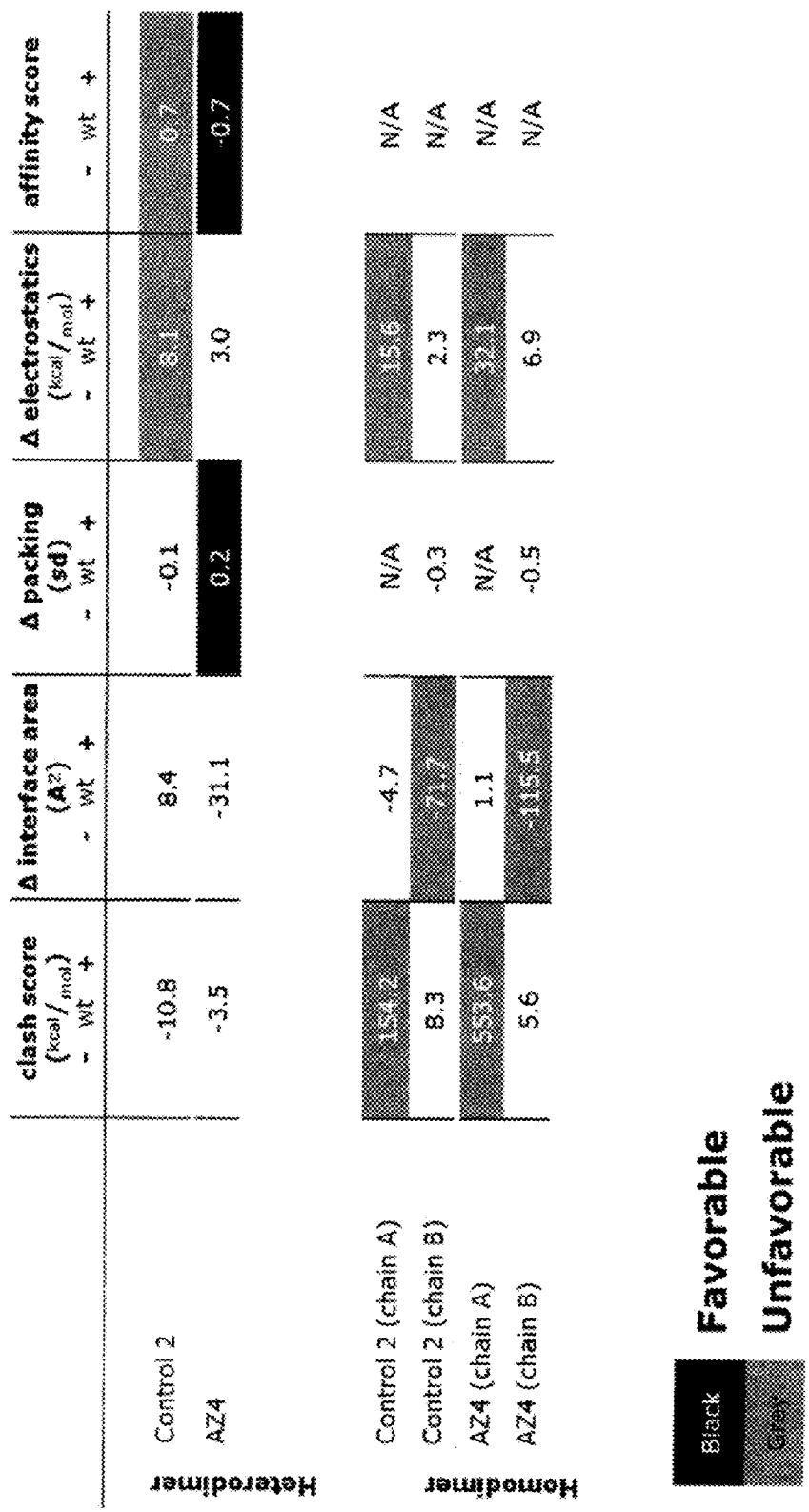
FIG. 10 is a table as FIG. 5 showing in silico calculations for AZ4 heterodimer and homodimers.
Figure 11:
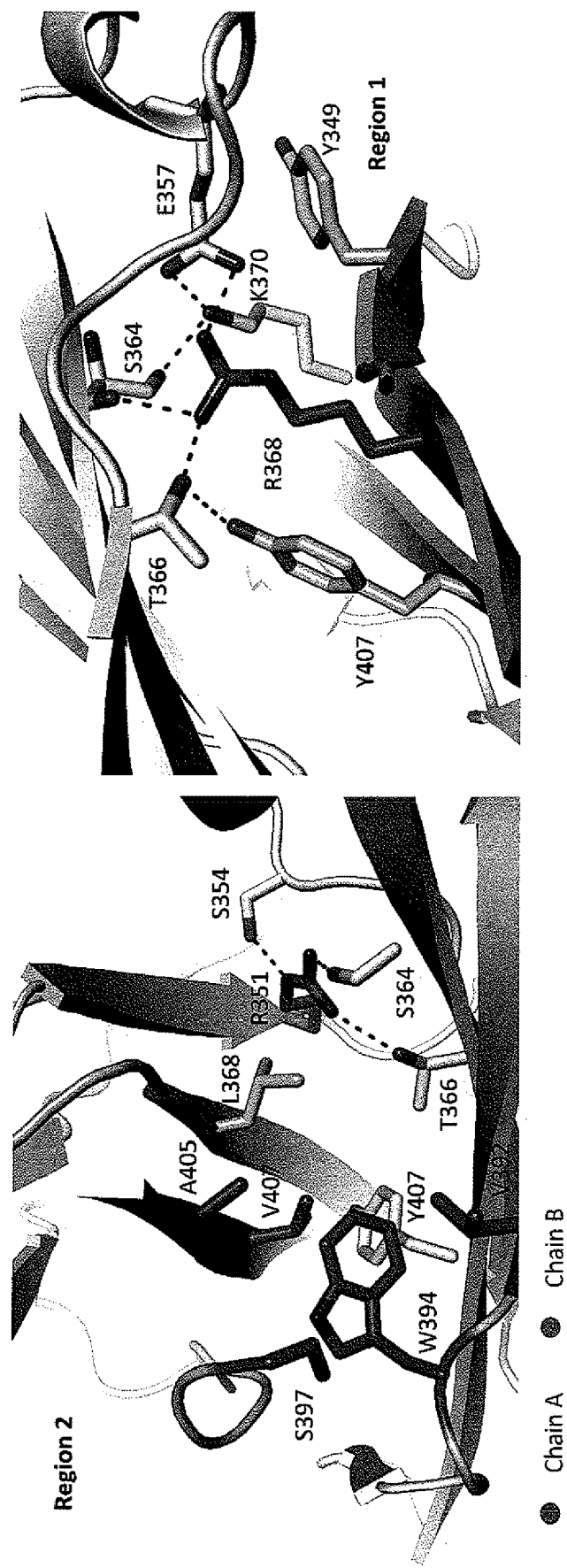
FIG. 11 is a graphical representation of CH3 variants AZ5 (left) and AZ6 (right)
Figure 13:
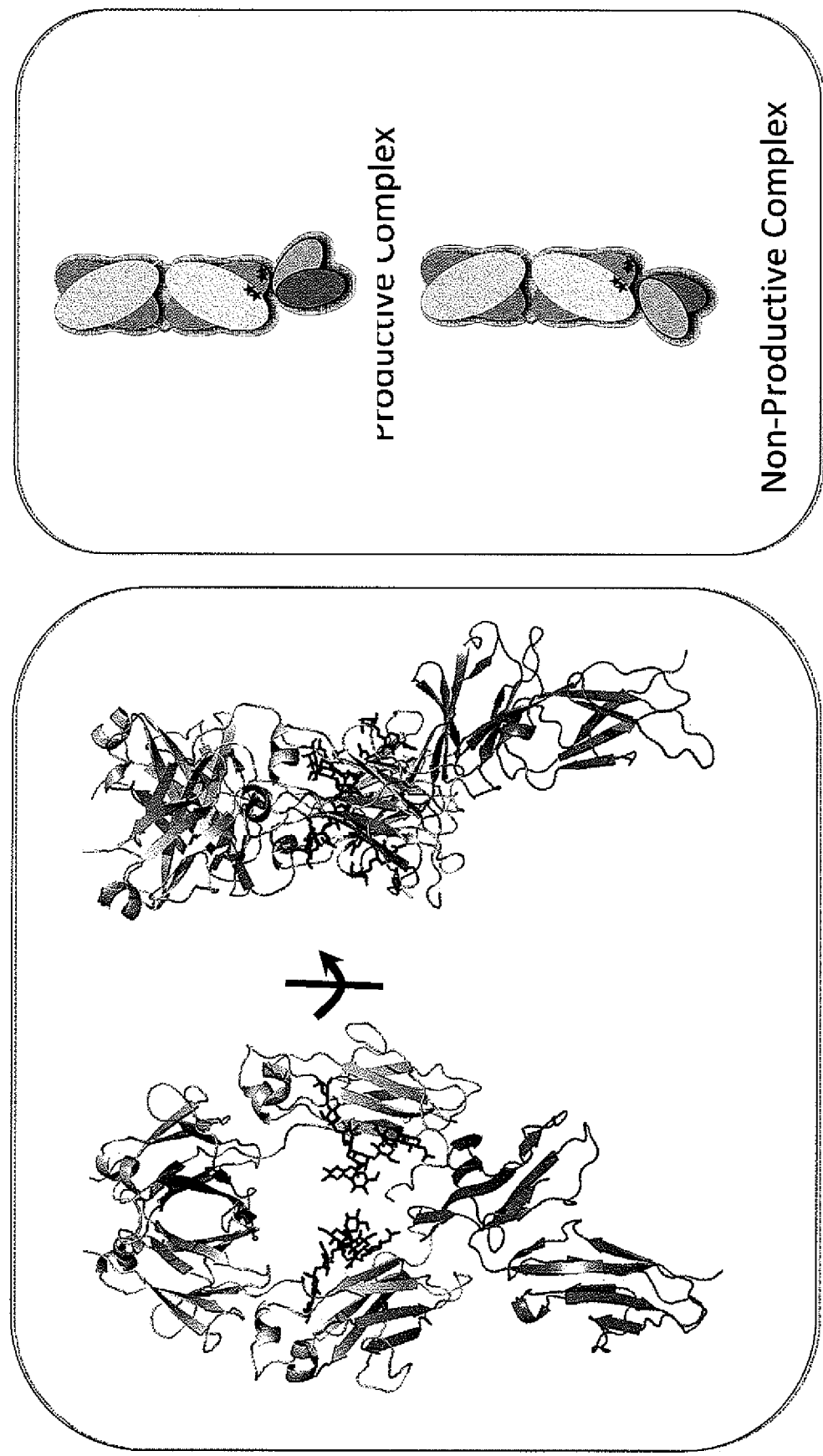
FIG. 13 is a graphical 3-D representation of an antibody on the left, with a drawing of the possibilities of binding characteristics at the receptor region using a heterodimeric approach.

FIG. 25C. Shows a non-reducing SDS-PAGE assay to determine heterodimer purity of Scaffold 1 variants. The Fc variants were expressed with different relative ratios of chain A (His) vs chain B (RFP) and analyzed by non-reducing SDS-PAGE as described in FIG. 2. Specifically, Ratio 1:3 is equivalent to a LC,HC_His,HC_mRFP ratio of 25%,10%,65%; Ratio 1:1 of 25%,20%,55% and Ratio 3:1 of 25%, 40%,35% respectively (the apparent 1:1 expression of chain A (His) to chain B (RFP) has been determined to be close to 20%/55% (His/RFP) for WT Fc).

FIG. 26 shows Fc Heterodimer variants expressed with a specific ratio of chain A (His) vs chain B (RFP) (See, Table 2), purified by Protein A affinity chromatography and analyzed by non-reducing SDS-PAGE as described in FIG. 25.

FIG. 26A illustrates how different variants have been binned into categories of purity based on the visual inspection of the SDS-PAGE results. For comparison the equivalent amount of Protein A purified product was loaded on the gel. This definition of purity based on non-reducing SDS-PAGE has been confirmed by LC/MS on selected variants (see FIG. 28).

FIG. 26B Example SDS-PAGE results of selected Protein A purified heterodimer variants of Scaffold 1 and 2 (AZ94, AZ86, AZ70, AZ33 and AZ34).

FIG. 27 illustrates DSC analysis to determine the melting temperature of the CH3-CH3 domain wherein two independent methods were used.

Figure 27A:
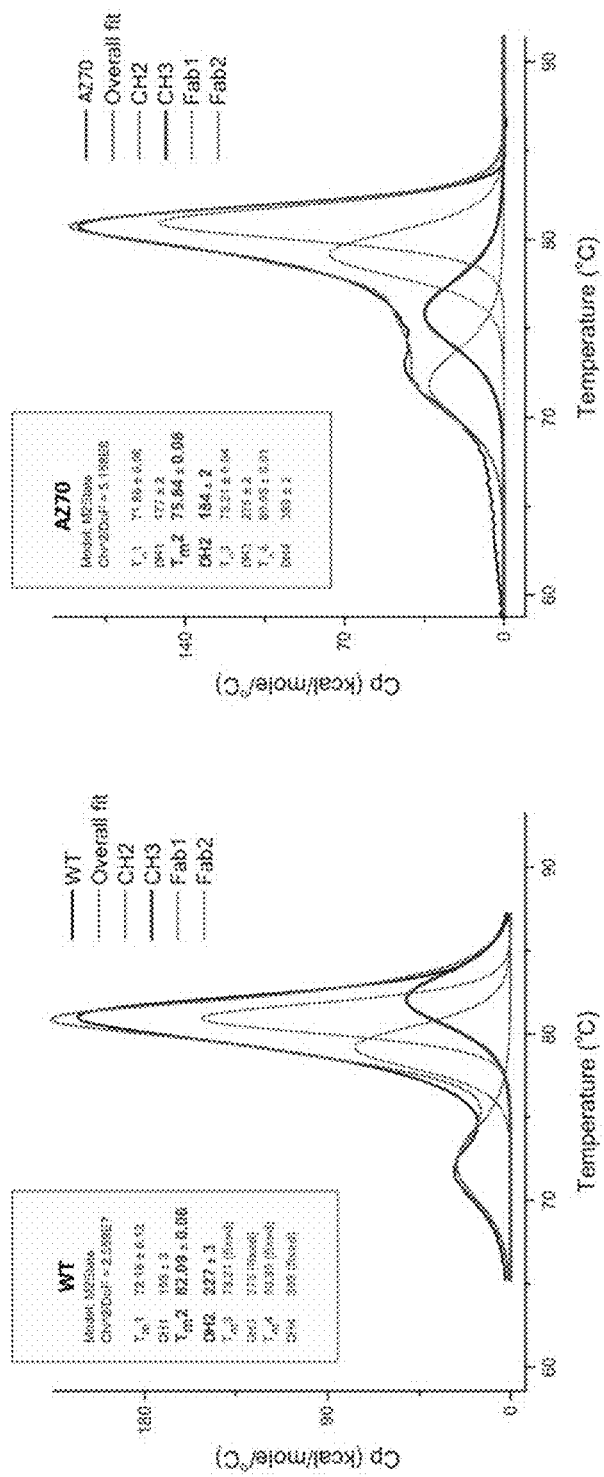

FIG. 27A The thermograms were fitted to 4 independent Non-2-State-transitions and optimized to yield values for the CH2 and Fab transitions close to the reported literature values for Herceptin of ~72° C. (CH2) and ~82° C. (Fab).

Figure 27B:
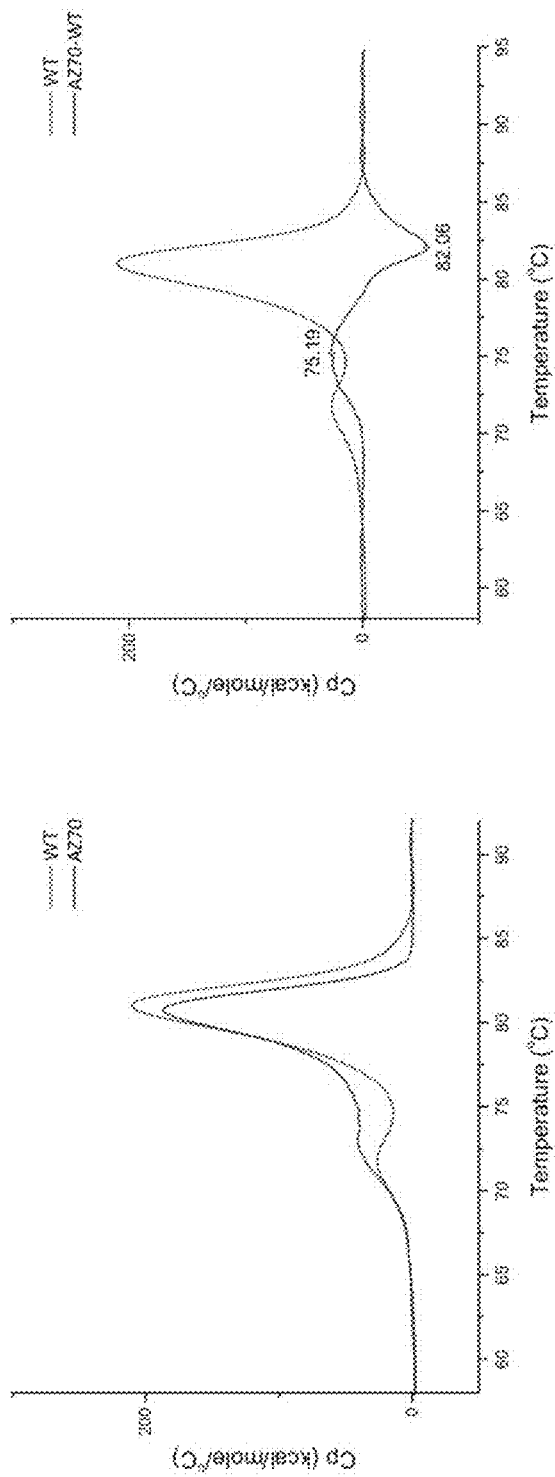

FIG. 27B. The normalized and baseline corrected thermograms for the heterodimer variants were subtracted from the WT to yield a positive and negative difference peak for only the CH3 transition.

Figure 28:
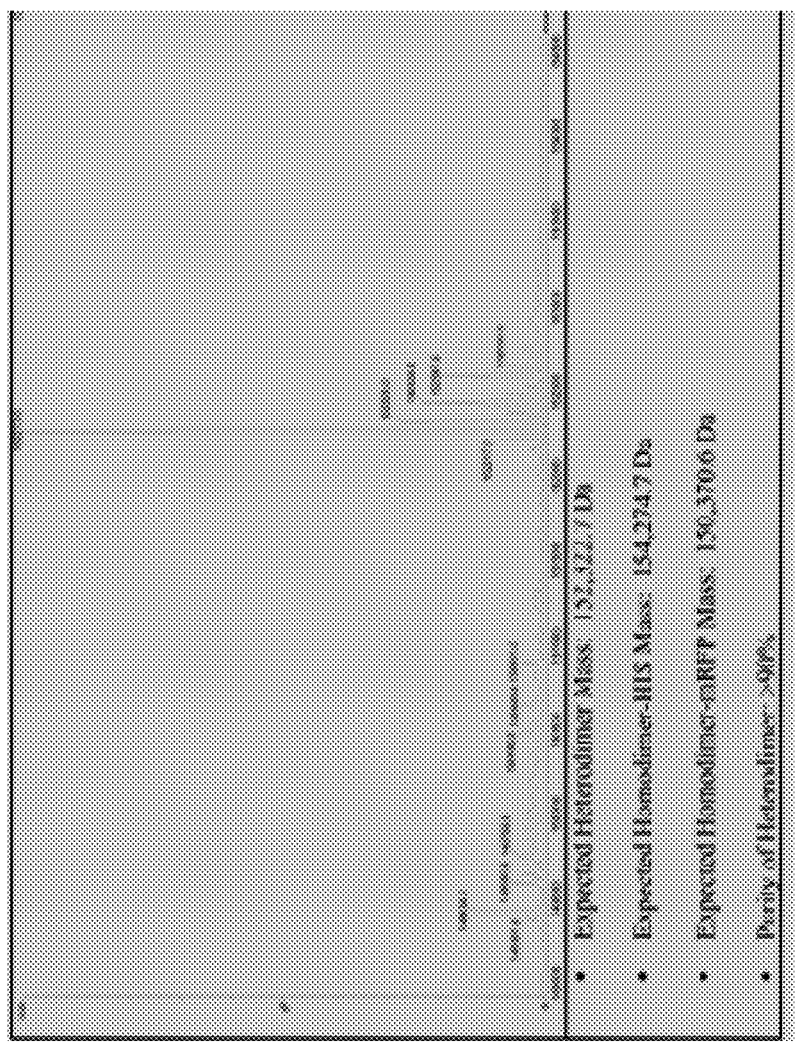

FIG. 28 illustrates the LC/MS analysis of example variant AZ70 as described in the example 2. The expected (calculated average) masses for the glycosylated heterodimer and homodimers are indicated. The region consistent with the heterodimer mass contains major peaks corresponding to the loss of a glycine (−57 Da) and the addition of 1 or 2 hexoses (+162 Da and +324 Da, respectively). The Heterodimer purity is classified as >90% if there are no significant peaks corresponding to either of the homodimers.

Figure 29A:
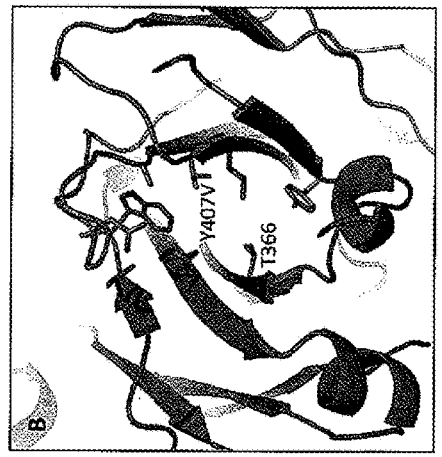
Figure 29B:
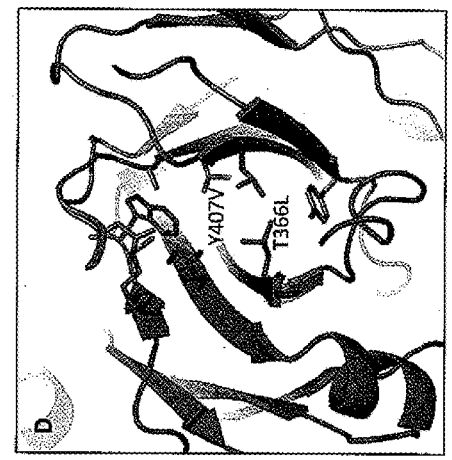
Figure 29C:
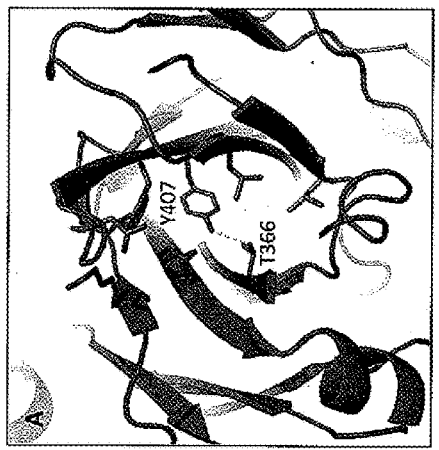
Figure 29D:
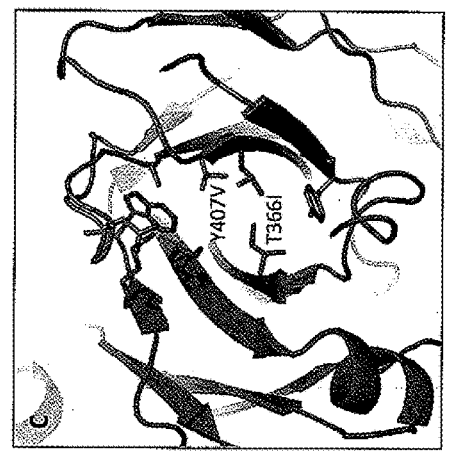

FIG. 29 shows the CH3 interface of FIG. 29A WT Fc; FIG. 29B AZ6; FIG. 29C AZ33; FIG. 29D AZ19. The comprehensive in silico analysis, as described in the detailed description section, and the comparison of the variants to the WT indicated that one of the reasons for the lower than WT stability of the initial AZ33 heterodimer is the loss of the core interaction/packing of Y407 and T366. The initial AZ33 shows non-optimal packing at this hydrophobic core as illustrated FIG. 29B, suggesting that optimization of this region, particularly at position T366 would improve the stability of AZ33. This is illustrated in FIG. 29C and FIG. 29D with T366I and T366L. The experimental data correlates with this structural analysis and shows that T366L gives the greatest improvement in Tm. See, Example 5.

FIG. 30 illustrates the utility and importance of the conformational dynamics analysis, exemplified at the initial Scaffold 1 variant AZ8. The structure after in silico mutagenesis (backbone conformation close to WT) is superimposed with a representative structure of a 50 ns Molecular Dynamics simulation analysis. The figure highlights the large conformational difference in the loop region D399-5400 of AZ8 variant vs. WT, which in turn exposes the hydrophobic core to solvent and causes decreased stability of the AZ8 heterodimer.

FIG. 31 illustrates how the information from the comprehensive in silico analysis and the MD simulation was used in the described positive design strategy. As illustrated in FIG. 30, one of the reasons for the lower than WT stability of AZ8 is the weakened interaction of the loop 399-400 to 409, which is mainly due to the loss of the F405 packing interactions (see comparison of FIG. 31A (WT) vs FIG. 31B (AZ8)). One of the positive design strategies was optimization of the hydrophobic packing of area, to stabilize the 399-400 loop conformation. This was achieved by the K392M mutation that is illustrated in FIG. 31C. FIG. 31C represents the heterodimer AZ33, which has a Tm of 74° vs. 68° of the initial negative design variant AZ8.

Figures 32A, 32B, 32C:

FIG. 32 illustrates the dynamics of the Fc molecule observed using principal component analysis of a molecular dynamics trajectory. FIG. 32A shows a backbone trace of the Fc structure as reference. FIGS. 32B and C represent an overlay of dynamics observed along the top 2 principal modes of motion in the Fc structure. The CH2 domains of chain A and B exhibits significant opening/closing motion relative to each other while the CH3 domains are relatively rigid. Mutations at the CH3 interface impact the relative flexibility and dynamics of this open/close motion in the CH2 domains.

Figures 33A, 33B, 33C:
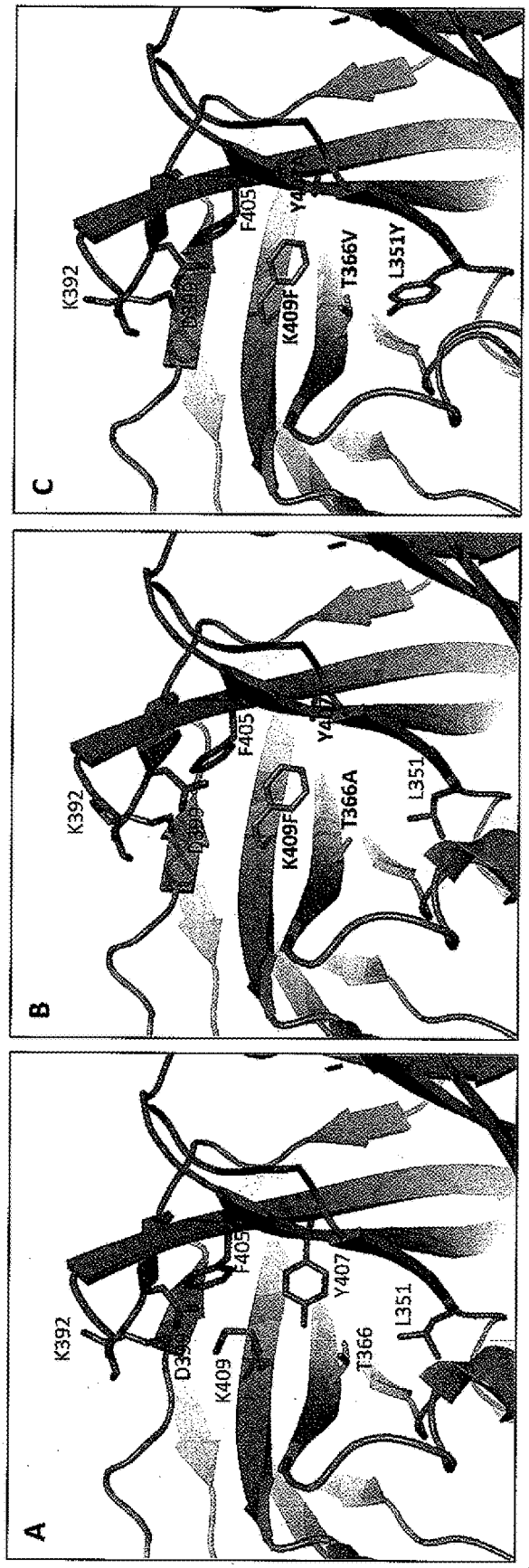

FIG. 33 Illustrates the hydrophobic core packing of two Scaffold-2 variants vs. WT. FIG. 33A WT Fc; FIG. 33B AZ63; and FIG. 33C AZ70. The comprehensive in-silico analysis of the initial Scaffold-2 variant suggested that loss of the core WT interactions of Y407-T366 is one of the reasons for the lower than WT stability for the initial Scaffold-2 variants. The loss of Y407-T366 is partially compensated by the mutations K409F, but as illustrated in FIG. 33B, particularly the T366A mutation leaves a cavity in the hydrophobic core, which destabilizes the variant vs. WT. Targeting this hydrophobic core by additional mutations T366V L351Y, as shown by Fc variant AZ70 in FIG. 33C, proved to be successful; AZ70 has an experimentally determined Tm of 75.5° C. See, Table 4 and Example 6.

Figures 34A, 34B, 34C:
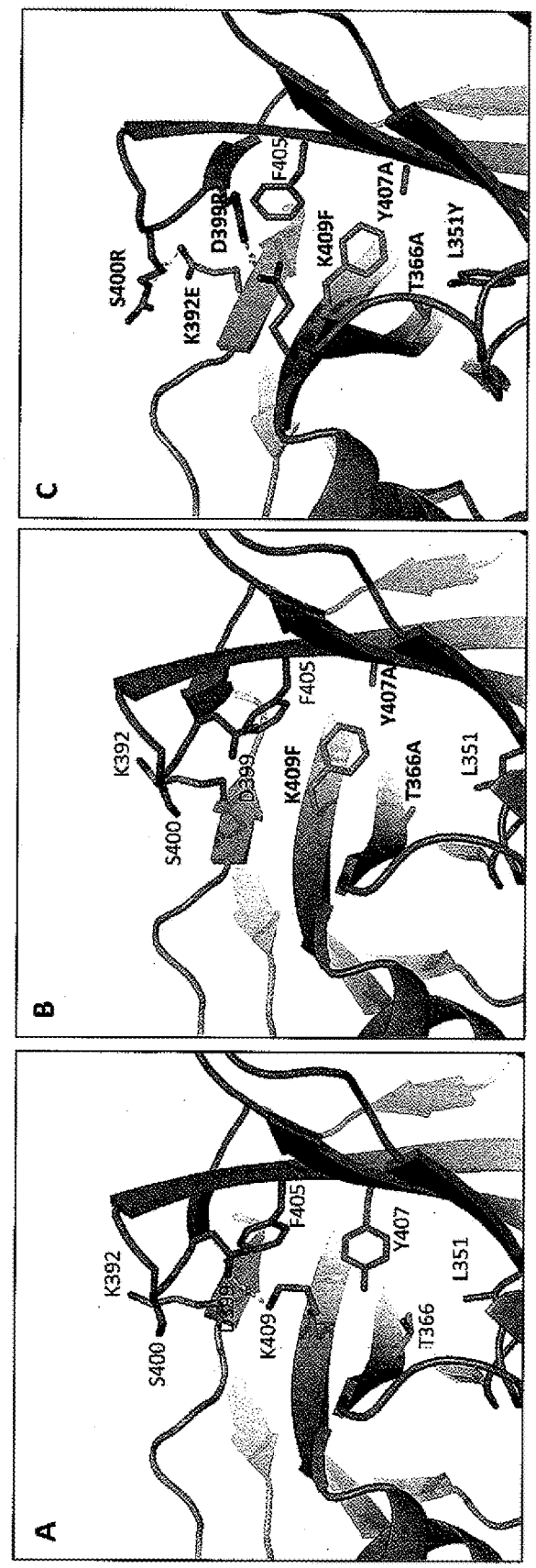

FIGS. 34A, 34B and 34C illustrate the interactions of the loop 399-400 of two Scaffold-2 variants vs. the WT:
FIG. 34A WT Fc;
FIG. 34B AZ63; and
FIG. 34C AZ94. The comprehensive in-silico analysis of the initial Scaffold-2 variant suggested that loss of the WT salt-bridge K409-D399 (FIG. 34A) due to the mutation K409F and the hence unsatisfied D399 (FIG. 34B) causes a more 'open' conformation of the 399-400 loop. This leads furthermore to a greater solvent exposure of the hydrophobic core and a further destabilization of the variant vs WT. One of the strategies employed to stabilize the 399-400 loop and compensate for the loss of the K409-D399 interaction was the design of additional salt bridges D399R-T411E and S400R-K392E as illustrated in FIG. 34C for variant AZ94. Experimental data showed a purity of >95% and Tm of 74° C. See, Table 4 and Example 6. Further, although AZ94 has a considerably higher purity and stability compared to the initial Scaffold-2 variant (purity <90%, Tm 71° C.), the hydrophobic core mutations of AZ94 are less preferred than the 'best' hydrophobic core mutations identified in variant AZ70 (FIG. 33). Since the mutations at the hydrophobic core in AZ70 (T366V L351Y) are distal from the salt-bridge mutations of AZ94 at the loop 399-400, the combination of AZ70 amino acid mutations and the additional AZ94 mutations, is expected to have a higher melting temperature then AZ70 or AZ94. This combination can be tested as described in Examples 1-4.

Figure 35:
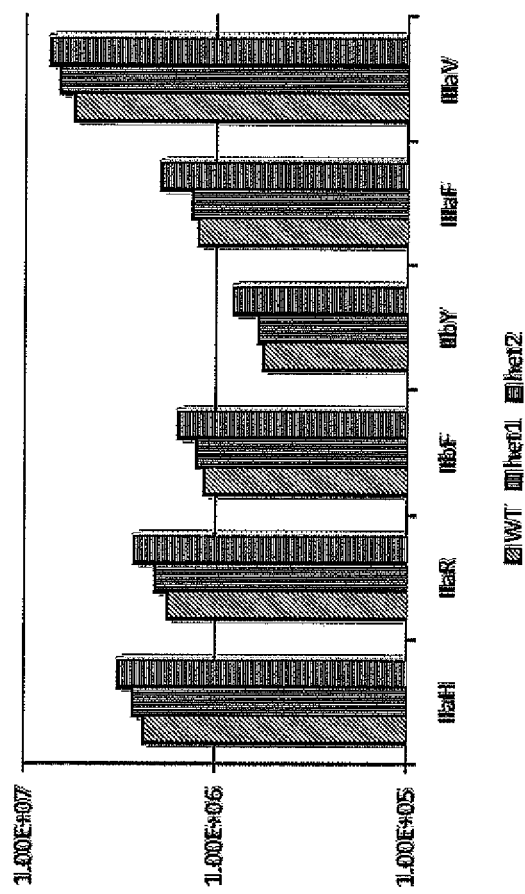

FIG. 35 Illustrates the association constant ($Ka(M^{-1})$) of homodimeric IgG1 Fc, the heterodimeric variants het1(Control 1): A:Y349C_T366S_L368A_Y407V/B: S354C_T366W and het2(Control 4): A:K409D_K392D/B: D399K_D356K binding to the six Fcgamma receptors. The heterodimeric Fc variants tend to show slightly altered binding to the Fcgamma receptors compared to the wild type IgG1 Fc. See, Example 7

Figure 36A:
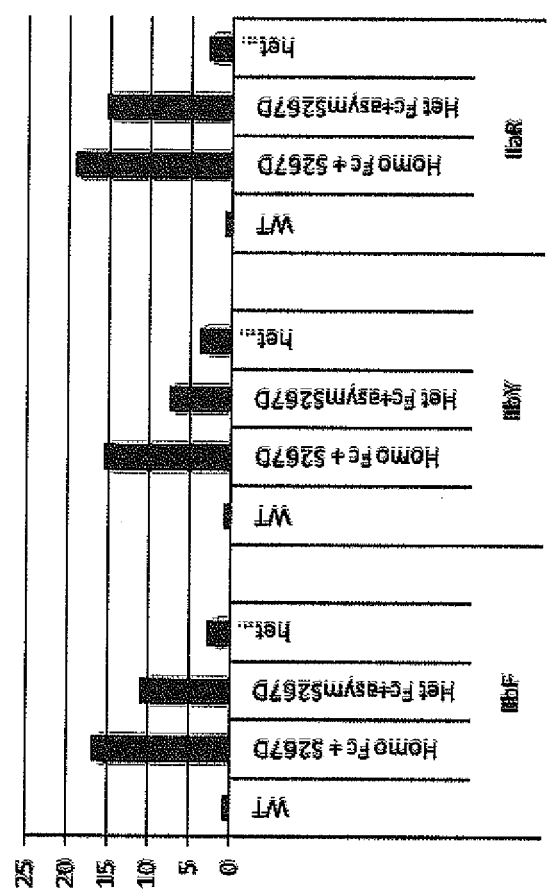

FIG. 36A shows the relative binding strength of a wild type IgG1 Fc and its various homodimeric and asymmetric mutant forms to the IIbF, IIBY and IIaR receptors, based on the wild type binding strength as reference. (Homo Fc+S267D) refers to the binding strength of a homodimeric Fc with the S267D mutation on both chains. (Het Fc+asym S267D) refers to the binding strength of a heterodimeric Fc with the S267D mutation introduced in one of the two chains in Fc. The average of the binding strength obtained by introducing the mutation on either of the two Fc chains is reported. Introduction of this mutation on one chain reduced the binding strength to roughly half the strength observed for the same mutation in a homodimeric manner. The (Het Fc+asym S267D+asym E269K) refers to the binding strength of a heterodimeric Fc with both the S267D and E269K mutations introduced in an asymmetric manner on one of the two Fc chains. The E269K mutation blocks the interaction of the FcgR to one of the faces of the Fc and is able to bring down the binding strength by roughly half of what was observed for the asymmetric S267D variant (Het Fc+S267D) by itself. The Het Fc here is comprised of CH3 mutations as indicated for the variant het2 (Control 4) in FIG. 35.

Figure 36B:
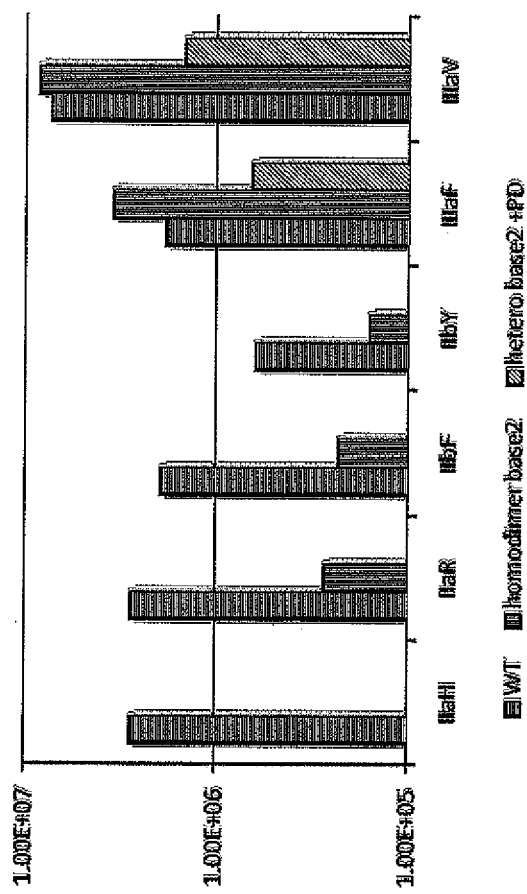

FIG. 36B shows the association constant ($Ka(M^{-1})$) of various Fc's and its variants with a number of FcgRIIa, FcgRIIb and FcgRIIIa allotypes. The Ka of wild type IgG1 Fc to various Fcg receptors is represented as columns with horizontal shade. The bars with vertical shades (homodimer base2) represent the Ka of homodimeric Fc with the mutations S239D/D265S/I332E/S298A. The columns with the slanted shade represent the Ka of heterodimeric Fc with asymmetric mutations A:S239D/D265S/I332E/E269K and B:S239D/D265S/S298A in the CH2 domain. The introduction of asymmetric mutations is able to achieve increased selectivity between the IIIa and IIa/IIb receptors. The Heterodimeric Fc here is comprised of CH3 mutations as indicated for the variant het2 (Control 4) in FIG. 35.

Figure 36C:
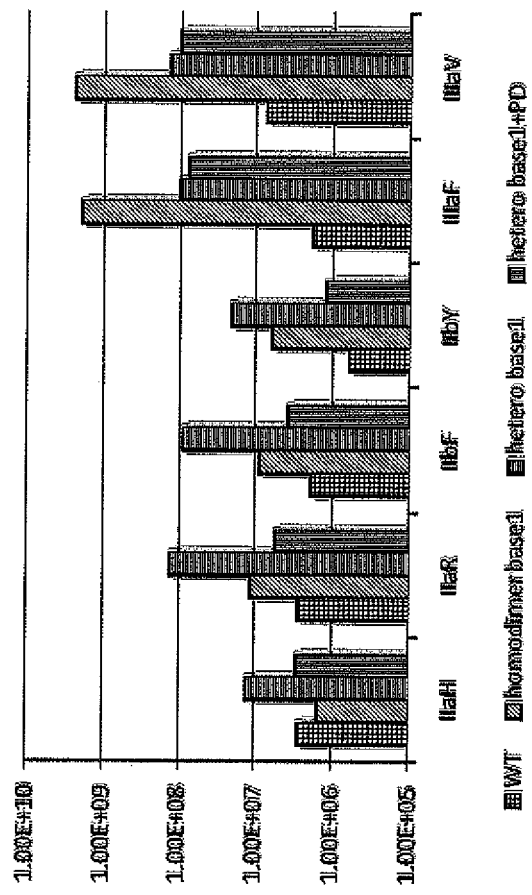

FIG. 36C shows the association constant ($Ka(M^{-1})$) for wild type IgG1 and three other variants involving homodimeric or asymmetric mutations in the CH2 domain of the Fc region. The Ka of wild type Fc is represented in the column shaded with grids. The Ka of Fc variant with the base mutation S239D/K326E/A330L/I332E/S298A introduced in a homodimeric manner (homodimer base1) on both the chains of Fc is shown with the slanted patterned column. Introduction of related mutations in an asymmetric manner in chains A and B of a heterodimeric Fc (hetero base1) is shown with the horizontal lines. The column with vertical shaded lines represents the asymmetric variant including the E269K mutation (hetero base 1+PD). The Heterodimeric Fc here is comprised of CH3 mutations as indicated for the variant het2 (Control 4) in FIG. 35.

FIGS. 37, 37A-37Z and 37Z1-37Z13—Table 6 Is a list of variants CH3 domains based on the third design phase as described in Example 5 for Scaffold 1.

FIG. 38A-38I—Table 7 is a list of variant CH3 domains based on the third design phase as described in Example 6 for scaffold 2.

DETAILED DESCRIPTION

The present invention provides modified CH3 domains comprising specific amino acid modifications to promote heterodimer formation. In one embodiment, the modified CH3 domains comprise specific amino acid modifications to promote heterodimer formation (See, for example Table 1). In another embodiment the modified CH3 domains comprise specific amino acid modifications to promote heterodimer formation with increased stability (See, for example Table 4, Table 6 and Table 7). Stability is measured as the melting temperature (Tm) of the CH3 domain and an increased stability refers to a Tm of about 70° C. or greater. The CH3 domains form part of the Fc region of a heteromultimeric or bispecific antibody. Thus, provided herein in one embodiment are heteromultimers comprising a heterodimer Fc region, wherein the heterodimer Fc region comprises a modified or variant CH3 domain comprising amino acid mutations to promote heterodimer formation wherein the variant CH3 domains are selected from the variants listed in Table 1. In a second embodiment, provided are heteromultimers comprising a heterodimer Fc region, wherein the heterodimer Fc region comprises a variant CH3 domain comprising amino acid mutations to promote heterodimer formation with increased stability, wherein the variant CH3 domain has a melting temperature (Tm) of about 70° C. or greater.

Amino acid modifications that may be utilized to generate a modified CH3 domain include, but are not limited to, amino acid insertions, deletions, substitutions, and rearrangements. The modifications of the CH3 domain and the modified CH3 domains are referred to herein collectively as "CH3 modifications", "modified CH3 domains", "variant CH3 domains" or "CH3 variants". These modified CH3 domains may be incorporated into a molecule of choice. Accordingly, in one embodiment are provided molecules, in particular polypeptides, more specifically immunoglobulins (e.g., antibodies) and other binding proteins, comprising an Fc region (as used herein "Fc region" and similar terms encompass any heavy chain constant region domain comprising at least a portion of the CH3 domain) incorporating a modified CH3 domain. Molecules comprising Fc regions comprising a modified CH3 domain (e.g., a CH3 domain comprising one or more amino acid insertions, deletions, substitutions, or rearrangements) are referred to herein as "Fc variants", "heterodimers" or "heteromultimers". The present Fc variants comprise a CH3 domain that has been asymmetrically modified to generate heterodimer Fc variants or regions. The Fc region is comprised of two heavy chain constant domain polypetides—Chain A and Chain B, which can be used interchangeably provided that each Fc region comprises one Chain A and one Chain B polypeptide. The amino acid modifications are introduced into the CH3 in an asymmetric fashion resulting in a heterodimer when two modified CH3 domains form an Fc variant (See, e.g., Table 1). As used herein, asymmetric amino acid modifications are any modification wherein an amino acid at a specific position on one polypeptide (e.g., "Chain A") is different from the amino acid on the second polypeptide (e.g., "Chain B") at the same position of the heterodimer or Fc variant. This can be a result of modification of only one of the two amino acids or modification of both amino acids to two different amino acids from Chain A and Chain B of the Fc variant. It is understood that the variant CH3 domains comprise one or more asymmetric amino acid modifications.

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, "about" means±10% of the indicated range, value, sequence, or structure, unless otherwise indicated. It should be understood that the terms "a" and "an" as used herein refer to "one or more" of the enumerated components unless otherwise indicated or dictated by its context. The use of the alternative (e.g., "or") should be understood to mean either one, both, or any combination thereof of the alternatives. As used herein, the terms "include" and "comprise" are used synonymously. In addition, it should be understood that the individual single chain polypeptides or heterodimers derived from various combinations of the structures and substituents (e.g., variant CH3 domains) described herein are disclosed by the present application to the same extent as if each single chain polypeptide or heterodimer were set forth individually. Thus, selection of particular components to form individual single chain polypeptides or heterodimers is within the scope of the present disclosure.

The "first polypeptide" is any polypeptide that is to be associated with a second polypeptide, also referred to herein as "Chain A". The first and second polypeptide meet at an "interface". The "second polypeptide" is any polypeptide that is to be associated with the first polypeptide via an "interface", also referred to herein as "Chain B". The "interface" comprises those "contact" amino acid residues in the first polypeptide that interact with one or more "contact" amino acid residues in the interface of the second polypeptide. As used herein, the interface comprises the CH3 domain of an Fc region that preferably is derived from an IgG antibody and most preferably a human IgG$_1$ antibody.

As used herein, "isolated" heteromultimer means a heteromultimer that has been identified and separated and/or recovered from a component of its natural cell culture environment. Contaminant components of its natural environment are materials that would interfere with diagnostic or therapeutic uses for the heteromultimer, and may include enzymes, hormones, and other proteinaceous or non-proteinaceous solutes.

The variant Fc heterodimers are generally purified to substantial homogeneity. The phrases "substantially homogeneous", "substantially homogeneous form" and "substantial homogeneity" are used to indicate that the product is substantially devoid of by-products originated from unde sired polypeptide combinations (e.g. homodimers). Expressed in terms of purity, substantial homogeneity means that the amount of by-products does not exceed 10%, and preferably is below 5%, more preferably below 1%, most preferably below 0.5%, wherein the percentages are by weight.

using only a negative design approach leads to high specificity with >95% heterodimers, but destabilizes the complex considerably (Supra). These negative design heterodimers posses a melting temperature, of the modified CH3 domain, of 69° C. or less, absent additional disulfide bonds as compared to the wild type. See, Table A below.

TABLE A

Published Fc Heterodimer Antibodies.

| | Chains | Engineering Approach | Source | Purity | Tm ° C. |
|---|---|---|---|---|---|
| Wild-Type | — | — | | | 81-83 |
| Control 4 | Y349C_T366S_L368A_Y407V S354C_T366W | Knobs-into-holes plus disulfide | Genentech (Merchant et al.) | 95% | >77** |
| Control 3 | K409D_K392D D399K | Electrostatic steering | Amgen (Gunaskekaran et al.) | <80% | NP |
| Control 2 | T366S_L368A_Y407V T366W | Knobs-into-holes | Genentech (Atwell et al.) | 95% | 69 |
| Control 1 | K409D_K392D D399K_E356K | Electrostatic steering | Amgen (Gunaskekaran et al.) | 100%* | 67 |
| Control 5 | IgG-IgA chimera | Strand Exchange | EMD Serono (Muda et al.) | >90% | 68 |

*We observed a purity of >90% for Control 1 in our assay system, but not 100% as previously reported in the literature.
**We observed a Tm greater than 77° C. for control 4 in our assay system; the Tm for this variant has not been published in the literature.
NP-The Tm for Control 3 has not been published and it was not tested in our assays systems. The melting temperature for wild-type IgG1 is shown as a range from 81-83 as the values in the literature vary depending on the assay system used, we report a value of 81.5° C. in our assay system.

Terms understood by those in the art of antibody technology are each given the meaning acquired in the art, unless expressly defined differently herein. Antibodies are known to have variable regions, a hinge region, and constant domains. Immunoglobulin structure and function are reviewed, for example, in Harlow et al, Eds., Antibodies: A Laboratory Manual, Chapter 14 (Cold Spring Harbor Laboratory, Cold Spring Harbor, 1988).

The design of variant Fc heterodimers from wildtype homodimers is illustrated by the concept of positive and negative design in the context of protein engineering by balancing stability vs. specificity, wherein mutations are introduced with the goal of driving heterodimer formation over homodimer formation when the polypeptides are expressed in cell culture conditions. Negative design strategies maximize unfavorable interactions for the formation of homodimers, by either introducing bulky sidechains on one chain and small sidechains on the opposite, for example the knobs-into-holes strategy developed by Genentech (Ridgway J B, Presta L G, Carter P. 'Knobs-into-holes' engineering of antibody CH3 domains for heavy chain heterodimerization. Protein Eng. 1996 July; 9(7):617-21; Atwell S, Ridgway J B, Wells J A, Carter P. Stable heterodimers from remodeling the domain interface of a homodimer using a phage display library. J Mol Biol. 270(1):26-35 (1997))), or by electrostatic engineering that leads to repulsion of homodimer formation, for example the electrostatic steering strategy developed by Amgen (Gunaskekaran K, et al. Enhancing antibody Fc heterodimer formation through electrostatic steering effects: applications to bispecific molecules and monovalent IgG. JBC 285 (25): 19637-19646 (2010)). In these two examples, negative design asymmetric point mutations were introduced into the wild-type CH3 domain to drive heterodimer formation. To date, only negative design strategies have been used to develop Fc heterodimers. Published results show that heterodimers designed In contrast to negative design, a general concept used to engineer proteins is positive design. In this instance amino acid modifications are introduced into polypeptides to maximize favorable interactions within or between proteins. This strategy assumes that when introducing multiple mutations that specifically stabilize the desired heterodimer while neglecting the effect on the homodimers, the net effect will be better specificity for the desired heterodimer interactions over the homodimers and hence a greater heterodimer specificity. It is understood in the context of protein engineering that positive design strategies optimize the stability of the desired protein interactions, but rarely achieve >90% specificity (Havranek J J & Harbury P B. Automated design of specificity in molecular recognition. Nat Struct Biol. 10(1):45-52 (2003); Bolon D N, Grant R A, Baker T A, Sauer R T. Specificity versus stability in computational protein design. Proc Natl Acad Sci USA. 6; 102(36):12724-9 (2005); Huang P S, Love J J, Mayo S L. A de novo designed protein protein interface Protein Sci. 16(12):2770-4 (2007)). And thus, to date, positive design strategies have not been used to design Fc heterodimers as specificity was more important than stability for therapeutic antibody manufacturing and development. In addition, beneficial positive design mutations can be hard to predict. Other methodologies for improving stability, such as additional disulfide bonds, have been tried to improve stability in Fc heterodimers with limited success on improvements to the molecule. (See, Table A) This may be because all engineered Fc CH3 domain disulfide bonds are solvent exposed, which results in a short lifetime of the disulfide bond and therefore a significant impact on the long-term stability of the heterodimer—especially when the engineered CH3 domain has a Tm of less than 70° C. without the additional disulfide bond (as in Control 4 which has a Tm of 69° C. without the disulfide (see Control 2). It is contemplated that other methodologies to improve stability, such as disulfide bonds, can also be used with the present Fc variants, provided the intrinsic stability (measured as melting temperature) of the CH3 domain is 70° C. or greater without the disulfide bond, in particular when the intrinsic stability (measured as melting temperature) of the CH3 domain is 72° C. or greater without the disulfide bond.

Therefore, we herein disclose a novel method for designing Fc heterodimers that results in both stable and highly specific heterodimer formation. This design method combines both negative and positive design strategies along with structural and computational modeling guided protein engineering techniques. This powerful method has allowed us to design novel combinations of mutations in the IgG1 CH3 domain wherein using only standard cell culture conditions heterodimers were formed with more than 90% purity compared to homodimers and the resulting heterodimers had a melting temperature of 70° C. or greater. In exemplary embodiments, the Fc variant heterodimers have a melting temperature of 73° C. or greater and a purity of greater than 98%. In other exemplary embodiments, the Fc variant heterodimers have a melting temperature of 75° C. or greater and a purity of greater than 90%.

In certain embodiments, an isolated heteromultimer comprising a heterodimer Fc region is provided wherein the heterodimer Fc region comprises a variant CH3 domain comprising amino acid mutations to promote heterodimer formation with increased stability, wherein the variant CH3 domain has a melting temperature (Tm) of 70° C. or greater. As used herein "increased stability" or "stable heterodimer", refers to a variant CH3 domain, in heterodimer formation, with a melting temperature of about 70° C. or greater. In addition, it is understood that the term "to promote heterodimer formation" refers herein to the amino acid mutations in the CH3 domain that result in greater than 90% heterodimer formation compared to homodimer formation.

In a further embodiment, this increased stability is in the absence of an additional disulfide bond. Specifically, the increased stability is in the absence of an additional disulfide bond in the CH3 domain. In one embodiment, the variant CH3 domain does not comprise an additional disulfide bond as compared to wild-type CH3 domain. In an alternative embodiment, the variant CH3 comprises at least one disulfide bond as compared to wild-type CH3 domain, provided that the variant CH3 has a melting temperature of 70° C. or greater in the absence of the disulfide bond. In one embodiments, the variant CH3 domain comprises at least one disulfide bond as compared to wild-type CH3 domain, and the variant CH3 domain has a melting temperature (Tm) of about 77.5° C. or greater. In an embodiment, the variant CH3 domain comprises at least one disulfide bond as compared to wild-type CH3 domain, and the variant CH3 domain has a melting temperature (Tm) of about 78° C. or greater. In another embodiment, the variant CH3 domain comprises at least one disulfide bond as compared to wild-type CH3 domain, and the variant CH3 domain has a melting temperature (Tm) of greater than about 78° C., or greater than about 78.5° C., or greater than about 79° C., or greater than about 79.5° C., or greater than about 80° C., or greater than about 80.5° C., or greater than about 81° C.

In one embodiment, the variant CH3 domain has a melting temperature of greater than about 70° C., or greater than about 70.5° C., or greater than about 71° C., or greater than about 71.5° C., or greater than about 72° C., or greater than about 72.5° C., or greater than about 73° C., or greater than about 73.5° C., or greater than about 74° C., or greater than about 74.5° C., or greater than about 75° C., or greater than about 75.5° C., or greater than about 76° C., or greater than about 76.5° C., or greater than about 77° C., or greater than about 77.5° C., or greater than about 78° C., or greater than about 78.5° C., or greater than about 79° C., or greater than about 79.5° C., or greater than about 80° C., or greater than about 80.5° C., or greater than about 81° C. In another embodiment, the variant CH3 domain has a melting temperature of about 70° C., or about 70.5° C., or about 71° C., or about 71.5° C., or about 72° C., or about 72.5° C., or about 73° C., or about 73.5° C., or about 74° C., or about 74.5° C., or about 75° C., or about 75.5° C., or about 76° C., or about 76.5° C., or about 77° C., or about 77.5° C., or about 78° C., or about 78.5° C., or about 79° C., or about 79.5° C., or about 80° C., or about 80.5° C., or about 81° C. In yet another embodiment, the variant CH3 domain has a melting temperature of about 70° C. to about 81° C., or about 70.5° C. to about 81° C., or about 71° C. to about 81° C., or about 71.5° C. to about 81° C., or about 72° C. to about 81° C., or about 72.5° C. to about 81° C., or about 73° C. to about 81° C., or about 73.5° C. to about 81° C., or about 74° C. to about 81° C., or about 74.5° C. to about 81° C., or about 75° C. to about 81° C., or about 75.5° C. to about 81° C., or 76° C. to about 81° C., or about 76.5° C. to about 81° C., or about 77° C. to about 81° C., or about 77.5° C. to about 81° C., or about 78° C. to about 81° C., or about 78.5° C. to about 81° C., or about 79° C. to about 81° C. In yet another embodiment, the variant CH3 domain has a melting temperature of about 71° C. to about 76° C., or about 72° C. to about 76° C., or about 73° C. to about 76° C., or about 74° C. to about 76° C.

In addition to improved stability, the heterodimer Fc region comprises a variant CH3 domain comprising amino acid mutations to promote heterodimer formation. It is understood that these amino acid mutations to promote heterodimer formation are as compared to homodimer formation. This heterodimer formation as compared to homodimer formation is referred jointly herein as "purity" or "specificity" or "heterodimer purity" or "heterodimer specificity". It is understood that the heterodimer purity refers to the percentage of desired heterodimer formed as compared to homodimer species formed in solution under standard cell culture conditions prior to selective purification of the heterodimer species. For instance, a heterodimer purity of 90% indicates that 90% of the dimer species in solution is the desired heterodimer. In one embodiment, the Fc variant heterodimers have a purity of greater than about 90%, or greater than about 91%, or greater than about 92%, or greater than about 93%, or greater than about 94%, or greater than about 95%, or greater than about 96%, or greater than about 97%, or greater than about 98%, or greater than about 99%. In another embodiment, the Fc variant heterodimers have a purity of about 90%, or about 91%, or about 92%, or about 93%, or about 94%, or about 95%, or about 96%, or about 97%, or about 98%, or about 99%, or about 100%.

In a specific embodiment, the isolated heteromultimer comprising a heterodimer Fc region, wherein the heterodimer Fc region comprises a variant CH3 domain comprising amino acid mutations to promote heterodimer formation with increased stability, wherein the variant CH3 domain has a melting temperature (Tm) of 70° C. or greater and the resulting heterodimer has a purity greater than 90%. In one aspect, the resulting Fc variant heterodimer has a purity greater than 90% and the variant CH3 domain has a melting temperature of greater than about 70° C., or greater than about 71° C., or greater than about 72° C., or greater than about 73° C., or greater than about 74° C., or greater than about 75° C., or greater than about 76° C., or greater than about 77° C., or greater than about 78° C., or greater than about 79° C., or greater than about 80° C. or greater than about 81° C. In a further aspect, the variant CH3 domain has a melting temperature of 70° C. or greater and the resulting Fc variant heterodimer has a purity greater than about 90%, or greater than about 91%, or greater than about 92%, or greater than about 93%, or greater than about 94%, or greater than about 95%, or greater than about 96%, or greater than about 97%, or greater than about 98%, or greater than about 99%.

In order to design these Fc variants with improved stability and purity we employed an iterative process of computational design and experimental screening to select the most successful combinations of positive and negative design strategies (See, FIG. 24).

Specifically, in the initial design phase different negative design Fc variant heterodimers were made and tested for expression and stability as described in Examples 1-3. The initial design phase included Fc variant heterodimers AZ1-AZ16 (See, Table 1). From this initial set of negative design Fc variant heterodimers, which were expected to have low stability (e.g., a Tm of less than 71° C.), the Fc variant heterodimers with greater than 90% purity and a melting temperature of about 68° C. or greater were selected for further development. This included Fc variant heterodimers AZ6, AZ8 and AZ15. In the second design phase, those selected Fc variant heterodimers were further modified to drive both stability and purity using positive design strategies following a detailed computational and structural analysis. The selected Fc variant heterodimers (AZ6, AZ8, and AZ15) were each analyzed with computational methods and comprehensive structure function analysis to identify the structural reasons these Fc variants had a lower stability than the wild-type Fc homodimer, which is 81° C. for IgG1. See, Table 4 for the list of Fc variant heterodimers and the Tm values.

In certain embodiments, the variant CH3 domain is selected from AZ1, or AZ2, or AZ3, or AZ4, or AZ5, or AZ6, or AZ7, or AZ8, or AZ9, or AZ10, or AZ11, or AZ12, or AZ13, or AZ14, or AZ15, or AZ16. In selected embodiments, the variant CH3 domain is AZ6, or AZ8 or AZ15.

The computational tools and structure-function analysis included, but were not limited to molecular dynamic analysis (MD), sidechain/backbone re-packing, Knowledge Base Potential (KBP), cavity and (hydrophobic) packing analysis (LJ, CCSD, SASA, dSASA(carbon/all-atom)), electrostatic-GB calculations, and coupling analysis. (See, FIG. 24 for an overview of the computational strategy)

An aspect of our protein engineering approach relied on combining structural information of the Fc IgG protein derived from X-ray crystallography with computational modeling and simulation of the wild type and variant forms of the CH3 domain. This allowed us to gain novel structural and physico-chemical insights about the potential role of individual amino acids and their cooperative action. These structural and physico-chemical insights, obtained from multiple variant CH3 domains, along with the resulting empirical data pertaining to their stability and purity helped us develop an understanding for the relationship between purity and stability of the Fc heterodimer as compared to the Fc homodimers and the simulated structural models. In order to execute our simulations we started by building complete and realistic models and refining the quality of the wild type Fc structure of an IgG1 antibody. Protein structures derived from X-ray crystallography are lacking in detail regarding certain features of the protein in aqueous medium under physiological condition and our refinement procedures addressed these limitations. These include building missing regions of the protein structure, often flexible portions of the protein such as loops and some residue side chains, evaluating and defining the protonation states of the neutral and charged residues and placement of potential functionally relevant water molecules associated with the protein.

Molecular dynamics (MD) algorithms are one tool we used, by simulating the protein structure, to evaluate the intrinsic dynamic nature of the Fc homodimer and the variant CH3 domains in an aqueous environment. Molecular dynamics simulations track the dynamic trajectory of a molecule resulting from motions arising out of interactions and forces acting between all the atomic entities in the protein and its local environment, in this case the atoms constituting the Fc and its surrounding water molecules. Following molecular dynamics simulations, various aspects of the trajectories were analyzed to gain insight into the structural and dynamic characteristics of the Fc homodimer and variant Fc heterodimer, which we used to identify specific amino acid mutations to improve both purity and stability of the molecule.

Therefore, the generated MD trajectories were studied using methods such as the principal component analysis to reveal the intrinsic low frequency modes of motion in the Fc structure. This provides insight into the potential conformational sub-states of the protein (See, FIG. 32). While the critical protein-protein interactions between chain A and B in the Fc region occur at the interface of the CH3 domains, our simulations indicated that this interface acts as a hinge in a motion that involves the "opening" and "closing" of the N-terminal ends of the CH2 domains relative to each other. The CH2 domain interacts with FcgR's at this end as seen in FIG. 16. Thus, while not wishing to be bound by a theory, it appears that introduction of amino acid mutations at the CH3 interface impacts the magnitude and nature of the open/close motion at the N-terminal end of the Fc and therefore how the Fc interacts with the FcgR's. See, example 4 and Table 5.

The generated MD trajectories were also studied to determine the mutability of specific amino acid residue positions in the Fc structure based on profiling their flexibility and analysis of their environment. This algorithm allowed us to identify residues that could affect protein structure and function, providing unique insight into residue characteristics and mutability for subsequent design phases of the variant CH3 domains. This analysis also enabled us to compare multiple simulations, and assess mutability based on outliers following profiling.

The generated MD trajectories were also studied to determine correlated residue motions in the protein and the formation of networks of residues as a result of coupling between them. Finding dynamic correlations and networks of residues within the Fc structure is a critical step in understanding the protein as a dynamic entity and for developing insight into the effects of mutations at distal sites. See, e.g. Example 6

Thus, we studied in detail the impact of mutations on the local environment of the site of mutation. The formation of a well packed core at the CH3 interface between chain A and B is critical for the spontaneous pairing of the two chains in a stable Fc structure. Good packing is the result of strong structural complementarity between interacting molecular partners coupled with favorable interactions between the contacting groups. The favorable interactions result from either buried hydrophobic contacts well removed from solvent exposure and/or from the formation of complementary electrostatic contacts between hydrophilic polar groups. These hydrophobic and hydrophilic contacts have entropic and enthalpic contributions to the free energy of dimer formation at the CH3 interface. We employ a variety of algorithms to accurately model the packing at the CH3 interface between chain A and chain B and subsequently evaluate the thermodynamic properties of the interface by scoring a number of relevant physicochemical properties.

We employed a number of protein packing methods including flexible backbones to optimize and prepare model structures for the large number of variants we computationally screened. Following packing we evaluated a number of terms including contact density, clash score, hydrogen bonds, hydrophobicity and electrostatics. The use of the solvation models allowed us to more accurately address the effect of solvent environment and contrast the free energy differences following mutation of specific positions in the protein to alternate residue types. Contact density and clash score provide a measure of complementarity, a critical aspect of effective protein packing. These screening procedures are based on the application of knowledge-based potentials or coupling analysis schemes relying on pair-wise residue interaction energy and entropy computations.

This comprehensive in-silico analysis provided a detailed understanding of the differences of each Fc variant compared to wild-type with respect to interface hotspots, sites of asymmetry, cavities and poorly packed regions, structural dynamics of individual sites and sites of local unfolding. These combined results of the described computational analysis identified specific residues, sequence/structural motifs and cavities that were not optimized and in combination responsible for the lower stability (e.g., Tm of 68° C.) and/or lower specificity of <90% purity. In the second design phase we used targeted positive design to specifically address these hypothesis by additional point-mutations and tested these by in-silico engineering using the above described methodology and analysis (See, FIG. 24). The Fc variant heterodimers designed to improve stability and purity for each targeted design in phase two (Fc variant heterodimers AZ17-AZ101) were validated experimentally for expression and stability as described in Examples 1-4.

In certain embodiments, provided herein are isolated heteromultimers comprising a heterodimer Fc region, wherein the heterodimer Fc region comprises a variant CH3 domain comprising amino acid mutations to promote heterodimer formation with increased stability, wherein the variant CH3 domain is AZ17, or AZ18, or AZ19, or AZ20, or AZ21, or AZ22, or AZ23, or AZ24, or AZ25, or AZ26, or AZ27, or AZ28, or AZ29, or AZ30, or AZ21, or AZ32, or AZ33, or AZ34, or AZ35, or AZ36, or AZ37, or AZ38, or AZ39, or AZ40, or AZ41, or AZ42, or AZ43, or AZ44, or AZ45, or AZ46, or AZ47, or AZ48, or AZ49, or AZ50, or AZ51, or AZ52, or AZ53, or AZ54, or AZ55, or AZ56 or AZ57, or AZ58, or AZ59, or AZ60, or AZ61, or AZ62, or AZ63, or AZ64, or AZ65, or AZ66, or AZ67, or AZ68, or AZ69, or AZ70, or AZ71, or AZ72, or AZ73, or AZ74, or AZ75, or AZ76, or AZ77, or AZ78, or AZ79, or AZ80, or AZ81, or AZ82, or AZ83, or AZ84, or AZ85, or AZ86, or AZ87, or AZ88, or AZ89, or AZ90, or AZ91, or AZ92, or AZ93, or AZ94, or AZ95, or AZ96, or AZ97, or AZ98, or AZ99, or AZ100 or AZ101. In an exemplary embodiment, the variant CH3 domain is AZ17, or AZ18, or AZ19, or AZ20, or AZ21, or AZ22, or AZ23, or AZ24, or AZ25, or AZ26, or AZ27, or AZ28, or AZ29, or AZ30, or AZ21, or AZ32, or AZ33, or AZ34, or AZ38, or AZ42, or AZ43, or AZ 44, or AZ45, or AZ46, or AZ47, or AZ48, or AZ49, or AZ50, or AZ52, or AZ53, or AZ54, or AZ58, or AZ59, or AZ60, or AZ61, or AZ62, or AZ63, or AZ64, or AZ65, or AZ66, or AZ67, or AZ68, or AZ69, or AZ70, or AZ71, or AZ72, or AZ73, or AZ74, or AZ75, or AZ76, or AZ77, or AZ78, or AZ79, or AZ81, or AZ82, or AZ83, or AZ84, or AZ85, or AZ86, or AZ87, or AZ88, or AZ89, or AZ91, or AZ92, or AZ93, or AZ94, or AZ95, or AZ98, or AZ99, or AZ100 or AZ101. In a specific embodiment, the variant CH3 domain is AZ33 or AZ34. In another embodiment, the variant CH3 domain is AZ70 or AZ90.

In an exemplary embodiment, the CH3 domain comprises a first and second polypeptide (also referred to herein as Chain A and Chain B) wherein the first polypeptide comprises amino acid modifications L351Y, F405A, and Y407V and wherein the second polypeptide comprises amino acid modifications T366I, K392M and T394W. In another embodiment, a first polypeptide comprises amino acid modifications L351Y, S400E, F405A and Y407V and the second polypeptide comprises amino acid modifications T366I, N390R, K392M and T394W.

This iterative process of computational structure-function analysis, targeted engineering and experimental validation was used to design the remaining Fc variants listed in Table 1 in subsequent design phases and resulting in Fc variant heterodimers with a purity greater than 90% and an increased stability with a CH3 domain melting temperature greater than 70° C. In certain embodiments, the Fc variants comprise amino acid mutations selected from AZ1 to AZ 136. In further embodiments, the Fc variants comprise amino acid mutations selected from the Fc variants listed in Table 4.

From the first and second design phases two core scaffolds were identified, Scaffold 1 and Scaffold 2, wherein additional amino acid modifications were introduced into these scaffolds to fine tune the purity and stability of the Fc variant heterodimers. See Example 5 for a detailed description of the development of Scaffold 1 including AZ8, AZ17-62 and the variants listed in Table 6. See Example 6 for a detailed description of the development of Scaffold 2 including AZ15 and AZ63-101 and the variants listed in Table 7.

The core mutations of Scaffold 1 comprise L351Y_F405A_Y407V/T394W. Scaffold 1a comprises the amino acid mutations T366I_K392M_T394W/F405A_Y407V and Scaffold 1b comprises the amino acid mutations T366L_K392M_T394W/F405A_Y407V. See, Example 5.

In certain embodiments, the variant CH3 domain comprises a first and second polypeptide (also referred to herein as Chain A and Chain B) wherein the first polypeptide comprises amino acid modifications L351Y, F405A and Y407V and the second polypeptide comprises amino acid modification T394W. In one aspect the variant CH3 domain further comprises point mutations at positions F405 and/or K392. These mutations at position K392 include, but are not limited to, K392V, K392M, K392R, K392L, K392F or K392E. These mutations at position F405 include, but are not limited to, F405I, F405M, F405S, F405S, F405V or F405W. In another aspect, the variant CH3 domain further comprises point mutations at positions T411 and/or S400. These mutations at position T411 include, but are not limited to, T411N, T411R, T411Q, T411K, T411D, T411E or T411W. These mutations at position S400 include, but are not limited to, S400E, S400D, S400R or S400K. In yet another embodiment, the variant CH3 domain comprises a first and second polypeptide wherein the first polypeptide comprises amino acid modifications L351Y, F405A and Y407V and the second polypeptide comprises amino acid modification T394W, wherein the first and/or second polypeptide comprises further amino acid modifications at positions T366 and/or L368. These mutations at position T366 include, but are not limited to, T366A, T366I, T366L, T366M, T366Y, T366S, T366C, T366V or T366W. In an exemplary embodiment, the amino acid mutation at position T366 is T366I. In another exemplary embodiment, the amino acid mutation at position T366 is T366L. The mutations at position L368 include, but are not limited to, L368D, L368R, L368T, L368M, L368V, L368F, L368S and L368A.

In certain embodiments, the variant CH3 domain comprises a first and second polypeptide (also referred to herein as Chain A and Chain B) wherein the first polypeptide comprises amino acid modifications L351Y, F405A and Y407V and the second polypeptide comprises amino acid modifications T366L and T394W. In another embodiment, the variant CH3 domain comprises a first and second polypeptide wherein the first polypeptide comprises amino acid modifications L351Y, F405A and Y407V and the second polypeptide comprises amino acid modifications T366I and T394W.

In certain other embodiments, the variant CH3 domain comprises a first and second polypeptide (also referred to herein as Chain A and Chain B) wherein the first polypeptide comprises amino acid modifications L351Y, F405A and Y407V and the second polypeptide comprises amino acid modifications T366L, K392M and T394W. In another embodiment, the variant CH3 domain comprises a first and second polypeptide wherein the first polypeptide comprises amino acid modifications L351Y, F405A and Y407V and the second polypeptide comprises amino acid modifications T366I, K392M and T394W.

In yet another embodiment, the variant CH3 domain comprises a first and second polypeptide (also referred to herein as Chain A and Chain B) wherein the first polypeptide comprises amino acid modifications F405A and Y407V and the second polypeptide comprises amino acid modifications T366L, K392M and T394W. In another embodiment, the variant CH3 domain comprises a first and second polypeptide wherein the first polypeptide comprises amino acid modifications F405A and Y407V and the second polypeptide comprises amino acid modifications T366I, K392M and T394W.

In certain embodiments, the variant CH3 domain comprises a first and second polypeptide (also referred to herein as Chain A and Chain B) wherein the first polypeptide comprises amino acid modifications F405A and Y407V and the second polypeptide comprises amino acid modifications T366L and T394W. In another embodiment, the variant CH3 domain comprises a first and second polypeptide wherein the first polypeptide comprises amino acid modifications F405A and Y407V and the second polypeptide comprises amino acid modifications T366I and T394W.

In an exemplary embodiment, provided herein are isolated heteromultimers comprising a heterodimer Fc region, wherein the heterodimer Fc region comprises a variant CH3 domain comprising amino acid mutations to promote heterodimer formation with increased stability, wherein the variant CH3 domain has a melting temperature (Tm) of about 74° C. or greater. In another embodiment, provided herein are isolated heteromultimers comprising a heterodimer Fc region, wherein the heterodimer Fc region comprises a variant CH3 domain comprising amino acid mutations to promote heterodimer formation with increased stability, wherein the variant CH3 domain has a melting temperature (Tm) of about 74° C. or greater and the heterodimer has a purity of about 98% or greater.

In certain embodiments, the isolated heteromultimer comprising a heterodimer Fc region, wherein the heterodimer Fc region comprises a variant CH3 domain comprising amino acid mutations to promote heterodimer formation with increased stability, wherein the variant CH3 domain has a melting temperature (Tm) greater than 70° C. and the variant CH3 domains are selected from Table 6.

The core mutations of Scaffold 2 comprise L351Y_Y407A/T366A_K409F. Scaffold 2a comprises the amino acid mutations L351Y_Y407A/T366V_K409F and Scaffold 2b comprises the amino acid mutations Y407A/T366A_K409F. See, Example 6.

In certain embodiments, the variant CH3 domain comprises a first and second polypeptide (also referred to herein as Chain A and Chain B) wherein the first polypeptide comprises amino acid modifications L351Y and Y407A and the second polypeptide comprises amino acid modifications T366A and K409F. In one aspect the variant CH3 domain further comprises point mutations at positions T366, L351, and Y407. These mutations at position T366 include, but are not limited to, T366I, T366L, T366M, T366Y, T366S, T366C, T366V or T366W. In a specific embodiment, the mutation at position T366 is T366V. The mutations at position L351 include, but are not limited to, L351I, L351D, L351R or L351F. The mutations at position Y407 include, but are not limited to, Y407V or Y407S. See, CH3 variants AZ63-AZ70 in Table 1 and Table 4 and Example 6.

In an exemplary embodiment, the variant CH3 domain comprises a first and second polypeptide (also referred to herein as Chain A and Chain B) wherein the first polypeptide comprises amino acid modifications L351Y and Y407A and the second polypeptide comprises amino acid modification T366V and K409F.

In an exemplary embodiment, provided herein are isolated heteromultimers comprising a heterodimer Fc region, wherein the heterodimer Fc region comprises a variant CH3 domain comprising amino acid mutations to promote heterodimer formation with increased stability, wherein the variant CH3 domain has a melting temperature (Tm) of about 75.5° C. or greater. In another embodiment, provided herein are isolated heteromultimers comprising a heterodimer Fc region, wherein the heterodimer Fc region comprises a variant CH3 domain comprising amino acid mutations to promote heterodimer formation with increased stability, wherein the variant CH3 domain has a melting temperature (Tm) of about 75° C. or greater and the heterodimer has a purity of about 90% or greater.

In other certain embodiments, the variant CH3 domain comprises a first and second polypeptide (also referred to herein as Chain A and Chain B) wherein the first polypeptide comprises amino acid modifications L351Y and Y407A and the second polypeptide comprises amino acid modification T366A and K409F, wherein the variant CH3 domain comprises one or more amino acid modifications at positions T411, D399, S400, F405, N390, and/or K392. These mutations at position D399 include, but are not limited to, D399R, D399W, D399Y or D399K. The mutations at position T411 includes, but are not limited to, T411N, T411R, T411Q, T411K, T411D, T411E or T411W. The mutations at position S400 includes, but are not limited to, S400E, S400D, S400R, or S400K. The mutations at position F405 includes, but are not limited to, F405I, F405M, F405S, F405V or F405W. The mutations at position N390 include, but are not limited to, N390R, N390K or N390D. The mutations at position K392 include, but are not limited to, K392V, K392M, K392R, K392L, K392F or K392E. See, CH3 variants AZ71-101 in Table 1 and Table 4 and Example 6.

In an exemplary embodiment, the variant CH3 domain comprises a first and second polypeptide (also referred to herein as Chain A and Chain B) wherein the first polypeptide comprises amino acid modification Y407A and the second polypeptide comprises amino acid modification T366A and K409F. In one aspect, this variant CH3 domain further comprises the amino acid modifications K392E, T411E, D399R and S400R. In a further embodiment, the variant CH3 domain comprises a first and second polypeptide wherein the first polypeptide comprises amino acid modification D399S, S400R and Y407A and the second polypeptide comprises amino acid modification T366A, K409F, K392E and T411E.

In an exemplary embodiment, provided herein are isolated heteromultimers comprising a heterodimer Fc region, wherein the heterodimer Fc region comprises a variant CH3 domain comprising amino acid mutations to promote heterodimer formation with increased stability, wherein the variant CH3 domain has a melting temperature (Tm) of about 74° C. or greater. In another embodiment, provided herein are isolated heteromultimers comprising a heterodimer Fc region, wherein the heterodimer Fc region comprises a variant CH3 domain comprising amino acid mutations to promote heterodimer formation with increased stability, wherein the variant CH3 domain has a melting temperature (Tm) of about 74° C. or greater and the heterodimer has a purity of about 95% or greater.

In certain embodiments, provided herein are isolated heteromultimers comprising a heterodimer Fc region, wherein the heterodimer Fc region comprises a variant CH3 domain comprising amino acid mutations to promote heterodimer formation with increased stability, wherein the variant CH3 domain has a melting temperature (Tm) greater than 70° C. and the variant CH3 domains are selected from Table 7.

Furthermore, this new method of designing Fc variant heterodimers with improved stability and purity can be applied to other classes and isotypes of Fc regions. In certain embodiments, the Fc region is a human IgG Fc region. In further embodiments, the human IgG Fc region is a human IgG1, IgG2, IgG3, or IgG4 Fc region. In some embodiments the Fc regions is from an immunoglobulin selected from the group consisting of IgG, IgA, IgD, IgE and IgM. In some embodiments, the IgG is of subtype selected from the group consisting of IgG1, IgG2a, IgG2b, IgG3 and IgG4.

TABLE 1

CH3 domain amino acid modifications for the generation of Fc variant heterodimers.

| Variant | | Chains | | | Fc Mutations | | | |
|---|---|---|---|---|---|---|---|---|
| Wild-Type IgG1 | | A | — | — | — | — | — | — |
| | | B | — | — | — | — | — | — |
| CH3 Variants | AZ1 | A | L368D | K370Q | — | — | — | — |
| | | B | E357R | L368R | — | — | — | — |
| | AZ2 | A | L351I | L368D | K370Q | — | — | — |
| | | B | E357R | L368R | — | — | — | — |
| | AZ3 | A | L351D | L368D | K370Q | — | — | — |
| | | B | E357R | L368R | — | — | — | — |
| | AZ4 | A | L368D | K370E | — | — | — | — |
| | | B | E357R | L368R | — | — | — | — |
| | AZ5 | A | L368D | K370E | — | — | — | — |
| | | B | E357K | L368R | — | — | — | — |
| | AZ6 | A | V397S | F405A | Y407V | — | — | — |
| | | B | K392V | T394W | — | — | — | — |
| | AZ7 | A | L351R | V397S | F405A | Y407V | — | — |
| | | B | K392V | T394W | — | — | — | — |
| | AZ8 | A | L351Y | V397S | F405A | Y407V | — | — |
| | | B | K392V | T394W | — | — | — | — |
| | AZ9 | A | V397S | F405A | Y407V | — | — | — |
| | | B | L368R | K392V | T394W | — | — | — |
| | AZ10 | A | V397T | F405I | — | — | — | — |
| | | B | K392V | T394H | — | — | — | — |
| | AZ11 | A | E357W | S364F | — | — | — | — |
| | | B | Y349A | L351Y | K370I | — | — | — |
| | AZ12 | A | E357H | S364F | — | — | — | — |
| | | B | L351Y | K370I | — | — | — | — |
| | AZ13 | A | E357W | S364F | — | — | — | — |
| | | B | Y349A | L351Y | K370F | — | — | — |
| | AZ14 | A | E357H | S364F | — | — | — | — |
| | | B | L351Y | K370F | — | — | — | — |
| | AZ15 | A | E357L | I366A | K409F | T411N | — | — |
| | | B | L351Y | Y407A | — | — | — | — |
| | AZ16 | A | E357L | T366A | K409Y | T411N | — | — |
| | | B | L351Y | L368T | Y407A | — | — | — |
| | AZ17 | A | L351Y | F405V | Y407V | — | — | — |
| | | B | T366I | T394W | — | — | — | — |
| | AZ18 | A | L351Y | V397T | F405M | Y407V | — | — |
| | | B | T366I | T394W | — | — | — | — |
| | AZ19 | A | L351Y | V397T | F405M | Y407V | — | — |
| | | B | T366L | T394W | — | — | — | — |
| | AZ20 | A | L351Y | V397T | F405M | Y407V | — | — |
| | | B | T366M | T394W | — | — | — | — |
| | AZ21 | A | L351Y | L368M | V397T | F405I | Y407V | — |
| | | B | T366L | T394W | — | — | — | — |

TABLE 1-continued

CH3 domain amino acid modifications for the generation of Fc variant heterodimers.

| Variant | Chains | Fc Mutations | | | | | |
|---|---|---|---|---|---|---|---|
| AZ22 | A | L351Y | L368M | V397T | F405I | Y407V | — |
| | B | T366M | T394W | — | — | — | — |
| AZ23 | A | L351Y | V397T | F405M | Y407V | — | — |
| | B | L351I | T366I | T394W | — | — | — |
| AZ24 | A | L351Y | V397T | L398D | F405M | Y407V | — |
| | B | S354E | T366I | T394W | — | — | — |
| AZ25 | A | L351Y | V397T | L398D | S400E | F405M | Y407V |
| | B | T366I | N390R | T394W | — | — | — |
| AZ26 | A | R344H | L351Y | V397T | S400E | F405M | Y407V |
| | B | Q362R | T366I | T394W | — | — | — |
| AZ27 | A | R344H | L351Y | V397T | D401E | F405M | Y407V |
| | B | Q362R | T366I | T394W | — | — | — |
| AZ28 | A | Q347R | L351Y | V397T | F405M | Y407V | — |
| | B | S354E | K360E | T366I | T394W | — | — |
| AZ29 | A | Q347R | L351Y | V397T | F405M | Y407V | — |
| | B | S354N | K360E | T366I | T394W | — | — |
| AZ30 | A | T350V | L351Y | V397T | S400E | F405M | Y407V |
| | B | T350V | T366I | T394W | T411R | — | — |
| AZ31 | A | R344H | L351Y | V397T | L398D | F405M | Y407V |
| | B | T366I | T394W | T411R | — | — | — |
| AZ32 | A | Q347R | T350V | L351Y | V397T | F405M | Y407V |
| | B | T350V | K360E | T366I | T394W | T411R | — |
| AZ33 | A | L351Y | F405A | Y407V | — | — | — |
| | B | T366I | K392M | T394W | — | — | — |
| AZ34 | A | L351Y | S400E | F405A | Y407V | — | — |
| | B | T366I | N390R | K392M | T394W | — | — |
| AZ35 | A | L351Y | K370Q | G371D | F405M | Y407V | — |
| | B | Q362R | T366I | T394W | K409R | T411Q | — |
| AZ36 | A | L351Y | K370Q | G371D | F405S | Y407V | — |
| | B | Q362R | T366I | T394W | K409R | T411Q | — |
| AZ37 | A | R344H | L351Y | K370Q | G371D | L398D | F405M | Y407V |
| | B | Q362R | T366I | T394W | K409R | T411Q | — |
| AZ38 | A | R344H | L351Y | K370Q | G371D | S400E | F405M | Y407V |
| | B | Q362R | T366I | N390R | T394W | K409R | T411Q |
| AZ39 | A | L351Y | K370Q | G371D | F405M | Y407V | — |
| | B | T366I | T394W | T411R | — | — | — |
| AZ40 | A | L351Y | K370Q | G371D | F405M | Y407V | — |
| | B | T366I | T394W | K409M | — | — | — |
| AZ41 | A | R344H | L351Y | K370Q | G371D | L398D | F405M | Y407V |
| | B | T366I | T394W | K409M | T411R | — | — |
| AZ42 | A | R344H | L351Y | K370Q | G371D | S400E | F405M | Y407V |
| | B | T366I | N390R | T394W | K409M | T411R | — |
| AZ43 | A | L351Y | K370T | G371D | F405I | Y407V | — |
| | B | E357Q | S364R | T394W | — | — | — |
| AZ44 | A | L351Y | K370T | G371D | F405M | Y407V | — |
| | B | E357Q | S364R | T394W | K409I | — | — |
| AZ45 | A | R344H | L351Y | K370T | G371D | S400E | F405M | Y407V |
| | B | E357Q | S364R | T366I | N390R | T394W | K409I |
| AZ46 | A | R344H | L351Y | K370T | G371D | F405M | Y407V | — |
| | B | E357Q | S364R | T366I | T394W | K409I | T411R |
| AZ47 | A | L351Y | K370A | G371S | D399R | F405S | Y407V |
| | B | E357Q | Q362R | T364Y | T366I | T394W | K409S |
| AZ48 | A | L351Y | V397S | D399W | F405M | Y407V | — |
| | B | Q362R | T366I | T394W | K409M | — | — |
| AZ49 | A | L351Y | V397S | D399Y | F405M | Y407V | — |
| | B | Q362R | T366I | T394W | K409I | — | — |
| AZ50 | A | R344H | L351Y | V397T | L398D | D399W | F405M | Y407V |
| | B | Q362R | T366I | T394W | K409M | — | — |
| AZ51 | A | R344H | L351Y | V397T | D399W | S400E | F405M | Y407V |
| | B | Q362R | T366I | T394W | K409M | — | — |
| AZ52 | A | L368V | K370F | F405I | Y407V | — | — |
| | B | E357Q | S364Y | T366I | T394W | — | — |
| AZ53 | A | L368V | K370Y | F405I | Y407V | — | — |
| | B | E357Q | S364Y | T394W | — | — | — |
| AZ54 | A | R344H | L368V | K370Y | F405M | Y407V | — |
| | B | E357Q | Q362R | S364Y | T394W | — | — |
| AZ55 | A | L368V | K370Y | S400E | F405M | Y407V | — |
| | B | E357Q | S364Y | N390R | T394W | — | — |
| AZ56 | A | L368V | K370Y | L398D | F405M | Y407V | — |
| | B | E357Q | S364Y | T394W | T411R | — | — |
| AZ57 | A | R344H | L351Y | K370Y | F405M | Y407V | — |
| | B | E357Q | Q362R | T364T | T366I | T394W | — |
| AZ58 | A | L368V | V397T | F405M | Y407V | — | — |
| | B | T366Y | T394W | — | — | — | — |
| AZ59 | A | L368V | K370Q | V397T | F405M | Y407V | — |
| | B | T366Y | T394W | — | — | — | — |

TABLE 1-continued

CH3 domain amino acid modifications for the generation of Fc variant heterodimers.

| Variant | Chains | Fc Mutations | | | | | |
|---|---|---|---|---|---|---|---|
| AZ60 | A | R344H | L368V | V397T | S400E | F405M | Y407V |
|  | B | Q362R | T366Y | T394W | — | — | — |
| AZ61 | A | L368V | V397T | S400E | F405M | Y407V | — |
|  | B | T366Y | N390R | T394W | — | — | — |
| AZ62 | A | L368V | V397T | L398D | F405M | Y407V | — |
|  | B | T366Y | T394W | T411R | — | — | — |
| AZ63 | A | T366A | K409F | — | — | — | — |
|  | B | Y407A | — | — | — | — | — |
| AZ64 | A | T366A | K409F | — | — | — | — |
|  | B | L351Y | Y407A | — | — | — | — |
| AZ65 | A | T366A | K409F | — | — | — | — |
|  | B | L351F | Y407A | — | — | — | — |
| AZ66 | A | T366S | K409F | — | — | — | — |
|  | B | Y407A | — | — | — | — | — |
| AZ67 | A | T366C | K409F | — | — | — | — |
|  | B | Y407A | — | — | — | — | — |
| AZ68 | A | T366L | K409F | — | — | — | — |
|  | B | Y407A | — | — | — | — | — |
| AZ69 | A | T366M | K409F | — | — | — | — |
|  | B | Y407A | — | — | — | — | — |
| AZ70 | A | T366V | K409F | — | — | — | — |
|  | B | L351Y | Y407A | — | — | — | — |
| AZ71 | A | T366A | K409F | — | — | — | — |
|  | B | L351I | T366S | L368F | Y407A | — | — |
| AZ72 | A | T366A | K409F | — | — | — | — |
|  | B | D399W | Y407A | — | — | — | — |
| AZ73 | A | T366A | K409F | — | — | — | — |
|  | B | D399W | S400D | Y407A | — | — | — |
| AZ74 | A | T366A | K409F | — | — | — | — |
|  | B | D399W | S400E | Y407A | — | — | — |
| AZ75 | A | T366A | K409F | T411R | — | — | — |
|  | B | D399W | S400D | Y407A | — | — | — |
| AZ76 | A | T366A | K409F | T411R | — | — | — |
|  | B | G371D | D399W | Y407A | — | — | — |
| AZ77 | A | T366A | K409F | T411R | — | — | — |
|  | B | K370Q | G371D | D399W | Y407A | — | — |
| AZ78 | A | T366A | N390R | K409F | — | — | — |
|  | B | D399Y | S400D | Y407A | — | — | — |
| AZ79 | A | Q362R | T366A | K409F | T411K | — | — |
|  | B | Y407A | — | — | — | — | — |
| AZ80 | A | Q362R | T366A | K409F | T411R | — | — |
|  | B | Y407A | — | — | — | — | — |
| AZ81 | A | Q362K | T366A | K409F | T411R | — | — |
|  | B | Y407A | — | — | — | — | — |
| AZ82 | A | T366A | N390K | K392R | K409F | T411R | — |
|  | B | S400E | Y407A | — | — | — | — |
| AZ83 | A | T366A | N390K | K392R | K409F | T411K | — |
|  | B | S400E | Y407A | — | — | — | — |
| AZ84 | A | T366A | N390K | K409F | T411R | — | — |
|  | B | S400D | Y407A | — | — | — | — |
| AZ85 | A | T366A | K392L | K409F | T411D | — | — |
|  | B | D399R | Y407A | — | — | — | — |
| AZ86 | A | T366A | K392L | K409F | T411E | — | — |
|  | B | D399R | Y407A | — | — | — | — |
| AZ87 | A | T366A | K392L | K409F | T411D | — | — |
|  | B | D399K | Y407A | — | — | — | — |
| AZ88 | A | T366A | K392L | K409F | T411E | — | — |
|  | B | D399K | Y407A | — | — | — | — |
| AZ89 | A | T366A | K392M | K409F | T411E | — | — |
|  | B | D399R | Y407A | — | — | — | — |
| AZ90 | A | T366A | K392M | K409F | T411D | — | — |
|  | B | D399R | Y407A | — | — | — | — |
| AZ91 | A | T366A | K392F | K409F | T411D | — | — |
|  | B | D399R | F405V | Y407A | — | — | — |
| AZ92 | A | T366A | K409F | T411E | — | — | — |
|  | B | D399R | S400E | Y407A | — | — | — |
| AZ93 | A | T366A | K409F | T411E | — | — | — |
|  | B | D399R | S400D | Y407A | — | — | — |
| AZ94 | A | T366A | K392E | K409F | T411E | — | — |
|  | B | D399R | S400R | Y407A | — | — | — |
| AZ95 | A | T366A | K392E | K409F | T411D | — | — |
|  | B | D399R | S400R | Y407A | — | — | — |
| AZ96 | A | Q362E | T366A | K409F | T411W | — | — |
|  | B | D399R | Y407A | — | — | — | — |
| AZ97 | A | Q362D | T366A | K409F | T411W | — | — |
|  | B | D399R | Y407A | — | — | — | — |

TABLE 1-continued

CH3 domain amino acid modifications for the generation of Fc variant heterodimers.

| Variant | Chains | Fc Mutations | | | | | |
|---|---|---|---|---|---|---|---|
| AZ98 | A | S364Y | T366A | K409F | T411R | — | — |
|  | B | Y407A | — | — | — | — | — |
| AZ99 | A | T366V | K409W | — | — | — | — |
|  | B | L368V | Y407S | — | — | — | — |
| AZ100 | A | T366V | K409W | — | — | — | — |
|  | B | L351Y | L368S | Y407A | — | — | — |
| AZ101 | A | T366V | K409W | — | — | — | — |
|  | B | L351Y | Y407A | — | — | — | — |
| AZ102 | A | E357Q | S364F | K392E | — | — | — |
|  | B | K370F | V397R | S400R | — | — | — |
| AZ103 | A | E357Q | S364F | K392E | V397E | — | — |
|  | B | K370F | V397R | S400R | — | — | — |
| AZ104 | A | E357Q | S364F | N390D | K392E | — | — |
|  | B | K370F | V397R | S400K | — | — | — |
| AZ105 | A | E357Q | S364F | K370E | G371W | — | — |
|  | B | E357Q | K360R | S364N | K370F | — | — |
| AZ106 | A | S354R | D356K | E357Q | S364F | — | — |
|  | B | S354E | K370F | K439E | — | — | — |
| AZ107 | A | Q347R | E357Q | S364F | — | — | — |
|  | B | Q347E | K360E | K370F | — | — | — |
| AZ108 | A | E357Q | S364F | K370E | — | — | — |
|  | B | E357R | K370F | — | — | — | — |
| AZ109 | A | E357Q | S364F | L368D | K370E | — | — |
|  | B | E357R | K370F | — | — | — | — |
| AZ110 | A | E357Q | S364F | K370T | G371D | — | — |
|  | B | E357Q | S364R | K370F | — | — | — |
| AZ111 | A | E357Q | S364Y | K392E | — | — | — |
|  | B | K370F | V397R | S400K | — | — | — |
| AZ112 | A | E357Q | S364Y | K392E | — | — | — |
|  | B | L368A | K370F | V397R | S400K | — | — |
| AZ113 | A | K409F | T411E | — | — | — | — |
|  | B | L368V | D399R | S400D | — | — | — |
| AZ114 | A | K409F | T411E | — | — | — | — |
|  | B | L368V | D399K | S400D | — | — | — |
| AZ115 | A | K409F | — | — | — | — | — |
|  | B | L368V | D399Y | — | — | — | — |
| AZ116 | A | E357Q | K409F | T411R | — | — | — |
|  | B | L368A | K370F | — | — | — | — |
| AZ117 | A | S354R | D356K | K409F | T411R | — | — |
|  | B | S354E | L368V | S400E | K439E | — | — |
| AZ118 | A | K360E | K370E | — | — | — | — |
|  | B | Y349R | E357R | — | — | — | — |
| AZ119 | A | K360E | K370E | — | — | — | — |
|  | B | Y349K | E357R | — | — | — | — |
| AZ120 | A | S354E | K360E | K370E | — | — | — |
|  | B | Y349R | E357R | — | — | — | — |
| AZ121 | A | K360E | L368D | K370E | — | — | — |
|  | B | Y349R | E357R | — | — | — | — |
| AZ122 | A | K360E | L368D | K370E | — | — | — |
|  | B | Y349R | E357R | T411R | — | — | — |
| AZ123 | A | K360E | K370T | G371D | — | — | — |
|  | B | Y349R | E357Q | S364R | — | — | — |
| AZ124 | A | K360E | K370T | G371D | — | — | — |
|  | B | Y349R | E357Q | S364K | — | — | — |
| AZ125 | A | S364E | K370T | G371D | — | — | — |
|  | B | E357Q | S364R | G371R | — | — | — |
| AZ126 | A | S364E | K370T | G371D | — | — | — |
|  | B | E357Q | S364R | G371K | — | — | — |
| AZ127 | A | G371D | T411E | — | — | — | — |
|  | B | G371D | T411R | — | — | — | — |
| AZ128 | A | G371D | T411E | — | — | — | — |
|  | B | G371K | T411R | — | — | — | — |
| AZ129 | A | Y349C | L351Y | V397T | F405M | Y407V | — |
|  | B | S354C | T366I | T394W | — | — | — |
| AZ130 | A | L351Y | S354C | V397T | F405M | Y407V | — |
|  | B | Y349C | T366I | T394W | — | — | — |
| AZ132 | A | L368A | F405W | Y407V | — | — | — |
|  | B | T366W | — | — | — | — | — |

The Fc region as defined herein comprises a CH3 domain or fragment thereof, and may additionally comprise one or more addition constant region domains, or fragments thereof, including hinge, CH1, or CH2. It will be understood that the numbering of the Fc amino acid residues is that of the EU index as in Kabat et al., 1991, NIH Publication 91-3242, National Technical Information Service, Springfield, Va. The "EU index as set forth in Kabat" refers to the EU index numbering of the human IgG1 Kabat antibody. For convenience, Table B provides the amino acids numbered according to the EU index as set forth in Kabat of the CH2 and CH3 domain from human IgG1.

TABLE B

| CH2 Domain | | CH3 Domain | |
|---|---|---|---|
| EU No. | Amino Acid | EU No. | Amino Acid |
| 231 | A | 341 | G |
| 232 | P | 342 | Q |
| 233 | E | 343 | P |
| 234 | L | 344 | R |
| 235 | L | 345 | E |
| 236 | G | 346 | P |
| 237 | G | 347 | Q |
| 238 | P | 348 | V |
| 239 | S | 349 | Y |
| 240 | V | 350 | T |
| 241 | F | 351 | L |
| 242 | L | 352 | P |
| 243 | F | 353 | P |
| 244 | P | 354 | S |
| 245 | P | 355 | R |
| 246 | K | 356 | D |
| 247 | P | 357 | E |
| 248 | K | 358 | L |
| 249 | D | 359 | T |
| 250 | T | 360 | K |
| 251 | L | 361 | N |
| 252 | M | 362 | Q |
| 253 | I | 363 | V |
| 254 | S | 364 | S |
| 255 | R | 365 | L |
| 256 | T | 366 | T |
| 257 | P | 367 | C |
| 258 | E | 368 | L |
| 259 | V | 369 | V |
| 260 | T | 370 | K |
| 261 | C | 371 | G |
| 262 | V | 372 | F |
| 263 | V | 373 | Y |
| 264 | V | 374 | P |
| 265 | D | 375 | S |
| 266 | V | 376 | D |
| 267 | S | 377 | I |
| 268 | H | 378 | A |
| 269 | E | 379 | V |
| 270 | D | 380 | E |
| 271 | P | 381 | W |
| 272 | E | 382 | E |
| 273 | V | 383 | S |
| 274 | K | 384 | N |
| 275 | F | 385 | G |
| 276 | N | 386 | Q |
| 277 | W | 387 | P |
| 278 | Y | 388 | E |
| 279 | V | 389 | N |
| 280 | D | 390 | N |
| 281 | G | 391 | Y |
| 282 | V | 392 | K |
| 283 | E | 393 | T |
| 284 | V | 394 | T |
| 285 | H | 395 | P |
| 286 | N | 396 | P |
| 287 | A | 397 | V |
| 288 | K | 398 | L |
| 289 | T | 399 | D |
| 290 | K | 400 | S |
| 291 | P | 401 | D |
| 292 | R | 402 | G |
| 293 | E | 403 | S |
| 294 | E | 404 | F |
| 295 | Q | 405 | F |
| 296 | Y | 406 | L |
| 297 | N | 407 | Y |
| 298 | S | 408 | S |
| 299 | T | 409 | K |
| 300 | Y | 410 | L |
| 301 | R | 411 | T |
| 302 | V | 412 | V |
| 303 | V | 413 | D |
| 304 | S | 414 | K |
| 305 | V | 415 | S |
| 306 | L | 416 | R |
| 307 | T | 417 | W |
| 308 | V | 418 | Q |
| 309 | L | 419 | Q |
| 310 | H | 420 | G |
| 311 | Q | 421 | N |
| 312 | D | 422 | V |
| 313 | W | 423 | F |
| 314 | L | 424 | S |
| 315 | N | 425 | C |
| 316 | G | 426 | S |
| 317 | K | 427 | V |
| 318 | E | 428 | M |
| 319 | Y | 429 | H |
| 320 | K | 430 | E |
| 321 | C | 431 | A |
| 322 | K | 432 | L |
| 323 | V | 433 | H |
| 324 | S | 434 | N |
| 325 | N | 435 | H |
| 326 | K | 436 | Y |
| 327 | A | 437 | T |
| 328 | L | 438 | Q |
| 329 | P | 439 | K |
| 330 | A | 440 | S |
| 331 | P | 441 | L |
| 332 | I | 442 | S |
| 333 | E | 443 | L |
| 334 | K | 444 | S |
| 335 | T | 445 | P |
| 336 | I | 446 | G |
| 337 | S | 447 | K |
| 338 | K | | |
| 339 | A | | |
| 340 | K | | |

In certain embodiments, the Fc variant comprises a CH2 domain. In some embodiments, the CH2 domain is a variant CH2 domain. In some embodiments, the variant CH2 domains comprise asymmetric amino acid substitutions in the first and/or second polypeptide chain. In some embodiments, the heteromultimer comprises asymmetric amino acid substitutions in the CH2 domain such that one chain of said heteromultimer selectively binds an Fc receptor.

In certain embodiments, the heteromultimer selectively binds an Fc receptor. In some embodiments, Fc receptor is a member of Fcγ receptor family. In some embodiments, the receptor is selected from FcγRI, FcγRIIa, FcγRIIb, FcγRIIc, FcγRIIIa and FcγRIIIb. In one embodiment, the CH2 domain comprises asymmetric amino acid modifications that promote selective binding to Fcgamma receptors.

In some embodiments, the heteromultimer binds selectively to FcγRIIIa. In some embodiments, the heteromultimer comprises asymmetric amino acid substitutions selected from S267D, K392D and K409D. In some embodiments, the heteromultimer binds selectively to FcγRIIa. In some embodiments, the heteromultimer comprises asymmetric amino acid substitutions selected from S239D, K326E, A330L and I332E. In some embodiments, the heteromultimer binds selectively to FcγRIIb. In some embodiments, the heteromultimer comprises asymmetric amino acid substitutions selected from S239D, D265S, E269K and I332E. In some embodiments, the heteromultimer binds selectively to FcγRIIIa and FcγRIIa. In some embodiments, the heteromultimer comprises asymmetric amino acid substitutions selected from S239D, D265S, and S298A. In some embodiments, the heteromultimer binds selectively to FcγRIIIa and FcγRIIb. In some embodiments, the heteromultimer comprises asymmetric amino acid substitutions selected from S239D, S298A, K326E, A330L and I332E. In some embodiments, the heteromultimer binds selectively to FcγRIIa and FcγRIIb. In some embodiments, the heteromultimer comprises asymmetric amino acid substitutions selected from S239D, D265S, S298A and I332E.

In certain embodiments is a method of designing multifunctional therapeutics comprising heteromultimer described herein. In some embodiments is method of designing bi-functional therapeutics comprising a variant Fc heterodimer. In some embodiments is a method for the design of asymmetric mutations in the CH2 domain of a variant Fc heterodimer derived with mutations in the CH3 domain. In some embodiments is a method to design selectivity for the different Fc gamma receptors based on the mutations in the asymmetric Fc. In certain embodiments is a method to design mutations that bias binding of the Fc gamma receptors to one face of the Fc molecule. In certain embodiments is a method to design polarity drivers that bias the Fcγ□ receptors to interact with only one face of the asymmetric Fc scaffold of the heteromultimer described herein.

In some embodiments, is provided a polypeptide comprising mutations in the CH2 domain of the asymmetric Fc that lead to preferential Fc gamma receptor selectivity profiles. In some embodiments mutations in the CH3 domain lead to preferential formation of heterodimeric Fc. In certain embodiments is a method for designing bispecific therapeutic entities based on the asymmetric Fc described herein. In certain embodiments is a method to design multi-specific therapeutic entities based on the asymmetric Fc described herein.

Figure 14:
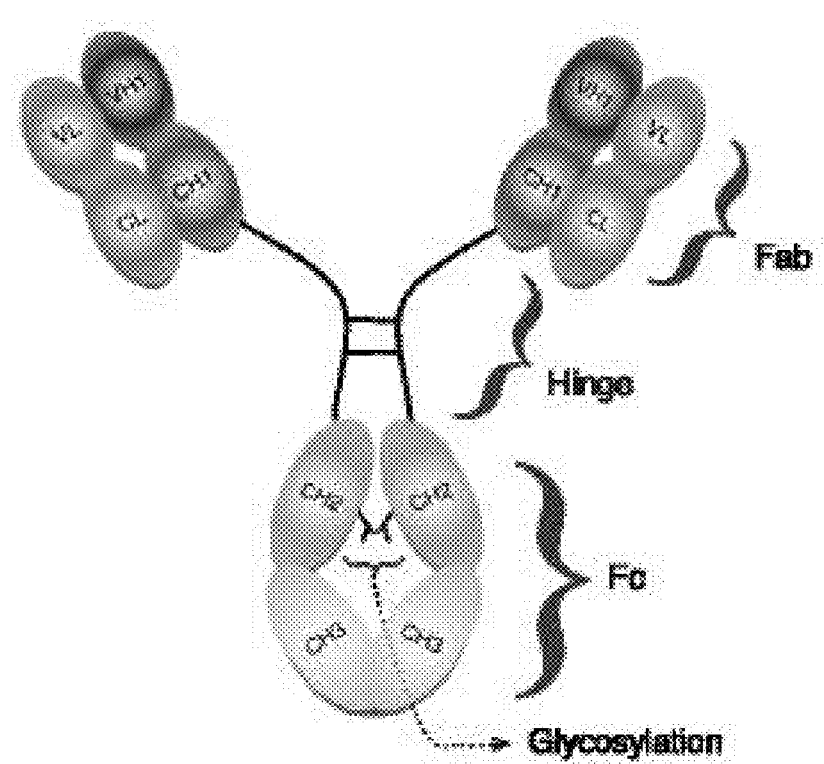
FIG. 14 is a schematic representation of the IgG molecule.

Monoclonal antibodies such as IgG are symmetric molecules composed of two equivalent heavy and two light polypeptide chains (FIG. 14), each comprising multiple immunoglobulin (Ig) structural domains. The IgG class of mAb's exists in one of four isoforms, IgG1, IgG2, IgG3, or IgG4. The heavy chain is composed of four (VH, CH1, CH2 and CH3) and the light chain of two (VL and CL) Ig domains, respectively. The VH and CH1 domains from each of the heavy chains combine with the VL and CL domains of light chain to form the two Fab ("fragment antigen binding") arms of the mAb. The CH3 and CH2 domains of the two heavy chains interact via protein-protein contacts across the CH3 domains and glycosylation in the CH2 domains to form the homodimeric Fc ("fragment crystallizable") region. The linker region between CH1 and CH2 domains of the antibody constitutes the hinge region of the antibody molecule. Apart from connecting the Fab and Fc regions of the mAb, the hinge also maintains disulphide links across the two heavy chains and holds them together. The number of amino acids and disulphide links in the hinge region is notably different among the four isotypes of IgG. The glycosylation pattern in IgG molecules can be significantly diverse, about 30 different carbohydrate moieties have been observed in IgG molecules [Arnold J. N.; Wormald M. R.; Sim R. B.; Rudd P. M. and Dwek R. A. (2007) Annual Reviews of Immunology 25, 21-50].

The symmetric nature of the monoclonal antibodies structure results in both Fab arms having their antigen binding capability affinity matured to recognize the same epitope. At the other end, the Fc portion of the antibody molecule is involved in interactions with various receptor molecules on the immune or "effector" cells, and some of these interactions are responsible for mediating effector functions such as antibody dependent cellular cytotoxicity (ADCC), antibody dependent cellular phagocytosis (ADCP) and complement activation. Generally, the effector function involves immune responses leading to pathogen or toxin neutralization and elimination, complement activation, and phagocytic response from the humoral immune system. The Fcγ receptor (FcγR) molecules on the effector cells contact the Fc of the activated IgG antibody involved in integral antibody-antigen immune complex to mediate and regulate the effector response. Optimizing the interaction of monoclonal antibody based protein therapeutic agents to these Fcγ receptors can lead to improvements in the efficacy of these drug candidates.

In humans there are three known classes of FcγR's with further polymorphic types within each class. The Fc in the IgG1 molecule is known to bind FcγRI (CD64) with dissociation constants in the nanomolar range while FcγRII (CD32) and fcγRIII (CD16) binding occurs at the micromolar range [Bruhns P.; Iannascoli B.; England P.; Mancardi D. A.; Fernandez N.; Jorieux S. and Daeron M. (2009) Blood 113: 3716-25]. The high affinity FcγRI receptors can bind IgG in monomeric forms while the low affinity FcγRII and FcγRIII receptors can only bind antigen-antibody immune complexes or IgG aggregates as a result of avidity effects. The different IgG forms have varying affinities for the different FcγR's; in particular, the IgG1 and IgG3 exhibit stronger activity. The Fcγ receptors are the extracellular domains of trans-membrane proteins and possess cytoplasmic domains that are involved in regulating signaling pathways within the cell. When clustered on the immune cell surface on association with the antibody mediated immune complexes, depending on the nature of signaling units linked to the FcγR's on the cytoplasmic end of these cell surface receptors, these molecules regulate the effector response [Nimmerjahn F. and Ravetch J. V. (2008) Nature Immu Rev 8(1):34-47].

At the human chromosomal level, three genes encode the FcγRI (FcγRIA, FcγRIB, FcγRIC) and FcγRII (FcγRIIA, FcγRIIB, FcγRIIC) and two genes encode the FcγRIII (FcγRIIIA, FcγRIIIB) Among the IgG binding human Fcγ receptors, the FcγRIA, FcγRIC and FcγRIIIA types have been shown to be membrane associated with a common γ-chain signal adaptor protein which contains a cytoplasmic immunoreceptor tyrosine based activation motif (ITAM) that leads to the activation of effector function. The FcγRIIA and FcγRIIC also comprise a cytoplasmic ITAM, but without the common γ-chain signal adaptor protein. At the same time, the FcγRIIB is linked to an immunoreceptor tyrosine-based inhibitory motif (ITIM). Activation of FcγRIIB resulting in ITIM phosphorylation results in inhibition of the activating signaling cascade. The FcγRIIIB, while lacking either of the tyrosine based immuno-modulatory cytoplasmic tails, has a GPI (glycosyl-phosphatidyl-inositol) anchor and has been shown to contribute to activation of some granulocytes in the presence of FcγRIIA.

TABLE C

Fcγ Receptor Characteristics

| Receptor | Alleles | Signaling Motif | Function | IgG Binding Affinity |
|---|---|---|---|---|
| FcγRI (CD64) | | ITAM | Activating | IgG1 ≈ IgG3 > IgG4 |
| FcγRIIa (CD32a) | 131(H/R) | ITAM | Activating | IgG1 > IgG3 > IgG2 > IgG4 |
| FcγRIIb (CD32b) | 232(I/T) | ITIM | Inhibitory | IgG3 ≈ IgG1 ≈ IgG4 > IgG2 |

TABLE C-continued

Fcγ Receptor Characteristics

| Receptor | Alleles | Signaling Motif | Function | IgG Binding Affinity |
|---|---|---|---|---|
| FcγRIIc (CD32c) | 57(Q/ Truncation) | ITAM | Activating | IgG3 ≈ IgG1 ≈ IgG4 > IgG2 |
| FcγRIIIa (CD16a) | 158(V/F) | ITAM | Activating | IgG3 > IgG1 > IgG4 > IgG2 |
| FcγRIIIb (CD16b) | NA1/2 SH/78(AID) | GPI | Activating | IgG3 > IgG1 |

ITAM: Immuno-receptor Tyrosine based Activation Motif; ITIM: Immuno-receptor Tyrosine based Inhibition Motif; GPI Glycophosphoinositol While the functional role of ITAM and ITIM motifs and the associated receptor molecules are known, the nature and mechanisms of the modulation of signaling in combination is not completely understood, especially when combined with the activity of a host of other immune cell surface receptors and adaptor molecules (e.g. BCR's, CD22, CD45 etc) involved in signal transduction. In this context, the design of Fc-like molecules that can interact with these Fcγ receptors with exquisite selectivity profiles is a valuable scaffold in any attempt to de-convolute and modulate the effect of such receptor molecules with subtle regulatory activities.

Figure 15:
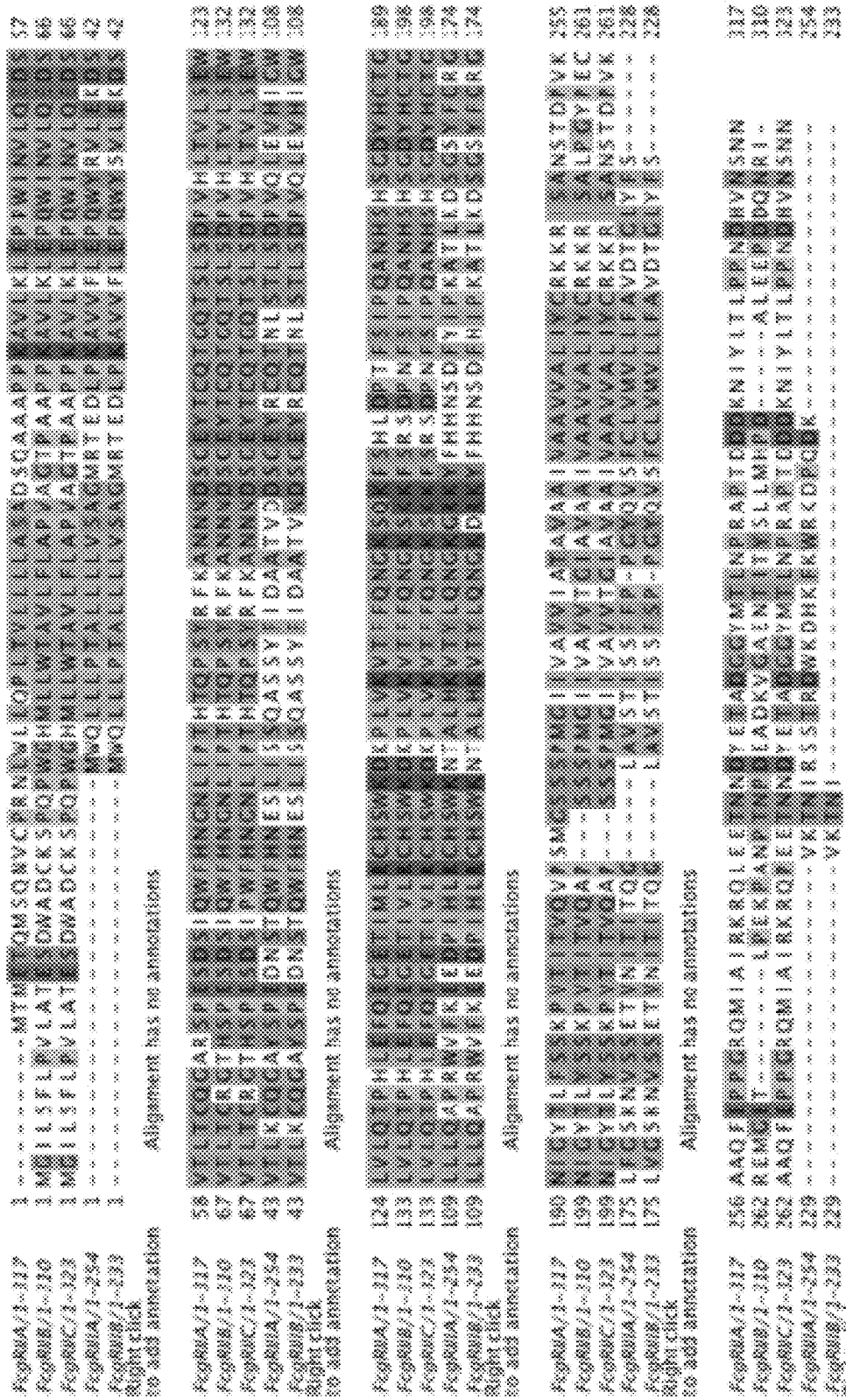
FIG. 15 shows multiple sequence alignment of Fcγ receptors. Genebank/Uniprot Sequence ID's.

In the context of designing antibody molecules that can differentiate the FcγR's, the effort is complicated by the fact that the extracellular Fc binding sections of the FcγRII and FcγRIII receptor types exhibit high sequence similarity (FIG. 15), which can be attributed at least in part to ancestral segmental duplication. The two major types of FcγRII receptors, A and B, have 69% sequence identity while the FcγRIIA and FcγRIIIA exhibit about 44% sequence identity. The FcγRIIB and FcγRIIC differ by only 2 residues in the extracellular region, although they are significantly different in the intracellular region, notable being the presence of ITIM and ITAM motifs respectively. As a result it can be anticipated that therapeutic antibody molecules required to bind one receptor would also potentially bind to other receptor classes, possibly resulting in unintended therapeutic effects.

Complicating matters further, each of the receptor class presents multiple single nucleotide polymorphisms (SNPs) and copy number variations (CNVs). The resulting receptor diversity differentially impact their affinity to IgG's and its mechanism of action. These genetic variations could affect the affinity of particular IgG subclasses for the Fcγ receptors, alter the downstream effector events or impact mechanisms that alter the levels of receptor expression resulting in functionally relevant phenotypes, non-functional or functionally unknown receptor variants (Bournazos S.; Woof J. M.; Hart S. P. and Dransfield I. (2009) Clinical and Experimental Immunology 157(2):244-54). They potentially lead to complex effects, altering the balance between activating and inhibitory receptor signaling, resulting in the creation of disease susceptible phenotypes.

Some of these allelic variations are listed in Table C. Notably, the R131 variant in FcγRII is a high responder with IgG1 while the alternate H131 variants show more efficient interactions with IgG2 and IgG3. In the case of FcγRIIIa, donors homozygous for V at position 158 exhibit increased NK cell activity in comparison to homozygous F/F158 individuals due to higher affinity of the former allotype for human IgG1, IgG3 and IgG4. The allelic variants NA1 and NA2 of FcγRIIIb is the result of a four amino acid substitution which in turn leads to differences in the glycosylation of the receptor. The NA1 allele presents enhanced binding and phagocytosis of the immune complex by neutrophils. The FcγRIIB has two known allelic variants, 232I and 232T. The 232T variant is known to be strongly impaired in its negative regulatory activity. The frequencies of FcγR polymorphisms and its associations to differential responsiveness to infections or predisposition to disease conditions such as systemic lupus erthematosus (SLE), rheumatoid arthritis (RA), vasculitis, immune-mediated thrombocytic purpura (ITP), myasthenia gravis, multiple sclerosis (MS), and immuno neuropathies (Guillian-Barre syndrome (GBS)) have been reported.

Copy number variation in the locus of FcγR genes, in particular for FcγRIIIB, FcγRIIc and FcγRIIIA has been demonstrated, and further correlation of these differences to cell surface expression of these receptors have been noted. In contrast FcγRIIa and FcγRIIb do not show gene copy number variation. Low copy number of FcγRIIIb has in fact been associated with glomerulonephritis in the autoimmune disease systemic lupus erythematosus (SLE) [Aitman T J et al. (2006) Nature 16; 439(7078):851-5]. This is particularly interesting given the fact that a non-signaling GPI module anchors the FcγRIIIb receptor. It can be hypothesized that the presence of these FcγRIIIb receptors could potentially act as competitive inhibitors of Fc interactions with other signaling FcγR's. The effect of copy number variation in FcγRIIc is also especially interesting. A C/T SNP at position 202 in FcγRIIc converts a glutamine residue to a stop codon preventing the generation of a functional protein. The functional open reading frame of FcγRIIc is expressed in 9% of healthy individuals (white population) and there is a significant overrepresentation (19%) of the allele in the ITP population implying a predisposition of these phenotypes for ITP [Breunis W B et al. (2008) Blood 111(3):1029-38]. It has been demonstrated that in individuals expressing functional FcγRIIc on NK cells, the ADCC achieved is mediated by these receptors to a greater extent than the FcγRIIIa. Such complexities associated with these polymorphisms and genetic variations highlights the need for personalized treatment strategies requiring high tailored therapeutics.

The various effector cells differ in the presentation of these Fcγ receptors as well as in their humoral and tissue distribution, thus contributing to variations in their mechanism of activation and action [Table D]. Tuning the selectivity of therapeutic antibodies towards the recognition of specific FcγR types and modulating the impact of certain classes of effector cells, leads to optimization of the effector mechanism for particular disease conditions. This is meant to selectively activate or inhibit specific effector modalities, depending on the disease condition being treated.

TABLE D

Cellular distribution of FcγR's.

| | FcγRI (CD64) | FcγRIIa (CD32a) | FcγRIIb (CD32b) | FcγRIIc (CD32c) | FcγRIIIa (CD16a) | FcγRIIIb (CD16b) | Distribution |
|---|---|---|---|---|---|---|---|
| Lymphoid | | | | | | | |
| B cell | | | ✓ | | | | Blood |
| Plasma cell | | | ✓ | | | | Tissue |
| NK cell | | | | ✓ | ✓ | | Blood |
| Myeloid | | | | | | | |
| Monocyte | ✓ | ✓ | ✓ | | ✓ | | Blood |
| Dendritic cell | ✓ | ✓ | ✓ | | ✓ | | Tissue |
| Platelet | | ✓ | | | | | Blood |
| Macrophage | ✓ | ✓ | ✓ | | ✓ | | Tissue |
| Neutrophil | ✓ | | ✓ | | | ✓ | Blood |
| Eosinophil | ✓ | | | | | ✓ | Blood |
| Basophil | | | ✓ | | | | Blood |
| Mast cell | | | ✓ | | | ✓ | Tissue |

In addition, FcγR's are also expressed by follicular dendritic cells, endothelial cells, microglial cells, osteoclasts and mesangial cells. Currently, the functional significance of FcγR expression on these other cells is not known.

The high affinity FcγRI is composed of three C-type immunoglobulin superfamily (IgSF) domains while the low affinity FcγRII and FcγRIII are constituted of two C-type IgSF domains each. The structure of FcγRIIa, FcγRIIb, FcγRIIIa and FcγRIIIb receptor proteins has been solved by crystallography. The two IgSF domains in these structures are positioned 50-55 degrees relative to each other and are connected by a hinge.

The publicly available structure of an Fc-FcγR co-complex is that of the Fc-FcγRIIIb system and the FcγR geometry in the complex is maintained very close to that observed in the apo state of the protein [Sondermann P.; Huber R.; Oosthuizen V. and Jacob U. (2000) Nature 406, 267-273.; Radaev S.; Motyaka S.; Fridman W.; Sautes-Fridman C. and Sun P. D. (2001) J Biol Chem 276, 16469-16477; Sondermann P. et al. Biochem Soc Trans. 2002 August; 30(4):481-6; Sondermann P, Oosthuizen V. Immunol Lett. 2002 Jun. 3; 82(1-2):51-6; Radaev S, Sun P. Mol Immunol. 2002 May; 38(14):1073-83.] [FIG. 16]. The strong sequence and structural similarity between the receptors forms the basis of comparative models of the Fc bound to the other receptors. On the other hand, the sequence and structural similarity between these receptor molecules also makes the design of Fc with the exquisite selectivity between the receptors and their diverse isotypes challenging.

Prior to the structural evaluation of Fc-FcγR complex based on crystallography, there were questions if the 2-fold axis of symmetry in the Fc molecule means two potential binding sites and an effective 2:1 stoichiometry for the Fc-FcγR association. Nuclear magnetic resonance (NMR) based structural studies of Fc-FcγR interactions indicate that binding an Fc to one FcγR on one face of the molecule induces a conformational change that precludes the binding of a second FcγR molecule to the Fc of the same antibody molecule [Kato K. et al (2000) J Mol Biol. 295(2):213-24]. The geometry of the available co-crystal complex of the Fc-FcγRIIIb confirms the association of the FcγR to Fc in an asymmetric orientation with a 1:1 stoichiometry. As shown in FIG. 16, the FcγR binds to a cleft on one end of the horseshoe-shaped Fc molecule, and is in contact with the CH2 domains from both the chains.

Alanine scanning mutagenesis [Shields R L et al. (2001) JBC 276(9): 6591-604] provides insight on the residues of the Fc interfacing with the diverse receptor types and hence involved in the Fc-FcγR interaction and recognition. Traditionally, optimization of the therapeutic antibodies has been focused around mutations that exhibit increased binding to the activating receptors FcγRIII [U.S. Pat. No. 6,737,056] or decreased affinity to FcγRIIb [US2009/0010920A1]. In all these alternate variants, mutations are introduced concurrently in both the chains.

Monoclonal antibodies often exhibit their therapeutic activity by inducing spatial localization of the target and effector immune cells. A natural antibody mediates this by interacting with the target using its Fab domains and the effector cell using Fc domain. They are able to juxtaposition the immune complex vis-à-vis the effector cell such that the cell mediated response can be induced. Avidity effects required for FcγR signaling, originating in the formation of immune complexes involving the targeting of a single target by multiple antibody molecules, is another example of significance of spatio-temporal organization in immune action.

There is also a spatio-temporal aspect to the cell signaling that is induced as part of the effector activity of mAb molecules. Cell signaling such as those based on FcγR molecule activation involves localization of the relevant receptor molecules within a region of membrane domain referred to as lipid rafts. Lipid rafts are enriched with glycosphingolipid and cholesterol and several classes of upstream signal transducers including the Src family kinases. Upon cell stimulation various signaling molecules, adaptor proteins and the signaling kinases as well as phosphatases are recruited. Molecular assembly at lipid rafts is important for signal transduction.

A non-natural design strategy, combining different antigen specificities and increased avidity to provide better binding properties is the basis of bispecific therapeutic design. Bispecific antibodies or other forms of bispecific or multifunctional protein therapeutics are designed to mediate interactions between the target and a variety of effector cells [Müller & Kontermann (2010) BioDrugs 24(2):89-98]. Multispecific therapeutic molecules are engineered to redirect the Helper T-cells or other immune effector cells against specific target cells.

In another embodiment, the invention relates to a method for identifying Fc variant polypeptides in silico based on calculated binding affinities to FcγRIIa, FcγRIIb and/or FcγRIIIa. In another embodiment, the method further comprises calculating in silico electrostatics, solvation, packing, packing density, hydrogen binding, and entropic effects of said Fc variant polypeptides. In yet another embodiment, the method of the current invention further includes constructing the Fc variant polypeptides and expressing said polypeptides in the context of a therapeutic antibody and further expressing said antibody in mammalian cells. In still another embodiment the method of the current invention comprises constructing the Fc variant polypeptides identified in silico by site directed mutagenesis, PCR based mutagenesis, cassette mutagenesis or de novo synthesis.

Factors taken into account in the design of the synthetic Fc scaffold include in silico calculations for steric repulsion, change in buried interface area, relative contact density, relative solvation and electrostatic effect. All these matrices were used to arrive at an affinity score.

In one aspect, this application describes a molecular design for achieving exquisite FcγR selectivity profiles via the design of an asymmetric scaffold built on a heterodimeric Fc. This scaffold allows for asymmetric mutations in the CH2 domain to achieve a variety of novel selectivity profiles. Further, the scaffold has inherent features for the engineering of multifunctional (bi, tri, tetra or penta functional) therapeutic molecules.

The asymmetric scaffold can be optimized for pH dependent binding properties to the neonatal Fc receptor (FcRn) to enable better recycling of the molecule and enhance its half life and related pharmacokinetic properties.

The asymmetric scaffold can be optimized for binding to the functionally relevant FcγRI receptor allotypes. FcγRI is a prominent marker on macrophages that are involved in chronic inflammatory disorders such as Rheumatoid Arthritis, Atopic Dermatitis, Psoriasis and a number of pulmonary diseases.

The asymmetric scaffold can be optimized for protein A binding. Protein A binding is often employed for separation and purification of antibody molecules. Mutations can be introduced in the asymmetric scaffold to avoid aggregation of the therapeutic during storage.

Therefore, it is specifically contemplated that the Fc variants of the invention may contain inter alia one or more additional amino acid residue substitutions, mutations and/or modifications which result in an antibody with preferred characteristics including but not limited to:

increased serum half life, increase binding affinity, reduced immunogenicity, increased production, enhanced or reduced ADCC or CDC activity, altered glycosylation and/or disulfide bonds and modified binding specificity.

It is contemplated that the Fc variants of the invention may have other altered characteristics including increased in vivo half-lives (e.g., serum half-lives) in a mammal; in particular a human, increased stability in vivo (e.g., serum half-lives) and/or in vitro (e.g., shelf-life) and/or increased melting temperature (Tm), relative to a comparable molecule. In one embodiment, an Fc variant of the invention has an in vivo half-life of greater then 15 days, greater than 20 days, greater than 25 days, greater than 30 days, greater than 35 days, greater than 40 days, greater than 45 days, greater than 2 months, greater than 3 months, greater than 4 months, or greater than 5 months. In another embodiment, an Fc variant of the invention has an in vitro half-live (e.g, liquid or powder formulation) of greater then 15 days, greater than 30 days, greater than 2 months, greater than 3 months, greater than 6 months, or greater than 12 months, or greater than 24 months, or greater than 36 months, or greater than 60 months.

It will also be appreciated by one skilled in the art that the Fc variants of the invention may have altered immunogenicity when administered to a subject. Accordingly, it is contemplated that the variant CH3 domain, which minimize the immunogenicity of the Fc variant are generally more desirable for therapeutic applications.

The Fc variants of the present invention may be combined with other Fc modifications, including but not limited to modifications that alter effector function. The invention encompasses combining an Fc variant of the invention with other Fc modifications to provide additive, synergistic, or novel properties in antibodies or Fc fusion proteins. Such modifications may be in the hinge, CH1, or CH2, (or CH3 provided it does not negatively alter the stability and purity properties of the present variant CH3 domains) domains or a combination thereof. It is contemplated that the Fc variants of the invention enhance the property of the modification with which they are combined. For example, if an Fc variant of the invention is combined with a mutant known to bind FcγRIIIA with a higher affinity than a comparable molecule comprising a wild type Fc region; the combination with a mutant of the invention results in a greater fold enhancement in FcγRIIIA affinity.

In one embodiment, the Fc variants of the present invention may be combined with other known Fc variants such as those disclosed in Duncan et al, 1988, Nature 332:563-564; Lund et al., 1991, J Immunol 147:2657-2662; Lund et al., 1992, Mol Immunol 29:53-59; Alegre et al, 1994, Transplantation 57:1537-1543; Hutchins et al., 1995, Proc Natl. Acad Sci USA 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, Immunol 157:4963-4969; Armour et al., 1999, Eur J Immunol 29:2613-2624; Idusogie et al, 2000, J Immunol 164:4178-4184; Reddy et al, 2000, J Immunol 164:1925-1933; Xu et al., 2000, Cell Immunol 200:16-26; Idusogie et al, 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. Nos. 5,624,821; 5,885,573; 6,194,551; U.S. Patent Application Nos. 60/601,634 and 60/608,852; PCT Publication Nos. WO 00/42072 and WO 99/58572.

One skilled in the art will understand that the Fc variants of the invention may have altered Fc ligand (e.g., FcγR, C1q) binding properties (examples of binding properties include but are not limited to, binding specificity, equilibrium dissociation constant ($K_D$), dissociation and association rates ($K_{off}$ and $K_{on}$ respectively), binding affinity and/or avidity) and that certain alterations are more or less desirable. It is well known in the art that the equilibrium dissociation constant ($K_D$) is defined as $k_{off}/k_{on}$. It is generally understood that a binding molecule (e.g., and antibody) with a low $K_D$ is preferable to a binding molecule (e.g., and antibody) with a high $K_D$. However, in some instances the value of the $k_{on}$ or $k_{off}$ may be more relevant than the value of the $K_D$. One skilled in the art can determine which kinetic parameter is most important for a given antibody application. For example a modified CH3 and/or CH2 that enhances Fc binding to one or more positive regulators (e.g., FcγRIIIA) while leaving unchanged or even reducing Fc binding to the negative regulator FcγRIIB would be more advantageous for enhancing ADCC activity. Alternatively, a modified CH3 and/or CH2 that reduced binding to one or more positive regulator and/or enhanced binding to FcγRIIB would be advantageous for reducing ADCC activity. Accordingly, the ratio of binding affinities (e.g., equilibrium dissociation constants ($K_D$)) can indicate if the ADCC activity of an Fc variant is enhanced or decreased. For example a decrease in the ratio of FcγRIIIA/FcγRIIB equilibrium dissociation constants ($K_D$), will correlate with improved ADCC activity, while an increase in the ratio will correlate with a decrease in ADCC activity.

As part of the characterization of the Fc variants they were tested for their binding affinity to FcγRIIIA (CD16a) and FcγRIIB(CD32b) reported as a ratio in comparison to wild-type IgG1. (See, Example 4 and Table 5) In this instance it was possible to evaluate the impact of the CH3 domain mutations on binding to these activating and inhibitory Fc receptors. In one embodiment, provided herein are isolated heteromultimers comprising a heterodimer Fc region, wherein the heterodimer Fc region comprises a variant CH3 domain comprising amino acid mutations to promote heterodimer formation with increased stability, wherein the variant CH3 domain has a melting temperature (Tm) greater than 70° C., wherein the heterodimer binding to CD16a is about the same as compared to wild-type homodimer. In certain embodiments the heterodimer binding to CD16a is increased as compared to wild-type homodimer. In an alternative embodiment, the heterodimer binding to CD16a is reduced as compared to wild-type homodimer.

In certain embodiments, provided herein are isolated heteromultimers comprising a heterodimer Fc region, wherein the heterodimer Fc region comprises a variant CH3 domain comprising amino acid mutations to promote heterodimer formation with increased stability, wherein the variant CH3 domain has a melting temperature (Tm) greater than 70° C., wherein the heterodimer binding to CD32b is about the same as compared to wild-type homodimer. In certain embodiments the heterodimer binding to CD32b is increased as compared to wild-type homodimer. In an alternative embodiment, the heterodimer binding to CD32b is reduced as compared to wild-type homodimer.

One of skill in the art will understand that instead of reporting the $K_D$ of binding CD16a and CD32b as a ratio Fc variant to wild-type homodimer, the $K_D$ could be reported as a ratio of Fc variant binding to CD16a to Fc variant binding to CD32b (data not shown). This ratio would provide an indication of the variant CH3 domain mutation on ADCC, either unchanged, increased to decreased compared to wild-type, described below in more detail.

The affinities and binding properties of the Fc variants of the invention for an FcγR are initially determined using in vitro assays (biochemical or immunological based assays) known in the art for determining Fc-FcγR interactions, i.e., specific binding of an Fc region to an FcγR including but not limited to ELISA assay, surface plasmon resonance assay, immunoprecipitation assays (See section entitled "Characterization and Functional Assays" infra) and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

It is contemplated that the binding properties of the molecules of the invention are also characterized by in vitro functional assays for determining one or more FcγR mediator effector cell functions (See section entitled "Characterization and Functional Assays" infra). In certain embodiments, the molecules of the invention have similar binding properties in in vivo models (such as those described and disclosed herein) as those in in vitro based assays. However, the present invention does not exclude molecules of the invention that do not exhibit the desired phenotype in in vitro based assays but do exhibit the desired phenotype in vivo.

The invention encompasses Fc variants that bind FcγRIIIA (CD16a) with increased affinity, relative to a comparable molecule. In a specific embodiment, the Fc variants of the invention bind FcγRIIIA with increased affinity and bind FcγRIIB (CD32b) with a binding affinity that is either unchanged or reduced, relative to a comparable molecule. In yet another embodiment, the Fc variants of the invention have a ratio of FcγRIIIA/FcγRIIB equilibrium dissociation constants ($K_D$) that is decreased relative to a comparable molecule.

Also encompassed by the present invention are Fc variants that bind FcγRIIIA (CD16a) with decreased affinity, relative to a comparable molecule. In a specific embodiment, the Fc variants of the invention bind FcγRIIIA with decreased affinity, relative to a comparable molecule and bind FcγRIIB with a binding affinity that is unchanged or increased, relative to a comparable molecule.

In one embodiment, the Fc variants bind with increased affinity to FcγRIIIA In a specific embodiment, said Fc variants have affinity for FcγRIIIA that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than that of a comparable molecule. In other embodiments, the Fc variants have an affinity for FcγRIIIA that is increased by at least 10%, or at least 20%, or at least 30%, or at least 40%, or at least 50%, or at least 60%, or at least 70%, or at least S0%, or at least 90%, or at least 100%, or at least 150%, or at least 200%, relative to a comparable molecule.

In another embodiment, the Fc variant has an equilibrium dissociation constant ($K_D$) for an Fc ligand (e.g., FcγR, C1q) that is decreased between about 2 fold and 10 fold, or between about 5 fold and 50 fold, or between about 25 fold and 250 fold, or between about 100 fold and 500 fold, or between about 250 fold and 1000 fold relative to a comparable molecule.

In a another embodiment, said Fc variants have an equilibrium dissociation constant ($K_D$) for FcγRIIIA that is reduced by at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or at least 400 fold, or at least 600 fold, relative to a comparable molecule. In another embodiment, the Fc variants have an equilibrium dissociation constant ($K_D$) for FcγRIIIA that is reduced by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In one embodiment, the Fc variant binds to FcγRIIB with an affinity that is unchanged or reduced. In a specific embodiment, said Fc variants have affinity for FcγRIIB that is unchanged or reduced by at least 1 fold, or by at least 3 fold, or by at least 5 fold, or by at least 10 fold, or by at least 20 fold, or by at least 50 fold, or by at least 100 fold, relative to a comparable molecule. In other embodiments, the Fc variants have an affinity for FcγRIIB that is unchanged or reduced by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In another embodiment, the Fc variants have an equilibrium dissociation constant ($K_D$) for FcγRIIB that is unchanged or increased by at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold relative to a comparable molecule. In another specific embodiment, the Fc variants have an equilibrium dissociation constant ($K_D$) for FcγRIIB that is unchanged or increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In still another embodiment, the Fc variants bind FcγRIIIA with increased affinity, relative to a comparable molecule and bind FcγRIIB with an affinity that is unchanged or reduced, relative to a comparable molecule. In a specific embodiment, the Fc variants have affinity for FcγRIIIA that is increased by at least 1 fold, or by at least 3 fold, or by at least 5 fold, or by at least 10 fold, or by at least 20 fold, or by at least 50 fold, or by at least 100 fold, relative to a comparable molecule. In another specific embodiment, the Fc variants have affinity for FcγRIIB that is either unchanged or is reduced by at least 2 fold, or at least 3 fold, or at least 5 fold, or at least 7 fold, or a least 10 fold, or at least 20 fold, or at least 50 fold, or at least 100 fold, relative to a comparable molecule. In other embodiments, the Fc variants have an affinity for FcγRIIIA that is increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule and the Fc variants have an affinity for FcγRIIB that is either unchanged or is increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In yet another embodiment, the Fc variants have a ratio of FcγRIIIA/FcγRIIB equilibrium dissociation constants ($K_D$) that is decreased relative to a comparable molecule. In a specific embodiment, the Fc variants have a ratio of FcγRIIIA/FcγRIIB equilibrium dissociation constants ($K_D$) that is decreased by at least 1 fold, or by at least 3 fold, or by at least 5 fold, or by at least 10 fold, or by at least 20 fold, or by at least 50 fold, or by at least 100 fold, relative to a comparable molecule. In another specific embodiment, the Fc variants have a ratio of FcγRIIIA/FcγRIIB equilibrium dissociation constants ($K_D$) that is decreased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In another embodiment, the Fc variants bind FcγRIIIA with a decreased affinity, relative to a comparable molecule. In a specific embodiment, said Fc variants have affinity for FcγRIIIA that is reduced by at least 1 fold, or by at least 3 fold, or by at least 5 fold, or by at least 10 fold, or by at least 20 fold, or by at least 50 fold, or by at least 100 fold, relative to a comparable molecule. In other embodiments, the Fc variants have an affinity for FcγRIIIA that is decreased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In still another embodiment, the Fc variants bind FcγRIIIA with decreased affinity and bind FcγRIIB with an affinity that is either unchanged or increased, relative to a comparable molecule. In a specific embodiment, the Fc variants have affinity for FcγRIIIA that is reduced by at least 1 fold, or by at least 3 fold, or by at least 5 fold, or by at least 10 fold, or by at least 20 fold, or by at least 50 fold, or by at least 100 fold relative to a comparable molecule. In another specific embodiment, the Fc variants have affinity for FcγRIIB that is at least 2 fold, or at least 3 fold, or at least 5 fold, or at least 7 fold, or a least 10 fold, or at least 20 fold, or at least 50 fold, or at least 100 fold, greater than that of a comparable molecule. In other embodiments, the Fc variants have an affinity for FcγRIIIA that is decreased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule and the Fc variants have an affinity for FcγRIIB that is increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In still another embodiment, the Fc variants have an equilibrium dissociation constant ($K_D$) for FcγRIIIA that are increased by at least 1 fold, or by at least 3 fold, or by at least 5 fold or by at least 10 or by at least 20 fold, or by at least 50 fold when compared to that of a comparable molecule. In a specific embodiment, said Fc variants have equilibrium dissociation constant ($K_D$) for FcγRIIB that are decreased at least 2 fold, or at least 3 fold, or at least 5 fold, or at least 7 fold, or a least 10 fold, or at least 20 fold, or at least 50 fold or at least 100 fold, relative to a comparable molecule.

CH2 Variations for fcγR Selectivity

The Fc-FcγR protein-protein interaction in this complex indicates that the two chains in the Fc molecule interact with two distinct sites on the FcγR molecule. Although there is symmetry in the two heavy chains in the natural Fc molecules, the local FcγR environment around residues on one chain is different from the FcγR residues surrounding the same residue position on the opposite Fc chain. The two symmetry related positions interact with different selection of FcγR residues.

Given the asymmetry in the association of Fc to FcγR, concurrent mutations in chain A and B of the Fc molecule do not impact the interactions with FcγR in a symmetric manner. When introducing mutations to optimize interactions on one chain of the Fc with its local FcγR environment, in a homodimeric Fc structure, the corresponding mutation in the second chain may be favorable, unfavorable or non-contributing to the required FcγR binding and selectivity profile.

Using a structure and computation guided approach, asymmetric mutations are engineered in the two chains of the Fc to overcome these limitations of traditional Fc engineering strategies, which introduce the same mutations on both the chains of Fc. One can achieve better binding selectivity between the receptors if the two chains of Fc are optimized independently for enhanced binding to their corresponding face of the receptor molecule.

For instance, mutations at a particular position on one chain of the Fc can be designed to enhance selectivity to a particular residue, a positive design effort, while the same residue position can be mutated to unfavorably interact with its local environment in an alternate Fcγ receptor type, a negative design effort, hence achieving better selectivity between the two receptors. In certain embodiments, is provided a method for designing asymmetric amino acid modifications in the CH2 domain that selectively bind one Fc gamma receptor as compared to a different Fc gamma receptor (e.g., selectively bind FcgRIIIa instead of FcgRIIb). In other certain embodiments, is provided a method for the design of asymmetric amino acid modifications in the CH2 domain of a variant Fc heterodimer comprising amino acid modifications in the CH3 domain to promote heterodimer formation. In another embodiment, is provided a method to design selectivity for the different Fc gamma receptors based on a variant Fc heterodimer comprising asymmetric amino acid modifications in the CH2 domain. In yet another embodiment, is provided a method for designing asymmetric amino acid modifications that bias binding of the Fc gamma receptors to one face of the Fc molecule. In other certain embodiments, is provided a method for designing polarity drivers that bias the Fcgamma receptors to interact with only one face of the variant Fc heterodimer comprising asymmetric amino acid modifications in the CH2 domain.

The asymmetric design of mutations in the CH2 domain can be tailored to recognize the FcγR on one face of the Fc molecule. This constitutes the productive face of the asymmetric Fc scaffold while the opposite face presents wild type like interaction propensity without the designed selectivity profile and can be considered a non-productive face. A negative design strategy can be employed to introduce mutations on the non-productive face to block FcγR interactions to this side of the asymmetric Fc scaffold, there by forcing the desired interaction tendencies to the Fcγ receptors.

TABLE E

| Variant Selectivity | Potentially InterestingSelectivity Profiles of Fc for different Fcγ Receptors Receptor Binding | | |
|---|---|---|---|
| | FcγRIIIa F/V | FcγRIIa H/R | FcγRIIb F/Y |
| | ↑/− | x | x |
| | x | ↑/− | x |
| | x | x | ↑/− |
| | ↑/− | ↑/− | x |
| | ↑/− | x | ↑/− |
| | x | ↑/− | ↑/− |

(↑/−) indicates a variant which exhibits an increased or wild type like binding to the particualr receptor typeor one of its allotype.
(x) indicates no noticeable binding to the receptor or a subset allotype.

The present invention also relates to fusion polypeptides comprising a binding domain fused to an Fc region, wherein the Fc region comprising a variant CH3 domain, comprising amino acid mutations to promote heterodimer formation with increased stability, wherein the variant CH3 domain has a melting temperature (Tm) greater than 70° C. It is specifically contemplated that molecules comprising a heterodimer comprising a variant CH3 domain may be generated by methods well known to one skilled in the art. Briefly, such methods include but are not limited to, combining a variable region or binding domain with the desired specificity (e.g., a variable region isolated from a phage display or expression library or derived from a human or non-human antibody or a binding domain of a receptor) with a variant Fc heterodimers. Alternatively, one skilled in the art may generate a variant Fc heterodimer by modifying the CH3 domain in the Fc region of a molecule comprising an Fc region (e.g., an antibody).

In one embodiment, the Fc variants are antibodies or Fc fusion proteins. In a specific embodiment, the invention provides antibodies comprising an Fc region comprising a variant CH3 domain, comprising amino acid mutations to promote heterodimer formation with increased stability, wherein the variant CH3 domain has a melting temperature (Tm) greater than 70° C. Such antibodies include IgG molecules that naturally comprise an Fc region containing a CH3 domain that can be modified to generate an Fc variant, or antibodies derivatives that have been engineered to contain an Fc region comprising a variant CH3 domain. Fc variants of the invention includes any antibody molecule that binds, preferably, specifically (i.e., competes off non-specific binding as determined by immunoassays well known in the art for assaying specific antigen-antibody binding) an antigen which comprises an Fc region incorporating a variant CH3 domain. Such antibodies include, but are not limited to, polyclonal, monoclonal, mono-specific, bi-specific, multi-specific, human, humanized, chimeric antibodies, single chain antibodies, Fab fragments, F(ab')2 fragments, disulfide-linked Fvs, and fragments containing either a VL or VH domain or even a complementary determining region (CDR) that specifically binds an antigen, in certain cases, engineered to contain or fused to a variant Fc heterodimer.

"Antibody-dependent cell-mediated cytotoxicity" or "ADCC" refers to a form of cytotoxicity in which secreted antibody bound onto Fc receptors (FcRs) present on certain cytotoxic cells (e.g., Natural Killer (NK) cells, neutrophils, and macrophages) enables these cytotoxic effector cells to bind specifically to an antigen-healing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement.

The ability of any particular antibody to mediate lysis of the target cell by ADCC can be assayed. To assess ADCC activity an antibody of interest is added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985, 79:277; Bruggemann et al., 1987, J Exp Med 166:1351; Wilkinson et al., 2001, J Immunol Methods 258:183; Patel et al., 1995 J Immunol Methods 184:29 and herein (see section entitled "Characterization and Functional Assays" infra). Alternatively, or additionally, ADCC activity of the antibody of interest may be assessed in vivo, e.g., in an animal model such as that disclosed in Clynes et al., 1998, PNAS USA 95:652.

It is contemplated that the Fc variants of the invention are characterized by in vitro functional assays for determining one or more FcγR mediator effector cell functions. In specific embodiments, the molecules of the invention have similar binding properties and effector cell functions in in vivo models (such as those described and disclosed herein)

as those in in vitro based assays However, the present invention does not exclude molecules of the invention that do not exhibit the desired phenotype in in vitro based assays but do exhibit the desired phenotype in vivo.

The present invention further provides Fc variants with enhanced CDC function. In one embodiment, the Fc variants have increased CDC activity. In one embodiment, the Fc variants have CDC activity that is at least 2 fold, or at least 3 fold, or at least 5 fold, or at least 10 fold, or at least 50 fold, or at least 100 fold greater than that of a comparable molecule. In another embodiment, the Fc variants bind C1q with an affinity that is at least 2 fold, or at least 3 fold, or at least 5 fold, or at least 7 fold, or a least 10 fold, or at least 20 fold, or at least 50 fold, or at least 100 fold, greater than that of a comparable molecule. In yet another embodiment, the Fc variants have CDC activity that is increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule. In a specific embodiment, the Fc variants of the invention bind C1q with increased affinity; have enhanced CDC activity and specifically bind to at least one antigen.

The present invention also provides Fc variants with reduced CDC function. In one embodiment, the Fc variants have reduced CDC activity. In one embodiment, the Fc variants have CDC activity that is at least 2 fold, or at least 3 fold, or at least 5 fold or at least 10 fold or at least 50 fold or at least 100 fold less than that of a comparable molecule. In another embodiment, an Fc variant binds C1q with an affinity that is reduced by at least 1 fold, or by at least 3 fold, or by at least 5 fold, or by at least 10 fold, or by at least 20 fold, or by at least 50 fold, or by at least 100 fold, relative to a comparable molecule. In another embodiment, the Fc variants have CDC activity that is decreased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule. In a specific embodiment, Fc variants bind to C1q with decreased affinity have reduced CDC activity and specifically bind to at least one antigen.

In some embodiments, the Fc variants comprise one or more engineered glycoforms, i.e., a carbohydrate composition that is covalently attached to a molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example β(1,4)-N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, Nat. Biotechnol 17:176-180; Davies et al., 20017 Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland). See, e.g., WO 00061739; EA01229125; US 20030115614; Okazaki et al., 2004, JMB, 336: 1239-49.

It is contemplated that Fc variants include antibodies comprising a variable region and a heterodimer Fc region, wherein the heterodimer Fc region comprises a variant CH3 domain comprising amino acid mutations to promote heterodimer formation with increased stability, wherein the variant CH3 domain has a melting temperature (Tm) greater than 70° C. The Fc variants which are antibodies may be produced "de novo" by combing a variable domain, of fragment thereof, that specifically binds at least one antigen with a heterodimer Fc region comprising a variant CH3 domain. Alternatively, heterodimer Fc variants may be produced by modifying the CH3 domain of an Fc region containing antibody that binds an antigen.

Antibodies of the invention may include, but are not limited to, synthetic antibodies, monoclonal antibodies, recombinantly produced antibodies, intrabodies, monospecific antibodies, multispecific antibodies, bispecific antibodies, human antibodies, humanized antibodies, chimeric antibodies, synthetic antibodies, single-chain FvFcs (scFvFc), single-chain Fvs (scFv), and anti-idiotypic (anti-Id) antibodies. In particular, antibodies used in the methods of the present invention include immunoglobulin molecules and immunologically active portions of immunoglobulin molecules. The immunoglobulin molecules of the invention can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule.

Antibodies of the invention may be from any animal origin including birds and mammals (e.g., human, murine, donkey, sheep, rabbit, goat, guinea pig, camel, horse, or chicken). In a specific embodiment, the antibodies are human or humanized monoclonal antibodies, in particular bi-specific monoclonal antibodies. As used herein, "human" antibodies include antibodies having the amino acid sequence of a human immunoglobulin and include antibodies isolated from human immunoglobulin libraries or from mice that express antibodies from human genes.

Antibodies like all polypeptides have an Isoelectric Point (pI), which is generally defined as the pH at which a polypeptide carries no net charge. It is known in the art that protein solubility is typically lowest when the pH of the solution is equal to the isoelectric point (pI) of the protein. It is possible to optimize solubility by altering the number and location of ionizable residues in the antibody to adjust the pI. For example the pI of a polypeptide can be manipulated by making the appropriate amino acid substitutions (e.g., by substituting a charged amino acid such as a lysine, for an uncharged residue such as alanine). Without wishing to be bound by any particular theory, amino acid substitutions of an antibody that result in changes of the pI of said antibody may improve solubility and/or the stability of the antibody. One skilled in the art would understand which amino acid substitutions would be most appropriate for a particular antibody to achieve a desired pI. The pI of a protein may be determined by a variety of methods including but not limited to, isoelectric focusing and various computer algorithms (see for example Bjellqvist et al., 1993, Electrophoresis 14:1023). In one embodiment, the pI of the Fc variants of the invention is between pH 6.2 and pH 8.0. In another embodiment, the pI of the antibodies of the invention is between pH 6.8 and pH 7.4. In one embodiment, substitutions resulting in alterations in the pI of the Fc variant of the invention will not significantly diminish its binding affinity for an antigen. It is contemplated that the variant CH3 domain with an increased stability may also result in a change in the pI. In one embodiment, variant Fc heterodimers are specifically chosen to effect both the increased stability and purity and, any desired change in pI.

Antibodies of the invention may be monospecific, bispecific, trispecific or have greater multispecificity. Multispecific antibodies may specifically bind to different epitopes of desired target molecule or may specifically bind to both the target molecule as well as a heterologous epitope, such as a heterologous polypeptide or solid support material. See, e.g., International Publication Nos. WO 94/04690; WO 93/17715; WO 92/08802; WO 91/00360; and WO 92/05793; Tutt, et al., 1991, J. Immunol. 147:60-69; U.S. Pat. Nos. 4,474,893; 4,714,681; 4,925,648; 5,573,920 and 5,601,819 and Kostelny et al., 1992, J. Immunol. 148:1547).

Various embodiments of multifunctional targeting molecules can be designed on the basis of this asymmetric scaffold as shown in FIG. 20.

Multispecific antibodies have binding specificities for at least two different antigens. While such molecules normally will only bind two antigens (i.e. bispecific antibodies, BsAbs), antibodies with additional specificities such as trispecific antibodies are encompassed by the instant invention. Examples of BsAbs include without limitation those with one arm directed against a tumor cell antigen and the other arm directed against a cytotoxic molecule, or both arms are directed again two different tumor cell antigens, or both arms are directed against two different soluable ligands, or one arm is directed against a soluable ligand and the other arm is directed against a cell surface receptor, or both arms are directed against two different cell surface receptors. Methods for making bispecific antibodies are known in the art.

According to a different approach, antibody variable domains with the desired binding specificities (antibody-antigen combining sites) are fused to immunoglobulin constant domain sequences. The fusion may be with an immunoglobulin heavy chain constant domain, comprising at least part of the hinge, CH2, and CH3 regions. It is contemplated that the first heavy-chain constant region (CH1) containing the site necessary for light chain binding is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. See, Example 1 and Table 2. It is, however, possible to insert the coding sequences for two or all three polypeptide chains in one expression vector when, the expression of at least two polypeptide chains in equal ratios results in high yields or when the ratios are of no particular significance.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Antibodies with more than two valencies incorporating variant CH3 domains and resulting Fc heterodimers of the invention are contemplated. For example, trispecific antibodies can be prepared. See, e.g., Tutt et al. J. Immunol. 147: 60 (1991).

Antibodies of the present invention also encompass those that have half-lives (e.g., serum half-lives) in a mammal, (e.g., a human), of greater than 15 days, greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present invention in a mammal, (e.g., a human), results in a higher serum titer of said antibodies or antibody fragments in the mammal, and thus, reduces the frequency of the administration of said antibodies or antibody fragments and/or reduces the concentration of said antibodies or antibody fragments to be administered. Antibodies having increased in vitro half-lives can be generated by techniques known to those of skill in the art. For example, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S. Patent Publication No. 2003/0190311).

In a specific embodiment the variant Fc heterodimer comprising the variant CH3 domain is a multi-specific antibody (referred to herein as an antibody of the invention), the antibody of the invention specifically binds an antigen of interest. In particular the antibody of the invention is a bi-specific antibody. In one embodiment, an antibody of the invention specifically binds a polypeptide antigen. In another embodiment, an antibody of the invention specifically binds a nonpolypeptide antigen. In yet another embodiment, administration of an antibody of the invention to a mammal suffering from a disease or disorder can result in a therapeutic benefit in that mammal.

Virtually any molecule may be targeted by and/or incorporated into a variant Fc heterodimer protein (e.g., antibodies, Fc fusion proteins) including, but not limited to, the following list of proteins, as well as subunits, domains, motifs and epitopes belonging to the following list of proteins:

renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VII, factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors such as, for example, EGFR, VEGFR; interferons such as alpha interferon (α-IFN), beta interferon (β-IFN) and gamma interferon (γ-IFN); protein A or D;

rheumatoid factors; a neurotrophic factor such as bone-derived neurotrophic factor (BDNF), neurotrophin-3, -4, -5, or -6 (NT-3, NT-4, NT-5, or NT-6), or a nerve growth factor; platelet-derived growth factor (PDGF); fibroblast growth factor such as AFGF and PFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and -II (IGF-I and IGF-II); des (1-3)-IGF-I (brain IGF-I), insulin-like growth factor binding proteins; CD proteins such as CD2, CD3, CD4, CD8, CD11a, CD14, CD18, CD19, CD20, CD22, CD23, CD25, CD33, CD34, CD40, CD40L, CD52, CD63, CD64, CD80 and CD147; erythropoietin; osteoinductive factors; immunotoxins; a bone morphogenetic protein (BMP); an interferon such as interferon-alpha, -beta, and -gamma; colony stimulating factors (CSFs), such as M-CSF, GM-CSF, and G-CSF; interleukins (ILs), e.g., IL-1 to IL-13; TNFα, superoxide dismutase; T-cell receptors; surface membrane proteins; decay accelerating factor; viral antigen such as, for example, a portion of the AIDS envelope, e.g., gp120; transport proteins; homing receptors; addressins; regulatory proteins; cell adhesion molecules such as LFA-1, Mac 1, p150.95, VLA-4, ICAM-1, ICAM-3 and VCAM, a4/p7 integrin, and (Xv/p3 integrin including either a or subunits thereof, integrin alpha subunits such as CD49a, CD49b, CD49c, CD49d, CD49e, CD49f, alpha7, alpha8, alpha9, alphaD, CD11a, CD11b, CD51, CD11c, CD41, alphaIIb, alphaIELb; integrin beta subunits such as, CD29, CD 18, CD61, CD104, beta5, beta6, beta7 and beta8; Integrin subunit combinations including but not limited to, αVβ3, αVβ5 and a4β7; a member of an apoptosis pathway; IgE; blood group antigens; flk2/flt3 receptor; obesity (OB) receptor; mp1 receptor; CTLA-4; protein C; an Eph receptor such as EphA2, EphA4, EphB2, etc.; a Human Leukocyte Antigen (HLA) such as HLA-DR; complement proteins such as complement receptor CR1, C1Rq and other complement factors such as C3, and C5; a glycoprotein receptor such as GpIbα, GPIIb/IIIa and CD200; and fragments of any of the above-listed polypeptides.

Also contemplated are antibodies of the invention that specifically bind cancer antigens including, but not limited to, ALK receptor (pleiotrophin receptor), pleiotrophin, KS 1/4 pan-carcinoma antigen; ovarian carcinoma antigen (CA125); prostatic acid phosphate; prostate specific antigen (PSA); melanoma-associated antigen p97; melanoma antigen gp75; high molecular weight melanoma antigen (HMW-MAA); prostate specific membrane antigen; carcinoembryonic antigen (CEA); polymorphic epithelial mucin antigen; human milk fat globule antigen; colorectal tumor-associated antigens such as:

CEA, TAG-72, CO17-1A, GICA 19-9, CTA-1 and LEA; Burkitt's lymphoma antigen-38.13; CD19; human B-lymphoma antigen-CD20; CD33; melanoma specific antigens such as ganglioside GD2, ganglioside GD3, ganglioside GM2 and ganglioside GM3; tumor-specific transplantation type cell-surface antigen (TSTA); virally-induced tumor antigens including T-antigen, DNA tumor viruses and Envelope antigens of RNA tumor viruses; oncofetal antigen-alpha-fetoprotein such as CEA of colon, 5T4 oncofetal trophoblast glycoprotein and bladder tumor oncofetal antigen; differentiation antigen such as human lung carcinoma antigens L6 and L20; antigens of fibrosarcoma; human leukemia T cell antigen-Gp37; neoglycoprotein; sphingolipids; breast cancer antigens such as EGFR (Epidermal growth factor receptor); NY-BR-16; NY-BR-16 and HER2 antigen (p185HER2); polymorphic epithelial mucin (PEM); malignant human lymphocyte antigen-APO-1; differentiation antigen such as I antigen found in fetal erythrocytes; primary endoderm I antigen found in adult erythrocytes; preimplantation embryos; I(Ma) found in gastric adenocarcinomas; M18, M39 found in breast epithelium; SSEA-1 found in myeloid cells; VEP8; VEP9; Myl; Va4-D5; $D_1$56-22 found in colorectal cancer; TRA-1-85 (blood group H); SCP-1 found in testis and ovarian cancer; C14 found in colonic adenocarcinoma; F3 found in lung adenocarcinoma; AH6 found in gastric cancer; Y hapten; Ley found in embryonal carcinoma cells; TL5 (blood group A); EGF receptor found in A431 cells; $E_1$ series (blood group B) found in pancreatic cancer; FC10.2 found in embryonal carcinoma cells; gastric adenocarcinoma antigen; CO-514 (blood group Lea) found in Adenocarcinoma; NS-10 found in adenocarcinomas; CO-43 (blood group Leb); G49 found in EGF receptor of A431 cells; MH2 (blood group ALeb/Ley) found in colonic adenocarcinoma; 19.9 found in colon cancer; gastric cancer mucins; $T_5A_7$ found in myeloid cells; $R_{24}$ found in melanoma; 4.2, $G_{D3}$, D1.1, OFA-1, $G_{M2}$, OFA-2, $G_{D2}$, and M1:22:25:8 found in embryonal carcinoma cells and SSEA-3 and SSEA-4 found in 4 to 8-cell stage embryos; Cutaneous Tcell Lymphoma antigen; MART-1 antigen; Sialy Tn (STn) antigen; Colon cancer antigen NY-CO-45; Lung cancer antigen NY-LU-12 valiant A; Adenocarcinoma antigen ART1; Paraneoplastic associated brain-testis-cancer antigen (onconeuronal antigen MA2; paraneoplastic neuronal antigen); Neuro-oncological ventral antigen 2 (NOVA2); Hepatocellular carcinoma antigen gene 520; TUMOR-ASSOCIATED ANTIGEN CO-029; Tumor-associated antigens MAGE-C1 (cancer/testis antigen CT7), MAGE-B1 (MAGE-XP antigen), MAGE-B2 (DAM6), MAGE-2, MAGE-4-a, MAGE-4-b and MAGE-X2; Cancer-Testis Antigen (NY-EOS-1) and fragments of any of the above-listed polypeptides.

In certain embodiments, the heteromultimer described herein, comprises at least one therapeutic antibody. In some embodiments, the therapeutic antibody binds a cancer target antigen. In an embodiment, the therapeutic antibody may be one of is selected from the group consisting of abagovomab, adalimumab, alemtuzumab, aurograb, bapineuzumab, basiliximab, belimumab, bevacizumab, briakinumab, canakinumab, catumaxomab, certolizumab pegol, cetuximab, daclizumab, denosumab, efalizumab, galiximab, gemtuzumab ozogamicin, golimumab, ibritumomab tiuxetan, infliximab, ipilimumab, lumiliximab, mepolizumab, motavizumab, muromonab, mycograb, natalizumab, nimotuzumab, ocrelizumab, ofatumumab, omalizumab, palivizumab, panitumumab, pertuzumab, ranibizumab, reslizumab, rituximab, teplizumab, tocilizumab/atlizumab, tositumomab, trastuzumab, Proxinium™, Rencarex™, ustekinumab, zalutumumab, and any other antibodies.

Antibodies of the invention include derivatives that are modified (i.e., by the covalent attachment of any type of molecule to the antibody such that covalent attachment). For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Antibodies or fragments thereof with increased in vivo half-lives can be generated by attaching polymer molecules such as high molecular weight polyethyleneglycol (PEG) to the antibodies or antibody fragments. PEG can be attached to the antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

Further, antibodies can be conjugated to albumin in order to make the antibody or antibody fragment more stable in vivo or have a longer half life in vivo. The techniques are well known in the art, see e.g., International Publication Nos. WO 93/15199, WO 93/15200, and WO 01/77137; and European Patent No. EP 413,622. The present invention encompasses the use of antibodies or fragments thereof conjugated or fused to one or more moieties, including but not limited to, peptides, polypeptides, proteins, fusion proteins, nucleic acid molecules, small molecules, mimetic agents, synthetic drugs, inorganic molecules, and organic molecules.

The present invention encompasses the use of antibodies or fragments thereof recombinantly fused or chemically conjugated (including both covalent and non-covalent conjugations) to a heterologous protein or polypeptide (or fragment thereof, for example, to a polypeptide of at least 10, at least 20, at least 30, at least 40, at least 50, at least 60, at least 70, at least 80, at least 90 or at least 100 amino acids) to generate fusion proteins. The fusion does not necessarily need to be direct, but may occur through linker sequences. For example, antibodies may be used to target heterologous polypeptides to particular cell types, either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452.

The present invention further includes compositions comprising heterologous proteins, peptides or polypeptides fused or conjugated to antibody fragments. For example, the heterologous polypeptides may be fused or conjugated to a Fab fragment, Fd fragment, Fv fragment, F(ab)$_2$ fragment, a VH domain, a VL domain, a VH CDR, a VL CDR, or fragment thereof. Methods for fusing or conjugating polypeptides to antibody portions are well known in the art. See, e.g., U.S. Pat. Nos. 5,336,603; 5,622,929; 5,359,046; 5,349,053; 5,447,851 and 5,112,946; European Patent Nos. EP 307,434 and EP 367,166; International publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins, e.g. of antibodies that specifically bind an antigen (e.g., supra), may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834,252 and 5,837,458, and Patten et al., 1997, Curr. Opinion Biotechnol. 8:724-33; Harayama, 1998, Trends Biotechnol. 16(2): 76-82; Hansson, et al., 1999, J. Mol. Biol. 287:265-76; and Lorenzo and Blasco, 1998, Biotechniques 24(2): 308-313. Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment, which portions specifically bind to an antigen may be recombined with one or more components, motifs, sections, parts, domains, fragments, etc. of one or more heterologous molecules.

The present invention further encompasses uses of variant Fc heterodimers or fragments thereof conjugated to a therapeutic agent.

An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include ribonuclease, monomethylauristatin E and F, paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclophosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). A more extensive list of therapeutic moieties can be found in PCT publications WO 03/075957.

Further, an antibody or fragment thereof may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, Onconase (or another cytotoxic RNase), *pseudomonas* exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Moreover, an antibody can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483; Peterson et al., 1999, Bioconjug. Chem. 10:553; and Zimmerman et al., 1999, Nucl. Med. Biol. 26:943.

Methods for fusing or conjugating antibodies to polypeptide moieties are known in the art. See, e.g., U.S. Pat. Nos. 5,336,603; 5,622,929; 5,359,046; 5,349,053; 5,447,851 and 5,112,946; EP 307,434; EP 367,166; PCT Publications WO 96/04388 and WO 91/06570; Ashkenazi et al., 1991, PNAS USA 88:10535; Zheng et al., 1995, J Immunol 154:5590; and Vil et al., 1992, PNAS USA 89:11337. The fusion of an antibody to a moiety does not necessarily need to be direct, but may occur through linker sequences. Such linker molecules are commonly known in the art and described in Denardo et al., 1998, Clin Cancer Res 4:2483; Peterson et al., 1999, Bioconjug Chem 10:553; Zimmerman et al., 1999, Nucl Med Biol 26:943; Garnett, 2002, Adv Drug Deliv Rev 53:171.

Recombinant expression of an Fc variant, derivative, analog or fragment thereof, (e.g., an antibody or fusion protein of the invention), requires construction of an expression vector containing a polynucleotide that encodes the Fc variant (e.g., antibody, or fusion protein). Once a polynucleotide encoding an Fc variant (e.g., antibody, or fusion protein) has been obtained, the vector for the production of the Fc variant (e.g., antibody, or fusion protein) may be produced by recombinant DNA technology using techniques well known in the art. Thus, methods for preparing a protein by expressing a polynucleotide containing an Fc variant (e.g., antibody, or fusion protein) encoding nucleotide sequence are described herein. Methods that are well known to those skilled in the art can be used to construct expression vectors containing Fc variant (e.g., antibody, or fusion protein) coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an Fc variant of the invention, operably linked to a promoter. Such vectors may include the nucleotide sequence encoding the constant region of the antibody molecule (see, e.g., International Publication No. WO 86/05807; International Publication No. WO 89/01036; and U.S. Pat. No. 5,122,464 and the variable domain of the antibody, or a polypeptide for generating an Fc variant may be cloned into such a vector for expression of the full length antibody chain (e.g. heavy or light chain), or complete Fc variant comprising a fusion of a non-antibody derived polypeptide and an Fc region incorporating at least the variant CH3 domain.

The expression vector is transferred to a host cell by conventional techniques and the transfected cells are then cultured by conventional techniques to produce an Fc variant of the invention. Thus, the invention includes host cells containing a polynucleotide encoding an Fc variant of the invention, operably linked to a heterologous promoter. In specific embodiments for the expression of Fc variants comprising double-chained antibodies, vectors encoding both the heavy and light chains may be co-expressed in the host cell for expression of the entire immunoglobulin molecule, as detailed below.

A variety of host-expression vector systems may be utilized to express the Fc variants of the invention (e.g., antibody or fusion protein molecules) (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an Fc variant of the invention in situ. These include but are not limited to microorganisms such as bacteria (e.g., *E. coli* and *B. subtilis*) transformed with recombinant bacteriophage DNA, plasmid DNA or cosmid DNA expression vectors containing Fc variant coding sequences; yeast (e.g., *Saccharomyces Pichia*) transformed with recombinant yeast expression vectors containing Fc variant coding sequences; insect cell systems infected with recombinant virus expression vectors (e.g., baculovirus) containing Fc variant coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing Fc variant coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In certain embodiments, bacterial cells such as *Escherichia coli*, or eukaryotic cells, are used for the expression of an Fc variant, which is a recombinant antibody or fusion protein molecules. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In a specific embodiment, the expression of nucleotide sequences encoding an Fc variant of the invention (e.g., antibody or fusion protein) is regulated by a constitutive promoter, inducible promoter or tissue specific promoter.

In bacterial systems, a number of expression vectors may be advantageously selected depending upon the use intended for the Fc variant (e.g., antibody or fusion protein) being expressed. For example, when a large quantity of such a protein is to be produced, for the generation of pharmaceutical compositions of an Fc variant, vectors that direct the expression of high levels of fusion protein products that are readily purified may be desirable. Such vectors include, but are not limited to, the *E. coli* expression vector pUR278 (Ruther et al., 1983, EMBO 12:1791), in which the Fc variant coding sequence may be ligated individually into the vector in frame with the lac Z coding region so that a lac Z-fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system *Autographa californica* nuclear polyhedrosis virus (AcNPV) is used as a vector to express foreign genes. The virus grows in *Spodoptera frugiperda* cells. The Fc variant (e.g., antibody or fusion protein) coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the Fc variant (e.g., antibody or fusion protein) coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the Fc variant (e.g., antibody or fusion protein) in infected hosts (e.g., see Logan & Shenk, 1984, Proc. Natl. Acad. Sci. USA 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:516-544).

The expression of an Fc variant (e.g., antibody or fusion protein) may be controlled by any promoter or enhancer element known in the art. Promoters which may be used to control the expression of the gene encoding an Fc variant (e.g., antibody or fusion protein) include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), the tetracycline (Tet) promoter (Gossen et al., 1995, Proc. Nat. Acad. Sci. USA 89:5547-5551); prokaryotic expression vectors such as the (3-lactamase promoter (Villa-Kamaroff et al, 1978, Proc. Natl. Acad. Sci. U.S.A. 75:3727-3731), or the tac promoter (DeBoer et al., 1983, Proc. Natl. Acad. Sci. U.S.A. 80:21-25; see also "Useful proteins from recombinant bacteria" in Scientific American, 1980, 242:74-94); plant expression vectors comprising the nopaline synthetase promoter region (Herrera-Estrella et al., Nature 303:209-213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286); neuronal-specific enolase (NSE) which is active in neuronal cells (Morelli et al., 1999, Gen. Virol. 80:571-83); brain-derived neurotrophic factor (BDNF) gene control region which is active in neuronal cells (Tabuchi et al., 1998, Biochem. Biophysic. Res. Com. 253:818-823); glial fibrillary acidic protein (GFAP) promoter which is active in astrocytes (Gomes et al., 1999, Braz J Med Biol Res 32(5): 619-631; Morelli et al., 1999, Gen. Virol. 80:571-83) and gonadotropic releasing hormone gene control region which is active in the hypothalamus (Mason et al., 1986, Science 234:1372-1378).

Expression vectors containing inserts of a gene encoding an Fc variant of the invention (e.g., antibody or fusion protein) can be identified by three general approaches: (a) nucleic acid hybridization, (b) presence or absence of "marker" gene functions, and (c) expression of inserted sequences. In the first approach, the presence of a gene encoding a peptide, polypeptide, protein or a fusion protein in an expression vector can be detected by nucleic acid hybridization using probes comprising sequences that are homologous to an inserted gene encoding the peptide, polypeptide, protein or the fusion protein, respectively. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding an antibody or fusion protein in the vector. For example, if the nucleotide sequence encoding the Fc variant (e.g., antibody or fusion protein) is inserted within the marker gene sequence of the vector, recombinants containing the gene encoding the antibody or fusion protein insert can be identified by the absence of the marker gene function. In the third approach, recombinant expression vectors can be identified by assaying the gene product (e.g., antibody or fusion protein) expressed by the recombinant. Such assays can be based, for example, on the physical or functional properties of the fusion protein in in vitro assay systems, e.g., binding with anti-bioactive molecule antibody.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells that possess the cellular machinery for proper processing of the primary transcript (e.g., glycosylation, and phosphorylation) of the gene product may be used. Such mammalian host cells include, but are not limited to, CHO, VERY, BHK, Hela, COS, MDCK, 293, 3T3, WI38, NS0, and in particular, neuronal cell lines such as, for example, SK-N-AS, SK-N-FI, SK-N-DZ human neuroblastomas (Sugimoto et al., 1984, J. Natl. Cancer Inst. 73: 51-57), SK-N-SH human neuroblastoma (Biochim. Biophys. Acta, 1982, 704: 450-460), Daoy human cerebellar medulloblastoma (He et al., 1992, Cancer Res. 52: 1144-1148) DBTRG-05MG glioblastoma cells (Kruse et al., 1992, In Vitro Cell. Dev. Biol. 28A: 609-614), IMR-32 human neuroblastoma (Cancer Res., 1970, 30: 2110-2118), 1321N1 human astrocytoma (Proc. Natl. Acad. Sci. USA, 1977, 74: 4816), MOG-G-CCM human astrocytoma (Br. J. Cancer, 1984, 49: 269), U87MG human glioblastoma-astrocytoma (Acta Pathol. Microbiol. Scand., 1968, 74: 465-486), A172 human glioblastoma (Olopade et al., 1992, Cancer Res. 52: 2523-2529), C6 rat glioma cells (Benda et al., 1968, Science 161: 370-371), Neuro-2a mouse neuroblastoma (Proc. Natl. Acad. Sci. USA, 1970, 65: 129-136), NB41A3 mouse neuroblastoma (Proc. Natl. Acad. Sci. USA, 1962, 48: 1184-1190), SCP sheep choroid plexus (Bolin et al., 1994, J. Virol. Methods 48: 211-221), G355-5, PG-4 Cat normal astrocyte (Haapala et al., 1985, J. Virol. 53: 827-833), Mpf ferret brain (Trowbridge et al., 1982, In Vitro 18: 952-960), and normal cell lines such as, for example, CTX TNA2 rat normal cortex brain (Radany et al., 1992, Proc. Natl. Acad. Sci. USA 89: 6467-6471) such as, for example, CRL7030 and Hs578Bst. Furthermore, different vector/host expression systems may effect processing reactions to different extents.

For long-term, high-yield production of recombinant proteins, stable expression is often preferred. For example, cell lines that stably express an Fc variant of the invention (e.g., antibody or fusion protein) may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express an Fc variant that specifically binds to an Antigen. Such engineered cell lines may be particularly useful in screening and evaluation of compounds that affect the activity of an Fc variant (e.g., a polypeptide or a fusion protein) that specifically binds to an antigen.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt-cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

Once an Fc variant (e.g., antibody, or a fusion protein) of the invention has been produced by recombinant expression, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

The Fc variant is generally recovered from the culture medium as a secreted polypeptide, although it also may be recovered from host cell lysate when directly produced without a secretory signal. If the Fc variant is membrane-bound, it can be released from the membrane using a suitable detergent solution (e.g. Triton-X 100).

When the Fc variant is produced in a recombinant cell other than one of human origin, it is completely free of proteins or polypeptides of human origin. However, it is necessary to purify the Fc variant from recombinant cell proteins or polypeptides to obtain preparations that are substantially homogeneous as to the Fc variant. As a first step, the culture medium or lysate is normally centrifuged to remove particulate cell debris.

Fc heterodimers having antibody constant domains can be conveniently purified by hydroxylapatite chromatography, gel electrophoresis, dialysis, or affinity chromatography, with affinity chromatography being the preferred purification technique. Other techniques for protein purification such as fractionation on an ion-exchange column, ethanol precipitation, reverse phase HPLC, chromatography on silica, chromatography on heparin Sepharose, chromatography on an anion or cation exchange resin (such as a polyaspartic acid column), chromatofocusing, SDS-PAGE, and ammonium sulfate precipitation are also available depending on the polypeptide to be recovered. The suitability of protein A as an affinity ligand depends on the species and isotype of the immunoglobulin Fc domain that is used. Protein A can be used to purify immunoglobulin Fc regions that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. Bound variant Fc heterodimers can be efficiently eluted either at acidic pH (at or above 3.0), or in a neutral pH buffer containing a mildly chaotropic salt. This affinity chromatography step can result in a variant Fc heterodimer preparation that is >95% pure.

The expression levels of an Fc variant (e.g., antibody or fusion protein) can be increased by vector amplification (for a review, see Bebbington and Hentschel, The use of vectors based on gene amplification for the expression of cloned genes in mammalian cells in DNA cloning, Vol. 3. (Academic Press, New York, 1987)). For example, when a marker in the vector system expressing an antibody or fusion protein is amplifiable, increase in the level of inhibitor present in culture of host cell will increase the number of copies of the marker gene. Since the amplified region is associated with the antibody gene, production of the antibody or fusion protein will also increase (Crouse et al., 1983, Mol. Cell. Biol. 3:257).

The host cell may be co-transfected with two expression vectors of the invention. For example, the first vector encoding a heavy chain derived polypeptide and the second vector encoding a light chain derived polypeptide. The two vectors may contain identical selectable markers, which enable equal expression of heavy and light chain polypeptides. Alternatively, a single vector may be used which encodes, and is capable of expressing, a fusion protein or both heavy and light chain polypeptides. The coding sequences for the fusion protein or heavy and light chains may comprise cDNA or genomic DNA.

Characterization and Functional Assays

Fc variants (e.g., antibodies or fusion proteins) of the present invention may be characterized in a variety of ways. In one embodiment, purity of the variant Fc heterodimers is assessed using techniques well known in the art including, but not limited to, SDS-PAGE gels, western blots, densitometry or mass spectrometry. Protein stability can be characterized using an array of techniques, not limited to, size exclusion chromatography, UV Visible and CD spectroscopy, mass spectroscopy, differential light scattering, bench top stability assay, freeze thawing coupled with other characterization techniques, differential scanning calorimetry, differential scanning fluorimetry, hydrophobic interaction chromatorgraphy, isoelectric focusing, receptor binding assays or relative protein expression levels. In en exemplary embodiment, stability of the variant Fc heterodimers is assessed by melting temperature of the variant CH3 domain, as compared to wild-type CH3 domain, using techniques well known in the art such as Differential Scanning calorimetry or differential scanning flourimetry.

Fc variants of the present invention may also be assayed for the ability to specifically bind to a ligand, (e.g., FcγRIIIA, FcγRIIB, C1q). Such an assay may be performed in solution (e.g., Houghten, Bio/Techniques, 13:412-421, 1992), on beads (Lam, Nature, 354:82-84, 1991, on chips (Fodor, Nature, 364:555-556, 1993), on bacteria (U.S. Pat. No. 5,223,409) on plasmids (Cull et al., Proc. Natl. Acad. Sci. USA, 89:1865-1869, 1992) or on phage (Scott and Smith, Science, 249:386-390, 1990; Devlin, Science, 249: 404-406, 1990; Cwirla et al., Proc. Natl. Acad. Sci. USA, 87:6378-6382, 1990; and Felici, J. Mol. Biol., 222:301-310, 1991). Molecules that have been identified to specifically bind to a ligand, (e.g., FcγRIIIA, FcγRIIB, C1q or to an antigen) can then be assayed for their affinity for the ligand.

Fc variants of the invention may be assayed for specific binding to a molecule such as an antigen (e.g., cancer antigen and cross-reactivity with other antigens) or a ligand (e.g., FcγR) by any method known in the art. Immunoassays which can be used to analyze specific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York).

The binding affinity of the Fc variants of the present invention to a molecule such as an antigen or a ligand, (e.g., FcγR) and the off-rate of the interaction can be determined by competitive binding assays. One example of a competitive binding assay is a radioimmunoassay comprising the incubation of labeled ligand, such as FcγR (e.g., 3H or 125I with a molecule of interest (e.g., Fc variants of the present invention) in the presence of increasing amounts of unlabeled ligand, such as FcγR, and the detection of the molecule bound to the labeled ligand. The affinity of the molecule of the present invention for the ligand and the binding off-rates can be determined from the saturation data by scatchard analysis.

The kinetic parameters of an Fc variant may also be determined using any surface plasmon resonance (SPR) based assays known in the art (e.g., BIAcore kinetic analysis). For a review of SPR-based technology see Mullet et al., 2000, Methods 22: 77-91; Dong et al., 2002, Review in Mol. Biotech., 82: 303-23; Fivash et al., 1998, Current Opinion in Biotechnology 9: 97-101; Rich et al., 2000, Current Opinion in Biotechnology 11: 54-61. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the invention.

Fluorescence activated cell sorting (FACS), using any of the techniques known to those skilled in the art, can be used for characterizing the binding of Fc variants to a molecule expressed on the cell surface (e.g., FcγRIIIA, FcγRIM) Flow sorters are capable of rapidly examining a large number of individual cells that contain library inserts (e.g., 10-100 million cells per hour) (Shapiro et al., Practical Flow, Cytometry, 1995). Flow cytometers for sorting and examining biological cells are well known in the art. Known flow cytometers are described, for example, in U.S. Pat. Nos. 4,347,935; 5,464,581; 5,483,469; 5,602,039; 5,643,796; and 6,211,477. Other known flow cytometers are the FACS Vantage™ system manufactured by Becton Dickinson and Company, and the COPAS™ system manufactured by Union Biometrica.

The Fc variants of the invention can be characterized by their ability to mediate FcγR-mediated effector cell function. Examples of effector cell functions that can be assayed include, but are not limited to, antibody-dependent cell mediated cytotoxicity (ADCC), phagocytosis, opsonization, opsonophagocytosis, C1q binding, and complement dependent cell mediated cytotoxicity (CDC). Any cell-based or cell free assay known to those skilled in the art for determining effector cell function activity can be used (For effector cell assays, see Perussia et al., 2000, Methods Mol. Biol. 121: 179-92; Baggiolini et al., 1998 Experientia, 44(10): 841-8; Lehmann et al., 2000 J. Immunol. Methods, 243(1-2): 229-42; Brown E J. 1994, Methods Cell Biol., 45: 147-64; Munn et al., 1990 J. Exp. Med., 172: 231-237, Abdul-Majid et al., 2002 Scand. J. Immunol. 55: 70-81; Ding et al., 1998, Immunity 8:403-411).

In particular, the Fc variants of the invention can be assayed for FcγR-mediated ADCC activity in effector cells, (e.g., natural killer cells) using any of the standard methods known to those skilled in the art (See e.g., Perussia et al., 2000, Methods Mol. Biol. 121: 179-92). An exemplary assay for determining ADCC activity of the molecules of the invention is based on a 51Cr release assay comprising of:

labeling target cells with [51Cr]Na$_2$CrO$_4$ (this cell-membrane permeable molecule is commonly used for labeling since it binds cytoplasmic proteins and although spontaneously released from the cells with slow kinetics, it is released massively following target cell necrosis); opsonizing the target cells with the Fc variants of the invention; combining the opsonized radiolabeled target cells with effector cells in a microtitre plate at an appropriate ratio of target cells to effector cells; incubating the mixture of cells for 16-18 hours at 37° C.; collecting supernatants; and analyzing radioactivity. The cytotoxicity of the molecules of the invention can then be determined, for example using the following formula:

% lysis=(experimental cpm−target leak cpm)/(detergent lysis cpm−target leak cpm)×100%. Alternatively, % lysis=(ADCC−AICC)/(maximum release−spontaneous release). Specific lysis can be calculated using the formula:

specific lysis=% lysis with the molecules of the invention−% lysis in the absence of the molecules of the invention. A graph can be generated by varying either the target:

effector cell ratio or antibody concentration.

Method to characterize the ability of the Fc variants to bind C1q and mediate complement dependent cytotoxicity (CDC) are well known in the art. For example, to determine C1q binding, a C1q binding ELISA may be performed. An exemplary assay may comprise the following:

assay plates may be coated overnight at 4 C with polypeptide variant or starting polypeptide (control) in coating buffer. The plates may then be washed and blocked. Following washing, an aliquot of human C1q may be added to each well and incubated for 2 hrs at room temperature. Following a further wash, 100 uL of a sheep anti-complement C1q peroxidase conjugated antibody may be added to each well and incubated for 1 hour at room temperature. The plate may again be washed with wash buffer and 100 ul of substrate buffer containing OPD (O-phenylenediamine dihydrochloride (Sigma)) may be added to each well. The oxidation reaction, observed by the appearance of a yellow color, may be allowed to proceed for 30 minutes and stopped by the addition of 100 ul of 4.5 NH2SO4. The absorbance may then read at (492-405) nm.

To assess complement activation, a complement dependent cytotoxicity (CDC) assay may be performed, (e.g. as described in Gazzano-Santoro et al., 1996, J. Immunol. Methods 202:163). Briefly, various concentrations of Fc variant and human complement may be diluted with buffer. Cells which express the antigen to which the Fc variant binds may be diluted to a density of about 1×106 cells/ml. Mixtures of the Fc variant, diluted human complement and cells expressing the antigen may be added to a flat bottom tissue culture 96 well plate and allowed to incubate for 2 hrs at 37 C. and 5% CO2 to facilitate complement mediated cell lysis. 50 uL of alamar blue (Accumed International) may then be added to each well and incubated overnight at 37 C. The absorbance is measured using a 96-well fluorometer with excitation at 530 nm n and emission at 590 nm. The results may be expressed in relative fluorescence units (RFU). The sample concentrations may be computed from a standard curve and the percent activity, relative to a comparable molecule (i.e., a molecule comprising an Fc region with an unmodified or wild type CH3 domain) is reported for the Fc variant of interest.

Complement assays may be performed with guinea pig, rabbit or human serum. Complement lysis of target cells may be detected by monitoring the release of intracellular enzymes such as lactate dehydrogenase (LDH), as described in Korzeniewski et al., 1983, Immunol. Methods 64(3): 313-20; and Decker et al., 1988, J. Immunol Methods 115(1): 61-9; or the release of an intracellular label such as europium, chromium 51 or indium 111 in which target cells are labeled.

Methods

The present invention encompasses administering one or more Fc variant of the invention (e.g., antibodies) to an animal, in particular a mammal, specifically, a human, for preventing, treating, or ameliorating one or more symptoms associated with a disease, disorder, or infection. The Fc variants of the invention are particularly useful for the treatment or prevention of a disease or disorder where an altered efficacy of effector cell function (e.g., ADCC, CDC) is desired. The Fc variants and compositions thereof are particularly useful for the treatment or prevention of primary or metastatic neoplastic disease (i.e., cancer), and infectious diseases. Molecules of the invention may be provided in pharmaceutically acceptable compositions as known in the art or as described herein. As detailed below, the molecules of the invention can be used in methods of treating or preventing cancer (particularly in passive immunotherapy), autoimmune disease, inflammatory disorders or infectious diseases.

The Fc variants of the invention may also be advantageously utilized in combination with other therapeutic agents known in the art for the treatment or prevention of a cancer, autoimmune disease, inflammatory disorders or infectious diseases. In a specific embodiment, Fc variants of the invention may be used in combination with monoclonal or chimeric antibodies, lymphokines, or hematopoietic growth factors (such as, e.g., IL-2, IL-3 and IL-7), which, for example, serve to increase the number or activity of effector cells which interact with the molecules and, increase immune response. The Fc variants of the invention may also be advantageously utilized in combination with one or more drugs used to treat a disease, disorder, or infection such as, for example anti-cancer agents, anti-inflammatory agents or anti-viral agents.

Accordingly, the present invention provides methods for preventing, treating, or ameliorating one or more symptoms associated with cancer and related conditions by administering one or more Fc variants of the invention. Although not intending to be bound by any mechanism of actions, an Fc variant of the invention that binds FcγRIIIA and/or FcγRIIA with a greater affinity than a comparable molecule, and further binds FcγRIIB with a lower affinity than a comparable molecule, and/or said Fc variant has an enhanced effector function, e.g., ADCC, CDC, phagocytosis, opsonization, etc. will result in the selective targeting and efficient destruction of cancer cells.

The invention further encompasses administering one or more Fc variants of the invention in combination with other therapies known to those skilled in the art for the treatment or prevention of cancer, including but not limited to, current standard and experimental chemotherapies, hormonal therapies, biological therapies, immunotherapies, radiation therapies, or surgery. In some embodiments, the molecules of the invention may be administered in combination with a therapeutically or prophylactically effective amount of one or more anti-cancer agents, therapeutic antibodies or other agents known to those skilled in the art for the treatment and/or prevention of cancer. Examples of dosing regimes and therapies which can be used in combination with the Fc variants of the invention are well known in the art and have been described in detail elsewhere (see for example, PCT publications WO 02/070007 and WO 03/075957).

Cancers and related disorders that can be treated or prevented by methods and compositions of the present invention include, but are not limited to, the following:

Leukemias, lymphomas, multiple myelomas, bone and connective tissue sarcomas, brain tumors, breast cancer, adrenal cancer, thyroid cancer, pancreatic cancer, pituitary cancers, eye cancers, vaginal cancers, vulvar cancer, cervical cancers, uterine cancers, ovarian cancers, esophageal cancers, stomach cancers, colon cancers, rectal cancers, liver cancers, gallbladder cancers, cholangiocarcinomas, lung cancers, testicular cancers, prostate cancers, penal cancers; oral cancers, salivary gland cancers pharynx cancers, skin cancers, kidney cancers, bladder cancers (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

The invention further contemplates engineering any of the antibodies known in the art for the treatment and/or prevention of cancer and related disorders, so that the antibodies comprise an Fc region incorporating a variant CH3 domain of the invention.

In a specific embodiment, a molecule of the invention (e.g., an antibody comprising a variant Fc heterodimer inhibits or reduces the growth of primary tumor or metastasis of cancerous cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth of primary tumor or metastasis in the absence of said molecule of the invention.

The present invention encompasses the use of one or more Fc variants of the invention for preventing, treating, or managing one or more symptoms associated with an inflammatory disorder in a subject. Although not intending to be bound by any mechanism of actions, Fc variants with enhanced affinity for FcγRIIB will lead to a dampening of the activating receptors and thus a dampening of the immune response and have therapeutic efficacy for treating and/or preventing an autoimmune disorder. Furthermore, antibodies binding more than one target, such as bispecific antibodies comprising a variant Fc heterodimer, associated with an inflammatory disorder may provide synergist effects over monovalent therapy.

The invention further encompasses administering the Fc variants of the invention in combination with a therapeutically or prophylactically effective amount of one or more anti-inflammatory agents. The invention also provides methods for preventing, treating, or managing one or more symptoms associated with an autoimmune disease further comprising, administering to said subject an Fc variant of the invention in combination with a therapeutically or prophylactically effective amount of one or more immunomodulatory agents. Examples of autoimmune disorders that may be treated by administering the Fc variants of the invention include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflamatory disorders include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections. Some autoimmune disorders are associated with an inflammatory condition, thus, there is overlap between what is considered an autoimmune disorder and an inflammatory disorder. Therefore, some autoimmune disorders may also be characterized as inflammatory disorders. Examples of inflammatory disorders which can be prevented, treated or managed in accordance with the methods of the invention include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections.

Fc variants of the invention can also be used to reduce the inflammation experienced by animals, particularly mammals, with inflammatory disorders. In a specific embodiment, an Fc of the invention reduces the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal, which is not administered the said molecule.

The invention further contemplates engineering any of the antibodies known in the art for the treatment and/or prevention of autoimmune disease or inflammatory disease, so that the antibodies comprise a variant Fc heterodimer of the invention.

The invention also encompasses methods for treating or preventing an infectious disease in a subject comprising administering a therapeutically or prophylactically effective amount of one or more Fc variants of the invention. Infectious diseases that can be treated or prevented by the Fc variants of the invention are caused by infectious agents including but not limited to viruses, bacteria, fungi, protozae, and viruses.

Viral diseases that can be treated or prevented using the Fc variants of the invention in conjunction with the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial diseases that can be treated or prevented using the Fc variants of the invention in conjunction with the methods of the present invention, that are caused by bacteria include, but are not limited to, mycobacteria *rickettsia, mycoplasma, neisseria, S. pneumonia, Borrelia burgdorferi* (Lyme disease), *Bacillus antracis* (anthrax), tetanus, *streptococcus, staphylococcus, mycobacterium*, tetanus, pertissus, cholera, plague, diptheria, *chlamydia, S. aureus* and *legionella*. Protozoal diseases that can be treated or prevented using the molecules of the invention in conjunction with the methods of the present invention, that are caused by protozoa include, but are not limited to, *leishmania*, kokzidioa, *trypanosoma* or malaria. Parasitic diseases that can be treated or prevented using the molecules of the invention in conjunction with the methods of the present invention, that are caused by parasites include, but are not limited to, *chlamydia* and *rickettsia*.

In some embodiments, the Fc variants of the invention may be administered in combination with a therapeutically or prophylactically effective amount of one or additional therapeutic agents known to those skilled in the art for the treatment and/or prevention of an infectious disease. The invention contemplates the use of the molecules of the invention in combination with other molecules known to those skilled in the art for the treatment and or prevention of an infectious disease including, but not limited to, antibiotics, antifungal agents and anti-viral agents.

The invention provides methods and pharmaceutical compositions comprising Fc variants of the invention (e.g., antibodies, polypeptides). The invention also provides methods of treatment, prophylaxis, and amelioration of one or more symptoms associated with a disease, disorder or infection by administering to a subject an effective amount of at least one Fc variant of the invention, or a pharmaceutical composition comprising at least one Fc variant of the invention. In a one aspect, the Fc variant, is substantially purified (i.e., substantially free from substances that limit its effect or produce undesired side-effects this includes homodimers and other cellular material). In a specific embodiment, the subject is an animal, such as a mammal including non-primates (e.g., cows, pigs, horses, cats, dogs, rats etc.) and primates (e.g., monkey such as, a cynomolgus monkey and a human). In a specific embodiment, the subject is a human. In yet another specific embodiment, the antibody of the invention is from the same species as the subject.

The route of administration of the composition depends on the condition to be treated. For example, intravenous injection may be preferred for treatment of a systemic disorder such as a lymphatic cancer or a tumor that has metastasized. The dosage of the compositions to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. Depending on the condition, the composition can be administered orally, parenterally, intranasally, vaginally, rectally, lingually, sublingually, buccally, intrabuccally and/or transdermally to the patient.

Accordingly, compositions designed for oral, lingual, sublingual, buccal and intrabuccal administration can be made without undue experimentation by means well known in the art, for example, with an inert diluent or with an edible carrier. The composition may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums, and the like.

Tablets, pills, capsules, troches and the like may also contain binders, recipients, disintegrating agent, lubricants, sweetening agents, and/or flavoring agents. Some examples of binders include microcrystalline cellulose, gum tragacanth and gelatin. Examples of excipients include starch and lactose. Some examples of disintegrating agents include alginic acid, cornstarch, and the like. Examples of lubricants include magnesium stearate and potassium stearate. An example of a glidant is colloidal silicon dioxide. Some examples of sweetening agents include sucrose, saccharin, and the like. Examples of flavoring agents include peppermint, methyl salicylate, orange flavoring, and the like. Materials used in preparing these various compositions should be pharmaceutically pure and non-toxic in the amounts used.

The pharmaceutical compositions of the present invention can be administered parenterally, such as, for example, by intravenous, intramuscular, intrathecal and/or subcutaneous injection. Parenteral administration can be accomplished by incorporating the compositions of the present invention into a solution or suspension. Such solutions or suspensions may also include sterile diluents, such as water for injection, saline solution, fixed oils, polyethylene glycols, glycerine, propylene glycol and/or other synthetic solvents. Parenteral formulations may also include antibacterial agents, such as, for example, benzyl alcohol and/or methyl parabens, antioxidants, such as, for example, ascorbic acid and/or sodium bisulfite, and chelating agents, such as EDTA. Buffers, such as acetates, citrates and phosphates, and agents for the adjustment of tonicity, such as sodium chloride and dextrose, may also be added. The parenteral preparation can be enclosed in ampules, disposable syringes and/or multiple dose vials made of glass or plastic. Rectal administration includes administering the composition into the rectum and/or large intestine. This can be accomplished using suppositories and/or enemas. Suppository formulations can be made by methods known in the art. Transdermal administration includes percutaneous absorption of the composition through the skin. Transdermal formulations include patches, ointments, creams, gels, salves, and the like. The compositions of the present invention can be administered nasally to a patient. As used herein, nasally administering or nasal administration includes administering the compositions to the mucous membranes of the nasal passage and/or nasal cavity of the patient.

The pharmaceutical compositions of the invention may be used in accordance with the methods of the invention for preventing, treating, or ameliorating one or more symptoms associated with a disease, disorder, or infection. It is contemplated that the pharmaceutical compositions of the invention are sterile and in suitable form for administration to a subject.

In one embodiment the compositions of the invention are pyrogen-free formulations that are substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with monoclonal antibodies, it is advantageous to remove even trace amounts of endotoxin. In a specific embodiment, endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

The invention provides methods for preventing, treating, or ameliorating one or more symptoms associated with a disease, disorder, or infection, said method comprising:

(a) administering to a subject in need thereof a dose of a prophylactically or therapeutically effective amount of a composition comprising one or more Fc variants and (b) administering one or more subsequent doses of said Fc variants, to maintain a plasma concentration of the Fc variant at a desirable level (e.g., about 0.1 to about 100 μg/ml), which continuously binds to an antigen. In a specific embodiment, the plasma concentration of the Fc variant is maintained at 10 μg/ml, 15 μg/ml, 20 μg/ml, 25 μg/ml, 30 μg/ml, 35 μg/ml, 40 μg/ml, 45 μg/ml or 50 μg/ml. In a specific embodiment, said effective amount of Fc variant to be administered is between at least 1 mg/kg and 8 mg/kg per dose. In another specific embodiment, said effective amount of Fc variant to be administered is between at least 4 mg/kg and 5 mg/kg per dose. In yet another specific embodiment, said effective amount of Fc variant to be administered is between 50 mg and 250 mg per dose. In still another specific embodiment, said effective amount of Fc valiant to be administered is between 100 mg and 200 mg per dose.

The present invention also encompasses protocols for preventing, treating, or ameliorating one or more symptoms associated with a disease, disorder, or infection which an Fc variant is used in combination with a therapy (e.g., prophylactic or therapeutic agent) other than an Fc variant and/or variant fusion protein. The invention is based, in part, on the recognition that the Fc variants of the invention potentiate and synergize with, enhance the effectiveness of, improve the tolerance of, and/or reduce the side effects caused by, other cancer therapies, including current standard and experimental chemotherapies. The combination therapies of the invention have additive potency, an additive therapeutic effect or a synergistic effect. The combination therapies of the invention enable lower dosages of the therapy (e.g., prophylactic or therapeutic agents) utilized in conjunction with Fc variants for preventing, treating, or ameliorating one or more symptoms associated with a disease, disorder, or infection and/or less frequent administration of such prophylactic or therapeutic agents to a subject with a disease disorder, or infection to improve the quality of life of said subject and/or to achieve a prophylactic or therapeutic effect. Further, the combination therapies of the invention reduce or avoid unwanted or adverse side effects associated with the administration of current single agent therapies and/or existing combination therapies, which in turn improves patient compliance with the treatment protocol. Numerous molecules which can be utilized in combination with the Fc variants of the invention are well known in the art. See for example, PCT publications WO 02/070007; WO 03/075957 and U.S. Patent Publication 2005/064514.

The present invention provides kits comprising one or more Fc variants with altered binding affinity to FcγRs and/or C1q and altered ADCC and/or CDC activity that specifically bind to an antigen conjugated or fused to a detectable agent, therapeutic agent or drug, in one or more containers, for use in monitoring, diagnosis, preventing, treating, or ameliorating one or more symptoms associated with a disease, disorder, or infection.

EXAMPLES

The examples below are given so as to illustrate the practice of this invention. They are not intended to limit or define the entire scope of this invention.

Example 1: Generation of Bivalent Monospecific Antibodies with Heterodimer Fc Domains The genes encoding the antibody heavy and light chains were constructed via gene synthesis using codons optimized for human/mammalian expression. The Fab sequences were generated from a known Her2/neu binding Ab (Carter P. et al. (1992) Humanization of an anti P185 Her2 antibody for human cancer therapy. *Proc Natl Acad Sci* 89, 4285.) and the Fc was an IgG1 isotype (SEQ ID NO:1). The final gene products were sub-cloned into the mammalian expression vector pTT5 (NRC-BRI, Canada) (Durocher, Y., Perret, S. & Kamen, A. High-level and high-throughput recombinant protein production by transient transfection of suspension-growing human HEK293-EBNA1 cells. *Nucleic acids research* 30, E9 (2002)). The mutations in the CH3 domain were introduced via site-directed mutagenesis of the pTT5 template vectors. See Table 1 and Table 6 and Table 7 for a list of the variant CH3 domain mutations made.

In order to estimate the formation of heterodimers and determine the ratio of homodimers vs. heterodimers the two heterodimer heavy chains were designed with C-terminal extensions of different size (specifically, chain A with C-terminal HisTag and chain B with C-terminal mRFP plus StrepTagII). This difference in molecular weight allows differentiation of homodimers vs. heterodimer in non-reducing SDS-PAGE as illustrated in FIG. 25A.

The HEK293 cells were transfected in exponential growth phase (1.5 to 2 million cells/mL) with aqueous 1 mg/mL 25 kDa polyethylenimine (PEI, Polysciences) at a PEI:DNA ratio of 2.5:1. (Raymond C. et al. A simplified polyethylenimine-mediated transfection process for large-scale and high-throughput applications. Methods. 55(1):44-51 (2011)). In order to determine the optimal concentration range for forming heterodimers, the DNA was transfected in three separate ratios of the two heavy chains. For example, this was done in 2 ml culture volume and transfection DNA, comprised of 5% GFP, 45% salmon sperm DNA, 25% light chain and 25% total heavy chains, where the heavy chain A plasmid (with C-terminal His-Tag) and the heavy chain B plasmid (with C-terminal StrepTagII plus RFP) at 65%/55%/35% or 10%/20%/40%) were sampled at 3 different relative ratios (chain_A(His)/chain_B(mRFP)) of 10%/65%; 20%/55%; 40%/35% (the apparent 1:1 expression ratio of a WT_His/WT_mRFP heterodimer was determined to be close to the DNA ratio 20%/55%). At 4 to 48 hours after transfection in F17 serum-free media (Gibco), TN1 peptone is added to a final concentration of 0.5%. Expressed antibody was analyzed by SDS-PAGE to determine the best ratio of heavy to light chain for optimal heterodimer formation (See FIGS. 25B and C).

A selected DNA ratio, for example 50% light chain plasmid, 25% heavy chain A plasmid, 25% heavy chain B of AZ33 and AZ34, with 5% GFP, and 45% salmon sperm DNA was used to transfect 150 mL of cell culture as described above. Transfected cells were harvested after 5-6 days with the culture medium collected after centrifugation at 4000 rpm and clarified using a 0.45 µm filter. See Table 2 below, for a list of the percentage of light and heavy chain A and B plasmids used in the scale up transfection assays for each of the antibodies with CH3 mutations generated for further analysis, including determination of purity and melting temperature.

TABLE 2

| Variant | LC/HCA/HCB |
|---|---|
| Wild-Type | 50%, 50% |
| AZ12 | 50%, 25%, 25% |
| AZ14 | 50%, 25%, 25% |
| AZ15 | 50%, 25%, 25% |
| AZ17 | 50%, 25%, 25% |
| AZ19 | 50%, 25%, 25% |
| AZ20 | 50%, 25%, 25% |
| AZ21 | 50%, 25%, 25% |
| AZ25 | 50%, 25%, 25% |
| AZ29 | 50%, 25%, 25% |
| AZ30 | 50%, 25%, 25% |
| AZ32 | 50%, 25%, 25% |
| AZ33 | 50%, 25%, 25% |
| AZ34 | 50%, 25%, 25% |
| AZ42 | 50%, 25%, 25% |
| AZ44 | 50%, 25%, 25% |
| AZ46 | 50%, 25%, 25% |
| AZ47 | 50%, 25%, 25% |
| AZ48 | 40%, 25%, 35% |
| AZ49 | 50%, 25%, 25% |
| AZ63 | 50%, 20%, 30% |
| AZ64 | 50%, 20%, 30% |
| AZ65 | 50%, 20%, 30% |
| AZ66 | 50%, 20%, 30% |
| AZ67 | 50%, 20%, 30% |
| AZ68 | 50%, 20%, 30% |
| AZ69 | 50%, 20%, 30% |
| AZ70 | 50%, 20%, 30% |
| AZ71 | 40%, 20%, 40% |
| AZ72 | 40%, 20%, 40% |
| AZ73 | 40%, 20%, 40% |
| AZ74 | 40%, 20%, 40% |
| AZ75 | 40%, 20%, 40% |
| AZ76 | 40%, 20%, 40% |
| AZ77 | 40%, 20%, 40% |
| AZ78 | 50%, 20%, 30% |
| AZ79 | 25%, 35%, 40% |
| AZ81 | 25%, 35%, 40% |
| AZ82 | 50%, 20%, 30% |
| AZ83 | 50%, 20%, 30% |
| AZ84 | 50%, 20%, 30% |
| AZ85 | 50%, 25%, 25% |
| AZ86 | 40%, 15%, 45% |
| AZ87 | 50%, 25%, 25% |
| AZ88 | 50%, 25%, 25% |
| AZ89 | 40%, 15%, 45% |
| AZ91 | 50%, 25%, 25% |
| AZ92 | 40%, 20%, 40% |
| AZ93 | 40%, 20%, 40% |
| AZ94 | 50%, 25%, 25% |
| AZ95 | 50%, 20%, 30% |
| AZ98 | 50%, 20%, 30% |
| AZ100 | 50%, 20%, 30% |
| AZ101 | 50%, 20%, 30% |
| AZ106 | 25%, 35%, 40% |
| AZ114 | 25%, 20%, 55% |
| AZ115 | 25%, 20%, 55% |
| AZ122 | 25%, 20%, 55% |
| AZ123 | 40%, 20%, 40% |
| AZ124 | 40%, 20%, 40% |
| AZ129 | 40%, 30%, 30% |
| AZ130 | 40%, 30%, 30% |

Example 2: Purification of Bivalent Monospecific Antibodies with Heterodimer Fc Domains The clarified culture medium was loaded onto a MabSelect SuRe (GE Healthcare) protein-A column and washed with 10 column volumes of PBS buffer at pH 7.2. The antibody was eluted with 10 column volumes of citrate buffer at pH 3.6 with the pooled fractions containing the antibody neutralized with TRIS at pH 11. The protein was finally desalted using an Econo-Pac 10DG column (Bio-Rad). The C-terminal mRFP tag on the heavy chain B was removed by incubating the antibody with enterokinase (NEB) at a ratio of 1:10,000 overnight in PBS at 25° C. The antibody was purified from the mixture by gel filtration. For gel filtration, 3.5 mg of the antibody mixture was concentrated to 1.5 mL and loaded onto a Sephadex 200 HiLoad 16/600 200 pg column (GE Healthcare) via an AKTA Express FPLC at a flow-rate of 1 mL/min. PBS buffer at pH 7.4 was used at a flow-rate of 1 mL/min. Fractions corresponding to the purified antibody were collected, concentrated to ~1 mg/mL and stored at −80° C.

Formation of heterodimers, as compared to homodimers, was assayed using non-reducing SDS-PAGE and mass spectrometry. Protein A purified antibody was run on a 4-12% gradient SDS-PAGE, non-reducing gel to determine the percentage of heterodimers formed prior to enterokinase (EK) treatment (See, FIG. 26). For mass spectrometry, all Trap LC/MS (ESI-TOF) experiments were performed on an Agilent 1100 HPLC system interfaced with a Waters Q-TOF2 mass spectrometer. Five µg of gel filtration purified antibody was injected into a Protein MicroTrap (1.0 by 8.0 mm), washed with 1% acetonitrile for 8 minutes, a gradient from 1 to 20% acetonitrile/0.1% formic acid for 2 minutes, then eluted with a 20 to 60% acetonitrile/0.1% formic acid gradient for 20 minutes. Eluate (30-50 µL/min) was directed to the spectrometer with spectrum acquired every second (m/z 800 to 4,000). (See, FIG. 28) Variants having greater than 90% heterodimers were selected for further analysis, with the exception of AZ12 and AZ14 which each had greater than 85% heterodimer formation.

Example 3: Stability Determination of Bivalent Monospecific Antibodies with Heterodimer Fc Domains Using Differential Scanning Calorimetry (DSC)

All DSC experiments were carried out using a GE VP-Capillary instrument. The proteins were buffer-exchanged into PBS (pH 7.4) and diluted to 0.4 to 0.5 mg/mL with 0.137 mL loaded into the sample cell and measured with a scan rate of 1° C./min from 20 to 100° C. Data was analyzed using the Origin software (GE Healthcare) with the PBS buffer background subtracted. (See, FIG. 27). See Table 3 for a list of variants tested and a melting temperature determined. See Table 4 for a list of the variants with a melting temperature of 70° C. and above and the specific Tm for each variant.

TABLE 3

Melting temperature measurements of variant CH3 domains in an IgG1 antibody having 90% or more heterodimer formation compared to homodimer formation

| Variant | Tm ° C. |
| --- | --- |
| Wild-Type | 81 |
| Control 1 | 69 |
| Control 2 | 69 |
| AZ3 | 65 |
| AZ6 | 68 |
| AZ8 | 68 |
| AZ12 | 77 |
| AZ14 | 77 |
| AZ15 | 71.5 |
| AZ16 | 68.5 |
| AZ17 | 71 |
| AZ18 | 69.5 |
| AZ19 | 70.5 |
| AZ20 | 70 |
| AZ21 | 70 |
| AZ22 | 69 |
| AZ23 | 69 |
| AZ24 | 69.5 |
| AZ25 | 70.5 |
| AZ26 | 69 |
| AZ27 | 68 |
| AZ28 | 69.5 |
| AZ29 | 70 |
| AZ30 | 71 |
| AZ31 | 68 |
| AZ32 | 71.5 |
| AZ33 | 74 |
| AZ34 | 73.5 |
| AZ38 | 69 |
| AZ42 | 70 |
| AZ43 | 67 |
| AZ44 | 71.5 |
| AZ46 | 70.5 |
| AZ47 | 70.5 |
| AZ48 | 70.5 |
| AZ49 | 71 |
| AZ50 | 69 |
| AZ52 | 68 |
| AZ53 | 68 |
| AZ54 | 67 |
| AZ58 | 69 |
| AZ59 | 69 |
| AZ60 | 67 |
| AZ61 | 69 |
| AZ62 | 68 |
| AZ63 | 71.5 |
| AZ64 | 74 |
| AZ65 | 73 |
| AZ66 | 72.5 |
| AZ67 | 72 |
| AZ68 | 72 |
| AZ69 | 71 |
| AZ70 | 75.5 |
| AZ71 | 71 |
| AZ72 | 70.5 |
| AZ73 | 71 |
| AZ74 | 71 |
| AZ75 | 70 |
| AZ76 | 71.5 |
| AZ77 | 71 |
| AZ78 | 70 |
| AZ79 | 70 |
| AZ81 | 70.5 |
| AZ82 | 71 |
| AZ83 | 71 |
| AZ84 | 71.5 |
| AZ85 | 71.5 |
| AZ86 | 72.5 |
| AZ87 | 71 |
| AZ88 | 72 |
| AZ89 | 72.5 |
| AZ91 | 71.5 |
| AZ92 | 71.5 |
| AZ93 | 71.5 |
| AZ94 | 73.5 |
| AZ95 | 72 |
| AZ98 | 70 |
| AZ99 | 69 |
| AZ100 | 71.5 |
| AZ101 | 74 |
| AZ106 | 74 |
| AZ114 | 71 |
| AZ115 | 70 |
| AZ117 | 69.5 |
| AZ122 | 71 |
| AZ123 | 70 |
| AZ124 | 70 |
| AZ125 | 69 |
| AZ126 | 69 |
| AZ129 | 70.5 |
| AZ130 | 71 |

TABLE 4

Melting temperature measurements of select variant CH3 domains in an IgG1 antibody

| Variant | Tm ° C. |
| --- | --- |
| Wild-Type | 81.5 |
| Control 1 | 69 |
| Control 2 | 69 |
| AZ12 | >77 |
| AZ14 | >77 |
| AZ15 | 71.5 |
| AZ17 | 71 |
| AZ19 | 70.5 |
| AZ20 | 70 |
| AZ21 | 70 |
| AZ25 | 70.5 |
| AZ29 | 70 |
| AZ30 | 71 |
| AZ32 | 71.5 |
| AZ33 | 74 |
| AZ34 | 73.5 |
| AZ42 | 70 |
| AZ44 | 71.5 |
| AZ46 | 70.5 |
| AZ47 | 70.5 |
| AZ48 | 70.5 |
| AZ49 | 71 |
| AZ63 | 71.5 |
| AZ64 | 74 |
| AZ65 | 73 |
| AZ66 | 72.5 |
| AZ67 | 72 |
| AZ68 | 72 |
| AZ69 | 71 |
| AZ70 | 75.5 |
| AZ71 | 71 |
| AZ72 | 70.5 |
| AZ73 | 71 |
| AZ74 | 71 |

TABLE 4-continued

Melting temperature measurements of select variant CH3 domains in an IgG1 antibody

| Variant | Tm ° C. |
|---|---|
| AZ75 | 70 |
| AZ76 | 71.5 |
| AZ77 | 71 |
| AZ78 | 70 |
| AZ79 | 70 |
| AZ81 | 70.5 |
| AZ82 | 71 |
| AZ83 | 71 |
| AZ84 | 71.5 |
| AZ85 | 71.5 |
| AZ86 | 72.5 |
| AZ87 | 71 |
| AZ88 | 72 |
| AZ89 | 72.5 |
| AZ91 | 71.5 |
| AZ92 | 71.5 |
| AZ93 | 71.5 |
| AZ94 | 73.5 |
| AZ95 | 72 |
| AZ98 | 70 |
| AZ100 | 71.5 |
| AZ101 | 74 |
| AZ106 | 74 |
| AZ114 | 71 |
| AZ115 | 70 |
| AZ122 | 71 |
| AZ123 | 70 |
| AZ124 | 70 |
| AZ129 | 70.5 |
| AZ130 | 71 |

Example 4: Evaluation of FcgammaR Binding Using Surface Plasmon Resonance

All binding experiments were carried out using a BioRad ProteOn XPR36 instrument at 25° C. with 10 mM HEPES, 150 mM NaCl, 3.4 mM EDTA, and 0.05% Tween 20 at pH 7.4. Recombinant HER-2/neu(p185, ErbB-2 (eBiosciences, Inc.)) was captured on the activated GLM sensorchip by injecting 4.0 µg/mL in 10 mM NaOAc (pH 4.5) at 25 µL/min until approx. 3000 resonance units (RUs) were immobilized with the remaining active groups quenched. 40 µg/mL of purified anti-HER-2/neu antibodies comprising the variant CH3 domains were indirectly captured on the sensorchip by binding the Her-2/neu protein when injected at 25 µL/min for 240 s (resulting in approx. 500 RUs) following a buffer injection to establish a stable baseline. FcgammaR (CD16a(f allotype) and CD32b) concentrations (6000, 2000, 667, 222, and 74.0 nM) were injected at 60 µL/min for 120 s with a 180 s dissociation phase to obtain a set of binding sensograms. Resultant $K_D$ values were determined from binding isotherms using the Equilibrium Fit model with reported values as the mean of three independent runs. Comparisons were made with the wild-type IgG1 Fc domain and binding is expressed as a ratio of the WT kD to the variant kD (See, Table 5).

TABLE 5

Ratio of kD wild-type IgG1 to variant CH3 domain antibody binding independently to CD16a and CD32b

| Variant | CD16a Ratio WT/Variant | CD32b Ratio WT/Variant |
|---|---|---|
| Control 1 | 1.28 | 1.68 |
| Control 2 | 1.1 | 1.13 |
| AZ3 | 1.75 | 1.87 |
| AZ6 | 1.38 | 1 |
| AZ8 | 1.75 | 1.64 |
| AZ12 | N/A | N/A |
| AZ14 | N/A | N/A |
| AZ15 | 0.72 | 0.59 |
| AZ16 | 0.95 | 0.64 |
| AZ17 | 2.28 | 2.37 |
| AZ18 | 1.53 | 1.7 |
| AZ19 | 1.55 | 1.89 |
| AZ20 | 2.56 | 1.93 |
| AZ21 | 2.41 | 3.28 |
| AZ22 | 2.02 | 2.37 |
| AZ23 | 1 | 2.16 |
| AZ24 | 1.79 | 2.26 |
| AZ25 | 2.02 | 2.37 |
| AZ26 | 2.38 | 2.59 |
| AZ27 | 2.27 | 2.38 |
| AZ28 | 1.45 | 2.15 |
| AZ29 | 1.62 | 2.13 |
| AZ30 | 1.61 | 2.38 |
| AZ31 | 1.63 | 2.29 |
| AZ32 | 1.82 | 2.48 |
| AZ33 | 1.91 | 1.89 |
| AZ34 | 1.88 | 1.88 |
| AZ38 | 1.78 | 1.44 |
| AZ42 | 1.28 | 1.09 |
| AZ43 | 1.63 | 1.73 |
| AZ44 | 2.76 | 3.07 |
| AZ46 | 2.16 | 2.66 |
| AZ47 | 1.76 | 2.12 |
| AZ48 | 2.02 | 1.59 |
| AZ49 | 2.09 | 2.9 |
| AZ50 | 2.33 | 1.86 |
| AZ52 | 1.55 | 1.5 |
| AZ53 | 1.87 | 1.27 |
| AZ54 | 1.36 | 1.64 |
| AZ58 | 2.33 | 1.48 |
| AZ59 | 1.18 | 1.57 |
| AZ60 | 1.51 | 1.23 |
| AZ61 | 1.41 | 1.75 |
| AZ62 | 1.53 | 1.88 |
| AZ63 | 0.9 | 0.95 |
| AZ64 | 0.95 | 0.9 |
| AZ65 | 0.93 | 0.9 |
| AZ66 | 1.26 | 1.19 |
| AZ67 | 1.21 | 1.13 |
| AZ68 | 1.02 | 1.1 |
| AZ69 | 0.96 | 1.05 |
| AZ70 | 1.06 | 1.11 |
| AZ71 | 0.89 | 0.95 |
| AZ72 | 1.04 | 1.02 |
| AZ73 | 1.09 | 1.07 |
| AZ74 | 1.25 | 1.17 |
| AZ75 | 1.34 | 1.22 |
| AZ76 | 0.99 | 1 |
| AZ77 | 1 | 1.08 |
| AZ78 | 0.9 | 1 |
| AZ79 | 1.01 | 0.8 |
| AZ81 | 1.01 | 0.84 |
| AZ82 | 0.97 | 0.94 |
| AZ83 | 0.94 | 0.94 |
| AZ84 | 0.93 | 1 |
| AZ85 | 1.01 | 1.14 |
| AZ86 | 1.22 | 1.18 |
| AZ87 | 1.03 | 1.1 |
| AZ88 | 1.11 | 1.15 |
| AZ89 | 1.12 | 1.24 |
| AZ91 | 1.11 | 1.11 |
| AZ92 | 1.21 | 1.24 |

TABLE 5-continued

Ratio of kD wild-type IgG1 to variant CH3 domain antibody binding independently to CD16a and CD32b

| Variant | CD16a Ratio WT/Variant | CD32b Ratio WT/Variant |
| --- | --- | --- |
| AZ93 | 1.21 | 1.18 |
| AZ94 | 1.17 | 1.19 |
| AZ95 | 0.86 | 0.96 |
| AZ98 | 0.79 | 0.82 |
| AZ99 | 1.16 | 1.15 |
| AZ100 | 1.13 | 1.12 |
| AZ101 | 1.24 | 1.23 |
| AZ106 | 0.76 | 0.64 |
| AZ114 | 1.3 | 0.84 |
| AZ115 | 1.13 | 0.82 |
| AZ117 | 0.89 | 1 |
| AZ122 | 0.89 | 0.92 |
| AZ123 | 0.85 | 0.92 |
| AZ124 | 0.99 | 1.09 |
| AZ125 | 1 | 1 |
| AZ126 | 0.86 | 0.9 |
| AZ129 | 1.91 | 2.57 |
| AZ130 | 1.91 | 2.54 |

Example 5: Rational Design of Fc Variants Using Fc_CH3 Engineering—Scaffold 1 (1a and 1b) and the Development of AZ17-62 and AZ133-AZ2438

To improve the initial negative design Fc variant AZ8 for stability and purity, the structural and computational strategies described above were employed. (See, FIG. 24) For example, the in depth structure-function analysis of AZ8 provided a detailed understanding for each of the introduced mutations of AZ8,L351Y_V397S_F405A_Y407V/K392V_T394W compared to wild-type human IgG1 and indicated that the important core heterodimer mutations were L351Y_F405A_Y407V/T394W, while V397S, K392V were not relevant for heterodimer formation. The core mutations (L351Y_F405A_Y407V/T394W) are herein referred to as "Scaffold 1" mutations. The analysis furthermore revealed that the important interface hotspots that are lost with respect to wild-type (WT) homodimer formation are the interactions of WT-F405-K409, Y407-T366 and the packing of Y407-Y407 and -F405 (See, FIG. 29). This was reflected in the packing, cavity and MD analysis, which showed a large conformational difference in the loop region D399-S400-D401 (See, FIG. 30) and the associated β-sheets at K370. This resulted in the loss of the interchain interactions K409-D399 (See, FIG. 30) and weakening of the strong K370 hydrogen bond to E357 (K370 is no longer in direct contact with S364 and E357, but is entirely solvent exposed). In the WT IgG1 CH3 domain these regions tether the interface at the rim protects the core interactions from bulk solvent competition and increases the dynamic occurrence of favorable hydrophobic van der Waals interactions. The consequence was a lower buried surface area of AZ8 compared to WT and a higher solvent accessibility of the hydrophobic core. This indicated the most important factors for the lower stability of AZ8 compared to WT stability was a) the loss of the WT-F405-K409 interaction and packing of F405, and b) the loss of the strong packing interaction of Y407-Y407 and Y407-T366. See, FIG. 29

Consequently, we identified the key residues/sequence motifs responsible for the low stability of AZ8 compared to WT. To improve the stability and heterodimer specificity of AZ8 the subsequent positive design engineering efforts were therefore specifically focused on stabilizing the loop conformation of positions 399-401 in a more 'closed'-WT like conformation (See, FIG. 30) and compensating for the overall slightly decreased (looser) packing of the hydrophobic core at positions T366 and L368 (See, FIG. 29).

To achieve this stabilization of the loop conformation of positions 399-401 the described computational approach was used to evaluate our different targeted design ideas. Specifically, three different independent options for Fc variant AZ8 were analyzed to optimize the identified key regions for improving stability. First, the cavity close to position K409 and F405A was evaluated for better hydrophobic packing to both protect the hydrophobic core and stabilize the loop conformation of 399-400 (See, FIG. 30). Those included, but were not limited to additional point mutations at positions F405 and K392. Second, options for improving the electrostatic interactions of positions 399-409 were evaluated, to stabilize the loop conformation of 399-400 and protect the hydrophobic core. This included, but was not limited to additional point mutations at positions T411 and S400. Third, the cavity at the core packing positions T366, T394W and L368 was evaluated to improve the core hydrophobic packing (See, FIG. 29). Those included, but were not limited to additional point mutations at positions T366 and L368. The different independent positive design ideas were tested in-silico and the best-ranked variants using the computational tools (AZ17-AZ62) were validated experimentally for expression and stability as described in Examples 1-4. See Table 4 for a list of Fc variants from this design phase with a melting temperature of 70° C. or greater.

Fc variant AZ33 is an example of the development of an Fc variant wherein Scaffold 1 was modified resulting in Scaffold 1a mutations to improve stability and purity. This Fc variant was designed based on AZ8 with the goal improving the hydrophobic packing at positions 392-394-409 and 366 to both protect the hydrophobic core and stabilize the loop conformation of 399-400. This Fc variant AZ33 heterodimer has two additional point mutations different from the core mutations of AZ8, K392M and T366I. The mutations T366I_K392M_T394W/F405A_Y407V are herein referred to as "Scaffold 1a" mutations. The mutation K392M was designed to improve the packing at the cavity close to position K409 and F405A to protect the hydrophobic core and stabilize the loop conformation of 399-400 (See, FIG. 31). T366I was designed to improve the core hydrophobic packing and to eliminate the formation of homodimers of the T394W chain (See, FIG. 29). The experimental data for AZ33 showed significantly improved stability over the initial negative design Fc variant AZ8 (Tm 68° C.) wherein AZ33 has a Tm of 74° C. and a heterodimer content of >98%. (See, FIG. 25C)

Development of Fc Variants Using Scaffold 1 Mutations in Phase Three Design of Fc Variant Heterodimers Although AZ33 provides a significant stability and specificity (or purity) improvement over the initial starting variant AZ8, our analysis indicates that further improvements to the stability of the Fc variant heterodimer can be made with further amino acid modifications using the experimental data of AZ33 and the above described design methods. The different design ideas have been independently tested for expression and stability, but the independent design ideas are transferable and the most successful heterodimer will contain a combination of the different designs. Specifically, for the optimization of AZ8 packing mutations at the cavity close to K409-F405A-K392 have been evaluated independently from mutations that optimize the core packing at residues L366T-L368. These two regions 366-368 and 409-

405-392 are distal from each other and are considered independent. Fc variant AZ33 for example has been optimized for packing at 409-405-392, but not at 366-368, because these optimization mutations were separately evaluated. The comparison of the 366-368 mutations suggests that T366L has an improved stability over T366 and also T366I, the point mutation used in the development of Fc variant AZ33. Consequently, the presented experimental data immediately suggest further optimization of AZ33 by introducing T366L instead of T366I, for example. Therefore, the amino acid mutations in the CH3 domain T366L_K392M_T394W/F405A_Y407V are herein referred to as "Scaffold 1b" mutations.

In a similar manner the complete experimental data has been analyzed to identify point mutations that can be used to further improve the current Fc variant heterodimer AZ33. These identified mutations were analyzed by the above described computational approach and ranked 100 to yield the list of additional Fc variant heterodimers based on AZ33 as shown in Table 6.

Example 6: Rational Design of Fc Variants Using Fc_CH3 Engineering—Scaffold 2 (a and b) and, the Development of AZ63-101 and AZ2199-AZ2524

To improve the initial negative design phase Fc variant AZ15 for stability and purity, the structural and computational strategies described above were employed (See, FIG. 24). For example, the in depth structure-function analysis of Fc variant AZ15 provided a detailed understanding for each of the introduced mutations of AZ15, L351Y_Y407A/E357L_T366A_K409F_T411N compared to wild-type (WT) human IgG1 and indicated that the important core heterodimer mutations were L351Y_Y407A/T366A_K409F, while E357L, T411N were not directly relevant for heterodimer formation and stability. The core mutations (L351Y_Y407A/T366A_K409F) are herein referred to as "Scaffold 2" mutations. The analysis furthermore revealed that the important interface hotspots that are lost with respect to wild-type (WT) homodimer formation are the salt bridge D399-K409, the hydrogen bond Y407-T366 and the packing of Y407-Y407. Our detailed analysis, provided below, describes how we improved the stability of our original Fc variant AZ15 and the positions and amino acid modifications made to achieve these Fc variants with improved stability.

Development of Fc Variants Using Scaffold 2 Mutations and the Further Development of Scaffold 2a Mutations.

Our in-silico analysis indicated a non-optimal packing of the Fc variant AZ15 mutations K409F_T366A_Y407A and an overall decreased packing of the hydrophobic core due to the loss of the WT-Y407-Y407 interactions. The positive design efforts in the subsequent engineering phase were focused on point mutations to compensate for these packing deficits in the initial Fc variant AZ15. The targeted residues included positions T366, L351, and Y407. Different combinations of these were tested in-silico and the best-ranked Fc variants using the computational tools (AZ63-AZ70) were validated experimentally for expression and stability as described in Examples 1-4.

Fc variant AZ70 is an example of the development of an Fc variant wherein Scaffold 2 was modified resulting in Scaffold 2a mutations to improve stability and purity. This Fc variant was designed based on AZ15 with the goal of achieving better packing at the hydrophobic core as described above. Fc variant AZ70 has the same Scaffold 2 core mutations (L351Y_Y407A/T366A_K409F) as described above except that T366 was mutated to T366V instead of T366A (FIG. 33). The L351Y mutation improves the 366A_409F/407A variant melting temperature from 71.5° C. to 74° C., and the additional change from 366A to 366V improves the Tm to 75.5° C. (See, AZ63, AZ64 and AZ70 in Table 4, with a Tm of 71.5° C., 74° C. and 75.5° C., respectively) The core mutations (L351Y_Y407A/T366V_K409F) are herein referred to as "Scaffold 2a" mutations. The experimental data for Fc variant AZ70 showed significantly improved stability over the initial negative design Fc variant AZ15 (Tm 71° C.) wherein AZ70 has a Tm of 75.5° C. and a heterodimer content of >90% (FIGS. 33 and 27).

Development of Fc Variants Using Scaffold 2 Mutations and the Further Development of Scaffold 2b Mutations.

The Molecular Dynamics simulation (MD) and packing analysis showed a preferred more 'open' conformation of the loop 399-400, which was likely due to the loss of the WT salt bridge K409-D399. This also results in the unsatisfied D399, which in turn preferred a compensating interaction with K392 and induced a more 'open' conformation of the loop. This more 'open' loop conformation results in an overall decreased packing and higher solvent accessibility of the core CH3 domain interface residues, which in turn significantly destabilized the heterodimer complex. Therefore, one of the targeted positive design efforts was the tethering of this loop in a more 'closed', WT-like conformation by additional point mutations that compensate for the loss of the D399-K409 salt bridge and the packing interactions of K409. The targeted residues included positions T411, D399, S400, F405, N390, K392 and combinations thereof. Different packing, hydrophobic- and electrostatic positive engineering strategies were tested in silico with respect to the above positions and the best-ranked Fc variants determined using the computational tools (AZ71-AZ101) were validated experimentally for expression and stability as described in Examples 1-4.

Fc variant AZ94 is an example of the development of an Fc variant wherein Scaffold 2 is modified resulting in Scaffold 2b mutations along with additional point mutations to improve stability and purity. This Fc variant was designed based on AZ15 with the goal of tethering loop 399-400 in a more 'closed', WT-like conformation and compensating for the loss of the D399-K409 salt bridge as described above. Fc variant AZ94 has four additional point mutations to Scaffold 2 (L351Y_Y407A/T366A_K409F) and returns L351Y to wild-type L351 leaving (Y407A/T366A_K409F) as the core mutations for this Fc variant. The core mutations Y407A/T366A_K409F are herein referred to as "Scaffold 2b" mutations. The four additional point mutations of AZ94 are K392E_T411E/D399R_S400R. The mutations T411E/D399R were engineered to form an additional salt bridge and compensate for the loss of the K409/D399 interaction (FIG. 34). Additionally, this salt bridge was designed to prevent homodimer formation by disfavoring charge-charge interactions in both potential homodimers. The additional mutations K392E/S400R were intended to form another salt bridge and hence further tether the 399_400 loop in a more 'closed', WT-like conformation (FIG. 34). The experimental data for AZ94 showed improved stability and purity over the initial negative design Fc variant AZ15 (Tm 71° C., >90% purity) wherein Fc variant AZ94 has a Tm of 74° C. and a heterodimer content or purity of >95%.

Development of Fc Variants Using Scaffold 2 Mutations in Phase Three Design of Fc Variant Heterodimers Both Fc variants AZ70 and AZ94 provide a significant improvement in stability and purity over the initial negative design Fc variant AZ15, but our analysis and the comparison of AZ70 and AZ94 directly indicate that further improvements to the stability of the Fc variant heterodimer can be made with further amino acid modifications. For example, Fc variants AZ70 and AZ94 were designed to target two distinct non-optimized regions in the initial variant AZ15, which was accomplished by improving the packing at the hydrophobic core and making mutations outside of the core interface residues resulting in additional salt bridges and hydrogen bonding to stabilize the loop conformation of positions 399-401. The additional point mutations of Fc variants AZ70 and AZ94 are distal from each other and are therefore independent and transferable to other Fc variants designed around the same Scaffold 2 core mutations, including 2a and 2b mutations. Specifically, AZ70 only carries the optimized core mutations L351Y_Y407A/T366A_K409F, but no additional salt bridges, whereas AZ94 comprises four additional electrostatic mutations (K392E_T411E/D399R_S400R), but has one less mutation in the hydrophobic core interface (Y407A/T366A_K409F). These Scaffold 2b mutations are less stable than AZ70 (See, for example AZ63, which has equivalent core mutations as AZ94 and Tm of 72° C.), but are compensated for by the addition of K392E_T411E/D399R_S400R mutations. The presented experimental stability and purity data indicates that combining the mutations of AZ70, which optimizes the hydrophobic core, and the electrostatic mutations of AZ94 should further improve stability and purity of the Fc variant heterodimers. In a similar manner the complete experimental data for Scaffold 2 Fc variants (AZ63-101) has been analyzed to identify point mutations that can be used to further improve the Fc variant heterodimers AZ70 and AZ94. These identified mutations were further analyzed by the above described computational approach and ranked to yield the list of additional Fc variant heterodimers based on AZ70 and AZ94 as shown in Table 7.

Example 7: Effect of Heterodimeric CH3 on FcgR Binding

As a prototypical example of heterodimeric Fc activity with FcgR, we have tested two variant antibodies with heterodimeric Fc region A:K409D_K392D/B:D399K_D356K (Control 1 (het 1 in FIG. 35)) and A:Y349C_T366S_L368A_Y407V/B:S354C_T366W (Control 4 (het 2 in FIG. 35)) with Her2 binding Fab arms in an SPR assay described in Example 4 for FcgR binding. As shown in FIG. 35, we observe that both the heterodimeric Fc regions bind the different Fcgamma receptors with the same relative strength as the wild type IgG1 Fc region, but overall, the heterodimeric Fc region bound each of the FcgR's slightly better than the wild type antibody. This indicates that mutations at the CH3 interface of Fc can impact the binding strength of the Fc region for Fcgamma receptors across the CH2 domains as observed in our molecular dynamics simulations and analysis.

Example 8: Effect of Asymmetric Mutations in CH2 of a Heterodimeric Fc on FcgR Binding Mutation of Serine at position 267 in the CH2 domain of the Fc region to an Aspartic acid (S267D) is known to enhance binding to Fcgamma IIbF, IIbY & IIaR receptors when introduced in a homodimeric manner in the two chains of CH2 domain. This mutation can be introduced on only one of the CH2 domains in an heterodimeric Fc molecule to gain roughly half the improvement in binding strength relative to when this mutation is introduced in a homodimeric CH2 Fc as the data presented in FIG. 36A indicates. On the other hand, the E269K mutation in a homodimeric CH2 domain of Fc prevents binding of the Fc region to FcgR. We present a scheme for enhanced manipulation of the binding strength of the Fc region for the FcgReceptors by the asymmetric introduction of these favorable and unfavorable mutations on one of the two chains in the CH2 domain of the Fc. The introduction of E269K mutation in an asymmetric manner on one CH2 chain in a heterodimeric Fc acts as a polarity driver by blocking binding of the FcgR at the face where it is present, while letting the other face of the Fc interact with the FcgR in a normal manner. The results from this experimentation are presented in FIG. 36A. The opportunity to selectively alter the binding strength via both the chains of Fc in an independent manner provides increased opportunity to manipulate the binding strength and selectivity between Fc and FcgRecptors. Thus, such asymmetric design of mutations in the CH2 domain allows us to introduce positive and negative design strategies to favor or disfavor certain binding models, providing greater opportunity to introduce selectivity.

In a subsequent experiment, we have altered the selectivity profile of the base Fc mutant S239D_D265S_I332E_S298A that shows increased binding strength to the Fcgamma IIIaF and IIIaV receptors while continuing to exhibit weaker binding to the Fcgamma IIaR, IIbF and IIbY receptors. This is shown in the binding profile shown in FIG. 36B. By introducing asymmetric mutations E269K in chain A and avoiding the I332E mutation in chain B, we are able to generate a novel FcgR binding profile that further weakens IIa and IIb receptor binding and makes the Fc more specific for the IIIa receptor binding.

In another example shown in FIG. 36C, asymmetric mutations are highlighted relative to the homodimeric Fc involving the mutation S239D/K326E/A330L/I332E/S298A in the CH2 domain. Relative to the wild type IgG1 Fc, this variant show increased binding to the IIIa receptor but also binds the IIa and IIb receptors slightly stronger than the wild type Fc. Introduction of these mutations in an asymmetric manner A:S239D/K326E/A330L/I332E and B:S298A while reducing the IIIa binding, also increases the IIa/IIb receptor binding, loosing selectivity in the process. By introducing an asymmetirc E269K mutation in this heterodimeric variant, i.e. A:S239D/K326E/A330L/I332E/E269K and B:S298A, we are able to reduce the IIa/IIb binding back to wild type levels. This highlights the fact that the use of asymmetric mutations in the CH2 domain of Fc is able to provide significant opportunity to design improved FcgammaR selectivity.

The reagents employed in the examples are commercially available or can be prepared using commercially available instrumentation, methods, or reagents known in the art. The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

All publications, patents and patent applications mentioned in this specification are herein incorporated by reference into the specification to the same extent as if each individual publication, patent or patent application was specifically and individually indicated to be incorporated herein by reference.

We claim:

1. An isolated heteromultimer comprising a heterodimer Fc region, the heterodimer Fc region comprising a variant CH3 domain comprising a first CH3 domain polypeptide and a second CH3 domain polypeptide, each of the first and second CH3 domain polypeptides comprising amino acid modifications that promote formation of the heterodimer Fc region, the heterodimer Fc region having a purity greater than 90% and the variant CH3 domain having a melting temperature (Tm) of 70° C. or greater,
wherein the heterodimer Fc region is an IgG Fc region, and wherein:
(a) the first CH3 domain polypeptide comprises the amino acid modifications L351Y and Y407A, and the second CH3 domain polypeptide comprises the amino acid modifications E357L, T366A, K409F and T411N (variant AZ15),
(b) the first CH3 domain polypeptide comprises the amino acid modification Y407A, and the second CH3 domain polypeptide comprises the amino acid modifications T366A and K409F (variant AZ63),
(c) the first CH3 domain polypeptide comprises the amino acid modifications L351Y and Y407A, and the second CH3 domain polypeptide comprises the amino acid modifications T366A and K409F (variant AZ64),
(d) the first CH3 domain polypeptide comprises the amino acid modifications L351F and Y407A, and the second CH3 domain polypeptide comprises the amino acid modifications T366A and K409F (variant AZ65),
(e) the first CH3 domain polypeptide comprises the amino acid modification Y407A, and the second CH3 domain polypeptide comprises the amino acid modifications T366S and K409F (variant AZ66),
(f) the first CH3 domain polypeptide comprises the amino acid modification Y407A, and the second CH3 domain polypeptide comprises the amino acid modifications T366C and K409F (variant AZ67), (g) the first CH3 domain polypeptide comprises the amino acid modification Y407A, and the second CH3 domain polypeptide comprises the amino acid modifications T366L and K409F (variant AZ68), (h) the first CH3 domain polypeptide comprises the amino acid modification Y407A, and the second CH3 domain polypeptide comprises the amino acid modifications T366M and K409F (variant AZ69), (i) the first CH3 domain polypeptide comprises the amino acid modifications L351Y and Y407A, and the second CH3 domain polypeptide comprises the amino acid modifications T366V and K409F (variant AZ70), (j) the first CH3 domain polypeptide comprises the amino acid modifications L351I, T366S, L368F and Y407A, and the second CH3 domain polypeptide comprises the amino acid modifications T366A and K409F (variant AZ71), (k) the first CH3 domain polypeptide comprises the amino acid modifications D399W and Y407A, and the second CH3 domain polypeptide comprises the amino acid modifications T366A and K409F (variant AZ72), (l) the first CH3 domain polypeptide comprises the amino acid modifications D399W, S400D and Y407A, and the second CH3 domain polypeptide comprises the amino acid modifications T366A and K409F (variant AZ73), (m) the first CH3 domain polypeptide comprises the amino acid modifications D399W, S400E and Y407A, and the second CH3 domain polypeptide comprises the amino acid modifications T366A and K409F (variant AZ74), (n) the first CH3 domain polypeptide comprises the amino acid modifications D399W, S400D and Y407A, and the second CH3 domain polypeptide comprises the amino acid modifications T366A, K409F and T411R (variant AZ75), (o) the first CH3 domain polypeptide comprises the amino acid modifications G371D, D399W and Y407A, and the second CH3 domain polypeptide comprises the amino acid modifications T366A, K409F and T411R (variant AZ76), (p) the first CH3 domain polypeptide comprises the amino acid modifications K370Q, G371D, D399W and Y407A, and the second CH3 domain polypeptide comprises the amino acid modifications T366A, K409F and T411R (variant AZ77), (q) the first CH3 domain polypeptide comprises the amino acid modifications D399Y, S400D and Y407A, and the second CH3 domain polypeptide comprises the amino acid modifications T366A, N390R and K409F (variant AZ78), (r) the first CH3 domain polypeptide comprises the amino acid modification Y407A, and the second CH3 domain polypeptide comprises the amino acid modifications Q362R, T366A, K409F and T411K (variant AZ79), (s) the first CH3 domain polypeptide comprises the amino acid modification Y407A, and the second CH3 domain polypeptide comprises the amino acid modifications Q362K, T366A, K409F and T411R (variant AZ81), (t) the first CH3 domain polypeptide comprises the amino acid modifications S400E and Y407A, and the second CH3 domain polypeptide comprises the amino acid modifications T366A, N390K, K392R, K409F and T411R (variant AZ82), (u) the first CH3 domain polypeptide comprises the amino acid modifications S400E and Y407A, and the second CH3 domain polypeptide comprises the amino acid modifications T366A, N390K, K392R, K409F and T411K (variant AZ83), (v) the first CH3 domain polypeptide comprises the amino acid modifications S400D and Y407A, and the second CH3 domain polypeptide comprises the amino acid modifications T366A, N390K, K409F and T411R (variant AZ84), (w) the first CH3 domain polypeptide comprises the amino acid modifications D399R and Y407A, and the second CH3 domain polypeptide comprises the amino acid modifications T366A, K392L, K409F and T411D (variant AZ85), (x) the first CH3 domain polypeptide comprises the amino acid modifications D399R and Y407A, and the second CH3 domain polypeptide comprises the amino acid modifications T366A, K392L, K409F and T411E (variant AZ86), (y) the first CH3 domain polypeptide comprises the amino acid modifications D399K and Y407A, and the second CH3 domain polypeptide comprises the amino acid modifications T366A, K392L, K409F and T411D (variant AZ87), (z) the first CH3 domain polypeptide comprises the amino acid modifications D399K and Y407A, and the second CH3 domain polypeptide comprises the amino acid modifications T366A, K392L, K409F and T411E (variant AZ88), (aa) the first CH3 domain polypeptide comprises the amino acid modifications D399R and Y407A, and the second CH3 domain polypeptide comprises the amino acid modifications T366A, K392M, K409F and T411E (variant AZ89), (bb) the first CH3 domain polypeptide comprises the amino acid modifications D399R, F405V and Y407A, and the second CH3 domain polypeptide comprises the amino acid modifications T366A, K392F, K409F and T411D (variant AZ91), (cc) the first CH3 domain polypeptide comprises the amino acid modifications D399R, S400E and Y407A, and the second CH3 domain polypeptide comprises the amino acid modifications T366A, K409F and T411E (variant AZ92), (dd) the first CH3 domain polypeptide comprises the amino acid modifications D399R, S400D and Y407A, and the second CH3 domain polypeptide comprises the amino acid modifications T366A, K409F and T411E (variant AZ93), (ee) the first CH3 domain polypeptide comprises the amino acid modifications D399R, S400R and Y407A, and the second CH3 domain polypeptide comprises the amino acid modifications T366A, K392E, K409F and T411E (variant AZ94), (ff) the first CH3 domain polypeptide comprises the amino acid modifications D399R, S400R and Y407A, and the second CH3 domain polypeptide comprises the amino acid modifications T366A, K392E, K409F and T411D (variant AZ95), (gg) the first CH3 domain polypeptide comprises the amino acid modification Y407A, and the second CH3 domain polypeptide comprises the amino acid modifications S364Y, T366A, K409F and T411R (variant AZ98), (hh) the first CH3 domain polypeptide comprises the amino acid modifications L351Y, L368S and Y407A, and the second CH3 domain polypeptide comprises the amino acid modifications T366V and K409W (variant AZ100), or (ii) the first CH3 domain polypeptide comprises the amino acid modifications L351Y and Y407A, and the second CH3 domain polypeptide comprises the amino acid modifications T366V and K409W (variant AZ101), and wherein the numbering of amino acid residues is according to the EU index as set forth in Kabat.

2. The isolated heteromultimer according to claim 1, wherein the heterodimer Fc region is a human IgG Fc region.

3. The isolated heteromultimer according to claim 2, wherein the IgG Fc region is an IgG1 Fc region.

4. The isolated heteromultimer according to claim 1, wherein the heteromultimer is an antibody.

5. The isolated heteromultimer according to claim 4, wherein the heteromultimer is a bispecific or multispecific antibody.

6. The isolated heteromultimer according to claim 4, wherein the antibody binds at least one cancer antigen.

7. The isolated heteromultimer according to claim 4, wherein the antibody is conjugated to a therapeutic agent.

8. A composition comprising the isolated heteromultimer of claim 1, and a pharmaceutically acceptable carrier.

* * * * *

UNITED STATES PATENT AND TRADEMARK OFFICE
CERTIFICATE OF CORRECTION

PATENT NO.       : 10,875,931 B2
APPLICATION NO.  : 15/409456
DATED            : December 29, 2020
INVENTOR(S)      : Thomas Spreter Von Kreudenstein et al.

It is certified that error appears in the above-identified patent and that said Letters Patent is hereby corrected as shown below:

On the Title Page

At the (73) Assignee, please delete "ZYMEWORKS, INC," and insert --ZYMEWORKS INC.--

Signed and Sealed this
Twenty-eighth Day of March, 2023

Katherine Kelly Vidal
*Director of the United States Patent and Trademark Office*

```
                        SEQUENCE LISTING

<160> NUMBER OF SEQ ID NOS: 6

<210> SEQ ID NO 1
<211> LENGTH: 212
<212> TYPE: PRT
<213> ORGANISM: Homo sapiens

<400> SEQUENCE: 1

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro Arg Glu Pro Gln
            100                 105                 110

Val Tyr Thr Leu Pro Pro Ser Arg Asp Glu Leu Thr Lys Asn Gln Val
        115                 120                 125

Ser Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Lys Leu Thr
                165                 170                 175

Val Asp Lys Ser Arg Trp Gln Gln Gly Asn Val Phe Ser Cys Ser Val
            180                 185                 190

Met His Glu Ala Leu His Asn His Tyr Thr Gln Lys Ser Leu Ser Leu
        195                 200                 205

Ser Pro Gly Lys
    210

<210> SEQ ID NO 2
<211> LENGTH: 317
<212> TYPE: PRT
<213> ORGANISM: Homo sapiens

<400> SEQUENCE: 2

Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
            20                  25                  30

Ser Gln Ala Ala Ala Pro Pro Lys Ala Val Leu Lys Leu Glu Pro Pro
        35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80
```

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser
            100                 105                 110

Asp Pro Val His Leu Thr Val Leu Ser Glu Trp Leu Val Leu Gln Thr
        115                 120                 125

Pro His Leu Glu Phe Gln Glu Gly Glu Thr Ile Met Leu Arg Cys His
    130                 135                 140

Ser Trp Lys Asp Lys Pro Leu Val Lys Val Thr Phe Phe Gln Asn Gly
145                 150                 155                 160

Lys Ser Gln Lys Phe Ser His Leu Asp Pro Thr Phe Ser Ile Pro Gln
                165                 170                 175

Ala Asn His Ser His Ser Gly Asp Tyr His Cys Thr Gly Asn Ile Gly
            180                 185                 190

Tyr Thr Leu Phe Ser Ser Lys Pro Val Thr Ile Thr Val Gln Val Pro
        195                 200                 205

Ser Met Gly Ser Ser Ser Pro Met Gly Ile Ile Val Ala Val Val Ile
    210                 215                 220

Ala Thr Ala Val Ala Ala Ile Val Ala Ala Val Val Ala Leu Ile Tyr
225                 230                 235                 240

Cys Arg Lys Lys Arg Ile Ser Ala Asn Ser Thr Asp Pro Val Lys Ala
                245                 250                 255

Ala Gln Phe Glu Pro Pro Gly Arg Gln Met Ile Ala Ile Arg Lys Arg
            260                 265                 270

Gln Leu Glu Glu Thr Asn Asn Asp Tyr Glu Thr Ala Asp Gly Gly Tyr
        275                 280                 285

Met Thr Leu Asn Pro Arg Ala Pro Thr Asp Asp Asp Lys Asn Ile Tyr
    290                 295                 300

Leu Thr Leu Pro Pro Asn Asp His Val Asn Ser Asn
305                 310                 315

<210> SEQ ID NO 3
<211> LENGTH: 310
<212> TYPE: PRT
<213> ORGANISM: Homo sapiens

<400> SEQUENCE: 3

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu

```
                130                 135                 140
Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Phe Ser Arg
                165                 170                 175

Ser Asp Pro Asn Phe Ser Ile Pro Gln Ala Asn His Ser His Ser Gly
                180                 185                 190

Asp Tyr His Cys Thr Gly Asn Ile Gly Tyr Thr Leu Tyr Ser Ser Lys
            195                 200                 205

Pro Val Thr Ile Thr Val Gln Ala Pro Ser Ser Pro Met Gly Ile
                210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Leu Pro
                245                 250                 255

Gly Tyr Pro Glu Cys Arg Glu Met Gly Glu Thr Leu Pro Glu Lys Pro
                260                 265                 270

Ala Asn Pro Thr Asn Pro Asp Glu Ala Asp Lys Val Gly Ala Glu Asn
                275                 280                 285

Thr Ile Thr Tyr Ser Leu Leu Met His Pro Asp Ala Leu Glu Glu Pro
290                 295                 300

Asp Asp Gln Asn Arg Ile
305                 310

<210> SEQ ID NO 4
<211> LENGTH: 323
<212> TYPE: PRT
<213> ORGANISM: Homo sapiens

<400> SEQUENCE: 4

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
                20                  25                  30

Ala Val Leu Phe Leu Ala Pro Val Ala Gly Thr Pro Ala Ala Pro Pro
            35                  40                  45

Lys Ala Val Leu Lys Leu Glu Pro Gln Trp Ile Asn Val Leu Gln Glu
        50                  55                  60

Asp Ser Val Thr Leu Thr Cys Arg Gly Thr His Ser Pro Glu Ser Asp
65                  70                  75                  80

Ser Ile Pro Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
                100                 105                 110

Cys Gln Thr Gly Gln Thr Ser Leu Ser Asp Pro Val His Leu Thr Val
            115                 120                 125

Leu Ser Glu Trp Leu Val Leu Gln Thr Pro His Leu Glu Phe Gln Glu
        130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Phe Ser Arg
                165                 170                 175

Ser Asp Pro Asn Phe Ser Ile Pro Gln Ala Asn His Ser His Ser Gly
                180                 185                 190
```

```
Asp Tyr His Cys Thr Gly Asn Ile Gly Tyr Thr Leu Tyr Ser Ser Lys
            195                 200                 205

Pro Val Thr Ile Thr Val Gln Ala Pro Ser Ser Pro Met Gly Ile
    210                 215                 220

Ile Val Ala Val Val Thr Gly Ile Ala Val Ala Ile Val Ala Ala
225                 230                 235                 240

Val Val Ala Leu Ile Tyr Cys Arg Lys Lys Arg Ile Ser Ala Asn Ser
            245                 250                 255

Thr Asp Pro Val Lys Ala Ala Gln Phe Glu Pro Pro Gly Arg Gln Met
                260                 265                 270

Ile Ala Ile Arg Lys Arg Gln Pro Glu Glu Thr Asn Asn Asp Tyr Glu
            275                 280                 285

Thr Ala Asp Gly Gly Tyr Met Thr Leu Asn Pro Arg Ala Pro Thr Asp
        290                 295                 300

Asp Asp Lys Asn Ile Tyr Leu Thr Leu Pro Pro Asn Asp His Val Asn
305                 310                 315                 320

Ser Asn Asn

<210> SEQ ID NO 5
<211> LENGTH: 254
<212> TYPE: PRT
<213> ORGANISM: Homo sapiens

<400> SEQUENCE: 5

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240
```

```
Lys Asp His Lys Phe Lys Trp Arg Lys Asp Pro Gln Asp Lys
                245                 250

<210> SEQ ID NO 6
<211> LENGTH: 233
<212> TYPE: PRT
<213> ORGANISM: Homo sapiens

<400> SEQUENCE: 6

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Ser Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
        210                 215                 220

Leu Tyr Phe Ser Val Lys Thr Asn Ile
225                 230
```